United States Patent
Dneprovskaia et al.

(10) Patent No.: US 12,312,337 B2
(45) Date of Patent: May 27, 2025

(54) COMPOUNDS AND METHODS FOR TREATING CANCER

(71) Applicant: ANTIDOTE IP HOLDINGS, LLC, Fort Lauderdale, FL (US)

(72) Inventors: Elena V. Dneprovskaia, San Diego, CA (US); Michael S. Holzwarth, San Diego, CA (US)

(73) Assignee: Antidote IP Holdings, LLC, Fort Lauderdale, FL (US)

( * ) Notice: Subject to any disclaimer, the term of this patent is extended or adjusted under 35 U.S.C. 154(b) by 807 days.

(21) Appl. No.: 17/608,434

(22) PCT Filed: May 7, 2020

(86) PCT No.: PCT/US2020/031876
§ 371 (c)(1),
(2) Date: Nov. 2, 2021

(87) PCT Pub. No.: WO2020/231739
PCT Pub. Date: Nov. 19, 2020

(65) Prior Publication Data
US 2022/0204482 A1   Jun. 30, 2022

Related U.S. Application Data

(60) Provisional application No. 62/846,390, filed on May 10, 2019.

(51) Int. Cl.

| | | |
|---|---|---|
| C07D 403/12 | (2006.01) |
| A61K 31/4365 | (2006.01) |
| A61K 31/4375 | (2006.01) |
| A61K 31/4709 | (2006.01) |
| A61K 31/496 | (2006.01) |
| A61K 31/498 | (2006.01) |
| A61K 31/4985 | (2006.01) |
| A61K 31/506 | (2006.01) |
| A61K 31/5377 | (2006.01) |
| C07D 215/48 | (2006.01) |
| C07D 265/36 | (2006.01) |
| C07D 401/12 | (2006.01) |
| C07D 401/14 | (2006.01) |
| C07D 409/14 | (2006.01) |
| C07D 413/14 | (2006.01) |
| C07D 417/14 | (2006.01) |
| C07D 471/04 | (2006.01) |
| C07D 495/04 | (2006.01) |

(52) U.S. Cl.
CPC ........ *C07D 403/12* (2013.01); *A61K 31/4365* (2013.01); *A61K 31/4375* (2013.01); *A61K 31/4709* (2013.01); *A61K 31/496* (2013.01); *A61K 31/498* (2013.01); *A61K 31/4985* (2013.01); *A61K 31/506* (2013.01); *A61K 31/5377* (2013.01); *C07D 215/48* (2013.01); *C07D 265/36* (2013.01); *C07D 401/12* (2013.01); *C07D 401/14* (2013.01); *C07D 409/14* (2013.01); *C07D 413/14* (2013.01); *C07D 417/14* (2013.01); *C07D 471/04* (2013.01); *C07D 495/04* (2013.01)

(58) Field of Classification Search
None
See application file for complete search history.

(56) References Cited

U.S. PATENT DOCUMENTS

| | | |
|---|---|---|
| 2012/0094992 A1 | 4/2012 | Brown et al. |
| 2019/0060282 A1 | 2/2019 | Ban et al. |

FOREIGN PATENT DOCUMENTS

| | | |
|---|---|---|
| EP | 2491025 B1 | 11/2013 |
| JP | 2019-052096 A | 4/2019 |
| WO | WO 03/028726 A1 | 4/2003 |
| WO | WO 2004/085436 | 10/2004 |
| WO | WO 2018/085348 A1 | 5/2018 |

OTHER PUBLICATIONS

Database Registry Chemical Abstracts Service, Columbus, Ohio, Accession No. RN 311322-56-2, Entered STN: Dec. 27, 2000.*
Database Registry Chemical Abstracts Service, Columbus, Ohio, Accession No. RN 2226196-35-4, Entered STN: May 31, 2018.*
Wang et al., "Discovery and structure-activity relationships of small molecules that block the human immunoglobulin G-human neonatal Fc receptor (hIgG-hFcRn) protein-protein interaction," Bioorg. Med. Chem. Lett. 23 (2013) 1253-1256.
Communication Pursuant to Article 94(3) EPC dated Oct. 16, 2024 for European patent application No. 20806367.7, filed Dec. 3, 2021.
Extended European Search Report with Annexes 1 and 2 dated Dec. 4, 2023 for European patent application No. 20806367.7, filed Dec. 3, 2021.
Tabatabaei-Dakhili, S. A. et al., "Untying the knot of transcription factor druggability: Molecular modeling study of FOXM1 inhibitors", Journal of Molecular Graphics and Modelling, 2018, vol. 80, pp. 197-210.

* cited by examiner

*Primary Examiner* — Samantha L Shterengarts
(74) *Attorney, Agent, or Firm* — Knobbe, Martens, Olson & Bear, LLP

(57) ABSTRACT

Compounds useful as modulators of AhR, methods of making such compounds, pharmaceutical compositions and medicaments comprising such compounds, and methods of using such compounds to treat, prevent or ameliorate AhR-mediated disorders such as cancers and inflammatory diseases are provided.

15 Claims, No Drawings

COMPOUNDS AND METHODS FOR TREATING CANCER

BACKGROUND

Field

The present application provides compounds useful as modulators of AhR, methods of making such compounds, pharmaceutical compositions and medicaments comprising such compounds, and methods of using such compounds to treat, prevent or ameliorate AhR-mediated disorders.

Description

The aryl hydrocarbon receptor (AhR) is a member of the Pern-Arnt-Sim (PAS) superfamily of transcription factors and is activated by a variety of small molecules from various external and internal sources, such as diet and metabolic degradation products, microorganisms and pollutants. Inactive AhR is localized in the cytoplasm as a part of the protein complex, consisting of HSP90, AIP, the co-shaperone p23 and possibly the c-Src protein kinase. Ligand binding triggers conformational changes in AhR that expose its nuclear localization signal. Upon ligand binding and activation, AhR dissociates from the complex and translocates from the cytoplasm into the nucleus where it forms a heterodimer with the AhR nuclear translocator (ARNT). The AhR-ARNT hetero-dimer controls the transcription of a wide variety of target genes. In particular it binds to specific cognate DNA sequence elements known as dioxin/xenobiotic response elements (DRE/XRE) present in the regulatory region of target genes, including certain xenobiotic-metabolizing enzymes such as CYP1A1, CYP1A2, CYP2B1 and UGT1A6. In addition, genes affected directly and indirectly by the TCDD/AhR-complex code for both inhibitory and stimulatory growth factors and their gene products affect cellular growth and differentiation leading to tumor promotion and carcinogenicity as well as other forms of toxicity. Aryl Hydrocarbon Receptor (AhR) affects signaling pathways critical to cell survival, proliferation and differentiation.

Cancer cells commonly over-express indoleamine-2,3-dioxygenases 1 and 2 (IDO-½) and tryptophan-2,3-dioxygenase (TDO2) enzymes responsible for tryptophan catabolism and its conversion into Kynurenine, one of the several metabolic products. Secreted metabolic products of the IDO1 and TDO2 pathways, i.e. kynurenines, have been shown to have an immunosuppressive effect on tumor microenvironment by increasing the number and function of immunosuppressive regulatory T cells and decreasing the number and function of cytotoxic CD8+ T cells. Kynurenine has been shown to inhibit proliferation of $CD4^+$ and $CD8^+$ T cells in a concentration-dependent manner. It is believed that Kynurenine is an endogenous AhR ligand that binds to the AhR with an apparent Kd of about 4 uM and acts as an agonist. Upon ligand binding, AhR translocates to the nucleus where it controls the transcription of a wide variety of target genes. Thus, small molecules capable of competing with endogenous ligands for binding to AhR and alleviating AhR-mediated immunosuppression represent a novel approach to cancer immunotherapy. See Jae Eun Cheong et al., Trends in Pharmacological Sciences 2018, 39(3):307-325; Yuying Liu et al, Cancer Cell 2018, 33:480-494; C. A. Opitz et al, Nature 2011, 478:197-203; and Lijie Zhai et al, Clinical Cancer Res 2015, 21(24):5427-5433.

SUMMARY

Some embodiments of the present disclosure relate to compounds having the structure of Formula (I):

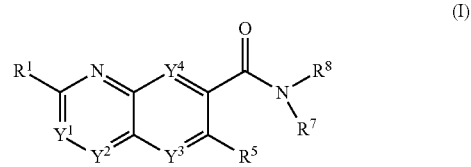

or a pharmaceutically acceptable salt thereof, wherein
$Y^1$ is N or $CR^2$;
$Y^2$ is N or $CR^3$;
$Y^3$ is N or $CR^4$;
$Y^4$ is N or $CR^6$; provided that $Y^1$ and $Y^2$ are not both N;
$R^1$ is selected from the group consisting of H, $C_{2-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkoxy)$C_{1-6}$ alkyl, —O—$(C_{1-6}$ alkoxy)$C_{1-6}$ alkyl, halo, azido, cyano, nitro, SEM, —$NR^9R^{10}$, —$OR^{11}$, —$C(O)R^{12}$, —$C(O)OR^{13}$, —$C(O)NR^{14}R^{15}$, —$S(O)_2NR^{14}R^{15}$, —$NR^{16}C(O)R^{17}$, —$S(O)_2R^{18}$, —$NR^{16}S(O)_2R^{18}$, phenyl, 5-6 membered heteroaryl and 5-6 membered heterocyclyl, wherein each of phenyl, 5-6 membered heteroaryl and 5-6 membered heterocyclyl is independently optionally substituted with one or more $R^{22}$;
each of $R^2$, $R^3$, $R^4$, $R^5$ and $R^6$ is independently selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkoxy)$C_{1-6}$ alkyl, —O—$(C_{1-6}$ alkoxy)$C_{1-6}$ alkyl, halo, azido, cyano, nitro, SEM, —$NR^9R^{10}$, —$OR^{11}$, —$C(O)R^{12}$, —$C(O)OR^{13}$, —$C(O)NR^{14}R^{15}$, —$S(O)_2NR^{14}R^{15}$, —$NR^{16}C(O)R^{17}$, —$S(O)_2R^{18}$, —$NR^{16}S(O)_2R^{18}$, phenyl, 5-6 membered heteroaryl and 5-6 membered heterocyclyl, wherein each of phenyl, 5-6 membered heteroaryl and 5-6 membered heterocyclyl is independently optionally substituted with one or more $R^{22}$;
$R^7$ is H or $C_{1-6}$ alkyl;
$R^8$ is selected from the group consisting of $C_{6-10}$ aryl, 5-6 membered heteroaryl, and 9-10 membered heteroaryl, each optionally substituted with one or more $R^4$;
each of $R^9$, $R^{10}$, $R^{14}$, $R^{15}$ and $R^{16}$ is independently selected from the group consisting of H, optionally substituted $C_{1-6}$ alkyl, optionally substituted $C_{6-10}$ aryl, optionally substituted $C_{7-14}$ aralkyl, and optionally substituted $C_{3-7}$ carbocyclyl; or $R^9$ and $R^{10}$ together with the nitrogen atom to which they are attached form a 3 to 7 membered heterocyclyl optionally substituted with one or more $R^{22}$; or $R^{14}$ and $R^{15}$ together with the nitrogen atom to which they are attached form a 3 to 7 membered heterocyclyl optionally substituted with one or more $R^{22}$;
$R^{11}$ is selected from the group consisting of optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

each of $R^{12}$, $R^{17}$ and $R^{18}$ is independently selected from the group consisting of optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

$R^{13}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

each $R^A$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, halo, hydroxy, azido, cyano, nitro, SEM, —$NR^9R^{10}$, —C(O)$NR^{14}R^{15}$, —$(CH_2)_m R^{19}$, —$O(CH_2)_n R^{20}$, and —$(CH_2)_k$—$S(O)_2$—$R^{21}$;

$R^{19}$ is selected from the group consisting of phenyl, 3 to 7 membered heterocyclyl, 5 to 6 membered heteroaryl, and —$NR^9R^{10}$, wherein each phenyl, 3 to 7 membered heterocyclyl, and 5 to 6 membered heteroaryl is optionally substituted with one or more $R^{22}$;

$R^{20}$ is selected from the group consisting of $C_{1-6}$ haloalkyl, $C_{1-6}$ alkoxy, $C_{1-6}$ haloalkoxy, optionally substituted phenyl, optionally substituted 5 or 6 membered heteroaryl, and —$NR^9R^{10}$;

$R^{21}$ is selected from the group consisting of $C_{1-6}$ alkyl, $C_{1-6}$ haloalkyl, ($C_{1-6}$ alkoxy)$C_{1-6}$ alkyl, $C_{3-7}$ carbocyclyl, $C_{6-10}$ aryl, $C_{7-14}$ aralkyl, —$NR^9R^{10}$, 3 to 7 membered heterocyclyl, and 5 to 6 membered heteroaryl, each optionally substituted with one or more $R^{22}$;

each $R^{22}$ is independently selected from the group consisting of $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, $C_{3-7}$ cycloalkyl, —$(CH_2CH_2O)_p$ $CH_2CH_2N_3$, halo, hydroxy, SEM, nitro, azido, and cyano; or two germinal $R^{22}$ form oxo; and each k, m, n and p is independently an integer selected from 0 to 6.

In some embodiments of the compounds of Formula (I), when $Y^1$ is $CR^2$; $Y^2$ is $CR^3$; $Y^3$ is $CR^4$; $Y^4$ is $CR^6$; and each of $R^1$, $R^2$, $R^3$, $R^4$, $R^5$, $R^6$ and $R^7$ is H, and $R^8$ is phenyl, then $R^8$ is substituted with one or more $R^A$ selected from the group consisting of $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, halo, hydroxy, azido, cyano, nitro, SEM, —$NR^9R^{10}$, —C(O)$NR^{14}R^{15}$, —$(CH_2)_m R^{19}$, —$O(CH_2)_n R^{20}$, and —$(CH_2)_k$—$S(O)_2$—$R^{21}$. In some further embodiments, when $Y^1$ is $CR^2$; $Y^2$ is $CR^3$; $Y^3$ is $CR^4$; $Y^4$ is $CR^6$; $R^7$ is H; and $R^8$ is pyrazolyl, thiazolyl, pyrimidyl, quinolinyl, or thiadiazolyl, each optionally substituted with one or more substituents selected from the group consisting of methyl, t-butyl, chloro, and trifluoromethoxy; then at least one of $R^1$, $R^2$, $R^3$, $R^4$, $R^5$, and $R^6$ is not H. In some further embodiments, when $Y^1$ is $CR^2$; $Y^2$ is $CR^3$; $Y^3$ is $CR^4$; $Y^4$ is $CR^6$; $R^7$ is methyl; and $R^8$ is 4-chloro-phenyl, then at least one of $R^1$, $R^2$, $R^3$, $R^4$, $R^5$, and $R^6$ is not H. In some further embodiments, when $Y^1$ is $CR^2$; $Y^2$ is $CR^3$; $Y^3$ is $CR^4$; $Y^4$ is $CR^6$; $R^7$ is H or methyl; and $R^8$ is phenyl or pyridyl optionally substituted with one or more substituents selected from the group consisting of $C_{1-6}$ alkyl, $C_{1-6}$ haloalkyl, $C_{1-6}$ alkoxy, $C_{1-6}$ haloalkoxy, halo, —$NR^9R^{10}$, —C(O)$NR^{14}R^{15}$, cyano, —$(CH_2)_m R^{19}$, —$O(CH_2)_n R^{20}$, and —$(CH_2)_k$—$S(O)_2$—$R^{21}$; then one of $R^1$, $R^2$, $R^3$, $R^4$, $R^5$, and $R^6$ is selected from the group consisting of $C_{2-6}$ alkyl, $C_{2-6}$ alkenyl, $C_{2-6}$ alkynyl, $C_{1-6}$ haloalkyl, $C_{2-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, azido, bromo, cyano, iodo, nitro, SEM, —$NR^9R^{10}$, —$OR^{11}$, —C(O)$R^{12}$, —C(O)$OR^{13}$, —C(O)$NR^{14}R^{15}$, —$S(O)_2NR^{14}R^{15}$, —$NR^{16}C(O)R^{17}$, —$S(O)_2R^{18}$, —$NR^{16}S(O)_2R^{18}$, phenyl, 5-6 membered heteroaryl, and 5-6 membered heterocyclyl, wherein each of phenyl, 5-6 membered heteroaryl and 5-6 membered heterocyclyl is independently optionally substituted with one or more $R^{22}$.

Some embodiments of the present disclosure relate to compounds having the structure of Formula (II):

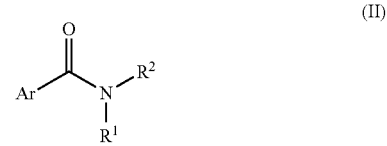

(II)

or a pharmaceutically acceptable salt thereof, wherein $R^1$ is H or $C_{1-6}$ alkyl;

$R^2$ is selected from the group consisting of $C_{6-10}$ aryl, 5-6 membered heteroaryl, and 9-10 membered heteroaryl, each optionally substituted with one or more $R^A$;

Ar is a 9 membered heteroaryl optionally substituted with one or more $R^B$;

each $R^A$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy) $C_{1-6}$ alkyl, halo, hydroxy, azido, cyano, nitro, SEM, —$NR^9R^{10}$, —C(O)$NR^{14}R^{15}$, —$(CH_2)_m R^{19}$, —$O(CH_2)_n R^{20}$, and —$(CH_2)_k$—$S(O)_2$—$R^{21}$;

each $R^B$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy) $C_{1-6}$ alkyl, —O—($C_{1-6}$ alkoxy)$C_{1-6}$ alkyl, halo, hydroxy, azido, cyano, nitro, SEM, —$NR^9R^{10}$, —$OR^{11}$, —C(O)$R^{12}$, —C(O)$OR^{13}$, —C(O)$NR^{14}R^{15}$, —$S(O)_2NR^{14}R^{15}$, —$NR^{16}C(O)R^{17}$, —$S(O)_2R^{18}$, —$NR^{16}S(O)_2R^{18}$, phenyl, 5-6 membered heteroaryl and 5-6 membered heterocyclyl, wherein each of phenyl, 5-6 membered heteroaryl and 5-6 membered heterocyclyl is independently optionally substituted with one or more $R^{22}$;

each of $R^9$, $R^{10}$, $R^{14}$, $R^{15}$ and $R^{16}$ is independently selected from the group consisting of H, optionally substituted $C_{1-6}$ alkyl, optionally substituted $C_{6-10}$ aryl, optionally substituted $C_{7-14}$ aralkyl, and optionally substituted $C_{3-7}$ carbocyclyl; or $R^9$ and $R^{10}$ together with the nitrogen atom to which they are attached form a 3 to 7 membered heterocyclyl optionally substituted with one or more $R^{22}$; or $R^{14}$ and $R^{15}$ together with the nitrogen atom to which they are attached form a 3 to 7 membered heterocyclyl optionally substituted with one or more $R^{22}$;

$R^{11}$ is selected from the group consisting of optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

each of $R^{12}$, $R^{17}$ and $R^{18}$ is independently selected from the group consisting of optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

$R^{13}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

$R^{19}$ is selected from the group consisting of phenyl, 3 to 7 membered heterocyclyl, 5 to 6 membered heteroaryl, and —$NR^9R^{10}$, wherein each phenyl, 3 to 7 membered heterocyclyl, and 5 to 6 membered heteroaryl is optionally substituted with one or more $R^{22}$;

$R^{20}$ is selected from the group consisting of $C_{1-6}$ haloalkyl, $C_{1-6}$ alkoxy, $C_{1-6}$ haloalkoxy, optionally substituted phenyl, optionally substituted 5 or 6 membered heteroaryl, and —$NR^9R^{10}$;

$R^{21}$ is selected from the group consisting of $C_{1-6}$ alkyl, $C_{1-6}$ haloalkyl, ($C_{1-6}$ alkoxy)$C_{1-6}$ alkyl, $C_{3-7}$ carbocyclyl, $C_{6-10}$ aryl, $C_{7-14}$ aralkyl, —$NR^9R^{10}$, 3 to 7 membered heterocyclyl, and 5 to 6 membered heteroaryl, each optionally substituted with one or more $R^{22}$;

each $R^{22}$ is independently selected from the group consisting of $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, $C_{3-7}$ cycloalkyl, —$(CH_2CH_2O)_p$ $CH_2CH_2N_3$, halo, hydroxy, SEM, nitro, azido, and cyano; or two germinal $R^{11}$ form oxo; and each k, m, n and p is independently an integer selected from 0 to 6.

Some embodiments of the present disclosure relate to compounds having the structure of Formula (III):

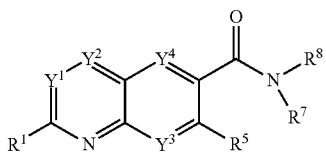

(III)

or a pharmaceutically acceptable salt thereof, wherein
$Y^1$ is N or $CR^2$;
$Y^2$ is N or $CR^3$;
$Y^3$ is N or $CR^4$;
$Y^4$ is N or $CR^6$; provided that $Y^1$ and $Y^2$ are not both N;
each of $R^1$, $R^2$, $R^3$, $R^4$, $R^5$ and $R^6$ is independently selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, halo, hydroxy, azido, cyano, nitro, SEM, —$NR^9R^{10}$, —$OR^{11}$, —$C(O)R^{12}$, —$C(O)OR^{13}$, —$C(O)NR^{14}R^{15}$, —$S(O)_2NR^{14}R^{15}$, —$NR^{16}C(O)R^{17}$, —$S(O)_2R^{18}$, —$NR^{16}S(O)_2R^{18}$, phenyl, 5-6 membered heteroaryl and 5-6 membered heterocyclyl, wherein each of phenyl, 5-6 membered heteroaryl and 5-6 membered heterocyclyl is independently optionally substituted with one or more $R^{22}$;
$R^7$ is H or $C_{1-6}$ alkyl;
$R^8$ is selected from the group consisting of $C_{6-10}$ aryl, 5-6 membered heteroaryl, and 9-10 membered heteroaryl, each optionally substituted with one or more $R^A$;

each of $R^9$, $R^{10}$, $R^{14}$, $R^{15}$ and $R^{16}$ is independently selected from the group consisting of H, optionally substituted $C_{1-6}$ alkyl, optionally substituted $C_{6-10}$ aryl, optionally substituted $C_{7-14}$ aralkyl, and optionally substituted $C_{3-7}$ carbocyclyl; or $R^9$ and $R^{10}$ together with the nitrogen atom to which they are attached form a 3 to 7 membered heterocyclyl optionally substituted with one or more $R^{22}$; or $R^{14}$ and $R^{15}$ together with the nitrogen atom to which they are attached form a 3 to 7 membered heterocyclyl optionally substituted with one or more $R^{22}$;

$R^{11}$ is selected from the group consisting of optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

each of $R^{12}$, $R^{17}$ and $R^{18}$ is independently selected from the group consisting of optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

$R^{13}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl; each $R^A$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, halo, hydroxy, azido, cyano, nitro, SEM, —$NR^9R^{10}$, —$C(O)NR^{14}R^{15}$, —$(CH_2)_mR^{19}$, —$O(CH_2)_nR^{20}$, and —$(CH_2)_k$—$S(O)_2$—$R^{21}$;

$R^{19}$ is selected from the group consisting of phenyl, 3 to 7 membered heterocyclyl, 5 to 6 membered heteroaryl, and —$NR^9R^{10}$, wherein each phenyl, 3 to 7 membered heterocyclyl, and 5 to 6 membered heteroaryl is optionally substituted with one or more $R^{22}$;

$R^{20}$ is selected from the group consisting of $C_{1-6}$ haloalkyl, $C_{1-6}$ alkoxy, $C_{1-6}$ haloalkoxy, optionally substituted phenyl, optionally substituted 5 or 6 membered heteroaryl, and —$NR^9R^{10}$;

$R^{21}$ is selected from the group consisting of $C_{1-6}$ alkyl, $C_{1-6}$ haloalkyl, ($C_{1-6}$ alkoxy)$C_{1-6}$ alkyl, $C_{3-7}$ carbocyclyl, $C_{6-10}$ aryl, $C_{7-14}$ aralkyl, —$NR^9R^{10}$, 3 to 7 membered heterocyclyl, and 5 to 6 membered heteroaryl, each optionally substituted with one or more $R^{22}$;

each $R^{22}$ is independently selected from the group consisting of $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, $C_{3-7}$ cycloalkyl, —$(CH_2CH_2O)_p$ $CH_2CH_2N_3$, halo, hydroxy, SEM, nitro, azido, and cyano; or two germinal $R^{22}$ form oxo; and each k, m, n and p is independently an integer selected from 0 to 6.

Some embodiments of the present disclosure relate to compounds having the structure of Formula (IV):

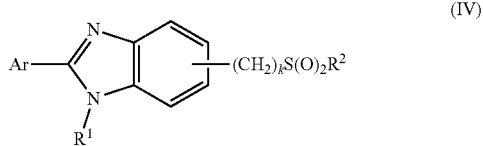

or a pharmaceutically acceptable salt thereof, wherein $R^1$ is H or $C_{1-6}$ alkyl;

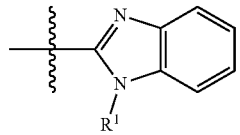

is further optionally substituted with one or more $R^A$;

Ar is a 9 or 10 membered heteroaryl optionally substituted with one or more $R^B$;

$R^2$ is selected from the group consisting of $-NR^9R^{10}$,

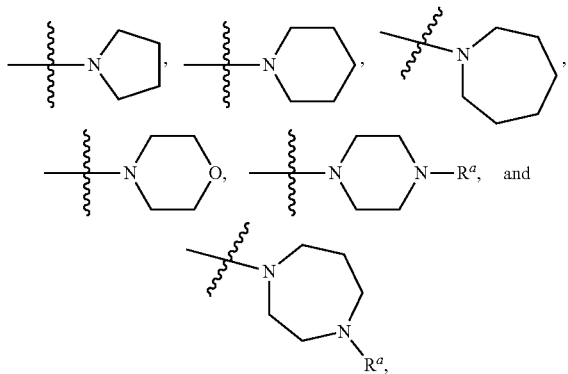

each optionally substituted with one or more $R^{22}$; and wherein each $R^a$ is independently H, $C_{1-6}$ alkyl, $C_{3-7}$ cycloalkyl, or $(C_{1-6}$ alkoxy$)C_{1-6}$ alkyl;

each $R^A$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkoxy$)C_{1-6}$ alkyl, halo, hydroxy, azido, cyano, nitro, SEM, $-(CH_2)_mR^{19}$, and $-O(CH_2)_nR^{20}$;

each $R^B$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkoxy$)C_{1-6}$ alkyl, $-O-(C_{1-6}$ alkoxy$)C_{1-6}$ alkyl, hydroxy, halo, azido, cyano, nitro, SEM, $-NR^9R^{10}$, $-OR^{11}$, $-C(O)R^{12}$, $-C(O)OR^{13}$, $-C(O)NR^{14}R^{11}$, $-S(O)_2NR^{14}R^{15}$, $-NR^{16}C(O)R^{17}$, $-S(O)_2R^{18}$, $-NR^{16}S(O)_2R^{18}$, phenyl and 5-6 membered heteroaryl, wherein each of phenyl and 5-6 membered heteroaryl is optionally substituted with one or more $R^{22}$;

each of $R^9$, $R^{10}$, $R^{14}$, $R^{15}$ and $R^{16}$ is independently selected from the group consisting of H, optionally substituted $C_{1-6}$ alkyl, optionally substituted $C_{6-10}$ aryl, optionally substituted $C_{7-14}$ aralkyl, and optionally substituted $C_{3-7}$ carbocyclyl; or $R^9$ and $R^{10}$ together with the nitrogen atom to which they are attached form a 3 to 7 membered heterocyclyl optionally substituted with one or more $R^{22}$; or $R^{14}$ and $R^{15}$ together with the nitrogen atom to which they are attached form a 3 to 7 membered heterocyclyl optionally substituted with one or more $R^{22}$;

$R^{11}$ is selected from the group consisting of optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

each of $R^{12}$, $R^{17}$ and $R^{18}$ is independently selected from the group consisting of optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

$R^{13}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;

$R^{19}$ is selected from the group consisting of phenyl, 3 to 7 membered heterocyclyl, 5 to 6 membered heteroaryl, and $-NR^9R^{10}$, wherein each phenyl, 3 to 7 membered heterocyclyl, and 5 to 6 membered heteroaryl is optionally substituted with one or more $R^{22}$;

$R^{20}$ is selected from the group consisting of $C_{1-6}$ haloalkyl, $C_{1-6}$ alkoxy, $C_{1-6}$ haloalkoxy, optionally substituted phenyl, optionally substituted 5 or 6 membered heteroaryl, and $-NR^9R^{10}$;

each $R^{22}$ is independently selected from the group consisting of $C_{1-6}$ alkyl, $C_{1-6}$ haloalkyl, $C_{1-6}$ alkoxy, $C_{1-6}$ haloalkoxy, $(C_{1-6}$ alkoxy$)C_{1-6}$ alkyl, $-O-(C_{1-6}$ alkoxy$)C_{1-6}$ alkyl, $C_{3-7}$ cycloalkyl, $-(CH_2CH_2O)_pCH_2CH_2N_3$, halo, hydroxy, SEM, nitro, azido, and cyano; or two germinal $R^{22}$ form oxo; and each k, m, n and p is independently an integer selected from 0 to 6.

In some embodiments of the compounds of Formula (IV), when Ar is quinolyl; k is 0; $R^1$ is H; $R^2$ is $-NH$-(4-Cl-Ph), $-NH$-(2-Cl-Ph), $-NH$-(3-$CF_3$-Ph),

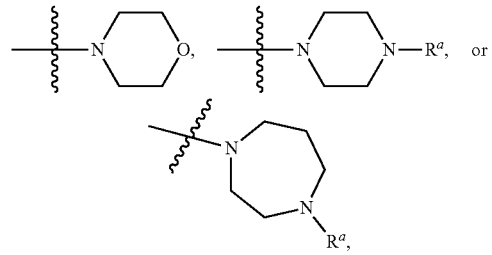

and wherein each $R^a$ is independently $-CH_3$ or $-(CH_2)_2OCH_3$; then Ar is substituted with one or more $R^B$ selected from the group consisting of $C_{2-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkoxy$)C_{1-6}$ alkyl, $-O-(C_{1-6}$ alkoxy$)C_{1-6}$ alkyl, hydroxy, halo, azido, cyano, nitro, SEM, $-NR^9R^{10}$, $-OR^{11}$, $-C(O)R^{12}$, $-C(O)OR^{13}$, $-C(O)NR^{14}R^{15}$, $-S(O)_2NR^{14}R^{15}$, $-NR^{16}C(O)R^{17}$, $-S(O)_2R^{18}$, $-NR^{16}S(O)_2R^{18}$, phenyl and 5-6 membered heteroaryl, wherein each of phenyl and 5-6 membered heteroaryl is optionally substituted with one or more $R^{22}$.

Some embodiments of the present disclosure relate to compounds having the structure of Formula (V):

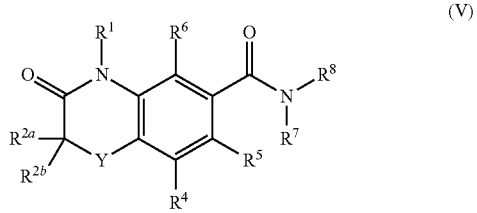

(V)

or a pharmaceutically acceptable salt thereof, wherein
Y is O or $NR^3$;
each of $R^1$, $R^3$ and $R^7$ is independently H or $C_{1-6}$ alkyl;
each of $R^{2a}$, $R^{2b}$, $R^4$, $R^5$ and $R^6$ is independently selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, halo, hydroxy, azido, cyano, nitro, SEM, —$NR^9R^{10}$, —$OR^{11}$, —$C(O)R^{12}$, —$C(O)OR^{13}$, —$C(O)NR^{14}R^{15}$, —$S(O)_2NR^{14}R^{15}$, —$NR^{16}C(O)R^{17}$, —$S(O)_2R^{18}$, —$NR^{16}S(O)_2R^{18}$, phenyl, 5-6 membered heteroaryl, and 5-6 membered heterocyclyl, wherein each of phenyl, 5-6 membered heteroaryl and 5-6 membered heterocyclyl is independently optionally substituted with one or more $R^{22}$;
$R^8$ is selected from the group consisting of $C_{6-10}$ aryl, 5-6 membered heteroaryl, and 9-10 membered heteroaryl, each optionally substituted with one or more $R^A$;
each of $R^9$, $R^{10}$, $R^{14}$, $R^{15}$ and $R^{16}$ is independently selected from the group consisting of H, optionally substituted $C_{1-6}$ alkyl, optionally substituted $C_{6-10}$ aryl, optionally substituted $C_{7-14}$ aralkyl, and optionally substituted $C_{3-7}$ carbocyclyl; or $R^9$ and $R^{10}$ together with the nitrogen atom to which they are attached form a 3 to 7 membered heterocyclyl optionally substituted with one or more $R^{22}$; or $R^{14}$ and $R^{15}$ together with the nitrogen atom to which they are attached form a 3 to 7 membered heterocyclyl optionally substituted with one or more $R^{22}$;
$R^{11}$ is selected from the group consisting of optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;
each of $R^{12}$, $R^{17}$ and $R^{18}$ is independently selected from the group consisting of optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;
$R^{13}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{6-10}$ aryl, optionally substituted 5 to 10 membered heteroaryl, optionally substituted $C_{7-14}$ aralkyl, optionally substituted 3 to 7 membered heterocyclyl, and optionally substituted $C_{3-7}$ carbocyclyl;
each $R^A$ is independently selected from the group consisting of $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, halo, hydroxy, azido, cyano, nitro, SEM, —$NR^9R^{10}$, —$C(O)NR^{14}R^{15}$, —$(CH_2)_mR^{19}$, —$O(CH_2)_nR^{20}$, and —$(CH_2)_k$—$S(O)_2$—$R^{21}$;
$R^{19}$ is selected from the group consisting of phenyl, 3 to 7 membered heterocyclyl, 5 to 6 membered heteroaryl, and —$NR^9R^{10}$, wherein each phenyl, 3 to 7 membered heterocyclyl, and 5 to 6 membered heteroaryl is optionally substituted with one or more $R^{22}$;
$R^{20}$ is selected from the group consisting of $C_{1-6}$ haloalkyl, $C_{1-6}$ alkoxy, $C_{1-6}$ haloalkoxy, optionally substituted phenyl, optionally substituted 5 or 6 membered heteroaryl, and —$NR^9R^{10}$;
$R^{21}$ is selected from the group consisting of $C_{1-6}$ alkyl, $C_{1-6}$ haloalkyl, ($C_{1-6}$ alkoxy)$C_{1-6}$ alkyl, $C_{3-7}$ carbocyclyl, $C_{6-10}$ aryl, $C_{7-14}$ aralkyl, —$NR^9R^{10}$, 3 to 7 membered heterocyclyl, and 5 to 6 membered heteroaryl, each optionally substituted with one or more $R^{22}$;
each $R^{22}$ is independently selected from the group consisting of $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, $C_{3-7}$ cycloalkyl, —($CH_2CH_2O)_p$ $CH_2CH_2N_3$, halo, hydroxy, SEM, nitro, azido, and cyano; or two germinal $R^{22}$ form oxo; and
each k, m, n and p is independently an integer selected from 0 to 6.

Some further embodiments of the present disclosure relate to pharmaceutical compositions comprising a compound of Formula (I), (II), (III), (IV) or (V) as described herein, or a pharmaceutically acceptable salt thereof, and a pharmaceutically acceptable carrier or excipient.

Some further embodiments of the present disclosure relate to or compounds of Formula (I), (II), (III), (IV) or (V) as described herein, or pharmaceutically acceptable salts thereof for use in inhibiting AhR in a subject in need thereof, or treating or ameliorating an AhR-mediated disorder in a subject in need thereof. Some additional embodiments of the present disclosure relate to methods of inhibiting AhR in a patient or treating or ameliorating an AhR-mediated disorder in a subject in need thereof, comprising administering a compound of Formula (I), (II), (III), (IV) or (V) as described herein, or a pharmaceutically acceptable salt thereof, or a pharmaceutical composition described herein to the subject. Some additional embodiments of the present disclosure relate to methods of inhibiting AhR in a biological sample, comprising contacting a compound of Formula (I), (II), (III), (IV) or (V) as described herein, or a pharmaceutically acceptable salt thereof, or a pharmaceutical composition described herein with the biological sample. In some embodiments, the AhR-mediated disorder is an inflammatory disorder or cancer. In some further embodiments, the cancer is selected from the group consisting breast cancer, melanoma, renal cancer, prostate cancer, colon cancer, lung cancer, bladder cancer, brain cancer, cervical cancer, head and neck cancer, esophageal and gastric cancers, osteosarcoma, multiple myeloma, acute myeloid leukemia, lymphomas, neuroendocrine cancer, hepatocellular carcinoma, renal cell cancer, pancreatic cancer, thyroid cancer, glioblastoma, ovarian and endometrial cancer. In some embodiments, the compound is an inhibitor of AhR. In some further embodiments, the compound may be used to affect PD-1 expression in T cells, for example, inhibits or blocks PD-1 expression on cell surface. In some further embodiments, the compound described herein may be used or co-administered to the subject with a second therapeutic agent.

DETAILED DESCRIPTION

Disclosed herein are compounds useful for the treatment of various diseases. In some embodiments, these compounds are modulators of the AhR pathway. In some further embodiments, these compounds are inhibitors of AhR, which may be useful in the treatment of AhR-mediated disorders, such as inflammatory diseases and cancers.

Definitions

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, except for the claims, a group of items linked with the conjunction 'and' should not be read as requiring that each and every one of those items be present in the grouping, but rather should be read as 'and/or' unless the context indicates otherwise. Similarly, except for the claims, a group of items linked with the conjunction 'or' should not be read as requiring mutual exclusivity among that group, but rather should be read as 'and/or' unless the context indicates otherwise.

All references cited herein are incorporated by reference in their entirety unless stated otherwise. To the extent publications and patents or patent applications incorporated by reference contradict the disclosure contained in the specification, the specification is intended to supersede and/or take precedence over any such contradictory material. In the event that there are a plurality of definitions for a term herein, those in this section prevail unless stated otherwise.

As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
Ac Acetyl
AhR Aryl hydrocarbon receptor
aq. Aqueous
ARNT Aryl hydrocarbon receptor nuclear translocator
Bn Benzyl
Bz Benzoyl
BOC or Boc tert-Butoxycarbonyl
Bu n-Butyl
° C. Temperature in degrees Centigrade
DCM Methylene chloride
ee % Enantiomeric excess
EtOH Ethanol
Et Ethyl
EtOAc Ethyl acetate
g Gram(s)
h or hr Hour(s)
iPr Isopropyl
m or min Minute(s)
MeOH MeOH
mL Milliliter(s)
PD-1 Programmed cell death protein 1
Ph Phenyl
ppt Precipitate
rt Room temperature
SEM [2-(Trimethylsilyl)ethoxy]methyl acetal
Tert, t tertiary
TLC Thin-layer chromatography
µL Microliter(s)

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a\text{-}b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1\text{-}4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1\text{-}4}$ alkyl" or similar designations. By way of example only, "$C_{1\text{-}4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyl.

As used herein, "alkoxy" refers to the formula —OR wherein R is an alkyl as is defined above, such as "$C_{1\text{-}9}$ alkoxy", including but not limited to methoxy, ethoxy, n-propoxy, 1-methylethoxy (isopropoxy), n-butoxy, iso-butoxy, sec-butoxy, and tert-butoxy.

As used herein, "alkylthio" refers to the formula —SR wherein R is an alkyl as is defined above, such as "$C_{1\text{-}9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, and tert-butylmercapto.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2\text{-}4}$ alkenyl" or similar designations. By way of example only, "$C_{2\text{-}4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2\text{-}4}$ alkynyl" or similar designations. By way of example only, "$C_{2\text{-}4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1\text{-}4}$ heteroalkyl" or similar designations. The heteroalkyl group may contain one or more heteroatoms. By way of example only, "$C_{1\text{-}4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio", including but not limited to phenyloxy.

An "aralkyl" or "arylalkyl" is an aryl group connected, as a substituent, via an alkylene group, such as "$C_{7-14}$ aralkyl", including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5, 6, 7, 8, 9 or 10 ring members or 5, 6, 7 or 8 ring members. The heteroaryl group may be designated as "5 to 8 membered heteroaryl," "5 to 10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a Ct-4 alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 7 carbon atoms. The carbocyclyl group may be designated as "$C_{3-7}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl. Some embodiments of the $C_{3-7}$ carbocyclyl group include $C_{3-7}$ cycloalkyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, and cycloheptylmethyl. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3, 4, 5, 6, or 7 ring members. The heterocyclyl group may be designated as "3 to 7 membered heterocyclyl" or similar designations. In preferred six or seven membered monocyclic heterocyclyls, the heteroatom(s) are selected from one up to three of O, N and S, and in preferred five membered monocyclic heterocyclyls, the heteroatom(s) are selected from one or two heteroatoms selected from O, N, and S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline. Some embodiments of the "heterocyclyl" described herein include monocyclic rings containing one to three heteroatoms that do not have any double or triple bond within the ring cycle.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

As used herein, an "aminoalkyl" group refers to an amino group connected via an alkylene group.

As used herein, an "alkoxyalkyl" group refers to an alkoxy group connected via an alkylene group, such as a "$C_{2-8}$ alkoxyalkyl" and ($C_{1-6}$ alkoxy)$C_{1-6}$ alkyl and the like.

As used herein, SEM group has the structure:

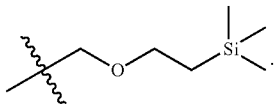 [SMILES: *COCC[Si](C)(C)C]

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, azido, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

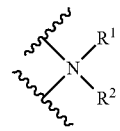

and R$^1$ and R$^2$ are defined as selected from the group consisting of hydrogen and alkyl, or R$^1$ and R$^2$ together with the nitrogen to which they are attached form a heterocyclyl, it is meant that R$^1$ and R$^2$ can be selected from hydrogen or alkyl, or alternatively, the substructure has structure:

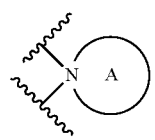

where ring A is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

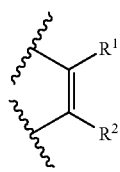

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

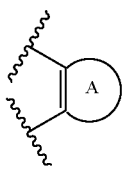

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

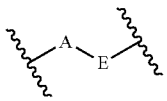

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes can be present in the compounds described. Each chemical element as represented in a compound structure can include any isotope of said element. For example, at any position of the compound that a hydrogen atom is be present, the hydrogen atom encompasses any isotope of hydrogen, including but not limited to hydrogen-1 (protium) and hydrogen-2 (deuterium). Thus, reference herein to a compound encompasses all potential isotopic forms unless the context clearly dictates otherwise. Deuteration replacement of a hydrogen-1 at a metabolically labile position of a compound may improve the pharmacokinetic properties of the compound.

As used herein, the term "partial agonist" is a compound that binds to and activates a given receptor, but have only partial efficacy at the receptor relative to a full agonist. In some instance, a partial agonist displays both agonistic and antagonistic effects when both a full agonist and partial agonist are present, the partial agonist actually acts as a competitive antagonist, competing with the full agonist for receptor occupancy and producing a net decrease in the receptor activation observed with the full agonist alone. For example, a partial agonist of AhR binds to and activates AhR receptor but may act as a competitive antagonist in the presence of a full agonist of AhR.

Compounds

Formula (A)

Some embodiments of the present disclosure relate to compounds of Formula (A).

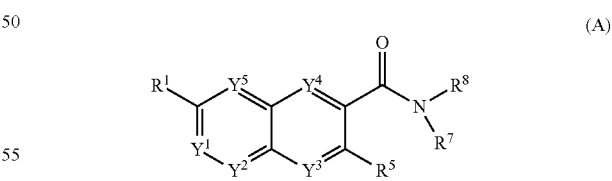

or a pharmaceutically acceptable salt thereof, wherein
$Y^1$ is N or $CR^2$;
$Y^2$ is N or $CR^3$;
$Y^3$ is N or $CR^4$;
$Y^4$ is N or $CR^6$;
$Y^5$ is N or $CR^{1'}$; provided that $Y^1$ and $Y^2$ are not both N;
$R^1$ is selected from the group consisting of H, $C_{2-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, halo, azido, cyano, nitro, SEM, —NR$^9$R$^{10}$, —OR$^{11}$, —C(O)R$^{12}$, —C(O)OR$^{13}$, —C(O)NR$^{14}$R$^{15}$, —S(O)$_2$NR$^{14}$R$^{15}$, —NR$^{16}$C(O)R$^{17}$, —S(O)$_2$R$^{18}$, —NR$^{16}$S(O)$_2$R$^{18}$, phenyl, and 5-6 membered heteroaryl, wherein each of phenyl and 5-6 membered heteroaryl is optionally substituted with one or more R$^{22}$;

each of R$^1$, R$^2$, R$^3$, R$^4$, R$^5$ and R$^6$ is independently selected from the group consisting of H, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, (C$_{1-6}$ alkoxy)C$_{1-6}$ alkyl, —O—(C$_{1-6}$ alkoxy)C$_{1-6}$ alkyl, halo, azido, cyano, nitro, SEM, —NR$^9$R$^{10}$, —OR$^{11}$, —C(O)R$^{12}$, —C(O)OR$^{13}$, —C(O)NR$^{14}$R$^{15}$, —S(O)$_2$NR$^{14}$R$^{15}$, —NR$^{16}$C(O)R$^{17}$, —S(O)$_2$R$^{18}$, —NR$^{16}$S(O)$_2$R$^{18}$, phenyl, 5-6 membered heteroaryl and 5-6 membered heterocyclyl, wherein each of phenyl, 5-6 membered heteroaryl and 5-6 membered heterocyclyl is independently optionally substituted with one or more R$^{22}$;

R$^7$ is H or C$_{1-6}$ alkyl;

R$^8$ is selected from the group consisting of C$_{6-10}$ aryl, 5-6 membered heteroaryl, and 9-10 membered heteroaryl, each optionally substituted with one or more R$^A$;

each of R$^9$, R$^{10}$, R$^{14}$, R$^{15}$ and R$^{16}$ is independently selected from the group consisting of H, optionally substituted C$_{1-6}$ alkyl, optionally substituted C$_{6-10}$ aryl, optionally substituted C$_{7-14}$ aralkyl, and optionally substituted C$_{3-7}$ carbocyclyl; or R$^9$ and R$^{10}$ together with the nitrogen atom to which they are attached form a 3 to 7 membered heterocyclyl optionally substituted with one or more R$^{22}$; or R$^{14}$ and R$^{15}$ together with the nitrogen atom to which they are attached form a 3 to 7 membered heterocyclyl optionally substituted with one or more R$^{22}$;

R$^{11}$ is selected from the group consisting of optionally substituted C$_{2-6}$ alkenyl, optionally substituted C$_{2-6}$ alkynyl, optionally substituted C$_{6-10}$ aryl, optionally substituted 5 to 10 membered heteroaryl, optionally substituted C$_{7-14}$ aralkyl, optionally substituted 3 to 7 membered heterocyclyl, and optionally substituted C$_{3-7}$ carbocyclyl;

each of R$^{12}$, R$^{17}$ and R$^{18}$ is independently selected from the group consisting of optionally substituted C$_{1-6}$ alkyl, optionally substituted C$_{2-6}$ alkenyl, optionally substituted C$_{2-6}$ alkynyl, optionally substituted C$_{6-10}$ aryl, optionally substituted 5 to 10 membered heteroaryl, optionally substituted C$_{7-14}$ aralkyl, optionally substituted 3 to 7 membered heterocyclyl, and optionally substituted C$_{3-7}$ carbocyclyl;

R$^{13}$ is selected from the group consisting of H, optionally substituted C$_{1-6}$ alkyl, optionally substituted C$_{2-6}$ alkenyl, optionally substituted C$_{2-6}$ alkynyl, optionally substituted C$_{6-10}$ aryl, optionally substituted 5 to 10 membered heteroaryl, optionally substituted C$_{7-4}$ aralkyl, optionally substituted 3 to 7 membered heterocyclyl, and optionally substituted C$_{3-7}$ carbocyclyl;

each R$^A$ is independently selected from the group consisting of C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, (C$_{1-6}$ alkoxy)C$_{1-6}$ alkyl, halo, hydroxy, azido, cyano, nitro, SEM, —NR$^9$R$^{10}$, —C(O)NR$^{14}$R$^{15}$, —(CH$_2$)$_m$R$^{19}$, —O(CH$_2$)$_n$R$^{20}$, and —(CH$_2$)$_k$—S(O)$_2$—R$^{21}$;

R$^{19}$ is selected from the group consisting of phenyl, 3 to 7 membered heterocyclyl, 5 to 6 membered heteroaryl, and —NR$^9$R$^{10}$, wherein each phenyl, 3 to 7 membered heterocyclyl, and 5 to 6 membered heteroaryl is optionally substituted with one or more R$^{22}$;

R$^{20}$ is selected from the group consisting of C$_{1-6}$ haloalkyl, C$_{1-6}$ alkoxy, C$_{1-6}$ haloalkoxy, optionally substituted phenyl, optionally substituted 5 or 6 membered heteroaryl, and —NR$^9$R$^{10}$;

R$^{21}$ is selected from the group consisting of C$_{1-6}$ alkyl, C$_{1-6}$ haloalkyl, (C$_{1-6}$ alkoxy)C$_{1-6}$ alkyl, C$_{3-7}$ carbocyclyl, C$_{6-10}$ aryl, C$_{7-14}$ aralkyl, —NR$^9$R$^{10}$, 3 to 7 membered heterocyclyl, and 5 to 6 membered heteroaryl, each optionally substituted with one or more R$^{22}$;

each R$^{22}$ is independently selected from the group consisting of C$_{1-6}$ alkyl, C$_{1-6}$ haloalkyl, C$_{1-6}$ alkoxy, C$_{1-6}$ haloalkoxy, (C$_{1-6}$ alkoxy)C$_{1-6}$ alkyl, —O—(C$_{1-6}$ alkoxy)C$_{1-6}$ alkyl, C$_{3-7}$ cycloalkyl, —(CH$_2$CH$_2$O)$_p$CH$_2$CH$_2$N$_3$, halo, hydroxy, SEM, nitro, azido, and cyano; or two germinal R$^{22}$ form oxo; and each k, m, n and p is independently an integer selected from 0 to 6.

In some embodiments of the compounds of Formula (A), when Y$^1$ is CR$^2$; Y$^2$ is CR$^3$; Y$^3$ is CR$^4$; Y$^4$ is CR$^6$; Y$^5$ is N; and each of R$^1$, R$^2$, R$^3$, R$^4$, R$^5$, R$^6$ and R$^7$ is H, and R$^8$ is phenyl, then R$^8$ is substituted with one or more R$^A$ selected from the group consisting of C$_{2-6}$ alkenyl, C$_{2-6}$ alkynyl, C$_{1-6}$ haloalkyl, C$_{1-6}$ alkoxy, C$_{1-6}$ haloalkoxy, (C$_{1-6}$ alkoxy)C$_{1-6}$ alkyl, halo, hydroxy, azido, cyano, nitro, SEM, —NR$^9$R$^{10}$, —C(O)NR$^{14}$R$^{15}$, —(CH$_2$)$_m$R$^{19}$, —O(CH$_2$)$_n$R$^{20}$, and —(CH$_2$)$_k$—S(O)$_2$—R$^{21}$. In some further embodiments, when Y$^1$ is CR$^2$; Y$^2$ is CR$^3$; Y$^3$ is CR$^4$; Y$^4$ is CR$^6$; Y$^5$ is N; R$^7$ is H; and R$^8$ is pyrazolyl, thiazolyl, pyrimidyl, quinolinyl, or thiadiazolyl, each optionally substituted with one or more substituents selected from the group consisting of methyl, t-butyl, chloro, and trifluoromethoxy; then at least one of R$^1$, R$^2$, R$^3$, R$^4$, R$^5$, and R$^6$ is not H. In some further embodiments, when Y$^1$ is CR$^2$; Y$^2$ is CR$^3$; Y$^3$ is CR$^4$; Y$^4$ is CR$^6$; Y$^5$ is N; R$^7$ is H; and R$^8$ is phenyl or pyridyl optionally substituted with one or more substituents selected from the group consisting of C$_{1-6}$ alkyl, C$_{1-6}$ haloalkyl, C$_{1-6}$ alkoxy, C$_{1-6}$ haloalkoxy, halo, —NR$^9$R$^{10}$, —C(O)NR$^{14}$R$^{15}$, cyano, —(CH$_2$)$_m$R$^{19}$, —O(CH$_2$)$_n$R$^{20}$, and —(CH$_2$)$_k$—S(O)$_2$—R$^{21}$; then one of R$^1$, R$^2$, R$^3$, R$^4$, R$^5$, and R$^6$ is selected from the group consisting of C$_{2-6}$ alkyl, C$_{2-6}$ alkenyl, C$_{2-6}$ alkynyl, C$_{1-6}$ haloalkyl, C$_{2-6}$ alkoxy, C$_{1-6}$ haloalkoxy, (C$_{1-6}$ alkoxy) C$_{1-6}$ alkyl, —O—(C$_{1-6}$ alkoxy)C$_{1-6}$ alkyl, azido, bromo, cyano, iodo, nitro, SEM, —NR$^9$R$^{10}$, —OR$^{11}$, —C(O)R$^{12}$, —C(O)OR$^1$, —C(O)NR$^{14}$R$^{15}$, —S(O)$_2$NR$^{14}$R$^{15}$, —NR$^{16}$C(O)R$^{17}$, —S(O)$_2$R$^{18}$, —NR$^{16}$S(O)$_2$R$^{18}$, phenyl, 5-6 membered heteroaryl and 5-6 membered heterocyclyl, wherein each of phenyl, 5-6 membered heteroaryl and 5-6 membered heterocyclyl is optionally substituted with one or more R$^{22}$. In some further embodiments, when Y$^1$ is CR$^2$; Y$^2$ is CR$^3$; Y$^3$ is CR$^4$; Y$^4$ is CR$^6$; Y$^5$ is N; R$^7$ is methyl; and R$^8$ is 4-chloro-phenyl, then at least one of R$^1$, R$^2$, R$^3$, R$^4$, R$^5$, and R$^6$ is not H.

In some embodiments of the compounds of Formula (A), Y$^5$ is N and the compound is also represented by Formula (I). In some other embodiments, Y$^2$ is N, Y$^1$ is CR$^2$, Y$^3$ is CR$^4$, Y$^4$ is CR$^6$, and Y$^5$ is CR$^{1'}$. In any embodiments of the compounds of Formula (A), R$^{11}$ is H. In any embodiments of the compounds of Formula (A), R$^{1'}$ is H.

Formula (I)

Some embodiments of the present disclosure relate to compounds having the structure of Formula (I) or pharmaceutically acceptable salts thereof as described herein.

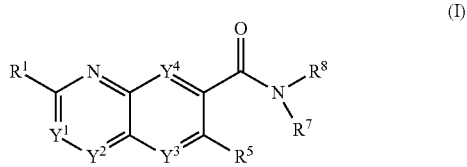
(I)

In some embodiments of the compounds of Formula (I), when $Y^1$ is $CR^2$; $Y^2$ is $CR^3$; $Y^3$ is $CR^4$; $Y^4$ is $CR^6$; and each of $R^1$, $R^2$, $R^3$, $R^4$, $R^5$, $R^6$ and $R^7$ is H, and $R^8$ is phenyl, then $R^8$ is substituted with one or more $R^A$ selected from the group consisting of $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, halo, hydroxy, azido, cyano, nitro, SEM, —$NR^9R^{10}$, —C(O)$NR^{14}R^{15}$, —$(CH_2)_mR^{19}$, —$O(CH_2)_nR^{20}$, and —$(CH_2)_k$—S(O)$_2$—$R^{21}$. In some further embodiments, when $Y^1$ is $CR^2$; $Y^2$ is $CR^3$; $Y^3$ is $CR^4$; $Y^4$ is $CR^6$; $R^7$ is H; and $R^8$ is phenyl or pyridyl optionally substituted with one or more substituents selected from the group consisting of $C_{1-6}$ alkyl, $C_{1-6}$ haloalkyl, $C_{1-6}$ alkoxy, $C_{1-6}$ haloalkoxy, halo, —$NR^9R^{10}$, —C(O)$NR^{14}R^{15}$, cyano, —$(CH_2)_mR^{19}$, —$O(CH_2)_nR^{20}$, and —$(CH_2)_k$—S(O)$_2$—$R^2$; then one of $R^1$, $R^2$, $R^3$, $R^4$, $R^5$, and $R^6$ is selected from the group consisting of $C_{2-6}$ alkyl, $C_{2-6}$ alkenyl, $C_{2-6}$ alkynyl, $C_{1-6}$ haloalkyl, $C_{2-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, azido, bromo, cyano, iodo, nitro, SEM, —$NR^9R^{10}$, —$OR^{11}$, —$C(O)R^{12}$, —$C(O)OR^{13}$, —$C(O)NR^{14}R^{15}$, —$S(O)_2NR^{14}R^{15}$, —$NR^{16}C(O)R^{17}$, —$S(O)_2R^1$, —$NR^{16}S(O)_2R^{18}$, phenyl, 5-6 membered heteroaryl and 5-6 membered heterocyclyl, wherein each of phenyl, 5-6 membered heteroaryl and 5-6 membered heterocyclyl is independently optionally substituted with one or more $R^{22}$. In some further embodiments, when $Y^1$ is $CR^2$; $Y^2$ is $CR^3$; $Y^3$ is $CR^4$; $Y^4$ is $CR^6$; $R^7$ is H, and $R^8$ is

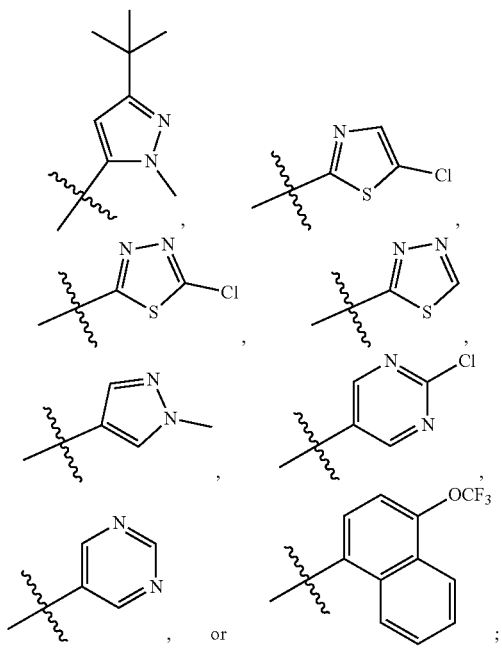

then at least one of $R^1$, $R^2$, $R^3$, $R^4$, $R^5$, and $R^6$ is not H. In some further embodiments, when $Y^1$ is $CR^2$; $Y^2$ is $CR^3$; $Y^3$ is $CR^4$; $Y^4$ is $CR^6$; $R^7$ is methyl; and $R_B$ is 4-chloro-phenyl, then at least one of $R^1$, $R^2$, $R^3$, $R^4$, $R^5$, and $R^6$ is not H.

In some embodiments of the Formula (A) or (I), $Y^1$ is $CR^2$, $Y^2$ is $CR^3$, $Y^3$ is $CR^4$, and $Y^4$ is $CR^6$. In some other embodiments, $Y^2$ is N, $Y^1$ is $CR^2$, $Y^3$ is $CR^4$, and $Y^4$ is $CR^6$. In some such embodiments, each of $R^2$, $R^4$ and $R^6$ is H. In some other embodiments, at least one of $R^2$, $R^4$ and $R^6$ is not H. For example, $R^4$ is methoxy, and $R^2$ and $R^6$ is independently H, halo, $C_{1-6}$ alkyl, $C_{1-6}$ haloalkyl, $C_{1-6}$ haloalkoxy (such as H, —Cl, —F, —Br, methyl, ethyl, methoxy, trifluoromethyl, trifluoromethoxy), —O-phenyl, —O-pyridyl, phenyl, 5-6 membered heteroaryl (e.g., pyridyl, pyrimidinyl, thienyl, thiazolyl, isothiazolyl, oxazolyl, isoxazolyl, pyrazolyl, imidazolyl, etc.) and 5-6 membered heterocyclyl (e.g., piperidyl, piperizinyl or morpholinyl), where each of the —O-phenyl, —O-pyridyl, phenyl, 5-6 membered heteroaryl and 5-6 membered heterocyclyl may be optionally substituted with one or more $R^{22}$. In some further embodiments, $R^2$ is H, halo, —O— phenyl, —O-pyridyl, thienyl, thiazolyl, isothiazolyl, pyrazolyl, oxazolyl, isoxazolyl, imidazolyl, pyridyl, pyrimidinyl or phenyl, wherein each of —O-phenyl, —O-pyridyl, thienyl, thiazolyl, isothiazolyl, pyrazolyl, oxazolyl, isoxazolyl, imidazolyl, pyridyl, pyrimidinyl and phenyl is independently optionally substituted with one or more $R^{22}$. In some further embodiments, each of —O-phenyl, —O-pyridyl, thienyl, thiazolyl, isothiazolyl, pyrazolyl, oxazolyl, isoxazolyl, imidazolyl, pyridyl, pyrimidinyl and phenyl is independently optionally substituted with one or more substituents independently selected from the group consisting of halo, hydroxy, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, and —O($C_{1-6}$ alkoxy)$C_{1-6}$ alkyl. In some embodiments, each $R^4$ and $R^6$ is H and $R^2$ is not H.

In some embodiments of the Formula (A) or (I), $Y^3$ is N. In some such embodiments, $Y^1$ is $CR^2$, $Y^2$ is $CR^3$, and $Y^4$ is $CR^6$. In some such embodiments, each of $R^2$, $R^3$ and $R^6$ is H. In some other embodiments, at least one of $R^2$, $R^3$ and $R^6$ is not H. For example, $R^3$ is methoxy, and each $R^2$ and $R^6$ is independently H, halo, $C_{1-6}$ alkyl, $C_{1-6}$ haloalkyl, $C_{1-6}$ haloalkoxy (such as H, —Cl, —F, —Br, methyl, ethyl, methoxy, trifluoromethyl, trifluoromethoxy), —O-phenyl, —O-pyridyl, phenyl, 5-6 membered heteroaryl (e.g., pyridyl, pyrimidinyl, thienyl, thiazolyl, isothiazolyl, oxazolyl, isoxazolyl, pyrazolyl, imidazolyl, etc.) and 5-6 membered heterocyclyl (e.g., piperidyl, piperizinyl or morpholinyl), where each of the —O-phenyl, —O-pyridyl, phenyl, 5-6 membered heteroaryl and 5-6 membered heterocyclyl may be optionally substituted with one or more $R^{22}$. In some further embodiments, $R^2$ is H, halo, —O-phenyl, —O-pyridyl, thienyl, thiazolyl, isothiazolyl, pyrazolyl, oxazolyl, isoxazolyl, imidazolyl, pyridyl, pyrimidinyl or phenyl, wherein each —O-phenyl, —O-pyridyl, thienyl, thiazolyl, isothiazolyl, pyrazolyl, oxazolyl, isoxazolyl, imidazolyl, pyridyl, pyrimidinyl and phenyl is independently optionally substituted with one or more substituents selected from the group consisting of halo, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, and —O($C_{1-6}$ alkoxy)$C_{1-6}$ alkyl. In some embodiments, each $R^4$ and $R^6$ is H and $R^2$ is not H.

In some embodiments of the Formula (A) or (I), both $Y^2$ and $Y^3$ are N. In some such embodiments, $Y^1$ is $CR^2$ and $Y^4$ is $CR^6$. In some such embodiments, each of $R^2$ and $R^6$ is H. In some other embodiments, at least one of $R^2$ and $R^6$ is not H. For example, $R^6$ is —Cl, and $R^2$ is H, halo, —O-phenyl, —O-pyridyl, thienyl, thiazolyl, isothiazolyl, pyrazolyl, oxazolyl, isoxazolyl, imidazolyl, pyridyl, pyrimidinyl or phenyl, wherein each of —O-phenyl, —O-pyridyl, thienyl, thiazolyl, isothiazolyl, pyrazolyl, oxazolyl, isoxazolyl, imidazolyl, pyridyl, pyrimidinyl and phenyl is independently optionally substituted with one or more $R^{22}$. In some further embodiments, each of —O-phenyl, —O-pyridyl, thienyl, thiazolyl, isothiazolyl, pyrazolyl, oxazolyl, isoxazolyl, imidazolyl, pyridyl, pyrimidinyl and phenyl is independently optionally substituted with one or more substituents independently selected from the group consisting of halo, hydroxy, $C_{1-6}$ alkyl, $C_{1-6}$ haloalkyl, $C_{1-6}$ alkoxy, $C_{1-6}$ haloalkoxy, $(C_{1-6}$ alkoxy$)C_{1-6}$ alkyl, and —O($C_{1-6}$ alkoxy) $C_{1-6}$ alkyl. In some embodiment, $R^6$ is H and $R^2$ is not H.

In some embodiments of the Formula (A) or (I), $Y^4$ is N. In some such embodiments, $Y^1$ is $CR^2$, $Y^2$ is $CR^3$, and $Y^3$ is $CR^4$. In some such embodiments, each of $R^2$, $R^3$ and $R^4$ is H. In some other embodiments, at least one of $R^2$, $R^3$ and $R^4$ is not H. For example, $R^3$ is methoxy, and $R^2$ and $R^4$ is independently H, halo, $C_{1-6}$ alkyl, $C_{1-6}$ haloalkyl, $C_{1-6}$ haloalkoxy (such as H, —Cl, —F, —Br, methyl, ethyl, methoxy, trifluoromethyl, trifluoromethoxy), —O-phenyl, —O-pyridyl, phenyl, 5-6 membered heteroaryl (e.g., pyridyl, pyrimidinyl, thienyl, thiazolyl, isothiazolyl, oxazolyl, isoxazolyl, pyrazolyl, imidazolyl, etc.) and 5-6 membered heterocyclyl (e.g., piperidyl, piperizinyl or morpholinyl), where each of the —O-phenyl, —O-pyridyl, phenyl, 5-6 membered heteroaryl and 5-6 membered heterocyclyl may be optionally substituted with one or more $R^{22}$. In some further embodiments, $R^2$ is H, halo, —O-phenyl, —O-pyridyl, thienyl, thiazolyl, isothiazolyl, pyrazolyl, oxazolyl, isoxazolyl, imidazolyl, pyridyl, pyrimidinyl or phenyl, wherein each of —O-phenyl, —O-pyridyl, thienyl, thiazolyl, isothiazolyl, pyrazolyl, oxazolyl, isoxazolyl, imidazolyl, pyridyl, pyrimidinyl and phenyl is independently optionally substituted with one or more substituents selected from the group consisting of halo, hydroxy, $C_{1-6}$ alkyl, $C_{1-6}$ haloalkyl, $C_{1-6}$ alkoxy, $C_{1-6}$ haloalkoxy, $(C_{1-6}$ alkoxy$)C_{1-6}$ alkyl, and —O($C_{1-6}$ alkoxy$)C_{1-6}$ alkyl. In some such embodiments, $R^4$ is H.

In some embodiments of the compounds of Formula (A) or (I), $R^7$ is H. In another embodiment, $R^7$ is methyl.

In some embodiments of the compounds of Formula (A) or (I), $R^8$ is phenyl, pyridyl, pyrazolyl, thiazolyl, imidazolyl, pyrimidyl, quinolinyl, or thiadiazolyl, each optionally substituted with one or more $R^4$. In some embodiments, $R^8$ is unsubstituted. In some embodiments, $R^8$ is substituted with one or more $R^4$. In one embodiment, $R^8$ is phenyl substituted with one or more $R^4$. In another embodiment, $R^8$ is pyridyl substituted with one or more $R^4$. In some such embodiments, $R^4$ is selected from the group consisting of $C_{1-6}$ alkyl, $C_{1-6}$ haloalkyl, $C_{1-6}$ alkoxy, $C_{1-6}$ haloalkoxy, and halo. In some other embodiments, $R^4$ is —C(O)$NR^{14}R^{15}$, where $R^{14}$ and $R^{15}$ together with the nitrogen atom to which they are attached form a 6 or 7 membered heterocyclyl selected from the group consisting of

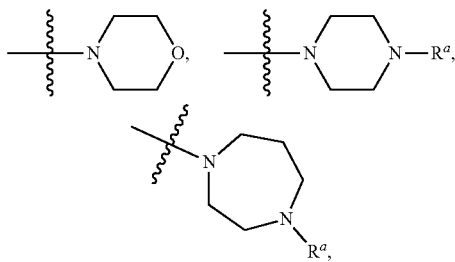

each optionally substituted with one or more $R^{22}$, and $R^a$ is independently H, $C_{1-6}$ alkyl, $C_{3-7}$ cycloalkyl, or $(C_{1-6}$ alkoxy$)C_{1-6}$ alkyl. In some embodiments, $R^a$ is H, methyl, cyclopentyl, or —(CH$_2$)$_2$OCH$_3$. In some other embodiments, $R^A$ is —(CH$_2$)$_m$$R^{19}$ and wherein m is 0, 1 or 2. In one embodiment, m is 0. In some embodiments, $R^{19}$ is phenyl optionally substituted with one or more substituents selected from the group consisting of halo, $C_{1-6}$ alkyl, $C_{1-6}$ haloalkyl, $C_{1-6}$ alkoxy, and $C_{1-6}$ haloalkoxy; or $R^{19}$ is a 6 or 7 membered heterocyclyl selected from the group consisting of

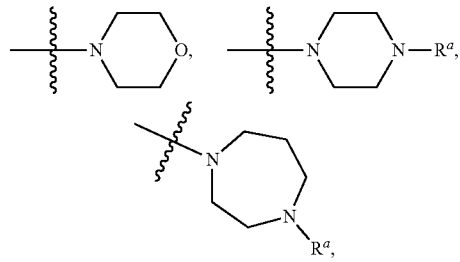

each optionally substituted with one or more $R^{22}$ and wherein $R^a$ is independently H, $C_{1-6}$ alkyl, $C_{3-7}$ cycloalkyl, or $(C_{1-6}$ alkoxy$)C_{1-6}$ alkyl. In some embodiments, $R^a$ is H, methyl, cyclopentyl, or —(CH$_2$)$_2$OCH$_3$. In some further embodiments, $R^{19}$ is substituted with one or more $R^{22}$; for example, $R^{19}$ is substituted with oxo formed by two adjacent $R^{22}$. In some other embodiments, $R^A$ is —(CH$_2$)$_k$—S(O)$_2$—$R^{21}$ and wherein k is 0, 1 or 2. In one embodiment, k is 0. In some embodiments, $R^{21}$ is a 5, 6 or 7 membered heterocyclyl selected from the group consisting of

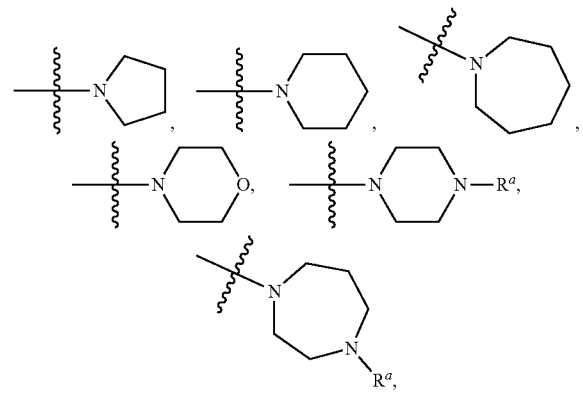

each optionally substituted with one or more $R^{22}$, and wherein $R^a$ is independently H, $C_{1-6}$ alkyl, $C_{3-7}$ cycloalkyl, or $(C_{1-6}$ alkoxy$)C_{1-6}$ alkyl. In some embodiments, $R^a$ is H, methyl, cyclopentyl, or —(CH$_2$)$_2$OCH$_3$. In some further embodiments, $R^{21}$ is substituted with one or more $R^{22}$; for example, $R^{21}$ is substituted with oxo formed by two adjacent $R^{22}$. In some other embodiments, $R^{21}$ is —$NR^9R^{10}$, and wherein each $R^9$ and $R^{10}$ is independently H, $C_{1-6}$ alkyl, optionally substituted phenyl, or optionally substituted $C_{3-7}$ cycloalkyl; for example, the phenyl or $C_{3-7}$ cycloalkyl may be optionally substituted with one or more $R^{22}$. In some further embodiments, $R^9$ is H or $C_{1-6}$ alkyl, and $R^{10}$ is $C_{1-6}$ alkyl, cyclopropyl, cyclopentyl, cyclohexyl, or phenyl. In some further embodiments, the phenyl group is substituted with halo, $C_{1-6}$ alkyl, or —O—($C_{1-6}$ alkoxy$)C_{1-6}$ alkyl; for example, methyl, —F, —Cl, or —(CH$_2$)$_2$OCH$_3$.

In some embodiments of the Formula (A) or (I), $R^8$ is a substituted pyrazolyl and the compounds have the structure of Formula (Ia):

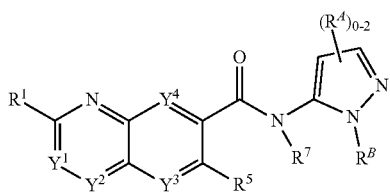

(Ia)

or a pharmaceutically acceptable salt thereof, wherein each $R^A$ is independently defined herein, $R^B$ is H, $C_{1-6}$ alkyl, $C_{1-6}$ haloalkyl, $(C_{1-6}$ alkoxy$)C_{1-6}$ alkyl, or phenyl optionally substituted with one or more $R^{22}$. In some embodiments, $R^B$ is H, $C_{1-6}$ alkyl, $C_{1-6}$ haloalkyl, $(C_{1-6}$ alkoxy$)C_{1-6}$ alkyl, or phenyl one or more substituents selected from the group consisting of $C_{1-6}$ alkyl, $C_{1-6}$ haloalkyl, $C_{1-6}$ alkoxy, $C_{1-6}$ haloalkoxy, halo, azido, cyano, and nitro.

In some further embodiments, the compound of Formula (Ta) is also represented by the structure of Formula (Ia-1), (Ia-2), (Ia-3), (Ia-4) or (Ia-5):

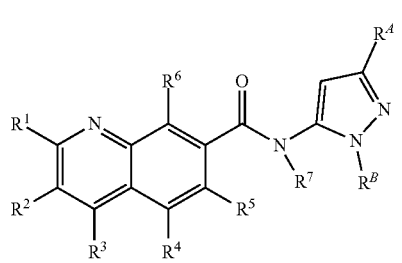

(Ia-1)

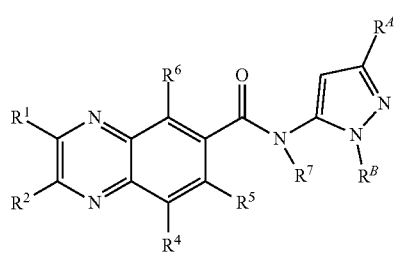

(Ia-2)

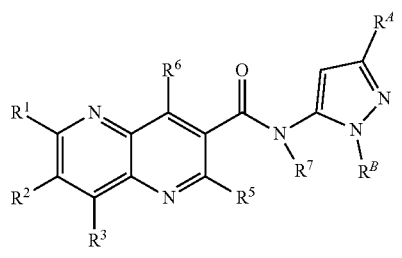

(Ia-3)

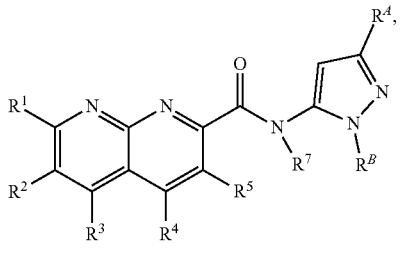

(Ia-4)

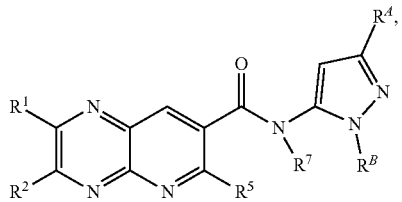

(Ia-5)

or a pharmaceutically acceptable salt thereof. In some such embodiments, $R^A$ is selected from the group consisting of $C_{1-6}$ alkyl, $C_{1-6}$ haloalkyl, $C_{1-6}$ alkoxy, $C_{1-6}$ haloalkoxy, halo, and $-(CH_2)_m R^{19}$. In some further embodiments, $R^A$ is tert-butyl, isobutyl, or $CF_3$. In some such embodiments, $R^A$ is $-(CH_2)_m R^{19}$, and wherein m is 0, and $R^{19}$ is phenyl optionally substituted with one or more substituents selected from the group consisting of halo, $C_{1-6}$ alkyl, $C_{1-6}$ haloalkyl, $C_{1-6}$ alkoxy, and $C_{1-6}$ haloalkoxy. In some further embodiments, $R^{19}$ is phenyl substituted with two substituents such as $C_{1-6}$ alkyl and halo, $C_{1-6}$ haloalkyl and halo, or $C_{1-6}$ alkyl and $C_{1-6}$ haloalkyl. In some embodiments, $R^B$ is selected from the group consisting of $CH_3$, $CF_3$, $CH_2CF_3$, isopropyl, and phenyl.

In any embodiments of the compounds of Formula (I), (Ta), (Ia-1), (Ia-2), (Ia-3), (Ia-4) or (Ia-5), $R^1$ is H.

In any embodiments of the compounds of Formula (I), (Ia), (Ia-1), (Ia-2), (Ia-3), (Ia-4) or (Ia-5), $R^2$ is H, halo, $-OR^{11}$, thienyl, thiazolyl, isothiazolyl, pyrazolyl, oxazolyl, isoxazolyl, imidazolyl, pyridyl, pyrimidinyl, or phenyl, wherein each thienyl, thiazolyl, isothiazolyl, pyrazolyl, oxazolyl, isoxazolyl, imidazolyl, pyridyl, pyrimidinyl, and phenyl is independently optionally substituted with one or more substituents selected from the group consisting of halo, hydroxy, $C_{1-6}$ alkyl, $C_{1-6}$ haloalkyl, $C_{1-6}$ alkoxy, $C_{1-6}$ haloalkoxy, $(C_{1-6}$ alkoxy$)C_{1-6}$ alkyl, and $-O(C_{1-6}$ alkoxy$)C_{1-6}$ alkyl. In some such embodiments, $R^{11}$ is phenyl or pyridyl, each optionally substituted with one or more $R^{22}$, for example, halo, hydroxy, $C_{1-6}$ alkyl, $C_{1-6}$ haloalkyl, $C_{1-6}$ alkoxy, $C_{1-6}$ haloalkoxy, $(C_{1-6}$ alkoxy$)C_{1-6}$ alkyl, or $-O(C_{1-6}$ alkoxy$)C_{1-6}$ alkyl.

In any embodiments of the compounds of Formula (I), (Ta), (Ia-1), (Ia-2), (Ia-3), (Ia-4) or (Ia-5), $R^3$ is H, $C_{1-6}$ alkoxy, $-N(C_{1-6}$ alkyl$)(C_{1-6}$ alkyl$)$, a 5-6 membered heterocyclyl or $-OR^{11}$. In some such embodiment, $R^3$ is H or methoxy. In one embodiment, $R^3$ is

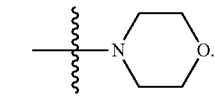

In another embodiment, $R^3$ is $-N(CH_3)_2$. In some such embodiments, $R^{11}$ is phenyl or pyridyl, each optionally substituted with one or more $R^{22}$, for example, halo, hydroxy, $C_{1-6}$ alkyl, $C_{1-6}$ haloalkyl, $C_{1-6}$ alkoxy, $C_{1-6}$ haloalkoxy, $(C_{1-6}$ alkoxy$)C_{1-6}$ alkyl, or $-O(C_{1-6}$ alkoxy$)C_{1-6}$ alkyl.

In any embodiments of the compounds of Formula (I), (Ta), (Ia-1), (Ia-2), (Ia-3), (Ia-4) or (Ia-5), each $R^4$, $R^5$ and $R^6$ is independently H, halo or $C_{1-6}$ alkyl. In one embodiment, each $R^4$, $R^5$ and $R^6$ is H.

In some embodiments of the compounds of Formula (A), (I) (Ia), (Ia-1), (Ia-2), (Ia-3), (Ia-4) or (Ia-5), $R^{19}$ is selected from 3, 4, 5, 6 or 7 membered heterocyclyl, or 5 to 6 membered heteroaryl, each optionally substituted with one or more $R^{22}$.

In further embodiments of the compounds of Formula (A), (I) (Ia), (Ia-1), (Ia-2), (Ia-3), (Ia-4) or (Ia-5), when each of $R^9$, $R^{10}$, $R^{14}$, $R^{15}$ and $R^{16}$ is independently optionally substituted $C_{1-6}$ alkyl, optionally substituted $C_{6-10}$ aryl, optionally substituted $C_{7-14}$ aralkyl, or optionally substituted $C_{3-7}$ carbocyclyl, each may be optionally substituted with one or more $R^{22}$ as defined herein. In addition, each of $R^{12}$, $R^{17}$ and $R^{18}$ may be optionally substituted with one more or $R^{22}$. When $R^{20}$ is optionally substituted phenyl, or optionally substituted 5 or 6 membered heteroaryl, each may also be optionally substituted with one or more $R^{22}$.

In some embodiments of the compounds of Formula (A), (I) (Ia), (Ia-1), (Ia-2), (Ia-3), (Ia-4) or (Ia-5), each $R^{11}$ is independently selected from the group consisting of halo, hydroxy, $C_{1-6}$ alkyl, $C_{1-6}$ haloalkyl, $(C_{1-6}$ alkoxy)$C_{1-6}$ alkyl, and —O—$(C_{1-6}$ alkoxy)$C_{1-6}$ alkyl. In some other embodiments, two adjacent $R^{22}$ form an oxo.

Additional embodiments of the compounds of Formula (I) are selected from the group consisting of compounds 1, 3-5, 9, 15, 17-19, 23-31, and 36-128 of Table 1, and pharmaceutically acceptable salts thereof.

Formula (II)

Some embodiments of the present disclosure relate to compounds having the structure of Formula (II) as described herein, or pharmaceutically acceptable salts thereof.

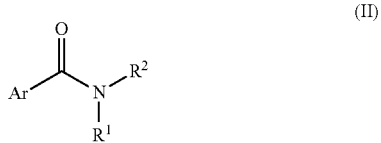

(II)

In some embodiments of the compounds of Formula (II), Ar contains one, two or three heteroatoms selected from the group consisting of N (nitrogen), O (oxygen) and S (sulfur), for example, Ar may be selected from the group consisting of benzothiazolyl, benzoxazolyl, benzimidazolyl, thienopyridyl, and indolyl, each optionally substituted with one or more $R^B$, for example, Ar is

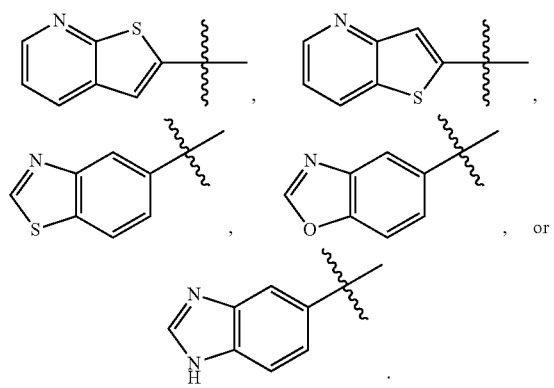

In some embodiments, Ar is unsubstituted. In some other embodiments, Ar is substituted with one or more $R^B$. In some further embodiments, Ar is

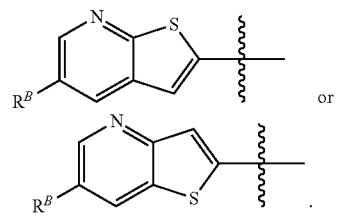

In some such embodiments, each $R^B$ is independently selected from the group consisting of halo, $C_{1-6}$ alkyl, $C_{1-6}$ haloalkyl, $C_{1-6}$ haloalkoxy (such as H, —Cl, —F, —Br, methyl, ethyl, methoxy, trifluoromethyl, trifluoromethoxy), —O-phenyl, —O-pyridyl, phenyl, 5-6 membered heteroaryl (e.g., pyridyl, pyrimidinyl, thienyl, thiazolyl, isothiazolyl, oxazolyl, isoxazolyl, pyrazolyl, imidazolyl, etc.) and 5-6 membered heterocyclyl (e.g., piperidyl, piperizinyl or morpholinyl), where each of the —O-phenyl, —O-pyridyl, phenyl, 5-6 membered heteroaryl and 5-6 membered heterocyclyl may be optionally substituted with one or more $R^{22}$. In some further embodiments, $R^B$ is halo, —O-phenyl, —O-pyridyl, thienyl, thiazolyl, isothiazolyl, pyrazolyl, oxazolyl, isoxazolyl, imidazolyl, pyridyl, pyrimidinyl, or phenyl, wherein each —O-phenyl, —O-pyridyl, thienyl, thiazolyl, isothiazolyl, pyrazolyl, oxazolyl, isoxazolyl, imidazolyl, pyridyl, pyrimidinyl, and phenyl is independently optionally substituted with one or more substituents selected from the group consisting of halo, hydroxy, $C_{1-6}$ alkyl, $C_{1-6}$ haloalkyl, $C_{1-6}$ alkoxy, $C_{1-6}$haloalkoxy, $(C_{1-6}$ alkoxy)$C_{1-6}$ alkyl, and —O$(C_{1-6}$ alkoxy)$C_{1-6}$ alkyl.

In some embodiments of the compounds of Formula (III), $R^1$ is H. In another embodiment, $R^1$ is methyl.

In some embodiments of the compounds of Formula (II), $R^2$ is phenyl, pyridyl, pyrazolyl, imidazolyl, thiazolyl, pyrimidyl, quinolinyl, or thiadiazolyl, each optionally substituted with one or more $R^A$. In one embodiment, $R^2$ is phenyl optionally substituted with one or more $R^A$. In another embodiment, $R^2$ is pyridyl optionally substituted with one or more $R^A$. In another embodiments, $R^2$ is pyrazolyl substituted with one or more $R^A$. For example, $R^2$ is

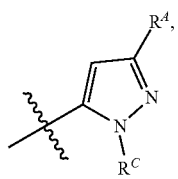

wherein $R^C$ is H, $C_{1-6}$ alkyl, $C_{1-6}$ haloalkyl, $(C_{1-6}$ alkoxy)$C_{1-6}$ alkyl, or phenyl optionally substituted with one or more $R^{22}$. In some embodiments, $R^C$ is H, $C_{1-6}$ alkyl, $C_{1-6}$ haloalkyl, $(C_{1-6}$ alkoxy)$C_{1-6}$ alkyl, or phenyl one or more substituents selected from the group consisting of $C_{1-6}$ alkyl, $C_{1-6}$ haloalkyl, $C_{1-6}$ alkoxy, $C_{1-6}$ haloalkoxy, halo, hydroxy, azido, cyano, and nitro.

In some embodiments of the compounds of Formula (II), $R^A$ is selected from the group consisting of $C_{1-6}$ alkyl, $C_{1-6}$ haloalkyl, $C_{1-6}$ alkoxy, $C_{1-6}$ haloalkoxy, and halo, for example, methyl, t-Bu, isobutyl, —Cl, —F, or —CF$_3$. In some other embodiments, $R^A$ is —$(CH_2)_m R^{19}$, and wherein m is 0 or 1, and $R^{19}$ is phenyl optionally substituted with one or more substituents selected from the group consisting of halo, $C_{1-6}$ alkyl, $C_{1-6}$ haloalkyl, $C_{1-6}$ alkoxy, and $C_{1-6}$ haloalkoxy. In some further embodiments, $R^{19}$ is phenyl substituted with two substituents such as $C_{1-6}$ alkyl and halo, $C_{1-6}$ haloalkyl and halo, or $C_{1-6}$ alkyl and $C_{1-6}$ haloalkyl. In some other embodiments, $R^{19}$ is a 6 or 7 membered heterocyclyl selected from the group consisting of

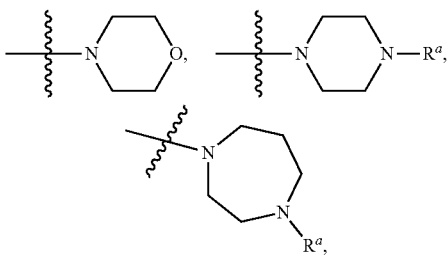

each optionally substituted with one or more $R^{22}$ and wherein $R^a$ is independently H, $C_{1-6}$ alkyl, $C_{3-7}$ cycloalkyl, or $(C_{1-6}$ alkoxy$)C_{1-6}$ alkyl. In some embodiments, $R^a$ is H, methyl, cyclopentyl, or $-(CH_2)_2OCH_3$. In some further embodiments, $R^{19}$ is substituted with one or more $R^{22}$; for example, $R^{19}$ is substituted with oxo formed by two adjacent $R^{22}$.

In some other embodiments, $R^4$ is $-C(O)NR^{14}R^{15}$, where $R^{14}$ and $R^{15}$ together with the nitrogen atom to which they are attached form a 6 or 7 membered heterocyclyl selected from the group consisting of

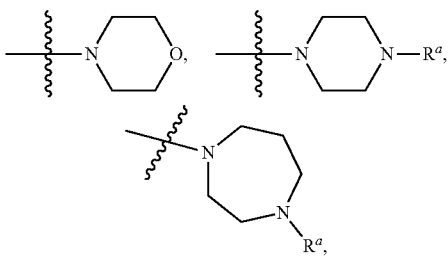

each optionally substituted with one or more $R^{22}$, and $R^a$ is independently H, $C_{1-6}$ alkyl, $C_{3-7}$ cycloalkyl, or $(C_{1-6}$ alkoxy$)C_{1-6}$ alkyl. In some embodiments, $R^a$ is H, methyl, cyclopentyl, or $-(CH_2)_2OCH_3$.

In some other embodiments, $R^4$ is $-(CH_2)_k-S(O)_2-R^{21}$ and wherein k is 0, 1 or 2. In one embodiment, k is 0. In some embodiments, $R^{21}$ is a 5, 6 or 7 membered heterocyclyl selected from the group consisting of

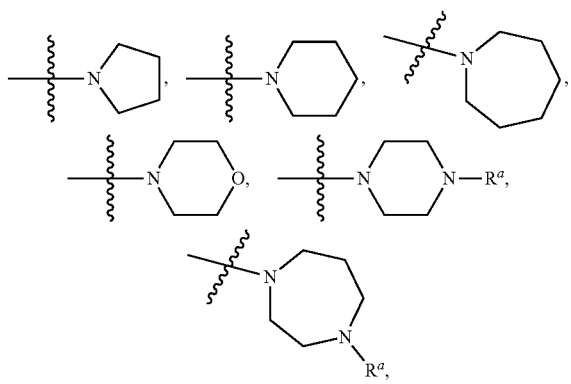

each optionally substituted with one or more $R^{22}$, and wherein $R^a$ is independently H, $C_{1-6}$ alkyl, $C_{3-7}$ cycloalkyl, or $(C_{1-6}$ alkoxy$)C_{1-6}$ alkyl. In some embodiments, $R^a$ is H, methyl, cyclopentyl, or $-(CH_2)_2OCH_3$. In some further embodiments, $R^{21}$ is substituted with one or more $R^{22}$; for example, $R^{21}$ is substituted with oxo formed by two adjacent $R^{22}$. In some other embodiments, $R^{21}$ is $-NR^9R^{10}$, and wherein each $R^9$ and $R^{10}$ is independently H, $C_{1-6}$ alkyl, optionally substituted phenyl, or optionally substituted $C_{3-7}$ cycloalkyl; for example, the phenyl or $C_{3-7}$ cycloalkyl may be optionally substituted with one or more $R^{22}$. In some further embodiments, $R^9$ is H or $C_{1-6}$ alkyl, and $R^{10}$ is $C_{1-6}$ alkyl, cyclopropyl, cyclopentyl, cyclohexyl, or phenyl. In some further embodiments, the phenyl group is substituted with halo, $C_{1-6}$ alkyl, or $-O-(C_{1-6}$ alkoxy$)C_{1-6}$ alkyl; for example, methyl, $-F$, $-Cl$, or $-(CH_2)_2OCH_3$.

In some embodiments of the compounds of Formula (II), when each of $R^9$, $R^{10}$, $R^{14}$, $R^{11}$ and $R^{16}$ is independently optionally substituted $C_{1-6}$ alkyl, optionally substituted $C_{6-10}$ aryl, optionally substituted $C_{7-14}$ aralkyl, or optionally substituted $C_{3-7}$ carbocyclyl, each may be optionally substituted with one or more $R^{22}$ as defined herein. In addition, each of $R^{12}$, $R^{17}$ and $R^{18}$ may be optionally substituted with one more or $R^{22}$. When $R^{20}$ is optionally substituted phenyl, or optionally substituted 5 or 6 membered heteroaryl, each may also be optionally substituted with one or more $R^{22}$.

In some embodiments of the compounds of Formula (II), $R^{19}$ is selected from 3, 4, 5, 6 or 7 membered heterocyclyl, or 5 to 6 membered heteroaryl, each optionally substituted with one or more $R^{22}$.

In some embodiments of the compounds of Formula (II), each $R^{22}$ is independently selected from the group consisting of halo, hydroxy, $C_{1-6}$ alkyl, $C_{1-6}$ haloalkyl, $(C_{1-6}$ alkoxy$)C_{1-6}$ alkyl, and $-O-(C_{1-6}$ alkoxy$)C_{1-6}$ alkyl. In some other embodiments, two adjacent $R^{22}$ form an oxo.

Additional embodiments of the compounds of Formula (II) are selected from the group consisting of Compounds 2, 129-154 and 165-168 of Table 1, and pharmaceutically acceptable salts thereof.

Formula (III)

Some embodiments of the present disclosure relate to compounds having the structure of Formula (III) as described herein, or pharmaceutically acceptable salts thereof.

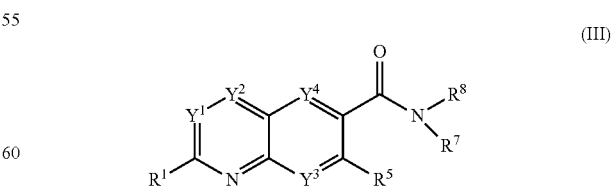

(III)

In some embodiments of the compounds of Formula (III), the 10 membered heteroaryl core of the compound is a quinolyl and the compounds are also represented by the structure of Formula (IIIa):

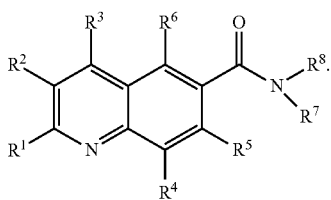

(IIIa)

Other embodiments of the 10-membered heteroaryl core may include:

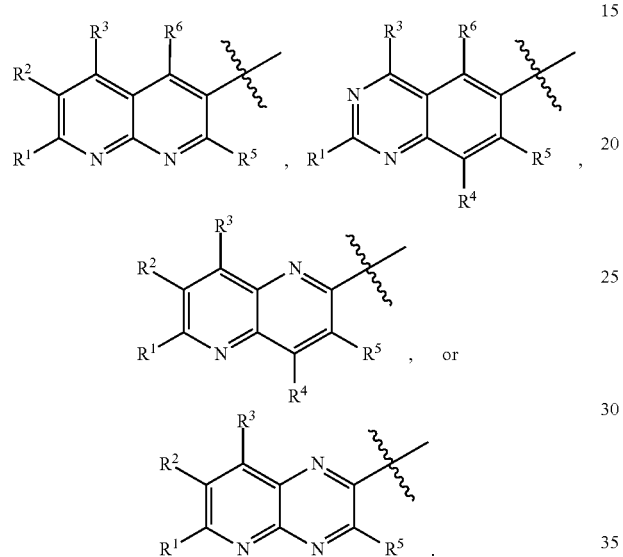

In some embodiments of the compounds of Formula (III) or (IIIa), $R^7$ is H. In another embodiment, $R^7$ is methyl.

In some embodiments of the compounds of Formula (III), $R^8$ is phenyl, pyridyl, pyrazolyl, imidazolyl, thiazolyl, pyrimidyl, quinolinyl, orthiadiazolyl, each optionally substituted with one or more $R^4$. In some embodiments, $R^8$ is unsubstituted. In one embodiment, $R^8$ is phenyl optionally substituted with one or more $R^4$. In another embodiment, $R^8$ is pyridyl optionally substituted with one or more $R^4$. In another embodiments, $R^8$ is pyrazolyl optionally substituted with one or more $R^4$. For example, $R^8$ is

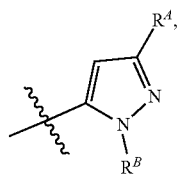

wherein $R^B$ is H, $C_{1-6}$ alkyl, $C_{1-6}$ haloalkyl, $(C_{1-6}$ alkoxy)$C_{1-6}$ alkyl, or phenyl optionally substituted with one or more $R^{22}$. In some embodiments, $R^B$ is H, $C_{1-6}$ alkyl, $C_{1-6}$ haloalkyl, $(C_{1-6}$ alkoxy)$C_{1-6}$ alkyl, or phenyl one or more substituents selected from the group consisting of $C_{1-6}$ alkyl, $C_{1-6}$ haloalkyl, $C_{1-6}$ alkoxy, $C_{1-6}$ haloalkoxy, halo, hydroxy, azido, cyano, and nitro.

In some embodiments of the compounds of Formula (III) or (IIIa), $R^4$ is selected from the group consisting of $C_{1-6}$ alkyl, $C_{1-6}$ haloalkyl, $C_{1-6}$ alkoxy, $C_{1-6}$ haloalkoxy, and halo, for example, methyl, t-Bu, isobutyl, —Cl, —F, or —CF$_3$. In some other embodiments, $R^4$ is —(CH$_2$)$_m$R$^{19}$, and wherein m is 0 or 1, and $R^{19}$ is phenyl optionally substituted with one or more substituents selected from the group consisting of halo, $C_{1-6}$ alkyl, $C_{1-6}$ haloalkyl, $C_{1-6}$ alkoxy, and $C_{1-6}$ haloalkoxy. In some further embodiments, $R^{19}$ is phenyl substituted with two substituents such as $C_{1-6}$ alkyl and halo, $C_{1-6}$ haloalkyl and halo, or $C_{1-6}$ alkyl and $C_{1-6}$ haloalkyl. In some other embodiments, $R^{19}$ is a 6 or 7 membered heterocyclyl selected from the group consisting of

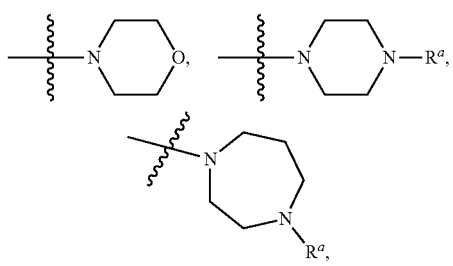

each optionally substituted with one or more $R^{22}$ and wherein $R^a$ is independently H, $C_{1-6}$ alkyl, $C_{3-7}$ cycloalkyl, or ($C_{1-6}$ alkoxy)$C_{1-6}$ alkyl. In some embodiments, $R^a$ is H, methyl, cyclopentyl, or —(CH$_2$)$_2$OCH$_3$. In some further embodiments, $R^{19}$ is substituted with one or more $R^{22}$; for example, $R^{19}$ is substituted with oxo formed by two adjacent $R^{22}$.

In some other embodiments of the compounds of Formula (III) or (IIIa), $R^4$ is —C(O)NR$^{14}$R$^{15}$, where $R^{14}$ and $R^{15}$ together with the nitrogen atom to which they are attached form a 6 or 7 membered heterocyclyl selected from the group consisting of

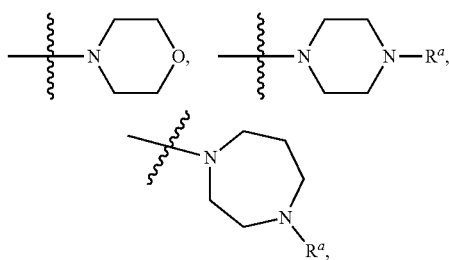

each optionally substituted with one or more $R^{22}$, and $R^a$ is independently H, $C_{1-6}$ alkyl, $C_{3-7}$ cycloalkyl, or ($C_{1-6}$ alkoxy)$C_{1-6}$ alkyl. In some embodiments, $R^a$ is H, methyl, cyclopentyl, or —(CH$_2$)$_2$OCH$_3$.

In some other embodiments of the compounds of Formula (III) or (IIIa), $R^4$ is —(CH$_2$)$_k$—S(O)$_2$—R$^{21}$ and wherein k is 0, 1 or 2. In one embodiment, k is 0. In some embodiments, $R^{21}$ is a 5, 6 or 7 membered heterocyclyl selected from the group consisting of,

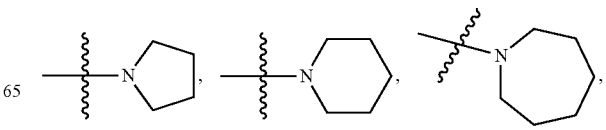

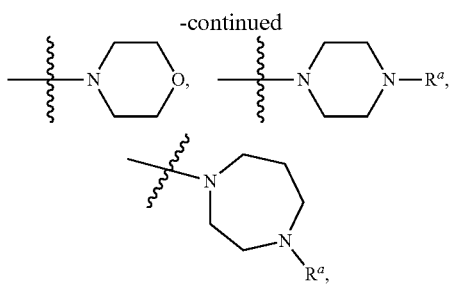

each optionally substituted with one or more $R^{22}$, and wherein $R^a$ is independently H, $C_{1-6}$ alkyl, $C_{3-7}$ cycloalkyl, or ($C_{1-6}$ alkoxy)$C_{1-6}$ alkyl. In some embodiments, $R^a$ is H, methyl, cyclopentyl, or —$(CH_2)_2OCH_3$. In some further embodiments, $R^{21}$ is substituted with one or more $R^{22}$; for example, $R^{21}$ is substituted with oxo formed by two adjacent $R^{22}$. In some other embodiments, $R^{21}$ is —$NR^9R^{10}$, and wherein each $R^9$ and $R^{10}$ is independently H, $C_{1-6}$ alkyl, optionally substituted phenyl, or optionally substituted $C_{3-7}$ cycloalkyl; for example, the phenyl or $C_{3-7}$ cycloalkyl may be optionally substituted with one or more $R^{22}$. In some further embodiments, $R^9$ is H or $C_{1-6}$ alkyl, and $R^{10}$ is $C_{1-6}$ alkyl, cyclopropyl, cyclopentyl, cyclohexyl, or phenyl. In some further embodiments, the phenyl group is substituted with halo, $C_{1-6}$ alkyl, or —O—($C_{1-6}$ alkoxy)$C_{1-6}$ alkyl; for example, methyl, —F, —Cl, or —$(CH_2)_2OCH_3$.

In any embodiments of the compounds of Formula (III) or (IIIa), $R^1$ is H, halo, —$OR^{11}$, thienyl, thiazolyl, isothiazolyl, imidazolyl, pyrazolyl, oxazolyl, isoxazolyl, pyridyl, pyrimidinyl or phenyl, wherein each of thienyl, thiazolyl, isothiazolyl, imidazolyl, pyrazolyl, oxazolyl, isoxazolyl, pyridyl, pyrimidinyl and phenyl is optionally substituted with one or more $R^{22}$. In some such embodiments, $R^{11}$ is phenyl or pyridyl, each optionally substituted halo, hydroxy, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, or —O($C_{1-6}$ alkoxy)$C_{1-6}$ alkyl.

In any embodiments of the compounds of Formula (III) or (IIIa), $R^3$ is H, $C_{1-6}$ alkoxy, or —$OR^{11}$. In some such embodiment, $R^3$ is H or methoxy. In some such embodiments, $R^{11}$ is phenyl or pyridyl, each optionally substituted with one or more $R^{22}$, for example, halo, hydroxy, $C_{1-6}$ alkyl, $C_{1-6}$ haloalkyl, $C_{1-6}$ alkoxy, $C_{1-6}$ haloalkoxy, (($C_{1-6}$ alkoxy) $C_{1-6}$ alkyl, or —O($C_{1-6}$ alkoxy)$C_{1-6}$ alkyl.

In any embodiments of the compounds of Formula (III) or (IIIa), each $R^2$, $R^4$, $R^5$ and $R^6$ is independently H, halo or $C_{1-6}$ alkyl. In one embodiment, each $R^2$, $R^4$, $R^5$ and $R^6$ is H.

In some embodiments of the compounds of Formula (III) or (IIIa), when each of $R^9$, $R^{10}$, $R^{14}$, $R^{15}$ and $R^{16}$ is independently optionally substituted $C_{1-6}$ alkyl, optionally substituted $C_{6-10}$ aryl, optionally substituted $C_{7-14}$ aralkyl, or optionally substituted $C_{3-7}$ carbocyclyl, each may be optionally substituted with one or more $R^{22}$ as defined herein. In addition, each of $R^{12}$, $R^{17}$ and $R^{11}$ may be optionally substituted with one more or $R^{22}$. When $R^{20}$ is optionally substituted phenyl, or optionally substituted 5 or 6 membered heteroaryl, each may also be optionally substituted with one or more $R^{22}$.

In some embodiments of the compounds of Formula (III) or (IIIa), $R^{19}$ is selected from 3, 4, 5, 6 or 7 membered heterocyclyl, or 5 to 6 membered heteroaryl, each optionally substituted with one or more $R^{22}$.

In some embodiments of the compounds of Formula (III) or (IIIa), each $R^{22}$ is independently selected from the group consisting of halo, hydroxy, $C_{1-6}$ alkyl, $C_{1-6}$ haloalkyl, ($C_{1-6}$ alkoxy)$C_{1-6}$ alkyl, and —O—($C_{1-6}$ alkoxy)$C_{1-6}$ alkyl. In some other embodiments, two adjacent $R^{22}$ form an oxo.

Additional embodiments of the compounds of Formula (III) or (IIIa) are selected from the group consisting of Compounds 156 and 158-161 of Table 1, and pharmaceutically acceptable salts thereof.

Formula (IV)

Some embodiments of the present disclosure relate to compounds having the structure of Formula (IV) as described herein, or pharmaceutically acceptable salts thereof.

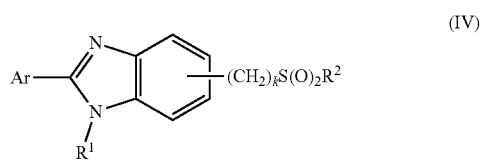

(IV)

In some embodiments of the compounds of Formula (IV), when Ar is

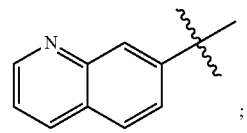 [SMILES: *c1ccc2cccnc2c1]

;

k is 0; $R^1$ is H; $R^2$ is —NH-(4-$C_1$-Ph), —NH-(2-$C_1$-Ph), —NH-(3-$CF_3$-Ph),

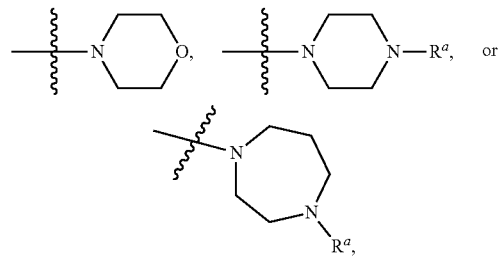

and wherein each $R^a$ is independently —$CH_3$ or —$(CH_2)_2$ $OCH_3$; then Ar is substituted with one or more $R^B$ selected from the group consisting of $C_{2-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, ($C_{1-6}$ alkoxy)$C_{1-6}$ alkyl, —O—($C_{1-6}$ alkoxy)$C_{1-6}$ alkyl, hydroxy, halo, azido, cyano, nitro, SEM, —$NR^9R^{10}$, —$OR^{11}$, —$C(O)$ $R^{12}$, —$C(O)OR^{13}$, —$C(O)NR^{14}R^{11}$, —$S(O)_2NR^{14}R^{15}$, —$NR^{16}C(O)R^{17}$, —$S(O)_2R^{18}$, —$NR^{16}S(O)_2R^{18}$, phenyl and 5-6 membered heteroaryl, wherein each of phenyl and 5-6 membered heteroaryl is optionally substituted with one or more $R^{22}$.

In some embodiments of the compounds of Formula (IV), Ar is a 10-membered heteroaryl selected from the group consisting of quinolyl

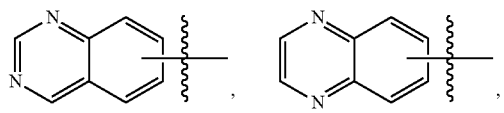

,

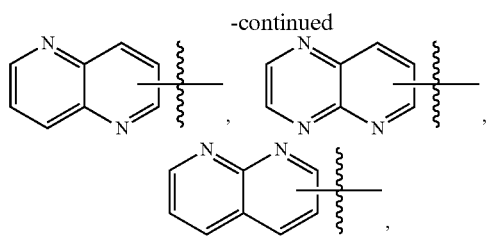 , 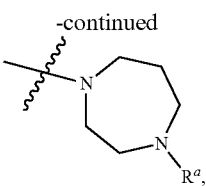 and

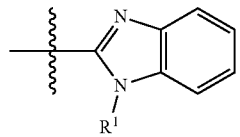

each optionally substituted with one or more $R^B$. In some embodiments, Ar is unsubstituted. In some other embodiments, Ar is substituted with one or more $R^B$. In one embodiment, Ar is quinolyl optionally substituted with one or more $R^B$. In some other embodiments, Ar is a 9-membered heteroaryl selected from the group consisting of benzothiazolyl, benzoxazolyl, benzimidazolyl, thienopyridyl, and indolyl, each optionally substituted with one or more $R^B$.

In some further embodiments, compounds of Formula (IV) also have the structure of Formula (IVa) or (IVb):

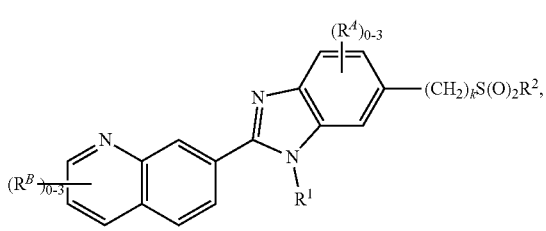 (IVa)

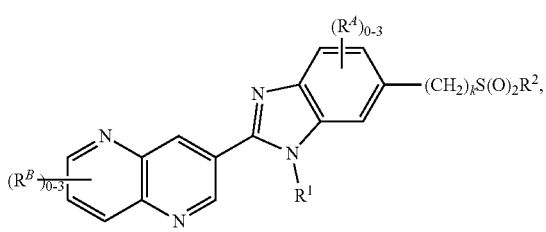 (IVb)

or a pharmaceutically acceptable salt thereof, where each $R^A$ is independently defined herein.

In some embodiments of the compounds of Formula (IV), (IVa) or (IVb), each $R_B$ is independently $C_{1-6}$ alkyl, $C_{1-6}$ haloalkyl, $C_{1-6}$ alkoxy, $C_{1-6}$ haloalkoxy, or halo. For example, each $R_B$ is independently methoxy, methyl, —C$_l$, —F, or —CF$_3$. In one embodiment, Ar is 4-methoxy quinolyl.

In some embodiments of the compounds of Formula (IV), (IVa) or (IVb), $R^1$ is H. In another embodiment, $R^1$ is methyl.

In some embodiments of the compounds of Formula (IV), (IVa) or (IVb), k is 0, 1 or 2. In one embodiment, k is 0.

In some embodiments of the compounds of Formula (IV), (IVa) or (IVb), $R^2$ is

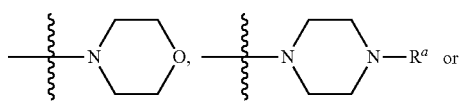 or each optionally substituted with one or more $R^{22}$. In some such embodiments, $R^a$ is independently H, $C_{1-6}$ alkyl (e.g., methyl, ethyl), $C_{3-7}$ cycloalkyl (e.g., cyclopropyl, cyclopentyl, cyclohexyl), or —(CH$_2$)$_2$OCH$_3$. In some further embodiments, $R^2$ is substituted with one or more $R^{22}$; for example, $R^2$ is substituted with oxo formed by two adjacent $R^{22}$.

In some other embodiments of the compounds of Formula (IV), (IVa) or (IVb), $R^2$ is —NR$^9$R$^{10}$, wherein each $R^9$ and $R^{10}$ is independently H, $C_{1-6}$ alkyl, phenyl or $C_{3-7}$ cycloalkyl, and wherein each phenyl and $C_{3-7}$ cycloalkyl is optionally substituted with one or more $R^{22}$. For example, $R^9$ is H or $C_{1-6}$ alkyl, and $R^{10}$ is $C_{1-6}$ alkyl, cyclopropyl, cyclopentyl, cyclohexyl, or phenyl. In some further embodiments, the phenyl group is substituted with halo, $C_{1-6}$ alkyl, or —O—($C_{1-6}$ alkoxy)$C_{1-6}$ alkyl; for example, methyl, —F, —Cl, or —(CH$_2$)$_2$OCH$_3$.

In some embodiments of the compounds of Formula (IV), (IVa) or (IVb),

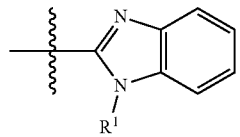

may further be substituted with one or more $R^A$ independently selected from the group consisting of $C_{1-6}$ alkyl, $C_{1-6}$ haloalkyl, $C_{1-6}$ alkoxy, $C_{1-6}$ haloalkoxy, and halo; for example, methyl, t-Bu, —Cl, —F, or —CF$_3$.

In some embodiments of the compounds of Formula (IV), (IVa) or (IVb), when each of $R^9$, $R^{10}$, $R^{14}$, $R^{15}$ and $R^{16}$ is independently optionally substituted $C_{1-6}$ alkyl, optionally substituted $C_{6-10}$ aryl, optionally substituted CY-14 aralkyl, or optionally substituted $C_{3-7}$ carbocyclyl, each may be optionally substituted with one or more $R^{22}$ as defined herein. In addition, each of $R^{12}$, $R^{17}$ and $R^{18}$ may be optionally substituted with one more or $R^{22}$. When $R^{20}$ is optionally substituted phenyl, or optionally substituted 5 or 6 membered heteroaryl, each may also be optionally substituted with one or more $R^{22}$.

In some embodiments of the compounds of Formula of the compounds of Formula (IV), (IVa) or (IVb), each $R^{22}$ is independently selected from the group consisting of halo, hydroxy, $C_{1-6}$ alkyl, $C_{1-6}$ haloalkyl, ($C_{1-6}$ alkoxy)$C_{1-6}$ alkyl, and —O—($C_{1-6}$ alkoxy)$C_{1-6}$ alkyl. In some other embodiments, two adjacent $R^{22}$ form an oxo.

Additional embodiments of the compounds of Formula (IV) are selected from the group consisting of compounds 10, 12-14, 16, 20 and 21 of Table 1, and pharmaceutically acceptable salts thereof.

In some embodiments, the compounds of Formula (IV), (IVa) or (IVb) may include tautomers thereof, depending on the specific synthetic procedures used in the preparation of the compounds.

Formula (V)

Some embodiments of the present disclosure relate to compounds having the structure of Formula (V) as described herein, or pharmaceutically acceptable salts thereof.

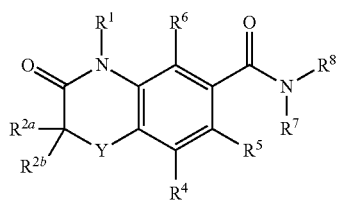

(V)

In some embodiments of the compounds of Formula (V), $R^1$ is H. In some other embodiments, $R^1$ is methyl.

In some embodiments of the compounds of Formula (V), Y is O. In other embodiments, Y is N($C_{1-6}$ alkyl), for example, N(methyl), N(ethyl), N(isopropyl), N(isobutyl) or N(t-butyl).

In some embodiments of the compounds of Formula (V), each $R^{2a}$ and $R^{2b}$ is independently H or $C_{1-6}$ alkyl. In one embodiment, both $R^{2a}$ and $R^{2b}$ are H. In another embodiment, both $R^{2a}$ and $R^{2b}$ are methyl. In other embodiments, $R^{2a}$ is H and $R^{2b}$ is halo, —$OR^{11}$, thienyl, thiazolyl, isothiazolyl, imidazolyl, pyrazolyl, oxazolyl, isoxazolyl, pyridyl, pyrimidinyl or phenyl, wherein each thienyl, thiazolyl, isothiazolyl, imidazolyl, pyrazolyl, oxazolyl, isoxazolyl, pyridyl, pyrimidinyl and phenyl is optionally substituted with one or more $R^{22}$. In some such embodiments, $R^{11}$ is phenyl or pyridyl, each optionally substituted halo, hydroxy, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, or —O($C_{1-6}$ alkoxy)$C_{1-6}$ alkyl.

In some embodiments of the compounds of Formula (V), each of $R^4$, $R^5$ and $R^6$ is independently H, halo, $C_{1-6}$ alkyl or $C_{1-6}$ alkoxy. In one embodiment, each $R^4$, $R^5$ and $R^6$ is H.

In some embodiments of the compounds of Formula (V), $R^7$ is H. In other embodiment, $R^7$ is methyl.

In some embodiments of the compounds of Formula (V), $R^8$ is phenyl, pyridyl or pyrazolyl, each optionally substituted with one or more $R^A$. In some such embodiments, each $R^A$ is independently selected from the group consisting of $C_{1-6}$ alkyl, $C_{1-6}$ haloalkyl, $C_{1-6}$ alkoxy, $C_{1-6}$ haloalkoxy, halo, —$(CH_2)_m R^{19}$ and —$(CH_2)_k$—$S(O)_2$—$R^{21}$; and wherein each m and k is independently 0 or 1. In some embodiments, $R^{19}$ is phenyl optionally substituted with one or more substituents selected from the group consisting of halo, $C_{1-6}$ alkyl, $C_{1-6}$ haloalkyl, $C_{1-6}$ alkoxy, and $C_{1-6}$ haloalkoxy. In some other embodiments, $R^{19}$ is a 6 or 7 membered heterocyclyl selected from the group consisting of

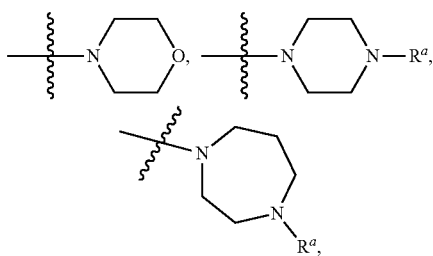

and wherein $R^a$ is H, $C_{1-6}$ alkyl, $C_{3-7}$ cycloalkyl, or ($C_{1-6}$ alkoxy)$C_{1-6}$ alkyl. In some embodiments, $R^{2'}$ is a 5 to 7 membered heterocyclyl selected from the group consisting of

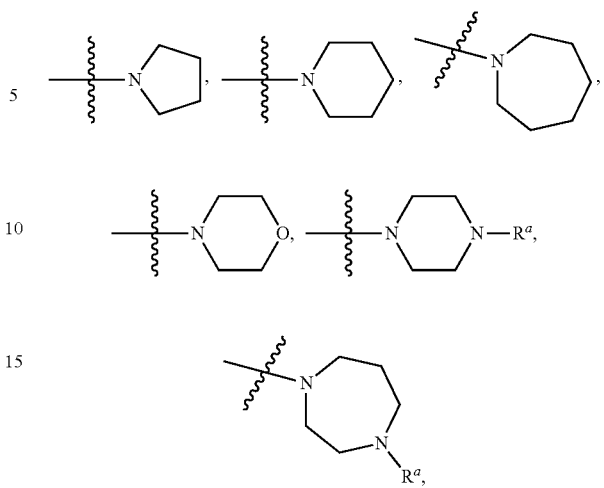

and wherein $R^a$ is independently H, $C_{1-6}$ alkyl, $C_{3-7}$ cycloalkyl, or ($C_{1-6}$ alkoxy)$C_{1-6}$ alkyl. In some other embodiments, $R^{21}$ is —$NR^9R^{10}$, and wherein each $R^9$ and $R^{10}$ is independently H, $C_{1-6}$ alkyl, optionally substituted phenyl, or optionally substituted $C_{3-7}$ cycloalkyl In some embodiments of the compounds of Formula (V), when each of $R^9$, $R^{10}$, $R^{14}$, $R^{15}$ and $R^{16}$ is independently optionally substituted $C_{1-6}$ alkyl, optionally substituted $C_{6-10}$ aryl, optionally substituted $C_{7-14}$ aralkyl, or optionally substituted $C_{3-7}$ carbocyclyl, each may be optionally substituted with one or more $R^{22}$ as defined herein. In addition, each of $R^{12}$, $R^{17}$ and $R^{18}$ may be optionally substituted with one more or $R^{22}$. When $R^{20}$ is optionally substituted phenyl, or optionally substituted 5 or 6 membered heteroaryl, each may also be optionally substituted with one or more $R^{22}$.

In some embodiments of the compounds of Formula (V), $R^{19}$ is selected from 3, 4, 5, 6 or 7 membered heterocyclyl, or 5 to 6 membered heteroaryl, each optionally substituted with one or more $R^{22}$.

In some embodiments of the compounds of Formula (V), each $R^{22}$ is independently selected from the group consisting of halo, hydroxy, $C_{1-6}$ alkyl, $C_{1-6}$ haloalkyl, ($C_{1-6}$ alkoxy)$C_{1-6}$ alkyl, and —O—($C_{1-6}$ alkoxy)$C_{1-6}$ alkyl. In some other embodiments, two adjacent $R^{22}$ form an oxo.

Additional embodiments of the compounds of Formula (V) are selected from the group consisting of Compounds 155, 157, 162-164, and 169-175 of Table 1, and pharmaceutically acceptable salts thereof.

In any embodiments of the compounds described herein, when a substituent is selected from a $C_{3-7}$ carbocyclyl, it includes $C_{3-7}$ cycloalkyl. When a substituent is select from 3 to 7 membered heterocyclyl (such as 5-6 membered heterocyclyl), it includes 3 to 7 membered monocyclic heterocycle rings with no double or triple bond within the ring structure. The description of various features of compounds of Formulas (I), (II), (III), (IV) and (V), and any substructures described herein also intends to cover the pharmaceutically acceptable salts of the compounds described herein.

Additional embodiments of the compounds described herein are illustrated in Table 1, or pharmaceutically acceptable salts thereof.

TABLE 1
Exemplary Compounds
| NO. | Structure |
|---|---|
| 1 | 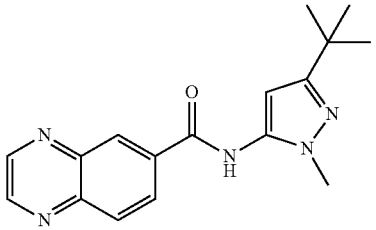 [SMILES: Cn1nc(C(C)(C)C)cc1NC(=O)c1ccc2nccnc2c1] |
| 2 | 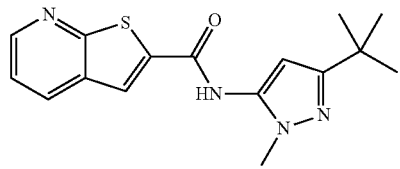 [SMILES: Cn1nc(C(C)(C)C)cc1NC(=O)c1cc2cccnc2s1] |
| 3 | 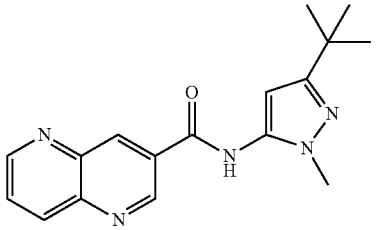 [SMILES: Cn1nc(C(C)(C)C)cc1NC(=O)c1cnc2cccnc2c1] |
| 4 | 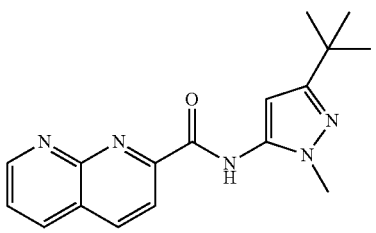 [SMILES: Cn1nc(C(C)(C)C)cc1NC(=O)c1ccc2cccnc2n1] |
| 5 | 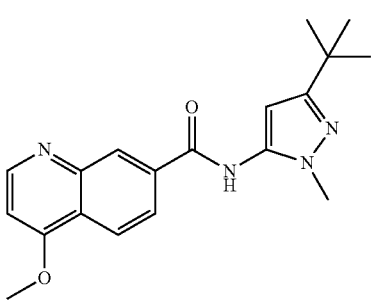 [SMILES: COc1ccnc2cc(C(=O)Nc3cc(C(C)(C)C)nn3C)ccc12] |
| 6 | 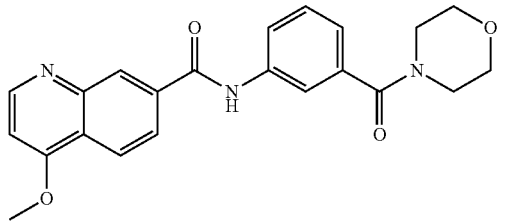 [SMILES: COc1ccnc2cc(C(=O)Nc3cccc(C(=O)N4CCOCC4)c3)ccc12] |

TABLE 1-continued
Exemplary Compounds
| NO. | Structure |
|---|---|
| 7 | 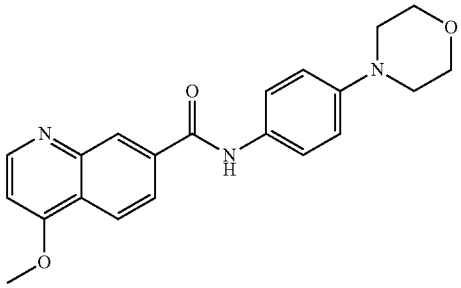 [SMILES: COc1ccnc2cc(C(=O)Nc3ccc(N4CCOCC4)cc3)ccc12] |
| 8 | 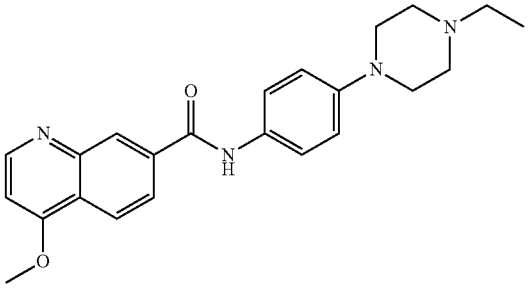 [SMILES: CCN1CCN(c2ccc(NC(=O)c3ccc4c(OC)ccnc4c3)cc2)CC1] |
| 9 | 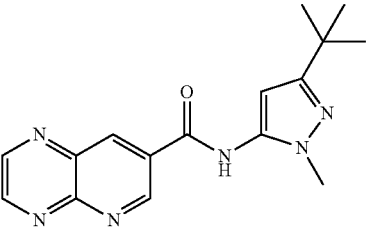 |
| 10 | 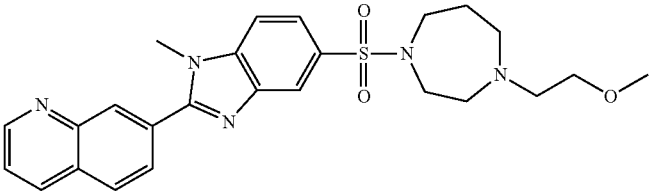 [SMILES: COCCN1CCCN(S(=O)(=O)c2ccc3c(c2)nc(-c2ccc4cccnc4c2)n3C)CC1] |
| 11 | 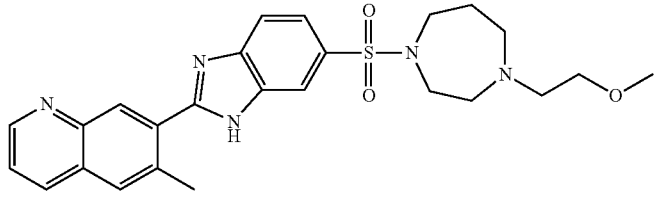 [SMILES: COCCN1CCCN(S(=O)(=O)c2ccc3nc(-c4cc5ncccc5cc4C)[nH]c3c2)CC1] |
| 12 | 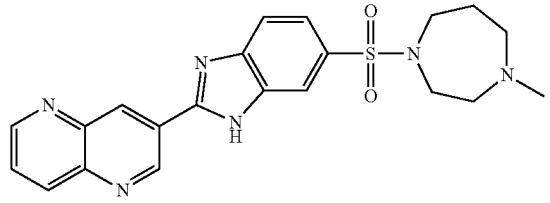 [SMILES: CN1CCCN(S(=O)(=O)c2ccc3nc(-c4cnc5cccnc5c4)[nH]c3c2)CC1] |

TABLE 1-continued

Exemplary Compounds

| NO. | Structure |
|---|---|
| 13 | 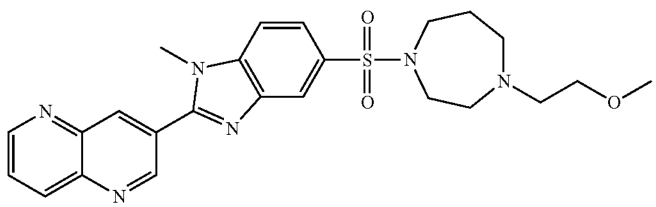 [SMILES: COCCN1CCCN(S(=O)(=O)c2ccc3c(c2)nc(-c2cnc4cccnc4c2)n3C)CC1] |
| 14 | 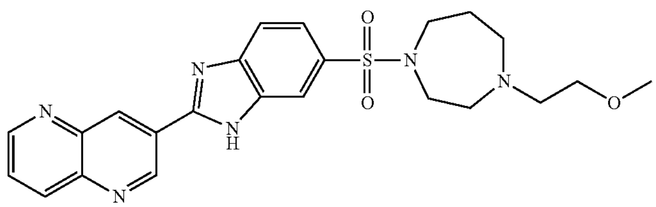 [SMILES: COCCN1CCCN(S(=O)(=O)c2ccc3nc(-c4cnc5cccnc5c4)[nH]c3c2)CC1] |
| 15 | 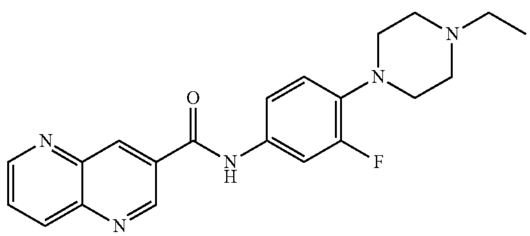 [SMILES: CCN1CCN(c2ccc(NC(=O)c3cnc4cccnc4c3)cc2F)CC1] |
| 16 | 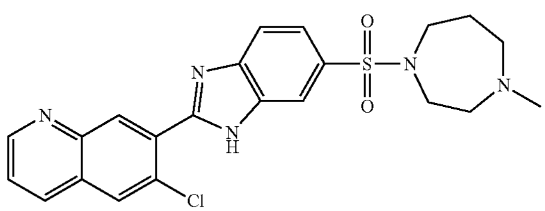 [SMILES: CN1CCCN(S(=O)(=O)c2ccc3nc(-c4cc5ncccc5cc4Cl)[nH]c3c2)CC1] |
| 17 | 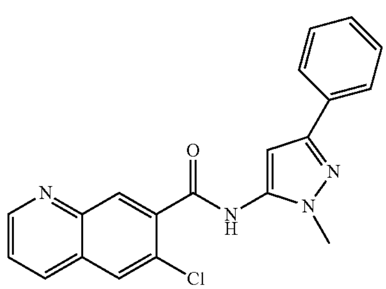 [SMILES: Cn1nc(-c2ccccc2)cc1NC(=O)c1cc2ncccc2cc1Cl] |
| 18 | 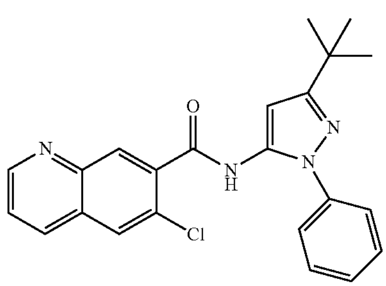 [SMILES: CC(C)(C)c1cc(NC(=O)c2cc3ncccc3cc2Cl)n(-c2ccccc2)n1] |

TABLE 1-continued

Exemplary Compounds

| NO. | Structure |
|---|---|
| 19 | 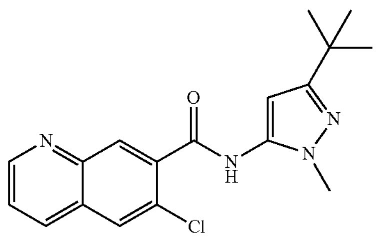 [SMILES: Cn1nc(C(C)(C)C)cc1NC(=O)c1cc2ncccc2cc1Cl] |
| 20 | 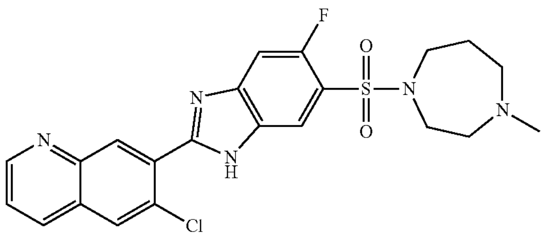 [SMILES: CN1CCCN(S(=O)(=O)c2cc3[nH]c(-c4cc5ncccc5cc4Cl)nc3cc2F)CC1] |
| 21 | 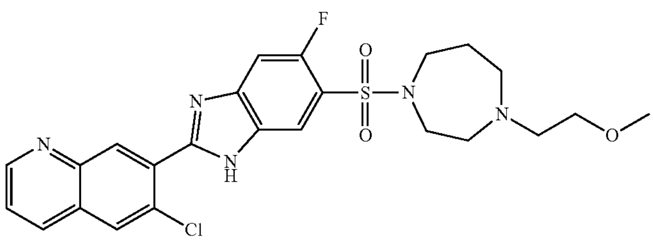 [SMILES: COCCN1CCCN(S(=O)(=O)c2cc3[nH]c(-c4cc5ncccc5cc4Cl)nc3cc2F)CC1] |
| 22 | 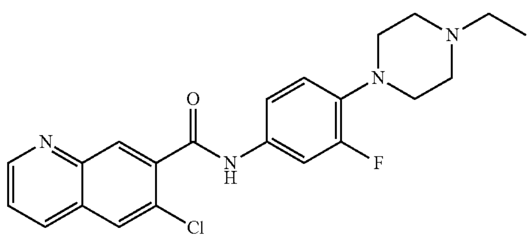 [SMILES: CCN1CCN(c2ccc(NC(=O)c3cc4ncccc4cc3Cl)cc2F)CC1] |
| 23 | 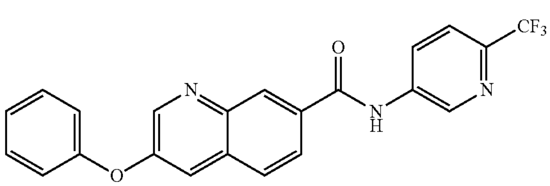 [SMILES: O=C(Nc1ccc(C(F)(F)F)nc1)c1ccc2cc(Oc3ccccc3)cnc2c1] |
| 24 | 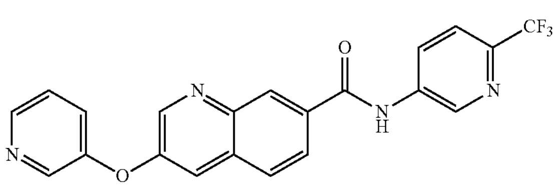 [SMILES: O=C(Nc1ccc(C(F)(F)F)nc1)c1ccc2cc(Oc3cccnc3)cnc2c1] |

TABLE 1-continued

Exemplary Compounds

| NO. | Structure |
|---|---|
| 25 | 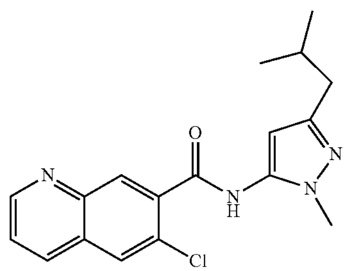 [SMILES: CC(C)Cc1cc(NC(=O)c2cc3ncccc3cc2Cl)n(C)n1] |
| 26 | 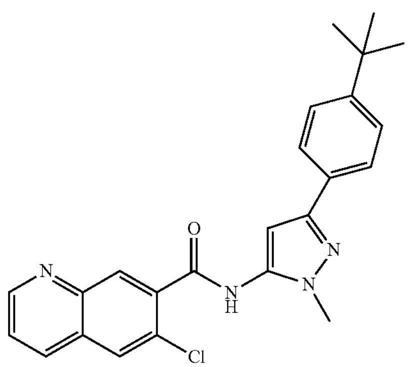 [SMILES: Cn1nc(-c2ccc(C(C)(C)C)cc2)cc1NC(=O)c1cc2ncccc2cc1Cl] |
| 27 | 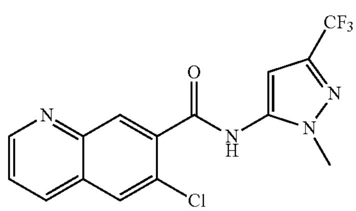 [SMILES: Cn1nc(C(F)(F)F)cc1NC(=O)c1cc2ncccc2cc1Cl] |
| 28 | 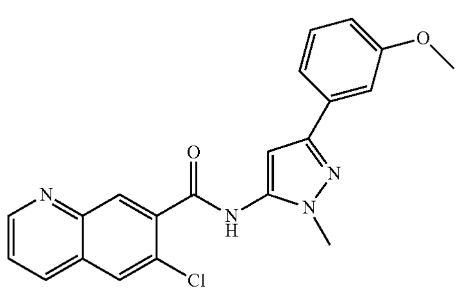 [SMILES: COc1cccc(-c2cc(NC(=O)c3cc4ncccc4cc3Cl)n(C)n2)c1] |
| 29 | 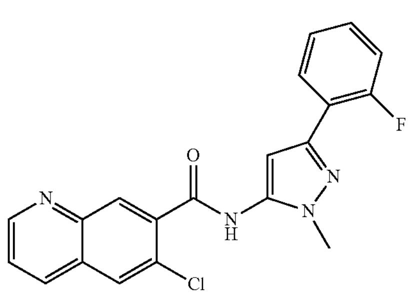 [SMILES: Cn1nc(-c2ccccc2F)cc1NC(=O)c1cc2ncccc2cc1Cl] |

TABLE 1-continued

Exemplary Compounds

| NO. | Structure |
|---|---|
| 30 | 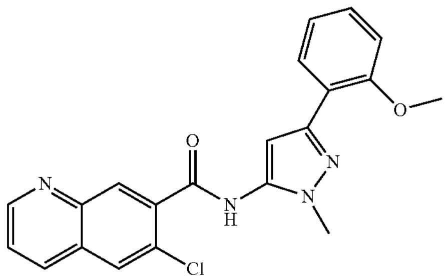 [SMILES: COc1ccccc1-c1cc(NC(=O)c2cc3ncccc3cc2Cl)n(C)n1] |
| 31 | 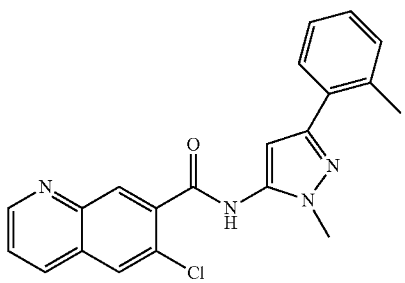 [SMILES: Cc1ccccc1-c1cc(NC(=O)c2cc3ncccc3cc2Cl)n(C)n1] |
| 32 | 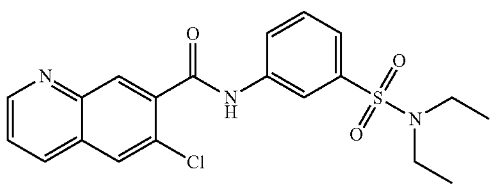 [SMILES: CCN(CC)S(=O)(=O)c1cccc(NC(=O)c2cc3ncccc3cc2Cl)c1] |
| 33 | 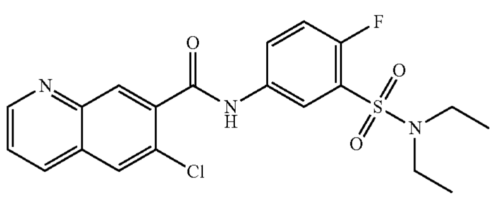 [SMILES: CCN(CC)S(=O)(=O)c1cc(NC(=O)c2cc3ncccc3cc2Cl)ccc1F] |
| 34 | 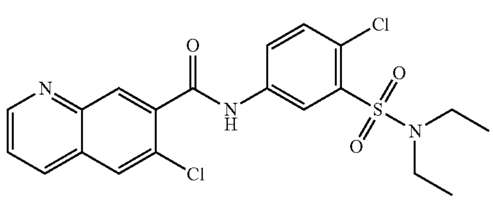 [SMILES: CCN(CC)S(=O)(=O)c1cc(NC(=O)c2cc3ncccc3cc2Cl)ccc1Cl] |
| 35 | 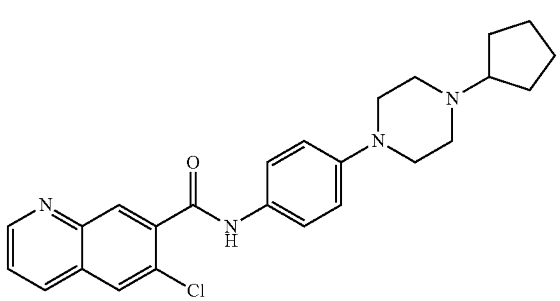 [SMILES: O=C(Nc1ccc(N2CCN(C3CCCC3)CC2)cc1)c1cc2ncccc2cc1Cl] |

TABLE 1-continued

Exemplary Compounds

| NO. | Structure |
|-----|-----------|
| 36 | 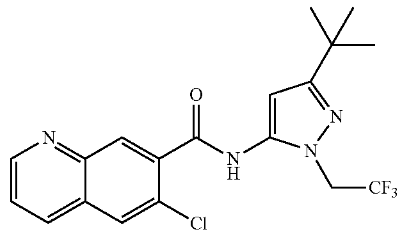 [SMILES: CC(C)(C)c1cc(NC(=O)c2cc3ncccc3cc2Cl)n(CC(F)(F)F)n1] |
| 37 | 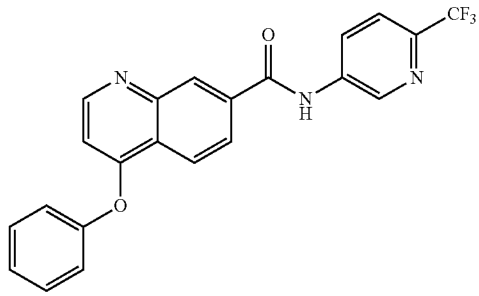 [SMILES: O=C(Nc1ccc(C(F)(F)F)nc1)c1ccc2c(Oc3ccccc3)ccnc2c1] |
| 38 | 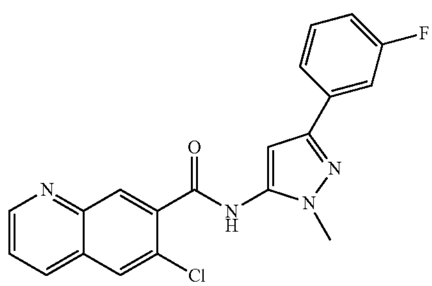 [SMILES: Cn1nc(-c2cccc(F)c2)cc1NC(=O)c1cc2ncccc2cc1Cl] |
| 39 | 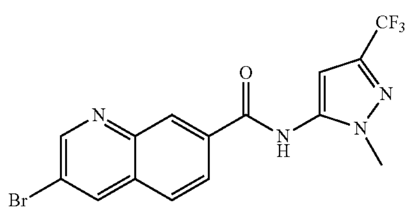 [SMILES: Cn1nc(C(F)(F)F)cc1NC(=O)c1ccc2cc(Br)cnc2c1] |
| 40 | 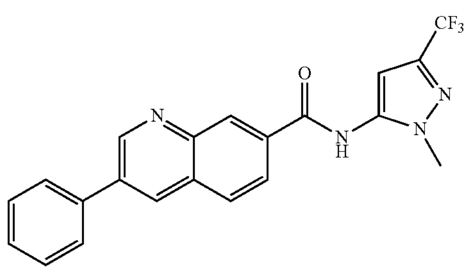 [SMILES: Cn1nc(C(F)(F)F)cc1NC(=O)c1ccc2cc(-c3ccccc3)cnc2c1] |
| 41 | 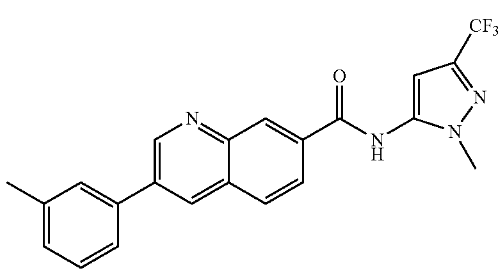 [SMILES: Cc1cccc(-c2cnc3cc(C(=O)Nc4cc(C(F)(F)F)nn4C)ccc3c2)c1] |

TABLE 1-continued

Exemplary Compounds

| NO. | Structure |
|---|---|
| 42 | 3-bromoquinoline-7-carboxylic acid (1-methyl-1H-pyrazol-5-yl)amide |
| 43 | 3-bromoquinoline-7-carboxylic acid (3-tert-butyl-1-methyl-1H-pyrazol-5-yl)amide |
| 44 | 6-chloroquinoline-7-carboxylic acid [1-methyl-3-(2-trifluoromethylphenyl)-1H-pyrazol-5-yl]amide |
| 45 | 3-phenylquinoline-7-carboxylic acid (1-methyl-1H-pyrazol-5-yl)amide |
| 46 | 3-phenylquinoline-7-carboxylic acid (3-tert-butyl-1-methyl-1H-pyrazol-5-yl)amide |
| 47 | 6-chloroquinoline-7-carboxylic acid [1-isopropyl-3-(2-trifluoromethylphenyl)-1H-pyrazol-5-yl]amide |

TABLE 1-continued

Exemplary Compounds

| NO. | Structure |
|---|---|
| 48 | 6-chloroquinoline-7-carboxamide linked via NH to 1-methyl-3-(3-(trifluoromethyl)phenyl)-1H-pyrazol-5-yl |
| 49 | 6-chloroquinoline-7-carboxamide linked via NH to 3-(3-chlorophenyl)-1-methyl-1H-pyrazol-5-yl |
| 50 | 6-chloroquinoline-7-carboxamide linked via NH to 3-(5-fluoro-2-methylphenyl)-1-methyl-1H-pyrazol-5-yl |
| 51 | 6-chloroquinoline-7-carboxamide linked via NH to 3-(5-chloro-2-methylphenyl)-1-methyl-1H-pyrazol-5-yl |
| 52 | 3-(o-tolyl)quinoline-7-carboxamide linked via NH to 1-methyl-3-(trifluoromethyl)-1H-pyrazol-5-yl |

TABLE 1-continued

Exemplary Compounds

| NO. | Structure |
|---|---|
| 53 | 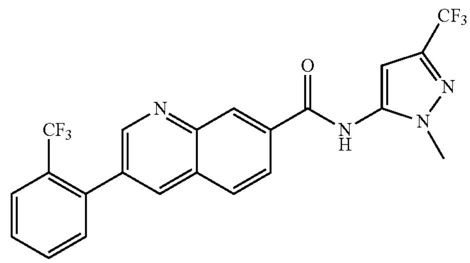 [SMILES: Cn1nc(C(F)(F)F)cc1NC(=O)c1ccc2cc(-c3ccccc3C(F)(F)F)cnc2c1] |
| 54 | 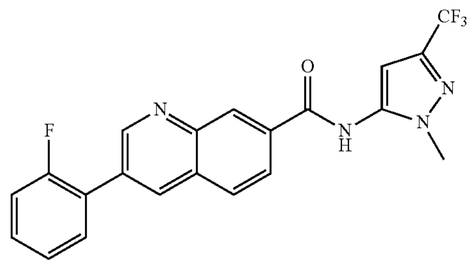 [SMILES: Cn1nc(C(F)(F)F)cc1NC(=O)c1ccc2cc(-c3ccccc3F)cnc2c1] |
| 55 | 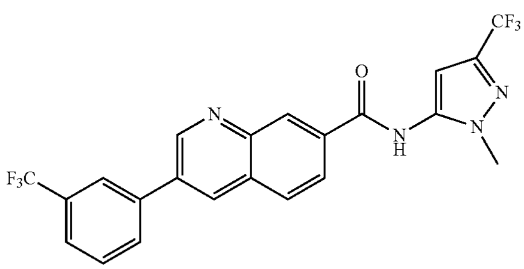 [SMILES: Cn1nc(C(F)(F)F)cc1NC(=O)c1ccc2cc(-c3cccc(C(F)(F)F)c3)cnc2c1] |
| 56 | 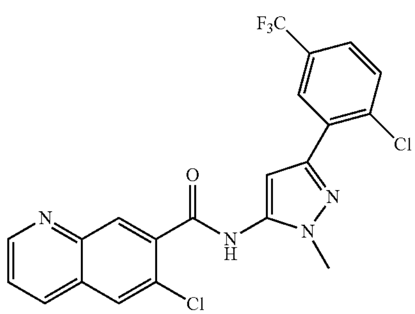 [SMILES: Cn1nc(-c2cc(C(F)(F)F)ccc2Cl)cc1NC(=O)c1cc2ncccc2cc1Cl] |
| 57 | 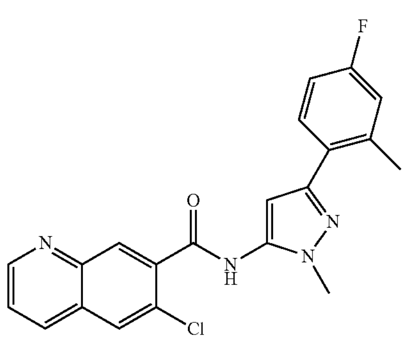 [SMILES: Cc1cc(F)ccc1-c1cc(NC(=O)c2cc3ncccc3cc2Cl)n(C)n1] |

TABLE 1-continued

| Exemplary Compounds | |
|---|---|
| NO. | Structure |
| 58 | (structure) |
| 59 | (structure) |
| 60 | (structure) |
| 61 | (structure) |
| 62 | (structure) |

TABLE 1-continued

| Exemplary Compounds | |
|---|---|
| NO. | Structure |
| 63 | 6-bromoquinoline-2-carboxamide with N-[3-fluoro-4-(4-ethylpiperazin-1-yl)phenyl] |
| 64 | 3-phenylquinoline-7-carboxamide with N-[3-fluoro-4-(4-ethylpiperazin-1-yl)phenyl] |
| 65 | 3-(3-chlorophenyl)quinoline-7-carboxamide with N-[3-(trifluoromethyl)-1-methyl-1H-pyrazol-5-yl] |
| 66 | 3-(2-chlorophenyl)quinoline-7-carboxamide with N-[3-(trifluoromethyl)-1-methyl-1H-pyrazol-5-yl] |
| 67 | 3-(thiophen-3-yl)quinoline-7-carboxamide with N-[3-(trifluoromethyl)-1-methyl-1H-pyrazol-5-yl] |

TABLE 1-continued

Exemplary Compounds

| NO. | Structure |
|---|---|
| 68 | 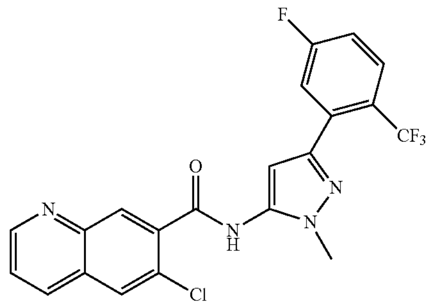 [SMILES: Cn1nc(-c2cc(F)ccc2C(F)(F)F)cc1NC(=O)c1cc2ncccc2cc1Cl] |
| 69 | 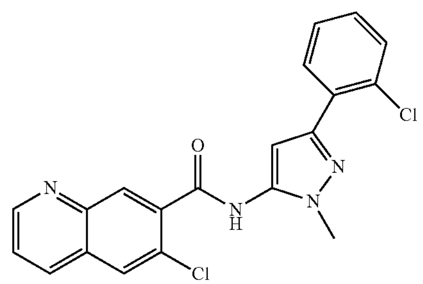 [SMILES: Cn1nc(-c2ccccc2Cl)cc1NC(=O)c1cc2ncccc2cc1Cl] |
| 70 | 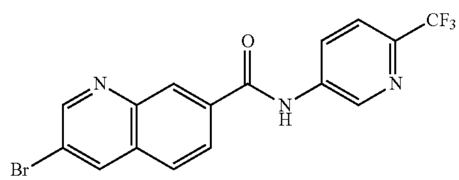 [SMILES: O=C(Nc1ccc(C(F)(F)F)nc1)c1ccc2cc(Br)cnc2c1] |
| 71 | 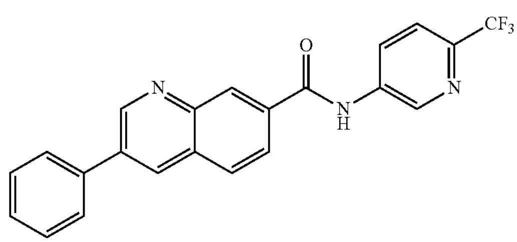 [SMILES: O=C(Nc1ccc(C(F)(F)F)nc1)c1ccc2cc(-c3ccccc3)cnc2c1] |
| 72 | 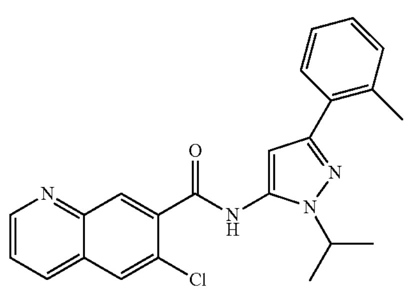 [SMILES: Cc1ccccc1-c1cc(NC(=O)c2cc3ncccc3cc2Cl)n(C(C)C)n1] |
| 73 | 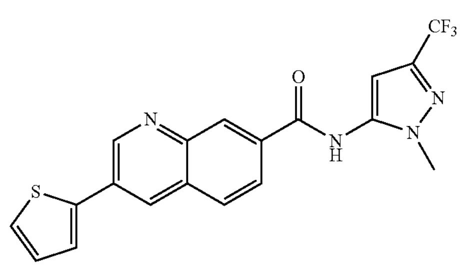 [SMILES: Cn1nc(C(F)(F)F)cc1NC(=O)c1ccc2cc(-c3cccs3)cnc2c1] |

TABLE 1-continued

| Exemplary Compounds | |
|---|---|
| NO. | Structure |
| 74 | (structure) |
| 75 | (structure) |
| 76 | (structure) |
| 77 | (structure) |
| 78 | (structure) |

TABLE 1-continued

Exemplary Compounds

| NO. | Structure |
|-----|-----------|
| 79  | 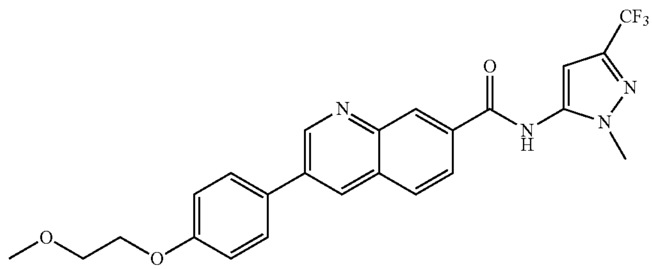 [SMILES: COCCOc1ccc(-c2cnc3cc(C(=O)Nc4cc(C(F)(F)F)nn4C)ccc3c2)cc1]          |
| 80  | 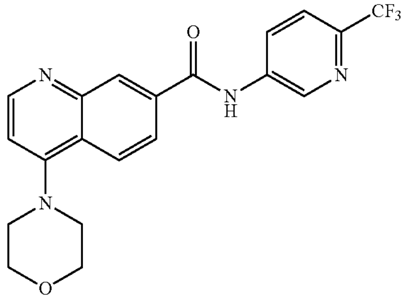 [SMILES: O=C(Nc1ccc(C(F)(F)F)nc1)c1ccc2c(N3CCOCC3)ccnc2c1]          |
| 81  | 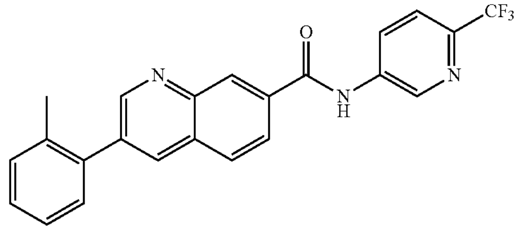          |
| 82  | 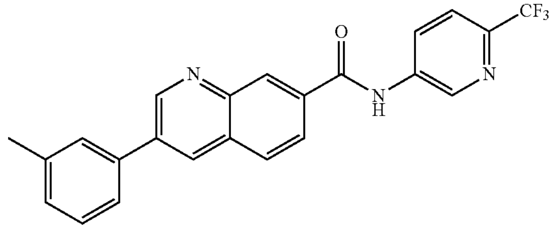 [SMILES: Cc1cccc(-c2cnc3cc(C(=O)Nc4ccc(C(F)(F)F)nc4)ccc3c2)c1]          |
| 83  | 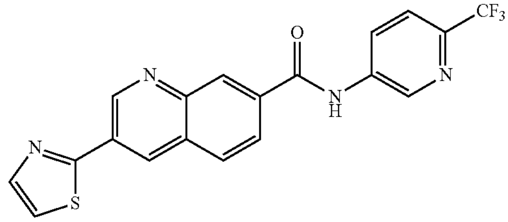 [SMILES: O=C(Nc1ccc(C(F)(F)F)nc1)c1ccc2cc(-c3nccs3)cnc2c1]          |

TABLE 1-continued

Exemplary Compounds

| NO. | Structure |
|---|---|
| 84 | 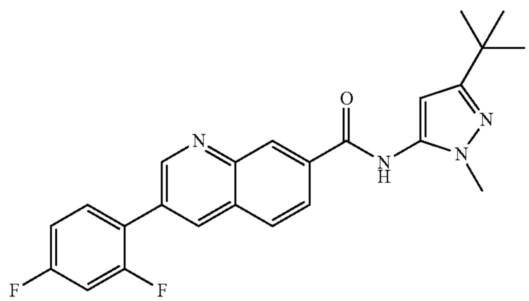 [SMILES: Cn1nc(C(C)(C)C)cc1NC(=O)c1ccc2cc(-c3ccc(F)cc3F)cnc2c1] |
| 85 | 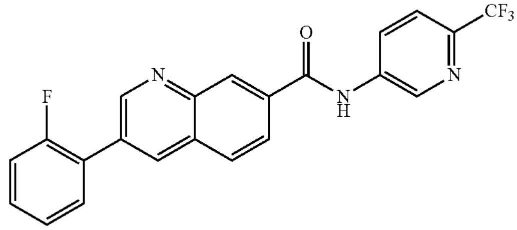 [SMILES: O=C(Nc1ccc(C(F)(F)F)nc1)c1ccc2cc(-c3ccccc3F)cnc2c1] |
| 86 | 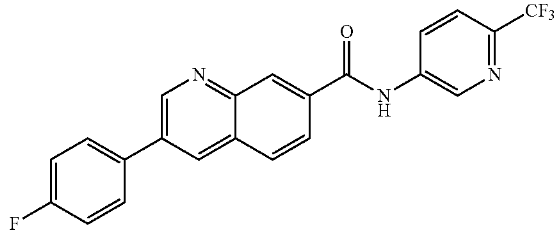 [SMILES: O=C(Nc1ccc(C(F)(F)F)nc1)c1ccc2cc(-c3ccc(F)cc3)cnc2c1] |
| 87 | 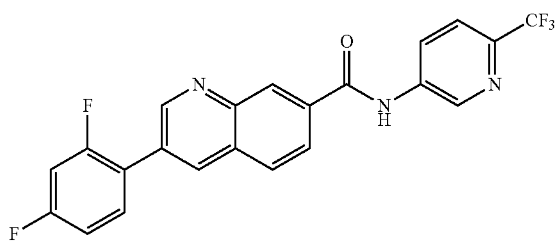 [SMILES: O=C(Nc1ccc(C(F)(F)F)nc1)c1ccc2cc(-c3ccc(F)cc3F)cnc2c1] |
| 88 | 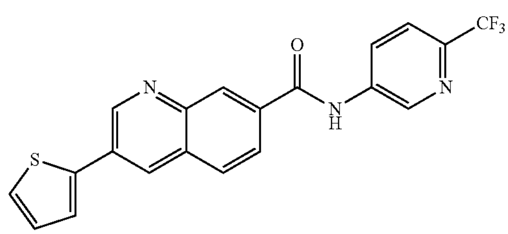 [SMILES: O=C(Nc1ccc(C(F)(F)F)nc1)c1ccc2cc(-c3cccs3)cnc2c1] |
| 89 | 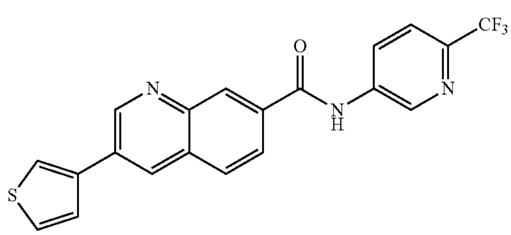 [SMILES: O=C(Nc1ccc(C(F)(F)F)nc1)c1ccc2cc(-c3ccsc3)cnc2c1] |

TABLE 1-continued

Exemplary Compounds

| NO. | Structure |
|---|---|
| 90 | 6-chloroquinoline-7-carboxamide linked via NH to 2-amino-1-methyl-4-phenylimidazole |
| 91 | 3-phenylquinoline-7-carboxamide linked via NH to 4-chloro-3-(N,N-diethylsulfamoyl)phenyl |
| 92 | 3-(2-fluorophenyl)quinoline-7-carboxamide linked via NH to 3-tert-butyl-1-methyl-1H-pyrazol-5-yl |
| 93 | 3-(thiazol-2-yl)quinoline-7-carboxamide linked via NH to 1-methyl-3-(trifluoromethyl)-1H-pyrazol-5-yl |
| 94 | 3-(4-fluorophenyl)quinoline-7-carboxamide linked via NH to 4-chloro-3-(N,N-diethylsulfamoyl)phenyl |

TABLE 1-continued
Exemplary Compounds
| NO. | Structure |
|---|---|
| 95 | 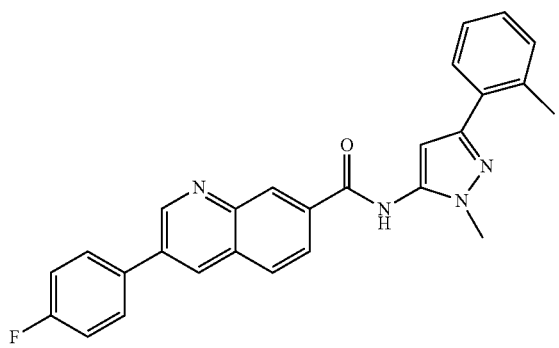 [SMILES: Cc1ccccc1-c1cc(NC(=O)c2ccc3cc(-c4ccc(F)cc4)cnc3c2)n(C)n1] |
| 96 | 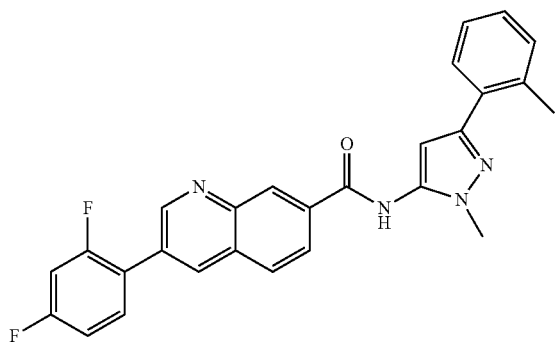 [SMILES: Cc1ccccc1-c1cc(NC(=O)c2ccc3cc(-c4ccc(F)cc4F)cnc3c2)n(C)n1] |
| 97 | 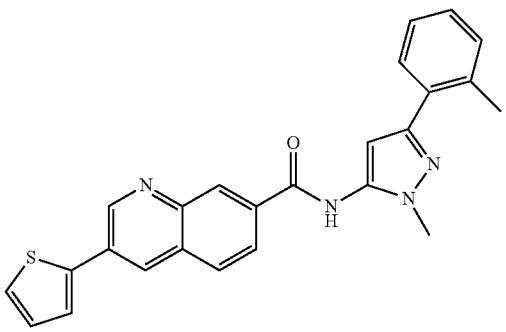 [SMILES: Cc1ccccc1-c1cc(NC(=O)c2ccc3cc(-c4cccs4)cnc3c2)n(C)n1] |
| 98 | 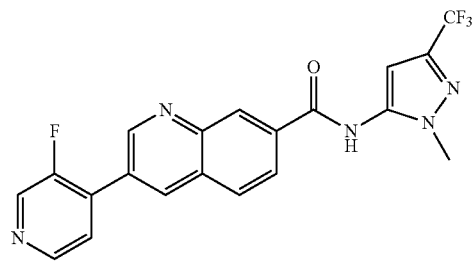 [SMILES: Cn1nc(C(F)(F)F)cc1NC(=O)c1ccc2cc(-c3ccncc3F)cnc2c1] |

TABLE 1-continued

Exemplary Compounds

| NO. | Structure |
|---|---|
| 99 | 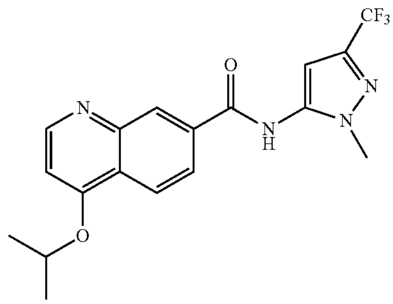 [SMILES: CC(C)Oc1ccnc2cc(C(=O)Nc3cc(C(F)(F)F)nn3C)ccc12] |
| 100 | 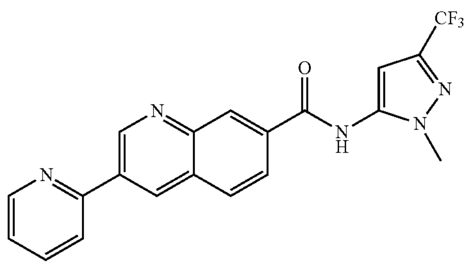 [SMILES: Cn1nc(C(F)(F)F)cc1NC(=O)c1ccc2cc(-c3ccccn3)cnc2c1] |
| 101 | 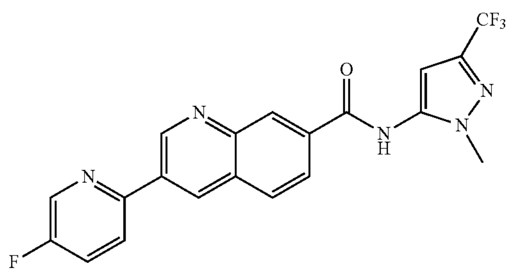 [SMILES: Cn1nc(C(F)(F)F)cc1NC(=O)c1ccc2cc(-c3ccc(F)cn3)cnc2c1] |
| 102 | 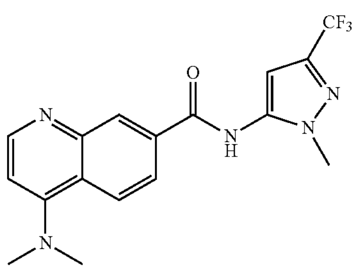 [SMILES: CN(C)c1ccnc2cc(C(=O)Nc3cc(C(F)(F)F)nn3C)ccc12] |
| 103 | 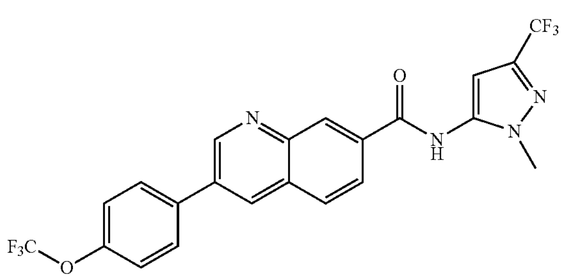 [SMILES: Cn1nc(C(F)(F)F)cc1NC(=O)c1ccc2cc(-c3ccc(OC(F)(F)F)cc3)cnc2c1] |

TABLE 1-continued

Exemplary Compounds

| NO. | Structure |
|---|---|
| 104 | 3-(2,6-difluorophenyl)-N-(1-methyl-3-(trifluoromethyl)-1H-pyrazol-5-yl)quinoline-7-carboxamide |
| 105 | N-(1-methyl-3-(trifluoromethyl)-1H-pyrazol-5-yl)-3-(2-(trifluoromethoxy)phenyl)quinoline-7-carboxamide |
| 106 | N-(1-methyl-3-(trifluoromethyl)-1H-pyrazol-5-yl)-3-(thiazol-5-yl)quinoline-7-carboxamide |
| 107 | 3-(1-methyl-1H-pyrazol-4-yl)-N-(1-methyl-3-(trifluoromethyl)-1H-pyrazol-5-yl)quinoline-7-carboxamide |
| 108 | 3-(1-methyl-1H-pyrazol-3-yl)-N-(1-methyl-3-(trifluoromethyl)-1H-pyrazol-5-yl)quinoline-7-carboxamide |

TABLE 1-continued

Exemplary Compounds

| NO. | Structure |
|---|---|
| 109 | 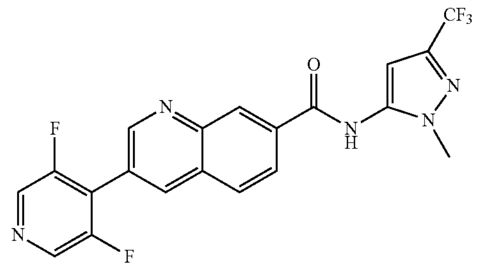 [SMILES: Cn1nc(C(F)(F)F)cc1NC(=O)c1ccc2cc(-c3c(F)cncc3F)cnc2c1] |
| 110 | 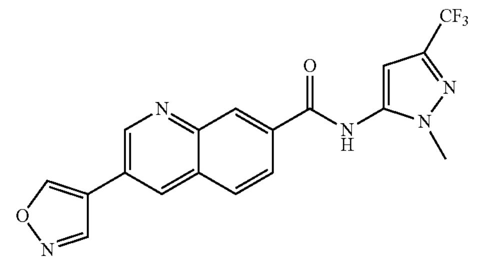 [SMILES: Cn1nc(C(F)(F)F)cc1NC(=O)c1ccc2cc(-c3cnoc3)cnc2c1] |
| 111 | 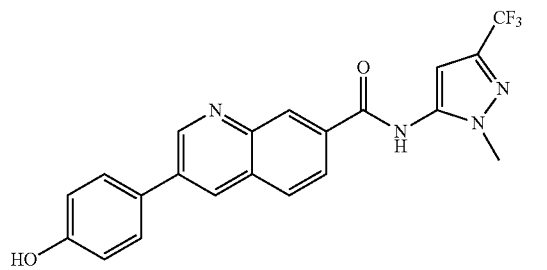 [SMILES: Cn1nc(C(F)(F)F)cc1NC(=O)c1ccc2cc(-c3ccc(O)cc3)cnc2c1] |
| 112 | 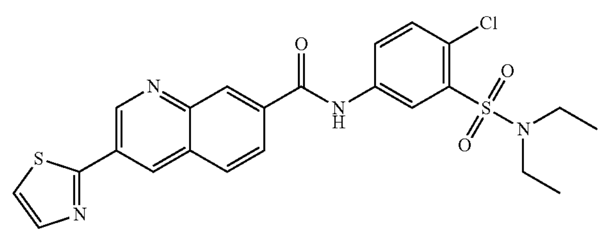 |
| 113 | 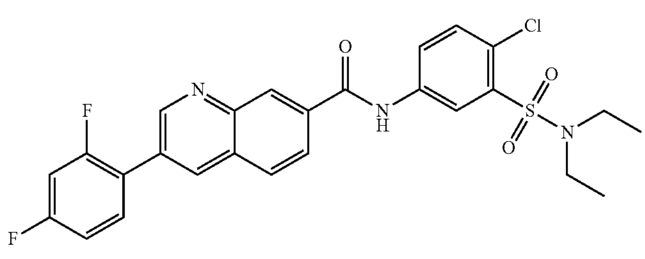 [SMILES: CCN(CC)S(=O)(=O)c1cc(NC(=O)c2ccc3cc(-c4ccc(F)cc4F)cnc3c2)ccc1Cl] |
| 114 | 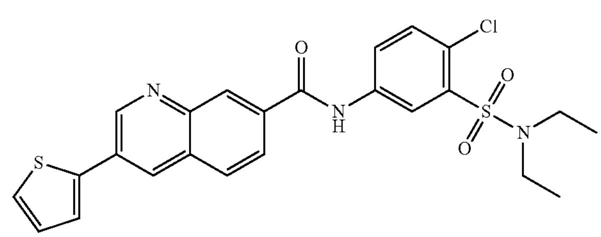 [SMILES: CCN(CC)S(=O)(=O)c1cc(NC(=O)c2ccc3cc(-c4cccs4)cnc3c2)ccc1Cl] |

TABLE 1-continued
Exemplary Compounds
| NO. | Structure |
|---|---|
| 115 | 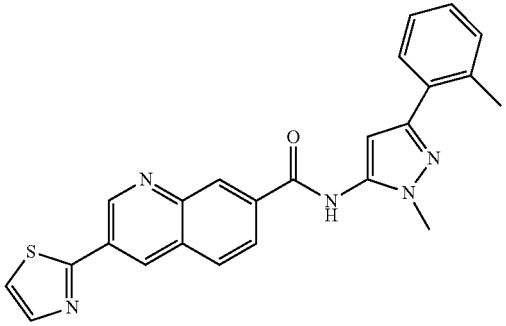 [SMILES: Cc1ccccc1-c1cc(NC(=O)c2ccc3cc(-c4nccs4)cnc3c2)n(C)n1] |
| 116 | 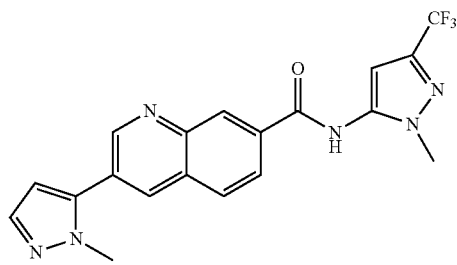 [SMILES: Cn1nc(C(F)(F)F)cc1NC(=O)c1ccc2cc(-c3ccnn3C)cnc2c1] |
| 117 | 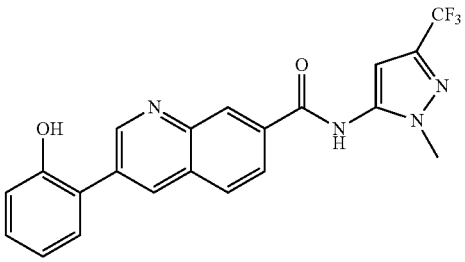 |
| 118 | 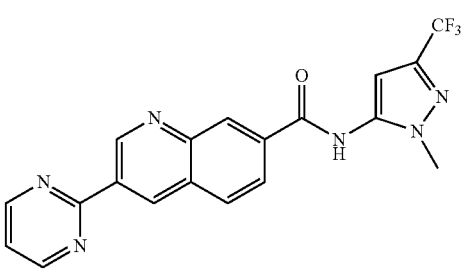 [SMILES: Cn1nc(C(F)(F)F)cc1NC(=O)c1ccc2cc(-c3ncccn3)cnc2c1] |
| 119 | 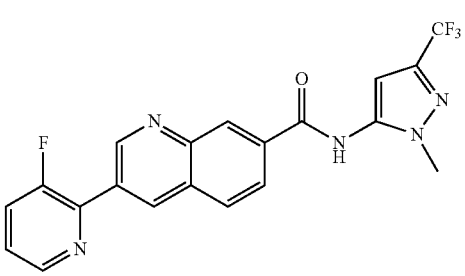 [SMILES: Cn1nc(C(F)(F)F)cc1NC(=O)c1ccc2cc(-c3ncccc3F)cnc2c1] |

TABLE 1-continued
Exemplary Compounds
| NO. | Structure |
|---|---|
| 120 | 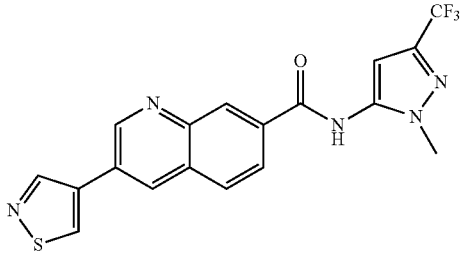 [SMILES: Cn1nc(C(F)(F)F)cc1NC(=O)c1ccc2cc(-c3cnsc3)cnc2c1] |
| 121 | 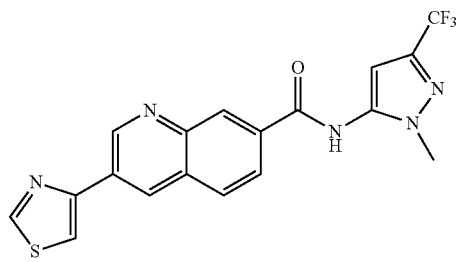 [SMILES: Cn1nc(C(F)(F)F)cc1NC(=O)c1ccc2cc(-c3cscn3)cnc2c1] |
| 122 | 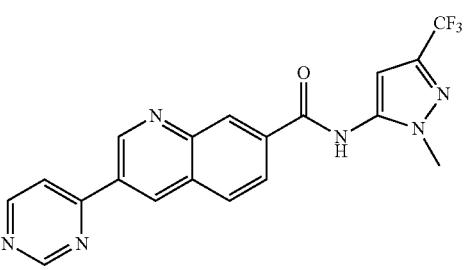 [SMILES: Cn1nc(C(F)(F)F)cc1NC(=O)c1ccc2cc(-c3ccncn3)cnc2c1] |
| 123 | 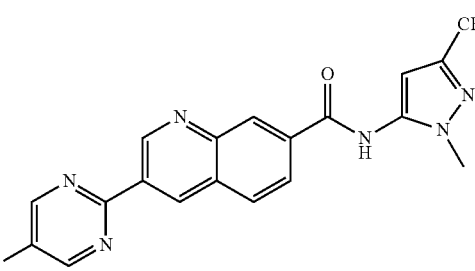 |
| 124 | 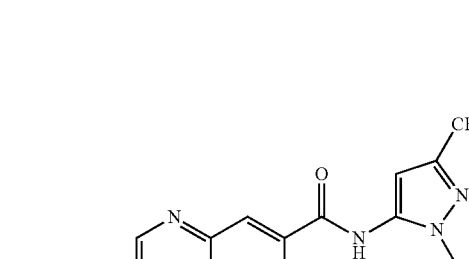 |

TABLE 1-continued

Exemplary Compounds

| NO. | Structure |
|---|---|
| 125 | 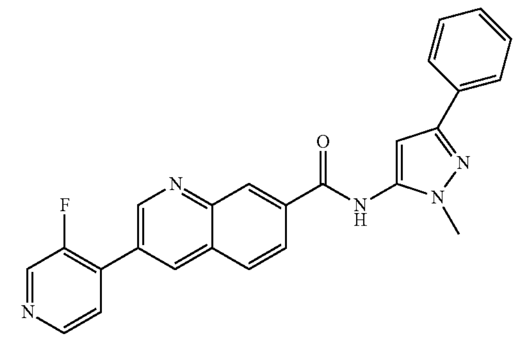 [SMILES: Cn1nc(-c2ccccc2)cc1NC(=O)c1ccc2cc(-c3ccncc3F)cnc2c1] |
| 126 | 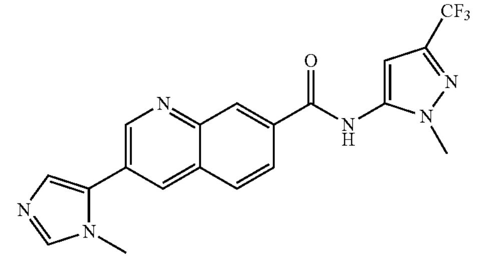 [SMILES: Cn1cncc1-c1cnc2cc(C(=O)Nc3cc(C(F)(F)F)nn3C)ccc2c1] |
| 127 | 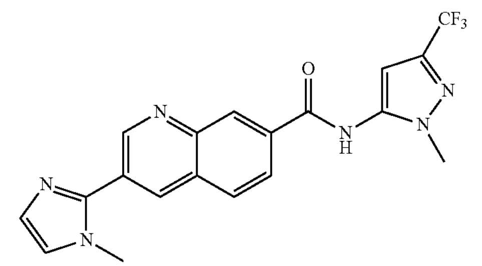 [SMILES: Cn1ccnc1-c1cnc2cc(C(=O)Nc3cc(C(F)(F)F)nn3C)ccc2c1] |
| 128 | 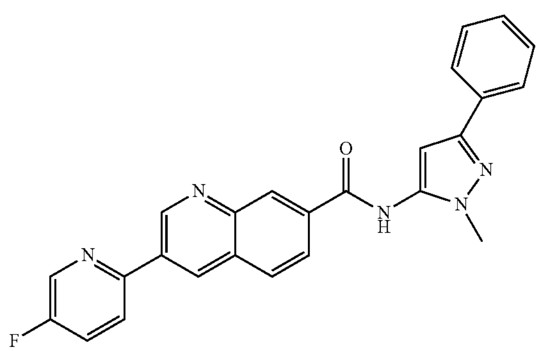 [SMILES: Cn1nc(-c2ccccc2)cc1NC(=O)c1ccc2cc(-c3ccc(F)cn3)cnc2c1] |
| 129 | 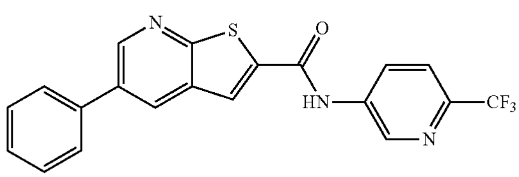 [SMILES: O=C(Nc1ccc(C(F)(F)F)nc1)c1cc2cc(-c3ccccc3)cnc2s1] |
| 130 | 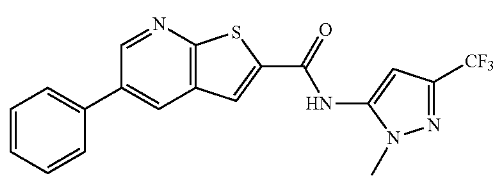 [SMILES: Cn1nc(C(F)(F)F)cc1NC(=O)c1cc2cc(-c3ccccc3)cnc2s1] |

TABLE 1-continued
Exemplary Compounds
| NO. | Structure |
|-----|-----------|
| 131 | 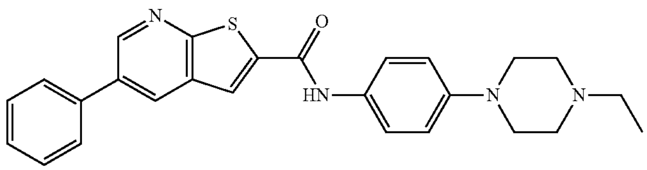 [SMILES: CCN1CCN(c2ccc(NC(=O)c3cc4cc(-c5ccccc5)cnc4s3)cc2)CC1] |
| 132 | 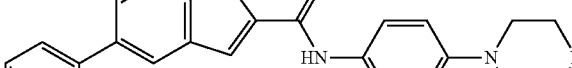 |
| 133 | 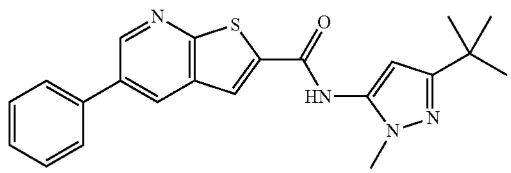 [SMILES: Cn1nc(C(C)(C)C)cc1NC(=O)c1cc2cc(-c3ccccc3)cnc2s1] |
| 134 | 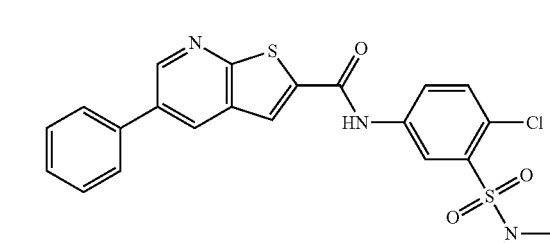 |
| 135 | 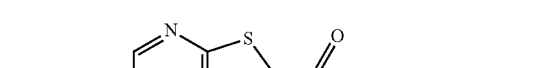 |
| 136 | 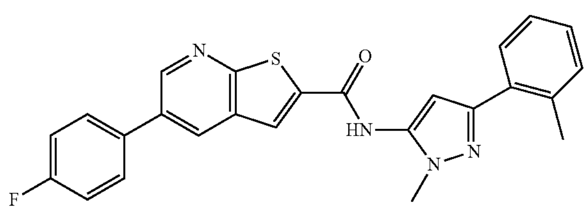 [SMILES: Cc1ccccc1-c1cc(NC(=O)c2cc3cc(-c4ccc(F)cc4)cnc3s2)n(C)n1] |
| 137 | 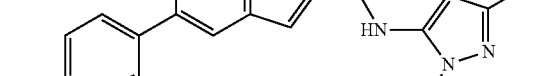 |

TABLE 1-continued

Exemplary Compounds

| NO. | Structure |
|---|---|
| 138 | 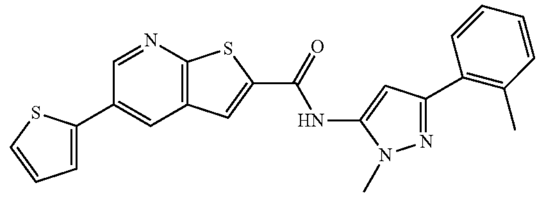 |
| 139 | 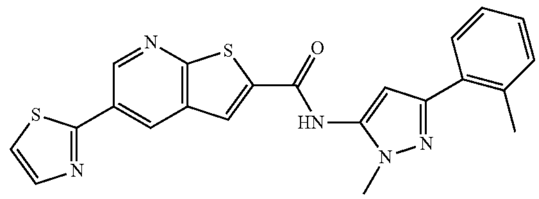 [SMILES: Cc1ccccc1-c1cc(NC(=O)c2cc3cc(-c4nccs4)cnc3s2)n(C)n1] |
| 140 | 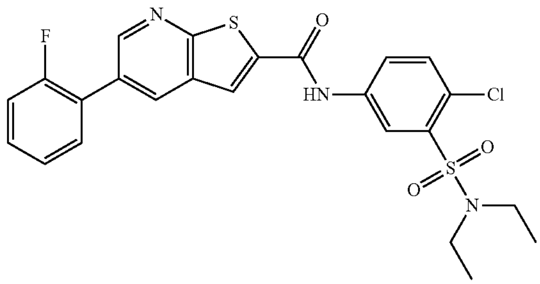 [SMILES: CCN(CC)S(=O)(=O)c1cc(NC(=O)c2cc3cc(-c4ccccc4F)cnc3s2)ccc1Cl] |
| 141 | 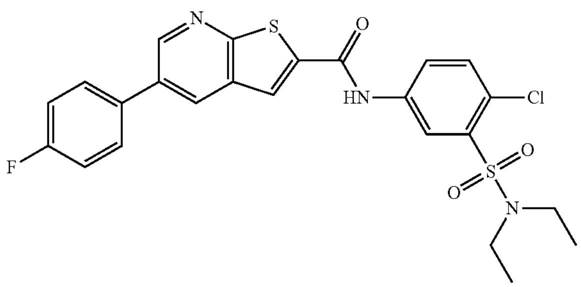 [SMILES: CCN(CC)S(=O)(=O)c1cc(NC(=O)c2cc3cc(-c4ccc(F)cc4)cnc3s2)ccc1Cl] |
| 142 | 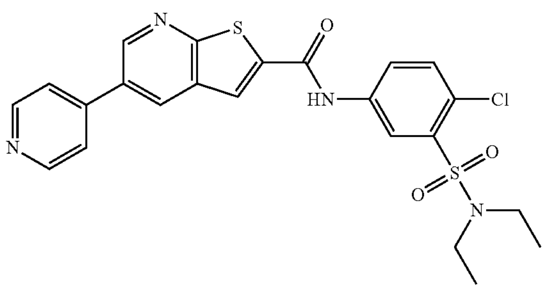 [SMILES: CCN(CC)S(=O)(=O)c1cc(NC(=O)c2cc3cc(-c4ccncc4)cnc3s2)ccc1Cl] |
| 143 | 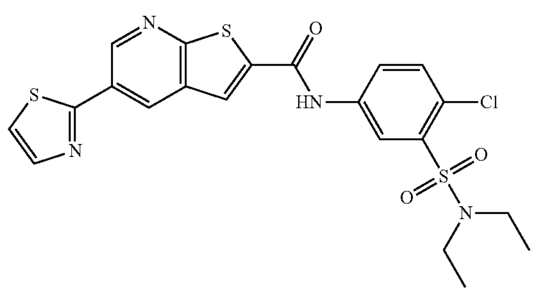 [SMILES: CCN(CC)S(=O)(=O)c1cc(NC(=O)c2cc3cc(-c4nccs4)cnc3s2)ccc1Cl] |

TABLE 1-continued

Exemplary Compounds

| NO. | Structure |
|---|---|
| 144 | 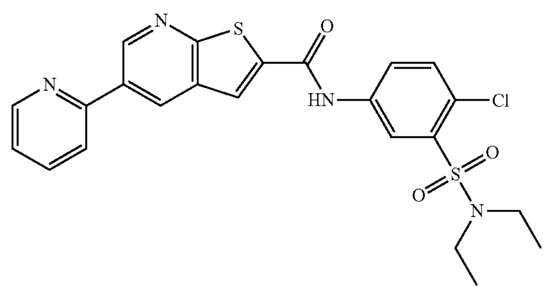 |
| 145 | 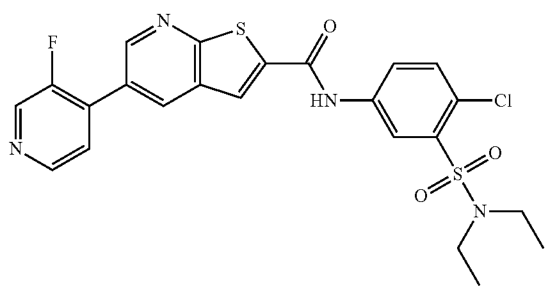 [SMILES: CCN(CC)S(=O)(=O)c1cc(NC(=O)c2cc3cc(-c4ccncc4F)cnc3s2)ccc1Cl] |
| 146 | 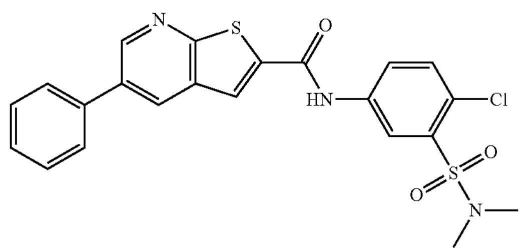 [SMILES: CN(C)S(=O)(=O)c1cc(NC(=O)c2cc3cc(-c4ccccc4)cnc3s2)ccc1Cl] |
| 147 | 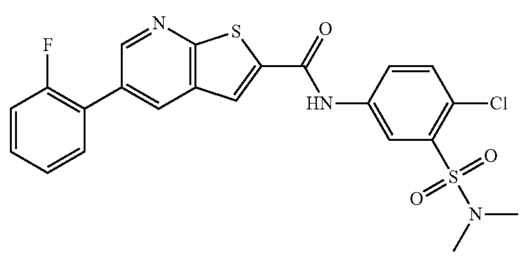 [SMILES: CN(C)S(=O)(=O)c1cc(NC(=O)c2cc3cc(-c4ccccc4F)cnc3s2)ccc1Cl] |
| 148 | 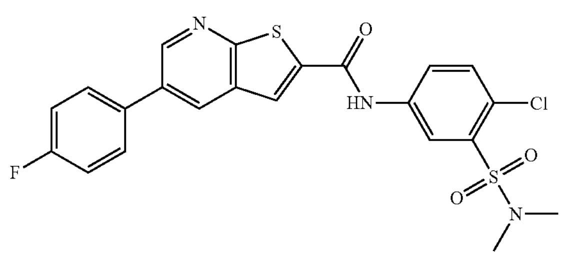 [SMILES: CN(C)S(=O)(=O)c1cc(NC(=O)c2cc3cc(-c4ccc(F)cc4)cnc3s2)ccc1Cl] |

TABLE 1-continued

Exemplary Compounds

| NO. | Structure |
|---|---|
| 149 | (structure) |
| 150 | (structure) |
| 151 | (structure) |
| 152 | (structure) |
| 153 | (structure) |
| 154 | (structure) |

TABLE 1-continued

Exemplary Compounds

| NO. | Structure |
|---|---|
| 155 | 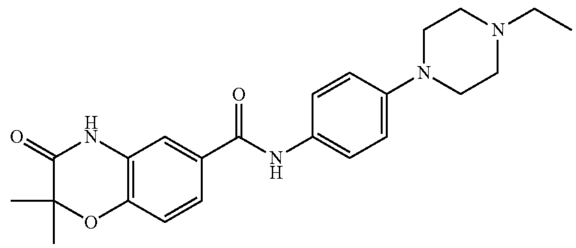 [SMILES: CCN1CCN(c2ccc(NC(=O)c3ccc4c(c3)NC(=O)C(C)(C)O4)cc2)CC1] |
| 156 | 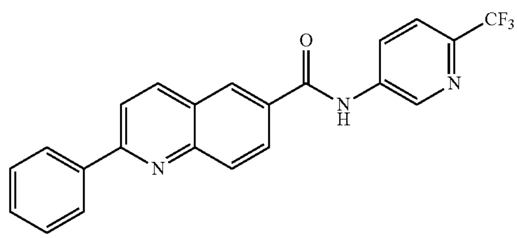 [SMILES: O=C(Nc1ccc(C(F)(F)F)nc1)c1ccc2nc(-c3ccccc3)ccc2c1] |
| 157 | 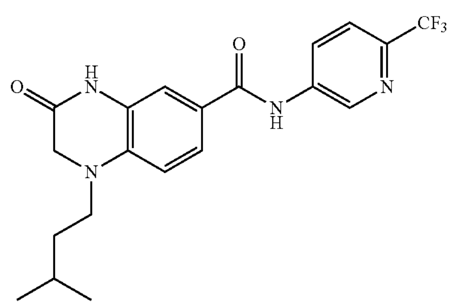 [SMILES: CC(C)CCN1CC(=O)Nc2cc(C(=O)Nc3ccc(C(F)(F)F)nc3)ccc21] |
| 158 | 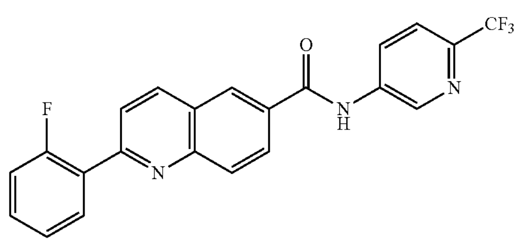 [SMILES: O=C(Nc1ccc(C(F)(F)F)nc1)c1ccc2nc(-c3ccccc3F)ccc2c1] |
| 159 | 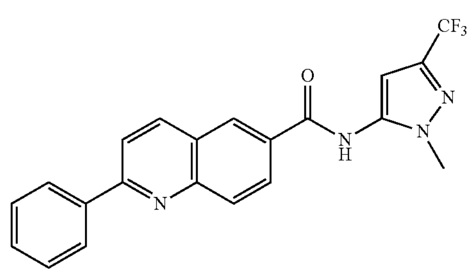 [SMILES: Cn1nc(C(F)(F)F)cc1NC(=O)c1ccc2nc(-c3ccccc3)ccc2c1] |
| 160 | 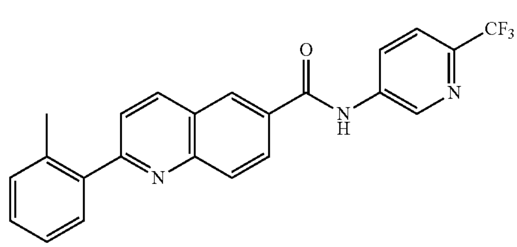 [SMILES: Cc1ccccc1-c1ccc2cc(C(=O)Nc3ccc(C(F)(F)F)nc3)ccc2n1] |

TABLE 1-continued
Exemplary Compounds
| NO. | Structure |
|---|---|
| 161 | 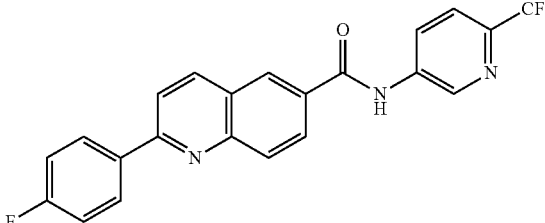 |
| 162 | 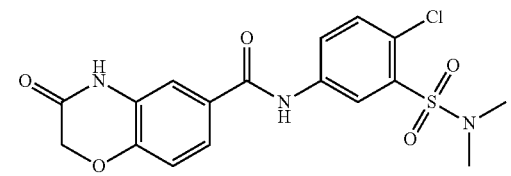 [SMILES: CN(C)S(=O)(=O)c1cc(NC(=O)c2ccc3c(c2)NC(=O)CO3)ccc1Cl] |
| 163 | 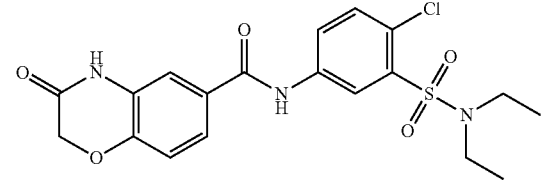 [SMILES: CCN(CC)S(=O)(=O)c1cc(NC(=O)c2ccc3c(c2)NC(=O)CO3)ccc1Cl] |
| 164 | 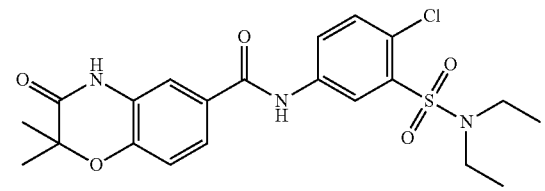 [SMILES: CCN(CC)S(=O)(=O)c1cc(NC(=O)c2ccc3c(c2)NC(=O)C(C)(C)O3)ccc1Cl] |
| 165 | 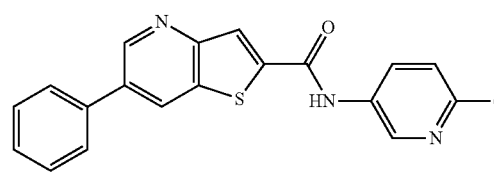 |
| 166 | 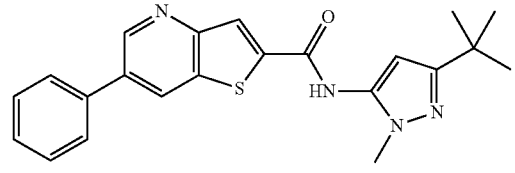 [SMILES: Cn1nc(C(C)(C)C)cc1NC(=O)c1cc2ncc(-c3ccccc3)cc2s1] |
| 167 | 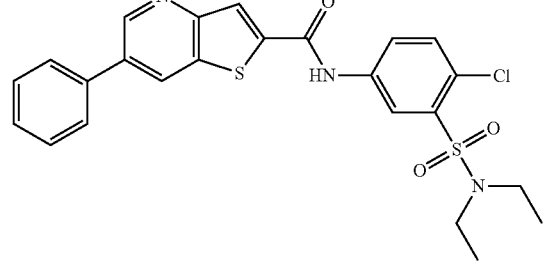 |

101
TABLE 1-continued
Exemplary Compounds
| NO. | Structure |
|---|---|
| 168 | 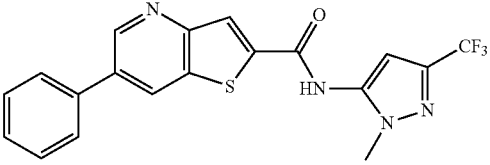 [SMILES: Cn1nc(C(F)(F)F)cc1NC(=O)c1cc2ncc(-c3ccccc3)cc2s1] |
| 169 | 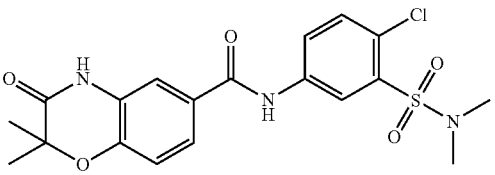 [SMILES: CN(C)S(=O)(=O)c1cc(NC(=O)c2ccc3c(c2)NC(=O)C(C)(C)O3)ccc1Cl] |
| 170 | 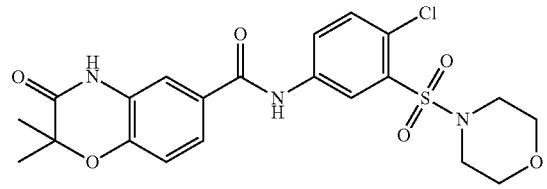 [SMILES: CC1(C)Oc2ccc(C(=O)Nc3ccc(Cl)c(S(=O)(=O)N4CCOCC4)c3)cc2NC1=O] |
| 171 | 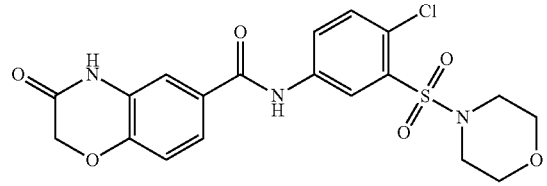 [SMILES: O=C1COc2ccc(C(=O)Nc3ccc(Cl)c(S(=O)(=O)N4CCOCC4)c3)cc2N1] |
| 172 | 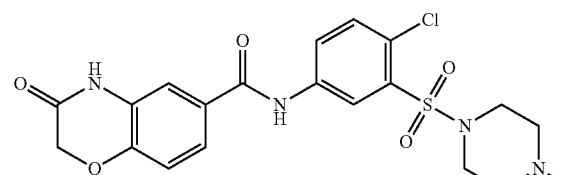 |
| 173 | 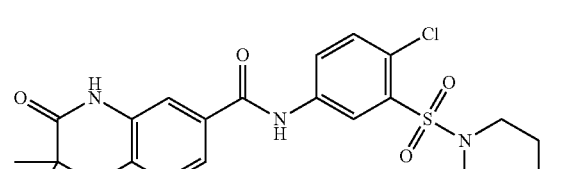 |
| 174 | 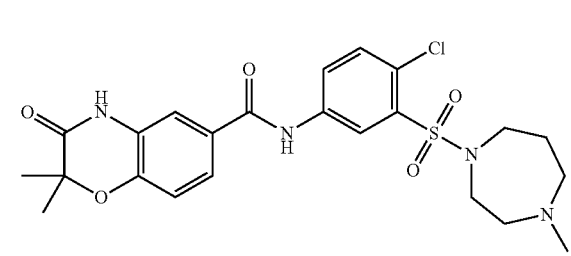 |

TABLE 1-continued

Exemplary Compounds

| NO. | Structure |
|---|---|
| 175 | (structure: 3-oxo-3,4-dihydro-2H-benzo[b][1,4]oxazine-6-carboxamide linked to N-H of a 4-chloro-3-[(4-methyl-1,4-diazepan-1-yl)sulfonyl]phenyl group) |

Additional compounds that may be used as AhR modulators are illustrated in Table 2, or pharmaceutically acceptable salts thereof.

TABLE 2

| NO. | Structure |
|---|---|
| A1 | quinoline-7-carboxamide N-linked to 3-tert-butyl-1-methyl-1H-pyrazol-5-yl |
| A2 | 4-methoxyquinoline-7-carboxamide N-linked to 3-(trifluoromethyl)phenyl |
| A3 | quinoline-7-carboxamide N-linked to 4-(4-ethylpiperazin-1-yl)-3-fluorophenyl |
| A4 | quinoline-7-carboxamide N-linked to 4-(4-ethylpiperazin-1-yl)phenyl |
| A5 | quinoline-7-carboxamide N-linked to 4-fluoro-3-(N,N-dimethylsulfamoyl)phenyl |

TABLE 2-continued

| NO. | Structure |
|---|---|
| A6 | 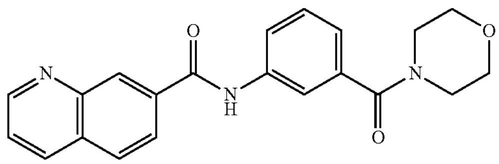 [SMILES: O=C(Nc1cccc(C(=O)N2CCOCC2)c1)c1ccc2cccnc2c1] |
| A7 | 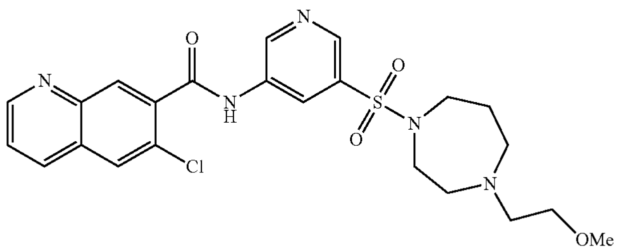 [SMILES: COCCN1CCCN(S(=O)(=O)c2cncc(NC(=O)c3cc4ncccc4cc3Cl)c2)CC1] |
| A8 | 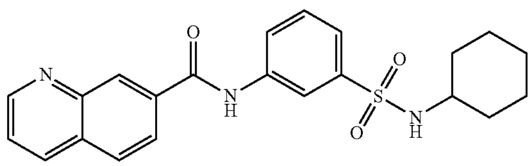 [SMILES: O=C(Nc1cccc(S(=O)(=O)NC2CCCCC2)c1)c1ccc2cccnc2c1] |
| A9 | 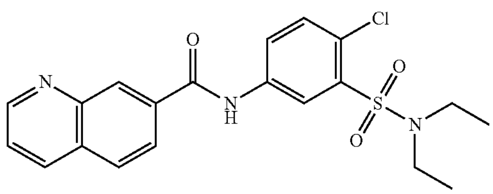 [SMILES: CCN(CC)S(=O)(=O)c1cc(NC(=O)c2ccc3cccnc3c2)ccc1Cl] |
| A10 | 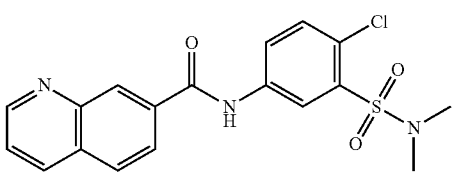 |
| A11 | 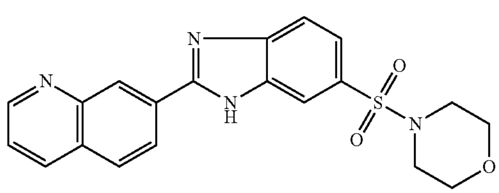 [SMILES: O=S(=O)(c1ccc2nc(-c3ccc4cccnc4c3)[nH]c2c1)N1CCOCC1] |
| A12 | 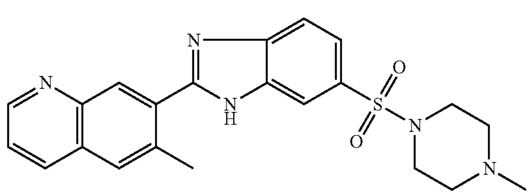 [SMILES: Cc1cc2cccnc2cc1-c1nc2ccc(S(=O)(=O)N3CCN(C)CC3)cc2[nH]1] |
| A13 | 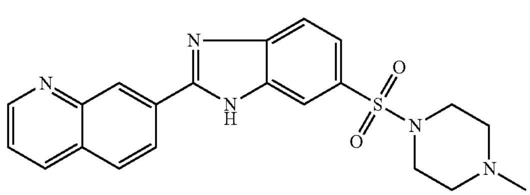 [SMILES: CN1CCN(S(=O)(=O)c2ccc3nc(-c4ccc5cccnc5c4)[nH]c3c2)CC1] |

TABLE 2-continued

| NO. | Structure |
|---|---|
| A14 | [Structure: quinoline-benzimidazole-sulfonyl-(4-methyl-1,4-diazepan-1-yl)] |
| A15 | [Structure: quinoline-benzimidazole-sulfonyl-piperazine-CH2CH2-OMe] |
| A16 | [Structure: quinoline-benzimidazole-sulfonyl-(1,4-diazepan-1-yl)-CH2CH2-OMe] |
| A17 | [Structure: quinoline (with methyl)-benzimidazole-sulfonyl-(4-methyl-1,4-diazepan-1-yl)] |

Administration and Pharmaceutical Compositions

Some embodiments include pharmaceutical compositions comprising: (a) a therapeutically effective amount of a compound of Formula (I), (II), (III), (IV) or (V) as described herein (including salts, enantiomers, diastereoisomers, tautomers, polymorphs, and solvates thereof), or pharmaceutically acceptable salts thereof, and (b) a pharmaceutically acceptable carrier, diluent, excipient or combination thereof. Compositions described herein may optionally include other drug actives.

The compounds are administered at a therapeutically effective dosage, e.g., a dosage sufficient to provide treatment for the disease states previously described. While human dosage levels have yet to be optimized for the compounds of the preferred embodiments, generally, a daily dose for most of the compounds described herein is from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. The amount of active compound administered will, of course, be dependent on the subject and disease state being treated, the severity of the affliction, the manner and schedule of administration and the judgment of the prescribing physician.

Administration of the compounds disclosed herein, or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, come embodiments include compositions containing a pharmaceutically acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically acceptable carriers well-known in the art may be used. Pharmaceutically acceptable carriers include, for example, solid or liquid fillers, diluents, hydrotropies, surface-active agents, and encapsulating substances. Optional pharmaceutically active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Pharmaceutically acceptable compositions of the compounds described herein may be orally administered in any orally acceptable dosage form including, but not limited to, capsules, tablets, aqueous suspensions or solutions. Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aq. solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically acceptable carriers suitable for preparation of such compositions are well known in the art. Typical components of carriers for syrups, elixirs, emulsions and suspensions include EtOH, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 5 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

Alternatively, pharmaceutically acceptable compositions of the compounds described herein may be administered in the form of suppositories for rectal administration. These can be prepared by mixing the agent with a suitable non-irritating excipient that is solid at rt but liquid at rectal temperature and therefore will melt in the rectum to release the drug. Such materials include cocoa butter, beeswax and polyethylene glycols.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The actual dose of the active compounds described herein depends on the specific compound, and on the condition to be treated; the selection of the appropriate dose is well within the knowledge of the skilled artisan.

Methods of Treatment/Uses of the Compounds

Some further embodiments of the present disclosure relate to compounds of Formula (I), (II), (III), (IV) or (V) as described herein, specific compounds selected from Table 1 or Table 2, or pharmaceutically acceptable salts thereof for use as AhR modulators, for examples, AhR inhibitors.

Some further embodiments of the present disclosure relate to compounds of Formula (I), (II), (III), (IV) or (V) as described herein, specific compounds selected from Table 1 or Table 2, or pharmaceutically acceptable salts thereof for use in inhibiting AhR in a subject in need thereof, or treating or ameliorating an AhR-mediated disorder in a subject in need thereof.

Some embodiments of the present disclosure relate to methods of modulating a AhR signaling pathway in a subject, comprising administering a therapeutically effective amount of a compound of Formula (I), (II), (III), (IV) or (V) as described herein, a specific compound selected from Table 1 or Table 2, or a pharmaceutically acceptable salt thereof, or a pharmaceutical composition described herein to a subject in need thereof. In some embodiments, the AhR signaling pathway is transcellular kynurenine (Kyn)-Aryl Hydrocarbon Receptor (AhR) pathway. The compounds may be an antagonist, or a partial agonist acting as a competitive antagonist in the presence of a full agonist of AhR.

Some additional embodiments of the present disclosure relate to methods of inhibiting AhR in a patient or treating or ameliorating an AhR-mediated disorder in a subject in need thereof, comprising administering a therapeutically effective amount of a compound of Formula (I), (II), (III), (IV) or (V) as described herein, a specific compound selected from Table 1 or Table 2, or a pharmaceutically acceptable salt thereof or a pharmaceutical composition described herein to the subject.

As used herein, the terms "AHR-mediated" disorders, diseases, and/or conditions as used herein means any disease or other deleterious condition in which AHR, or a mutant thereof, are known to play a role. AHR mediated disorders are well established in the art. The nexus between AHR and AHR mediated disorders diseases and/or conditions as recited herein is well established in the relevant arts. In some embodiments, the present disclosure provides a method for treating one or more disorders, diseases, and/or conditions wherein the disorder, disease, or condition is a proliferative disease such as cancer, an inflammatory disorder, or a viral infection.

Some additional embodiments of the present disclosure relate to methods of inhibiting AhR in a biological sample, comprising contacting a compound of Formula (I), (II), (III), (IV) or (V) as described herein, or a pharmaceutically acceptable salt thereof, or a pharmaceutical composition described herein with the biological sample.

Some additional embodiments of the present disclosure relate to methods of treating cancer by cancer immunotherapy, comprising administering a compound of Formula (I), (II), (III), (IV) or (V) as described herein, a specific compound selected from Table 1 or Table 2, or a pharmaceutically acceptable salt thereof, or a pharmaceutical composition described herein to a subject in need thereof.

In some embodiments, the compound described herein is an inhibitor or antagonist of AhR. In some such embodiments, the compound binds to and inhibits or blocks the AhR receptor pathway, for example, the transcellular kynurenine (Kyn)-Aryl Hydrocarbon Receptor (AhR) pathway, which may result in PD-1 downregulation.

In some other embodiments, the compound described herein is a partial agonist of AhR. In such embodiments, the compound described herein binds to and activates AhR, but have only partial efficacy at the receptor relative to a full agonist. In some instances, such partial agonist displays both agonistic and antagonistic effects when both a full agonist and partial agonist are present, the partial agonist actually acts as a competitive antagonist, competing with the full agonist for AhR receptor binding or occupancy and producing a net decrease in the AhR receptor activation observed with the full agonist alone. For example, the compound described herein may binds to and activates AhR receptor but act as a competitive antagonist in the presence of a full agonist of AhR. In some instances, such competitive binding results in PD-1 downregulation.

In some further embodiments, the compound described herein may be used to affect PD-1 expression in T cells, for example, inhibits or blocks PD-1 expression on cell surface. In some instance, this may result in activation of immune response against cancer cells.

Non-limiting examples of cancers described herein may be selected from the group consisting breast cancer, melanoma, renal cancer, prostate cancer, colon cancer, lung cancer, bladder cancer, brain cancer, cervical cancer, head and neck cancer, esophageal and gastric cancers, osteosarcoma, multiple myeloma, acute myeloid leukemia, lymphoma (including non-Hodgkin lymphoma and primary effusion lymphoma), neuroendocrine cancer, hepatocellular carcinoma, renal cell cancer, pancreatic cancer, thyroid cancer, glioblastoma, ovarian cancer, endometrial cancer, and liposarcoma. Compounds of the present disclosure may also be useful in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, Waldenstrom's macroglobulinemia, a mammary carcinoma, follicular carcinoma, undifferentiated carcinoma, papillary carcinoma, seminoma, melanoma, an MYD88-driven disorder, DLBCL, ABC DLBCL, an IL-1-driven disorder, Smoldering of indolent multiple myeloma, or a leukemia.

In some embodiments, the compounds disclosed herein may be used to treat cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer).

Some embodiments of the present disclosure relate to methods of inhibiting cancer cell growth by activating the immune system to attack cancer cells, comprising selecting a patient with a cancer that is responsive to immunotherapy, and providing an effective amount of a compound of Formula (I), (II), (III), (IV) or (V) as described herein, a specific compound selected from Table 1 or Table 2, or a pharmaceutically acceptable salt thereof, or a pharmaceutical composition described herein to a patient in need thereof.

In some other embodiments, compounds of the present disclosure are useful in the treatment of inflammatory or obstructive airways diseases, including intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), chronic bronchitis or dyspnea, emphysema, exacerbation of airways hyper-reactivity consequent to other drug therapy (in particular other inhaled drug therapy), and eosinophil related disorders. These compounds are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, *Pemphigus vulgaris, Pemphigus foliaceus*, paraneoplastic *Pemphigus*, epidermolysis bullosa acquisita, acne vulgaris, and other inflammatory or allergic conditions of the skin. These compounds are also useful in the treatment of inflammatory or allergic conditions of the eye, for example, ocular allergy, conjunctivitis, keratoconjunctivitis sicca, and vernal conjunctivitis, diseases affecting the nose including allergic rhinitis.

In some embodiments the inflammatory disease which can be treated according to the methods is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin-Associated Periodic Syndromes (CAPS), or osteoarthritis. In some embodiments, the inflammatory disease which can be treated according to the methods described herein is selected from a TH17-mediated disease. In some embodiments, the TH17-mediated disease is selected from Systemic lupus erythematosus, Multiple sclerosis, inflammatory bowel disease including Crohn's or ulcerative colitis.

In some other embodiments, compounds of the present disclosure are useful in the treatment a viral infection, disease, or condition. Non-limiting examples of a viral disease may include retroviral diseases, such as, HIV-1, HIV-2, human T-cell leukemia virus-I (HTLV-I), HTLV-II, HTLV-III, simian immunodeficiency virus (SIV), lymphadenopathy-associated virus (LAV-2), simian T-lymphotrophic virus-I (STLV-I), STLV-II, STLV-III, simian B-lymphotrophic (SBL) virus, Gibbon ape leukemia virus (GALV), bovine leukemia virus (BLV), equine infectious anemia virus (EIAV), feline leukemia virus (FELV), murine leukemia virus (MuLV), avian leukosis virus (ALV); other virus infections such as hepadnaviridae (Hepatitis B); herpesviridae; parvoviridae; papovaviridae; pox viruses.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Inhibition of enzymes in a biological sample is useful for a variety of purposes that are known to one of skill in the art. Examples of such purposes include, but are not limited to biological assays, gene expression studies, and biological target identification.

The terms "therapeutically effective amount," as used herein, refer to an amount of a compound sufficient to cure, ameliorate, slow progression of, prevent, or reduce the likelihood of onset of the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $IC_{50}$ is a measure of how effective a drug is. It indicates how much of a particular drug compound is needed to inhibit a given biological process (e.g., a cancer cell line) by half. It is commonly used as a measure of antagonist drug potency in pharmacological research. $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. However, pharmaceutical compositions that exhibit narrow therapeutic indices are also within the scope of the invention. The data obtained from cell culture assays and animal studies may be used in formulating a range of dosage for human use. The dosage contained in such compositions is preferably within a range of circulating concentrations that include an EDso with little or no toxicity. The dosage may vary within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In another aspect, treating a condition described herein results in a reduction in the rate of cellular proliferation. Preferably, after treatment, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating a condition described herein results in a reduction in the proportion of proliferating cells. Preferably, after treatment, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. In a preferred aspect, the proportion of proliferating cells is measured, for example, by quantifying the number of dividing cells relative to the number of non-dividing cells in a tissue sample. In another preferred aspect, the proportion of proliferating cells is equivalent to the mitotic index.

In another aspect, treating a condition described herein results in a decrease in size of an area or zone of cellular proliferation. Preferably, after treatment, size of an area or zone of cellular proliferation is reduced by at least 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. In a preferred aspect, size of an area or zone of cellular proliferation may be measured as a diameter or width of an area or zone of cellular proliferation.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In some embodiments, the agents are administered simultaneously. In some such embodiments, administration in combination is accomplished by combining the agents in a single dosage form. In some embodiments, the agents are administered sequentially. In some embodiments the agents are administered through the same route, such as orally. In some other embodiments, the agents are administered through different routes, such as one being administered orally and another being administered intravenously. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Synthesis

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

EXAMPLES

Additional embodiments are disclosed in further detail in the following examples, which are not in any way intended to limit the scope of the claims.

Example 1. Experimental Procedures

Compounds of the invention can be prepared using one of the general synthetic schemes exemplified below.
General Experimental Procedure I

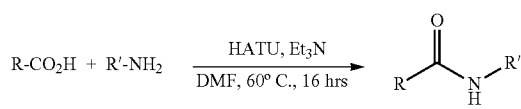

Corresponding carboxylic acid (1.0 equiv) and corresponding aniline (1.1 equiv) were suspended in dry N,N-dimethyl formamide under argon atmosphere followed by the addition of triethylamine (1.2 equiv). Then HATU (1-[bis(dimethylamino)methylene]-1H-1,2,3-triazolo[4,5-b]pyridinium 3-oxid hexafluorophosphate) (228 mg, 0.6 mmol, 1.2 equiv) was added, and the reaction mixture was stirred for 16 hours at rt. After dilution with water, the mixture was extracted with dichloromethane. The combined organic layers were dried over anhydrous $Na_2SO_4$, filtered and concentrated in vacuo. The crude product was purified on C18-silica gel (water/acetonitrile+0.1% trifluoroacetic acid). The fractions containing the desired product were combined and treated with saturated sodium bicarbonate solution. The mixture was extracted with dichloromethane. The combined organic layers were dried over anhydrous $Na_2SO_4$, filtered and concentrated in vacuo to give the desired product in >95% purity as determined by HPLC.
General Experimental Procedure II

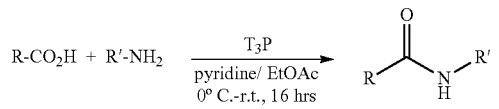

$T_3P$ (35.0 equiv., 50% solution in EtOAc) was added to a stirred solution of the corresponding acid (1.0 equiv.) in pyridine (0.8 M) at 0° C., and the reaction mixture was stirred for 15 minutes. Then, the corresponding aniline (1.0 equiv.) was added at 0° C., and the reaction mixture was left to stir at rt for additional 16 hours under Nitrogen atmosphere. The progress of the reaction was monitored by thin layer chromatography and LC/MS. Upon completion of the reaction, the reaction mixture was filtered through a neutral alumina pad twice to remove the excess of $T_3P$. The filtrate was concentrated in vacuo and the crude product was purified by prep-HPLC. After purification, the fractions containing the desired product were concentrated to a minimal volume, filtered through 0.4 m syringe filter and lyophilized to afford the product in >95% purity.

General Experimental Procedure III

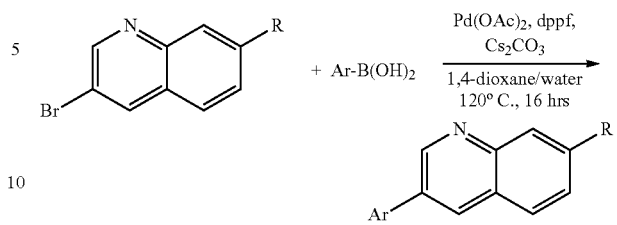

A vial was charged with the corresponding 3-bromoquinoline (1.0 equiv.), the corresponding boronic acid (1.2 equiv.), cesium carbonate (3.0 equiv.), palladium(II) acetate (0.2 equiv.) and 1,1'-Bis(diphenylphosphino)ferrocene (0.25 equiv.), then 1,4-dioxane (0.04 M) and water (0.12 M) were added. The reaction mixture was degassed by purging with nitrogen gas for 10 minutes before the vial was capped and heated at 120° C. for 16 hours. After cooling down to rt the volatiles were removed in vacuo. The residue was diluted with water and extracted with EtOAc (3×). Combined organic phases were washed with brine, dried over $Na_2SO_4$ and concentrated in vacuo. The crude product was purified on reversed phase silica. Fractions containing the desired product were combined, treated with saturated aqueous sodium bicarbonate solution and extracted into dichloromethane (3×). The combined organic phases were washed with brine, dried over $Na_2SO_4$, filtered and concentrated in vacuo to give the product.
General Experimental Procedure IV

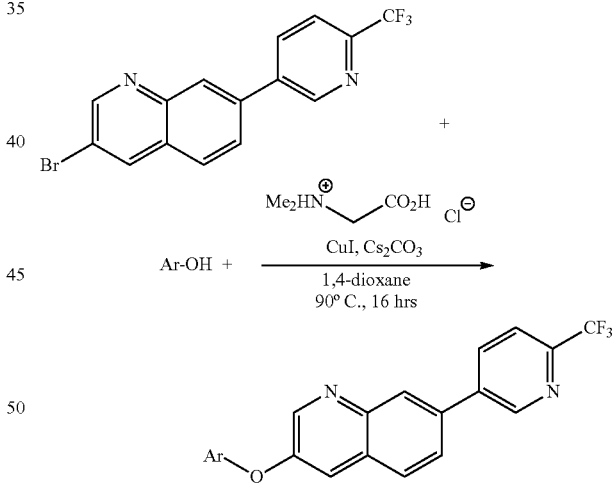

A vial was charged with 3-bromo-N-[6-(trifluoromethyl)pyridin-3-yl]quinoline-7-carboxamide (0.08 mmol, 30.0 mg), the corresponding phenol (0.12 mmol), cesium carbonate (0.16 mmol, 52.1 mg), copper(I) iodide (20 mol %) and N,N-dimethylglycine hydrochloride (40 mol %), then 1,4-dioxane (0.27 M) was added. The vial was sealed and heated at 90° C. for 16 hours. After cooling down to rt, the reaction mixture was diluted with water (5 mL) and extracted with EtOAc (3×10 mL). Combined organic layers were washed with brine, dried over $Na_2SO_4$ and concentrated in vacuo. The product was purified on silica gel. Fraction containing the desired product were combined and concentrated in vacuo to give the desired product.

General Experimental Procedure V

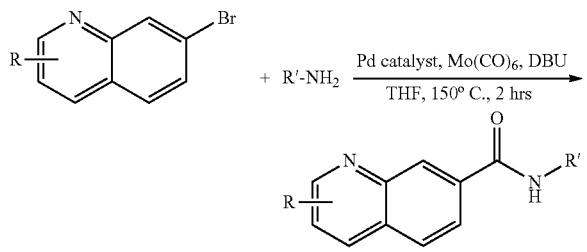

10 mL microwave vial was charged with the corresponding 7-bromoquinoline (1.0 equiv.), trans-Bis(acetato)bis[o-(di-o-tolylphosphino)benzyl]-dipalladium(II) (0.1 equiv.; CAS: 172418-32-5), molybdenum hexacarbonyl (1.0 equiv.), dry THF (0.4 M) and the corresponding aniline (3.0 equiv.). Then, 1,8-diazabicycloundec-7-ene (3.0 equiv.) was added and the microwave vial was immediately sealed (gas evolution was observed). The reaction mixture was heated at 150° C. for 2 hours. After cooling down to rt, the reaction mixture was filtered through Celite plug, the plug was washed with DCM, and the filtrate was concentrated in vacuo. The crude product was purified on C18-silica gel. The fractions containing the desired product were combined and treated with saturated aqueous sodium bicarbonate solution and the mixture was extracted with dichloromethane (3×). Combined organic layers were dried over anhydrous $Na_2SO_4$, filtered and concentrated in vacuo to give the desired product in >95% purity as determined by HPLC.

General Experimental Procedure VI

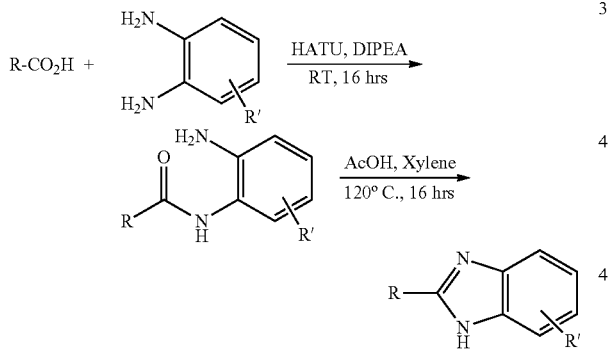

N,N-Diisopropylethylamine (DIPEA) (3 equiv.) was added to a stirred solution of carboxylic acid (1 equiv.) in DMF (15 mL), followed by HATU (1.5 equiv.) at 0° C., and the reaction mixture was stirred for 15 min. Then diamine (1 equiv.) was added to the reaction mixture at 0° C. The reaction mixture was stirred at rt for 16 hrs. The progress of the reaction was monitored by thin layer chromatography and LCMS. After completion of the reaction, the reaction mixture was diluted with water (250 mL) and extracted with EtOAc (2×30 mL). Combined organic layers were washed with water and brine, dried over anhydrous $Na_2SO_4$ and concentrated in vacuo. The resultant crude compound was triturated with diethyl ether to afford carboxamide as a dark-yellow or brown solid. The solid was dissolved in 15 mL of acetic acid and 5 mL of xylene was added. Then the reaction mixture was heated at 120° C. for 16 hrs. Upon completion, the reaction mixture was concentrated in vacuo to give crude material, which was passed through neutral alumina. The resultant crude product was purified by prep-HPLC. Fractions containing the desired product were concentrated to minimum volume, filtered through 0.4μ syringe filter and concentrated in vacuo to afford the final product as an off-white solid.

General Experimental Procedure VII

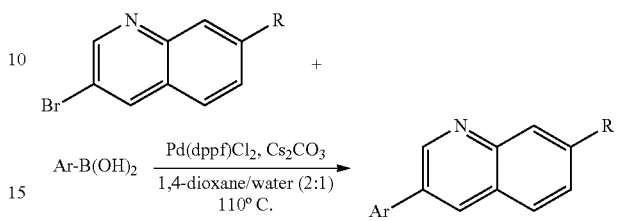

A vial was charged with the corresponding 3-bromoquinoline (1.0 equiv.), the corresponding boronic acid (1.2 equiv.), cesium carbonate (3.0 equiv.), and 1,1'-bis(diphenylphosphino)ferrocene]dichloropalladium(II) (0.1 equiv.), then 1,4-dioxane and water were added in 2:1 ratio. The reaction mixture was degassed by purging with nitrogen gas for 5 minutes before the vial was sealed and heated at 110° C. until no starting material was detected by LC/MS. After cooling down to rt, the volatiles were removed in vacuo. The residue was diluted with water and extracted with EtOAc (3×). Combined organic phases were washed with brine, dried over $Na_2SO_4$ and concentrated in vacuo. The crude product was purified on reversed phase silica gel column. Fractions containing the desired product were combined, treated with saturated aqueous sodium bicarbonate solution and extracted with DCM. The combined organic phases were washed with brine, dried over anhydrous $Na_2SO_4$, filtered and concentrated in vacuo to give the product as a free base.

General Experimental Procedure VIII

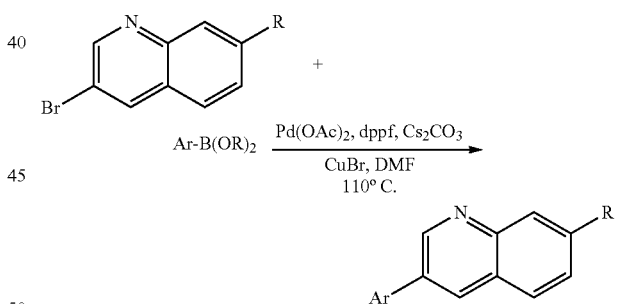

A vial was charged with the corresponding 3-bromoquinoline (1.0 equiv.), the corresponding boronic acid ester (2.0 equiv.), cesium carbonate (4.0 equiv.), copper(I) bromide (1.0 equiv), palladium (II) acetate (0.1 equiv), 1,1'-Ferrocenediyl-bis(diphenylphosphine), (0.2 equiv.), and anhydrous DMF. The reaction mixture was degassed by purging with nitrogen gas for 5 minutes. Then the vial was sealed and heated at 110° C. overnight. After cooling down to rt, the reaction mixture was diluted with dichloromethane and washed with water (3×). Organic phase was washed with brine, dried over anhydrous $Na_2SO_4$ and concentrated in vacuo. The crude product was purified on reversed phase silica gel column. Fractions containing the desired product were combined, treated with saturated aqueous sodium bicarbonate solution and extracted with DCM (3×). The combined organic phases were washed with brine, dried over anhydrous Na$_2$SO$_4$, filtered and concentrated in vacuo to give the product as a free base.

General Experimental Procedure IX

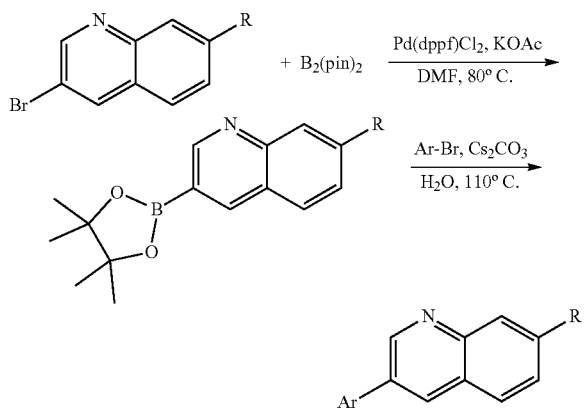

A vial was charged with the corresponding 3-bromoquinoline (1.0 equiv.), bis(pinacolato)diboron (1.4 equiv.), potassium acetate (3.0 equiv.), 1,1'-bis(diphenylphosphino)ferrocene]dichloropalladium(II) (0.1 equiv.), and anhydrous DMF. The reaction mixture was degassed by purging with nitrogen gas for 3 minutes. Then the vial was sealed and heated at 80° C. for 2 hrs. After cooling down to rt, the corresponding aryl bromide was added, followed by cesium carbonate (3.0 equiv.), 1,1'-bis(diphenylphosphino)ferrocene]dichloropalladium(II) (0.1 equiv.), and DI water. The reaction mixture was once again degassed by purging with nitrogen gas for 3 minutes. Then the vial was sealed and heated at 110° C. overnight. Then the reaction mixture was diluted with dichloromethane and washed with water (3×). Organic phase was washed with brine, dried over anhydrous Na$_2$SO$_4$ and concentrated in vacuo. The crude product was purified on reversed phase silica gel column. Fractions containing the desired product were combined, treated with saturated aqueous sodium bicarbonate solution and extracted with dichloromethane. The combined organic phases were washed with brine, dried over anhydrous Na$_2$SO$_4$, filtered and concentrated in vacuo to give the product as a free base.

Int-1: 7-Bromo-6-chloroquinoline

Concentrated H$_2$SO$_4$ (48 mL, 2.4 vol per g) was added slowly over a period of 24 min to a pre-chilled solution of 3-bromo-4-chloroaniline (20 g, 97.087 mmol) in nitrobenzene (10 mL, 97.087 mmol) and glycerol (17.69 g, 242.71 mmol) at 0° C. The reaction temperature was gradually increased to 150° C., and the reaction mixture was stirred at 150° C. for 6 hrs. Then it was allowed to cool down to rt, poured into crushed ice, and extracted with EtOAc (3×500 mL). The combined organic layers were washed with water and brine, dried over anhydrous Na$_2$SO$_4$ and concentrated under reduced pressure. The resultant crude compound was purified by column chromatography (100-200 silica) using 20% EtOAc in hexane as eluent to give 13 g of racemic mixture of 7-bromo-6-chloroquinoline and 5-bromo-6-chloroquinoline as a brown solid in 56% yield. The racemic mixture of two compounds (13 g) was separated by SFC purification using C$_{02}$ gas and IPA as a co-solvent to give 3.4 g (26% Yield) of Int-1. MS (ESI) m/z 241.9 [M+H]$^+$.

Int-2: Methyl 6-chloroquinoline-7-carboxylate

A mixture of Int-1 (1.0 g, 4.13 mmol, 1.0 eq) and NaOAc (1.02 g, 12.5 mmol, 3.0 eq) in 1:1 MeOH/DMF (20 mL) was de-gassed with argon for 10 min. Then PdCl$_2$(dppf). DCM (340 mg, 0.413 mol, 0.1 eq) was added and an the mixture was de-gassed with argon for another 15 min. Then the reaction mixture was heated at 70° C. in steel bomb under CO atmosphere for 6 hrs. The progress of the reaction was monitored by LCMS and TLC. After completion, the reaction mixture was concentrated in vacuo, and the crude product was purified by silica gel column chromatography to give 350 mg of Int-2 as a pale-yellow solid in 38% yield. MS (ESI) m/z=222.15 [M+H]$^+$.

Int-3: 6-Chloroquinoline-7-carboxylic acid

Lithium hydroxide monohydrate (114 mg, 2.71 mmol, 2.0 eq) was added to a solution of Int-2 (300 mg, 1.35 mmol, 1.0 eq) in 4:2:1 mixture of THF/H$_2$O/MeOH (1 mL), and the reaction mixture was stirred at rt for 2 hrs. The progress of the reaction was monitored by LCMS and TLC. Upon completion, the reaction mixture was concentrated in vacuo, diluted with DI water, acidified to pH ~ 4 with 1N HCl and extracted with EtOAc. The organic layers were combined, washed with water and brine, separated, dried over anhydrous Na$_2$SO$_4$, filtered and concentrated in vacuo to give 210 mg of Int-3 as a pale-yellow solid in 74% yield. MS (ESI) m/z=208.16 [M+H]$^+$. 99.46% purity by LCMS.

Int-4: 7-Bromo-6-methylquinoline

Concentrated H$_2$SO$_4$ (48 mL, 2.4 vol per g) was added slowly over a period of 24 min to a pre-chilled solution of 3-bromo-4-methylaniline (20 g, 107.5 mmol) in nitrobenzene (11.1 mL, 107.5 mmol) and glycerol (19.6 mL, 268.8 mmol) at 0° C. The reaction temperature was gradually increased to 150° C., and the reaction mixture was stirred at 150° C. for 6 hrs. Then it was cooled down to rt, poured into crushed ice, and extracted with EtOAc (3×500 mL). Combined organic layers were washed with water and brine, dried over anhydrous Na$_2$SO$_4$ and concentrated under reduced pressure. The resultant crude compound was purified by column chromatography to afford 15 g (63% yield) of isomeric mixture of 7-bromo-6-methylquinoline and 8-bromo-7-methylquinoline as a brown solid. The isomeric mixture of two compounds (13 g) was separated by prep-HPLC purification to afford 5 g (21% yield) of Int-4. MS (ESI) m/z 223.98 [M+H]$^+$.

Int-5: Methyl 6-methyl quinoline-7-carboxylate

A mixture of the compound Int-4 (1.0 g, 4.5 mmol, 1.0 eq) and NaOAc (1.13 g, 13.6 mmol, 3.0 eq) in 1:1 MeOH/DMF (20 mL) was de-gassed with argon for 10 min. Then Pd(dppf)Cl$_2$DCM (370 mg, 0.452 mmol, 0.1 eq) was added and the reaction mixture was de-gassed with argon for another 15 min, then heated at 70° C. in steel bomb under CO atmosphere for 6 hrs. Upon completion, the reaction mixture was distilled off, diluted with EtOAc and filtered through celite, and the celite pad was washed with EtOAc. The EtOAc layer was separated from filtrate and washed with water and brine, dried over anhydrous Na$_2$SO$_4$, filtered and concentrated in vacuo to give crude product. The crude product was purified by flash chromatography using EtOAc in hexane as eluent to provide 300 mg of Int-5 as a pale-yellow solid in 33% yield. MS (ESI) m/z 202.22 [M+H]$^+$. 99.01% purity by LCMS.

Int-6: 6-Methylquinoline-7-carboxylic acid

Lithium hydroxide monohydrate (125 mg, 2.98 mmol, 2.0 eq) was added to a solution of Int-5 (300 mg, 1.49 mmol, 1.0 eq) in 4:2:1 mixture of THF/H$_2$O/MeOH (3.0 mL), and the reaction mixture was stirred at rt for 2 hrs. After completion, the reaction mixture was concentrated in vacuo to give crude product. The crude product was diluted with DI water, acidified to pH ~ 4 with 1N HCl and extracted with EtOAc. The organic layers were combined, washed with water and brine, then dried over anhydrous Na$_2$SO$_4$, filtered and concentrated in vacuo to give 110 mg of Int-6 as a pale-yellow solid in 39% yield. MS (ESI) m/z 188.17 [M+H]$^+$. 98.85% purity by LCMS.

Int-7: 4-Chloroquinoline-7-carboxylic acid

A mixture of 4-chloro-7-(trifluoromethyl)quinoline (10.0 g, 43.29 mmol) and concentrated sulfuric acid (100 mL) was stirred in a 500 mL sealed tube at 200° C. for 16 hours. After LC/MS indicated complete consumption of the starting material, the reaction mixture was cooled to rt and poured into ice water (500 mL). The pH of the reaction mixture was adjusted to 3 with 1N NaOH. The resulting precipitate was collected by filtration, washed with water (2×100 mL) and dried under high vacuum to afford 7.0 g of Int-7 as a grey solid in 78% yield. MS (ESI) m z 207.9 [M+H]$^+$.

Int-8: 4-Methoxyquinoline-7-carboxylic acid

1 M solution of potassium tert-butoxide in THF (58 mL, 57.9 mmol) was added to a mixture of Int-7 (4.0 g, 19.3 mmol) in methanol (20 mL) and 1,4-dioxane (40 mL) in a 500 mL reaction tube. The tube was sealed, and the reaction mixture was heated at 100° C. for 16 hrs. After LC/MS indicated complete consumption of starting materials, the reaction mixture was cooled to rt. The volatiles were removed in vacuo and the residue was diluted with water and pH was adjusted to ~4.5 with 1 M HCl (aq.). The reaction mixture was extracted with EtOAc (2×150 mL). Combined organic layers were washed with water and brine, dried over anhydrous Na$_2$SO$_4$, and concentrated under reduced pressure to afford the crude product, which was purified by prep-HPLC to afford 929 mg of Int-8 as an off-white solid in 24% yield. MS (ESI) m/z 204.56 [M+H]$^+$.

Int-9: 4-Amino-3-nitrobenzenesulfonyl chloride

2-Nitroaniline (10 g, 72.37 mmol) was added slowly to a stirred pre-chilled (0° C.) solution of chlorosulfonic acid (20 mL, 289.5 mmol), and the reaction mixture was heated at 100° C. for 16 hrs in a sealed glass tube. After completion of the reaction, the reaction mixture was poured into crushed ice (100 g) and extracted with EtOAc (2×150 mL). Combined organic layers were washed with water and brine, dried over anhydrous Na$_2$SO$_4$ and concentrated under reduced pressure to afford crude product, which was purified by column chromatography using silica gel to afford 6.0 g of Int-9 as a yellow solid in 35% yield. MS (ESI) m/z 234.84 [M−H]$^−$ Int-10: 4-((4-(2-Methoxyethyl)-1,4-diazepan-1-yl)sulfonyl)-2-nitroaniline Triethylamine (10.64 mL, 76.27 mmol) was added to a stirred solution of Int-9 (3 g, 12.71 mmol) in dry THF (30 mL), followed by 1-(2-methoxyethyl)-1,4-diazepane (2.7 g, 15.25 mmol) at 0° C., and the reaction mixture was stirred at rt for 16 hrs. After completion of the reaction, the reaction mixture was diluted with water (150 mL) and extracted with EtOAc (2×100 mL). Combined organic layers were washed with water and brine, dried over anhydrous Na$_2$SO$_4$ and concentrated under reduced pressure. The resultant crude product was purified by column chromatography to afford 2.1 g of Int-10 as a brown solid in 46% yield. MS (ESI) m/z 359.09 [M+H]$^+$ Int-11: 4-(4-(2-methoxyethyl)-1,4-diazepan-1-ylsulfonyl)benzene-1,2-diamine 10% Pd/C (20% by wt) was added to a stirred solution of Int-10 (2.3 g, 6.42 mmol) in Ethanol (50 mL) at rt, and the reaction mixture was stirred for 6 hrs. After completion of the reaction, the reaction mixture was filtered through Celite pad. The filtrate was concentrated in vacuo to afford 1.7 g of Int-11 as a brown sticky solid in 80% yield. The obtained product was used in the next step without any purification. MS (ESI) m/z 329.04 [M+H]$^+$ Int-12: 4-Methylamino-3-nitrobenzenesulfonyl chloride 2-N-methylnitroaniline (10 g, 65.7 mmol) was slowly added to a pre-chilled stirred chlorosulfonic acid (20 mL, 289.5 mmol) at 0° C., and the reaction mixture was heated at 100° C. for 4 hrs. After completion of the reaction, the reaction mixture was poured into crushed ice (200 g) and extracted with EtOAc (2×150 mL). Combined organic layers were washed with water and brine, dried over anhydrous Na$_2$SO$_4$ and concentrated in vacuo to afford crude product, which was purified by column chromatography using silica gel to afford 6.0 g of Int-12 as a yellow solid in 36% yield. MS (ESI) n/z=249.06[M−H]$^−$ Int-13: N-Methyl[4-((4-(2-Methoxyethyl)-1,4-diazepan-1-yl)sulfonyl)]-2-nitroaniline K$_2$CO$_3$ (3.2 g, 24 mmol) was added to a stirred solution of Int-12 (3 g, 12 mmol) in dry THF (30 mL), followed by 1-(2-methoxyethyl)-1,4-diazepane (1.8 g, 12 mmol), and the reaction mixture was stirred at rt for 16 hrs. The progress of reaction was monitored by thin layer chromatography. After completion of the reaction, the reaction mixture was diluted with water (50 mL) and extracted with EtOAc (2×100 mL). Combined organic layers were washed with water and brine, dried over anhydrous Na$_2$SO$_4$ and concentrated under reduced pressure. The resultant crude compound was purified by column chromatography to afford 2 g of Int-13 as a yellow solid in 45% yield. MS (ESI) m/z 373.19 [M+H]$^+$.

Int-14: N-methyl-[4-(4-(2-methoxyethyl)-1,4-diazepan-1-ylsulfonyl)]benzene-1,2-diamine 10% Pd/C (20% by wt) was added to a stirred solution of Int-13 (2 g, 5.37 mmol) in Ethanol (50 mL), and the reaction mixture was stirred under Hydrogen atmosphere for 16 hrs. After completion of the reaction, the reaction mixture was filtered through a pad of Celite, and collected filtrates were concentrated under reduced pressure to afford 1.6 g of Int-14 as a brown sticky solid in 87% yield. The crude product was taken directly to the next step without further purification. MS (ESI) m/z 347.41 [M+H]$^+$.

Int-15: 4-(4-Methyl-1,4-diazepan-1-ylsulfonyl)-2-nitroaniline $K_2CO_3$ (3.4 g, 25.5 mmol) was added to a stirred solution of 4-amino-3-nitrobenzenesulfonyl chloride (3 g, 12.71 mmol) in dry THF (30 mL), followed by 1-methylhomopiperazine (2.7 g, 15.25 mmol). The reaction mixture was stirred at rt for 16 hrs. After completion of the reaction, the reaction mixture was diluted with water (150 mL) and extracted with EtOAc (2×100 mL). Combined organic layers were washed with water and brine, dried over anhydrous $Na_2SO_4$, and concentrated under reduced pressure. The resultant crude compound was purified by column chromatography to afford 2.2 g of Int-15 as a yellow solid in 54% yield. MS (ESI) m/z 359.09 $[M+H]^+$.

Int-16: 4-(4-Methyl-1,4-diazepan-1-ylsulfonyl)benzene-1,2-diamine

10% Pd/C (20% by wt) was added to a stirred solution of Int-15 (2.3 g, 6.42 mmol) in ethanol (50 mL) at rt, and the reaction mixture was stirred for 6 hrs. Upon completion of the reaction, the reaction mixture was filtered through Celite pad. The filtrate was concentrated under reduced pressure to afford Int-16 as a brown solid. The product was used in the next step without any purification. MS (ESI) m/z 285.04 $[M+H]^+$.

Int-17: 4-Amino-2-fluoro-5-nitrobenzenesulfonyl chloride 5-fluoro-2-nitroaniline (5 g, 32.0 mmol) was added slowly to a stirred pre-chilled (0° C.) solution of chlorosulfonic acid (10 mL, 289.5 mmol), and the reaction mixture was heated at 100° C. for 3 hrs in a sealed glass tube. After completion of the reaction, the reaction mixture was poured into crushed ice (100 g) and extracted with EtOAc (2×150 mL). Combined organic layers were washed with water and brine, dried over anhydrous $Na_2SO_4$ and concentrated under reduced pressure. The crude product was purified by column chromatography to afford 5 g Int-17 as a yellow solid in 61% yield.

Int-18: 5-Fluoro-4-(4-Methyl-1,4-diazepan-1-ylsulfonyl)-2-nitroaniline

Pyridine (0.627 g, 7.84 mmol) was added to a stirred solution of Int-17 (1 g, 3.92 mmol) in anhydrous $CH_2Cl_2$ (10 mL), followed by 1-methylhomopiperazine (0.536 g, 4.7 mmol). The reaction mixture was stirred at rt for 16 hrs. Then the mixture was diluted with water (50 mL) and extracted with EtOAc (2×50 mL). Combined organic layers were washed with water and brine, dried over anhydrous $Na_2SO_4$, filtered and concentrated under reduced pressure. The crude compound was purified by column chromatography to afford 1.0 g of Int-18 as a yellow solid in 77% yield.

Int-19: 4-Fluoro-5-(4-Methyl-1,4-diazepan-1-ylsulfonyl)benzene-1,2-diamine

10% Pd/C (20 wt %) was added to a stirred solution of Int-18 (1.0 g, 3.0 mmol) in ethanol (20 mL) at rt and the reaction mixture was stirred under hydrogen atmosphere (1 atm) for 4 hrs. Then the reaction mixture was filtered through Celite pad and Celite was washed with 25 mL ethanol. Combined filtrate was concentrated under reduced pressure to afford 0.72 g of Int-19. The crude product was used in the next step without any purification.

Int-20: 5-Fluoro-4-[4-(2-methoxyethyl)-1,4-diazepan-1-ylsulfonyl]-2-nitroaniline Pyridine (0.627 g, 7.84 mmol) was added to a stirred solution of Int-17 (1 g, 3.92 mmol) in anhydrous THE (10 mL), followed by 4-(2-methoxyethyl)-1,4-diazepane (0.743 g, 4.7 mmol), and the reaction mixture was stirred at rt for 16 hrs. Then the reaction mixture was diluted with water (50 mL) and extracted with EtOAc (2×50 mL). Combined organic layers were washed with water and brine, dried over anhydrous $Na_2SO_4$, filtered and concentrated under reduced pressure. The crude compound was purified by silica column chromatography to afford 0.9 g of Int-20 as a yellow solid in 61% yield.

Int-21: 4-Fluoro-5-[4-(2-methoxyethyl)-1,4-diazepan-1-ylsulfonyl]benzene-1,2-diamine 10% Pd/C (20 wt %) was added to a stirred solution of Int-20 (0.9 g, 2.39 mmol) in Ethanol (20 mL) at rt and the reaction mixture was stirred under hydrogen atmosphere (1 atm) for 4 hrs. Then the reaction mixture was filtered through Celite pad and Celite was washed with 25 mL of Ethanol. Combined filtrate was concentrated under reduced pressure to afford 0.68 g of Int-21 as a brown oily solid. The crude compound was used in the next step without any purification.

Int-22: N,N-Diethyl 2-fluoro-5-nitrobenzenesulfonamide

Anhydrous $K_2CO_3$ (2.16 g, 15.64 mmol) was added to a stirred solution of 2-fluoro-3-nitrobenzene-1-sulfonyl chloride (2.5 g, 10.43 mmol) in THE (20 mL) at rt, and the mixture was stirred for 5 min. Then diethylamine (0.83 g, 11.47 mmol) was added, and the reaction mixture was stirred for 6 hrs. The progress of the reaction was monitored by TLC and LCMS. After completion, THE was removed in vacuo, the reaction mixture was diluted with water and extracted with EtOAc (3×150 mL). Combined organic layers were washed with water (lx 50 mL), dried over anhydrous $Na_2SO_4$, and concentrated in vacuo to give 1.5 g of Int-22 as a yellow solid in 52% yield.

Int-23: N,N-diethyl 3-Amino-6-fluorobenzenesulfonamide

10% Pd/C (0.46 mmol) was added to a stirred solution of Int-22 (1.5 g, 5.43 mmol) in Ethanol (50 mL) at rt, and the reaction mixture was stirred for 6 hrs. After completion, the reaction mixture was filtered through Celite, and the filtrate was concentrated in vacuo to afford 0.82 g of Int-23 as a pink solid in 61.6% yield.

Int-24: N,N-diethyl 2-chloro-5-nitrobenzenesulfonamide

Anhydrous $K_2CO_3$ (2.02 g, 14.64 mmol) was added to a stirred solution of 2-chloro-5-nitrobezene-1-sulfonyl chloride (2.5 g, 9.76 mmol) in THF (30 mL) at rt, and the reaction mixture was stirred for 5 min. Then diethylamine (0.784 g, 10.73 mmol) was added, and the reaction mixture was stirred for 6 hrs. After completion, THE was removed in vacuo, the mixture was diluted with water and extracted with EtOAc (3×150 mL). Combined organic layers were washed with water (250 mL), dried over anhydrous $Na_2SO_4$, and concentrated in vacuo to afford 2.6 g of Int-24 as a yellow solid in 91% yield.

Int-25: N,N-Diethyl 3-Amino-6-chloro-benzenesulfonamide

10% Pd/C (0.87 mmol) was added to a stirred solution of N,N-diethyl 2-chloro-5-nitrobenzenesulfonamide (2.6 g, 8.88 mmol) in ethanol (50 mL) at rt, and the reaction mixture was stirred for 6 hrs. After completion, reaction mixture was filtered through Celite and the filtrate was concentrated in vacuo to provide 0.96 g of Int-25 as a brown solid in 41.7% yield.

Int-26: 7-Bromo-4-phenoxyquinoline

Phenol (498.8 mg, 5.3 mmol) and sodium hydroxide (30.0 mg, 0.75 mmol) were heated at 100° C. until a homogeneous solution was obtained. Then, 7-bromo-4-chloroquinoline (121.3 mg, 0.5 mmol) was added, and the reaction mixture was heated at 120° C. for 2 hrs. Then the hot solution was poured into vigorously stirring aqueous 2N NaOH solution, and the mixture was stirred for 30 minutes at rt. The resulting precipitate was isolated by centrifugation and washed with 2N aqueous NaOH solution (1×) and 4 M aqueous $NH_4OH$ solution (1×), then lyophilized for 18 hours to give 138 mg of Int-26 as brown highly viscous oil in 92% yield. MS m/z 301.5 $[M+H]^+$.

Int-27: 3-Bromo-N-(6-(trifluoromethyl)pyridin-3-yl) quinoline-7-carboxamide

Compound Int-27 was synthesized according to the General Experimental Procedure I starting from 3-bromoquinoline-7-carboxylic acid and 5-amino-2-(trifluoromethyl)pyridine, and the product was obtained as an off-white solid in 77% yield. MS (ESI) m/z=397.9 $[M+H]^+$.

Int-28: 1-Methyl-3-(2-(trifluoromethyl)phenyl)-1H-pyrazol-5-amine

NaH (0.47 g, 19.58 mmol) was added to a stirred solution of methyl 2-(trifluoromethyl)benzoate (2.0 g, 9.79 mmol) in Toluene (40 mL) at 0° C., and the reaction mixture was heated to 80° C. Then MeCN (2.01 g, 48.96 mmol) was added dropwise to the reaction mixture. The resulting mixture was heated at 80° C. for 16 hrs. Toluene was removed under reduced pressure and the reaction mass was diluted with $H_2O$ (100 mL), acidified to pH ~2 with 1N aq. HCl and extracted with EtOAc (3×100 mL). Combined organic layers were washed with $H_2O$ and brine, dried over anhydrous $Na_2SO_4$, filtered and concentrated in vacuo to afford 0.9 g of 3-oxo-3-(2-(trifluoromethyl)phenyl)propanenitrile as an off-white solid in 43% yield. 0.45 g of the solid was dissolved in 3 mL of MeOH and methylhydrazine (0.29 g, 6.30 mmol) was added. The resulting mixture was stirred at 120° C. for 1 h under microwave. Then MeOH was removed in vacuo and the crude compound was purified by reverse phase column chromatography (C18, 24 g) using 45% MeCN in $H_2O$ (10 mM Ammonium Bicarbonate) to afford 0.08 g of Int-28 as an off-white solid in 16% yield.

Int-29: 1-Isopropyl-3-(2-(trifluoromethyl)phenyl)-1H-pyrazol-5-amine

Isopropyl hydrazine HCl (0.78 g, 7.04 mmol) was added to a stirred solution of 3-oxo-3-(2-(trifluoromethyl)phenyl) propanenitrile (0.50 g, 2.34 mmol) in MeOH (3 mL), and the reaction mixture was heated at 120° C. for 1 hr under microwave. Then MeOH was removed in vacuo, and the crude compound was purified by reverse phase column chromatography (C18, 24 g) using 45% MeCN in $H_2O$ (10 mM Ammonium bicarbonate) to afford 0.06 g of Int-29 as an off-white solid in 10% yield.

Int-30: 1-Methyl-3-(3-(trifluoromethyl)phenyl)-1H-pyrazol-5-amine

NaH (0.47 g, 19.58 mmol) was added to a stirred solution of methyl 3-(trifluoromethyl) benzoate (2.0 g, 9.79 mmol) in toluene (40 mL) at 0° C., and the reaction mixture was heated to 80° C. Then MeCN (2.01 g, 48.96 mmol) was added dropwise to the reaction mixture. The resulting mixture was heated to 110° C. for 16 hrs. Toluene was removed in vacuo, and the reaction mass was diluted with $H_2O$ (100 mL), acidified to pH ~2 with 1N HCl and extracted with EtOAc (3×100 mL). Combined organic layers were washed with $H_2O$ (50 mL), brine (50 mL), dried over anhydrous $Na_2SO_4$, filtered and concentrated in vacuo to afford 1.6 g of 3-oxo-3-(3-(trifluoromethyl)phenyl)propanenitrile as an off-white solid in 77% yield. 0.5 g of the solid was dissolved in 3 mL of MeOH and methyl hydrazine (0.32 g, 7.04 mmol) was added. The resulting mixture was heated at 120° C. for 1 hr under microwave. Then MeOH was removed in vacuo, and the crude product was purified by reverse phase column chromatography (C18, 24 g) using 45% ACN in $H_2O$ (10 mM Ammonium bicarbonate) to afford 0.20 g of Int-30 as an off-white solid in 35% yield.

Int-31: 3-(3-Chlorophenyl)-1-methyl-1H-pyrazol-5-amine

NaH (0.56 g, 23.44 mmol) was added to a stirred solution of methyl 3-chlorobenzoate (2.0 g, 11.72 mmol) in THF (40 mL) at 0° C., and the reaction mixture was heated to 80° C. Then MeCN (1.44 g, 35.16 mmol) was added dropwise and the reaction mixture was heated at 80° C. for 30 min. After completion, THF was removed in vacuo, and the residue was diluted with $H_2O$ (100 mL), acidified to pH ~2 with 1N HCl and extracted with EtOAc (3×100 mL). Combined organic layers were washed with $H_2O$ (50 mL), brine (50 mL), dried over anhydrous $Na_2SO_4$, filtered and concentrated in vacuo to afford 0.9 g of 3-(3-chlorophenyl)-3-oxopropanenitrile as an off-white solid in 43% yield. 0.45 g of the solid was dissolved in 3 mL of MeOH and methyl hydrazine (0.35 g, 7.52 mmol) was added. The resulting mixture was heated at 120° C. for 1 h under microwave. Then MeOH was removed under reduced pressure, and the crude compound was purified by reverse phase column chromatography to afford Int-31 (0.24 g, 46%) as an off-white solid.

Int-32: 3-(5-Fluoro-2-methylphenyl)-1-methyl-1H-pyrazol-5-amine

NaH (0.285 g, 11.89 mmol) was added to a stirred solution of methyl 5-fluoro-2-methylbenzoate (1.0 g, 5.95 mmol) in anhydrous THF (20 mL) at 0° C., followed by dropwise addition of MeCN (1.22 g, 29.72 mmol). The resulting mixture was stirred at rt for 16 h. Then THF was removed in vacuo, and the residue was diluted with $H_2O$ (100 mL), acidified to pH ~2 with 1N HCl and extracted with EtOAc (3×100 mL). Combined organic layers were washed with $H_2O$ and brine, dried over anhydrous $Na_2SO_4$, filtered and concentrated in vacuo to afford 3-(5-fluoro-2-methylphenyl)-3-oxopropanenitrile (0.5 g, 48%) as an off-white solid.

3-(5-fluoro-2-methylphenyl)-3-oxopropanenitrile (0.5 g, 2.82 mmol) was dissolved in MeOH (3 mL), and methyl hydrazine (0.39 g, 8.46 mmol) was added. The resulting mixture was heated at 120° C. for 1 h under microwave. Then MeOH was removed in vacuo, and the crude product was purified by reverse phase column chromatography to afford 0.2 g of Int-32 as an off-white solid in 34% yield.

Int-33: 3-(5-Chloro-2-methylphenyl)-1-methyl-1H-pyrazol-5-amine

NaH (0.39 g, 16.3 mmol) was added to a stirred solution of methyl 5-chloro-2-methylbenzoate (1.5 g, 8.12 mmol) in anhydrous THE (30 mL) at 0° C., followed by dropwise addition of MeCN (1.67 g, 40.6 mmol). The resulting mixture was stirred at rt for 16 hrs. Then THE was removed in vacuo, and the residue was diluted with $H_2O$ (100 mL), acidified to pH ~2 with 1N HCl and extracted with EtOAc (3×100 mL). Combined organic layer was washed with $H_2O$ and brine, dried over anhydrous $Na_2SO_4$, filtered and concentrated in vacuo. Crude compound was purified by silica column chromatography to afford 1.3 g of 3-(5-chloro-2-methylphenyl)-3-oxopropanenitrile as a yellow solid in 83% yield. To a stirred solution of 3-(5-chloro-2-methylphenyl)-3-oxopropanenitrile (0.6 g, 3.10 mmol) in MeOH (5 mL) was added methyl hydrazine (0.57 g, 12.4 mmol), and the resulting mixture was heated at 120° C. for 1 h under microwave. Then MeOH was removed in vacuo, and the crude compound was purified by silica column chromatography to afford 0.25 g of Int-33 as an off-white solid in 36% yield.

Int-34: 3-(2-Chloro-5-(trifluoromethyl)phenyl)-1-methyl-1H-pyrazol-5-amine

Potassium tert-pentoxide (7 mL, 16.76 mmol) was added to a stirred solution of methyl 2-chloro-5-(trifluoromethyl) benzoate (2.0 g, 8.38 mmol) in toluene (20 mL) at 0° C. Then MeCN (1.03 g, 25.2 mmol) was added, and the resulting mixture was stirred at rt for 1 hr. Then toluene was removed in vacuo, and the residue was diluted with water (100 mL), acidified with sat. $NH_4Cl$ solution and extracted with EtOAc (3×100 mL). Combined organic layers were washed with $H_2O$ and brine, dried over anhydrous $Na_2SO_4$, filtered and concentrated. Crude compound was purified by silica column chromatography to afford 3-(2-chloro-5-(trifluoromethyl)phenyl)-3-oxopropanenitrile (1.4 g, 67%) as a pale yellow liquid. 0.5 g of 3-(2-chloro-5-(trifluoromethyl) phenyl)-3-oxopropanenitrile (0.5 g, 2.02 mmol) was dissolved in 5 mL of MeOH, and methyl hydrazine (0.186 g, 4.04 mmol) was added. The resulting mixture was heated to 120° C. for 1 h under microwave. Then MeOH was removed in vacuo. Crude product was purified by purified by reverse phase column chromatography to afford 0.26 g of Int-34 as a yellow solid in 47% yield.

Int-35: 3-(4-Fluoro-2-methylphenyl)-1-methyl-1H-pyrazol-5-amine

NaH (0.57 g, 23.78 mmol) was added to a stirred solution of methyl 4-fluoro-2-methylbenzoate (2.0 g, 11.89 mmol) in anhydrous THF (40 mL) at 0° C., followed by dropwise addition of MeCN (2.44 g, 59.45 mmol). The resulting mixture was stirred at rt for 16 hrs. Then THF was removed in vacuo, and the residue was diluted with $H_2O$ (100 mL), acidified to pH ~2 with 1N HCl and extracted with EtOAc (3×100 mL). Combined organic layers were washed with $H_2O$ and brine, dried over anhydrous $Na_2SO_4$, filtered and concentrated to afford 3-(4-fluoro-2-methylphenyl)-3-oxopropanenitrile (1.00 g, 47%) as an off-white solid. To a stirred solution of 3-(4-fluoro-2-methylphenyl)-3-oxopropanenitrile (1.0 g, 5.64 mmol) in MeOH (3 mL) was added methyl hydrazine (0.78 g, 16.93 mmol), and the resulting mixture was heated at 120° C. for 1 hr under microwave. Then MeOH was removed under in vacuo, and the crude compound was purified by reverse phase column chromatography to afford 0.4 g of Int-35 as an off-white solid in 34% yield.

Int-36: 3-(4-Chloro-2-methylphenyl)-1-methyl-1H-pyrazol-5-amine

NaH (60% oil dispersion, 0.87 g, 21.66 mmol) was added to a stirred solution of methyl 4-chloro-2-methylbenzoate (2.0 g, 10.83 mmol) in anhydrous THF (20 mL) at 0° C., followed by dropwise addition of MeCN (2.22 g, 54.2 mmol) at 80° C. The resulting mixture was heated at 80° C. for 16 hrs. Then the reaction mixture was diluted with $H_2O$ (100 mL), acidified with sat. aq. $NH_4C_1$ solution and extracted with EtOAc (3×100 mL). Combined organic layers were washed with $H_2O$ and brine, dried over anhydrous $Na_2SO_4$, filtered and concentrated to afford 3-(4-chloro-2-methylphenyl)-3-oxopropanenitrile (2.0 g, 95%) as a yellow solid. 0.45 g of 3-(4-chloro-2-methylphenyl)-3-oxopropanenitrile (0.45 g, 2.32 mmol) was dissolved in 4 mL of MeOH and methyl hydrazine (0.21 g, 4.65 mmol) was added. The resulting mixture was heated at 120° C. for 1 hr under microwave. Then MeOH was removed in vacuo and the crude product was purified by reverse phase column chromatography to afford 0.17 g of Int-36 as a yellow solid in 33% yield.

Int-37: 1-Methyl-3-(2-methyl-5-(trifluoromethyl) phenyl)-1H-pyrazol-5-amine

NaH (60% oil dispersion, 0.29 g, 7.3 mmol) was added to a stirred solution of methyl 2-methyl-5-(trifluoromethyl) benzoate (0.8 g, 3.7 mmol) in toluene (16 mL) at 0° C., followed by dropwise addition of MeCN (0.76 g, 18.5 mmol) at 80° C. The resulting mixture was heated at 80° C. for 16 hrs. Then the reaction mixture was diluted with $H_2O$ (100 mL), acidified to pH ~ 2 with 1N HCl solution and extracted with EtOAc (3×100 mL). Combined organic layers were washed with $H_2O$ and brine, dried over anhydrous $Na_2SO_4$, filtered and concentrated to afford 3-(2-methyl-5-(trifluoromethyl)phenyl)-3-oxopropanenitrile (0.6 g, 72%) as a reddish oil. 0.6 g of 3-(2-methyl-5-(trifluoromethyl) phenyl)-3-oxopropanenitrile (0.6 g, 2.64 mmol) was dissolved in 5 mL of in MeOH, and methyl hydrazine (0.36 g, 7.92 mmol) was added. The resulting mixture was heated at 120° C. for 1 h under microwave. Then MeOH was removed in vacuo and the crude compound was purified by silica column chromatography to afford 0.25 g of Int-37 as an off-white solid in 37% yield.

Int-38: 3-(5-Fluoro-2-(trifluoromethyl)phenyl)-1-methyl-1H-pyrazol-5-amine

EDC.HCl (4.15 g, 21.62 mmol) was added to a stirred solution of 5-fluoro-2-(trifluoromethyl)benzoic acid (3.0 g, 14.42 mmol) in DMF (30 mL) at 0° C., followed by HOBt (2.92 g, 21.62 mmol), and the mixture was stirred for 5 min. N,O-dimethylhydroxylamine.HCl (1.41 g, 14.42 mmol) and triethylamine (8.1 mL, 57.69 mmol) were added, and the reaction mixture was stirred at rt for 6 hrs. Then the reaction was quenched with cold water and extracted with EtOAc (2×100 mL). Combined organic layers were washed with water and brine, dried over anhydrous $Na_2SO_4$, filtered and concentrated in vacuo. Crude compound was purified by silica column chromatography using 15-20% EtOAc in petroleum ether as an eluent to afford 5-fluoro-N-methoxy-N-methyl-2-(trifluoromethyl) benzamide (2.3 g, 64%) as colorless liquid.

LDA (2M in THF, 9.15 mL, 18.31 mmol) was added dropwise to a stirred solution of MeCN (0.75 g, 18.31 mmol) in THF (15 mL) at −78° C., and the mixture was stirred for 15 min. Then 5-fluoro-N-methoxy-N-methyl-2-(trifluoromethyl) benzamide (2.3 g, 9.16 mmol) in THF (10 mL) was added dropwise at −78° C., and reaction mixture was allowed to warm up to rt and stirred at rt for 3 hrs. Then the reaction mixture was quenched with saturated aqueous $NH_4Cl$ solution and extracted with EtOAc. Combined organic layers were dried over anhydrous $Na_2SO_4$, filtered and concentrated in vacuo to afford 3-(5-fluoro-2-(trifluoromethyl)phenyl)-3-oxopropanenitrile (0.87 g, 41%) as a yellow solid.

Methyl hydrazine (0.35 g, 7.53 mmol) was added to a stirred solution of 3-(5-fluoro-2-(trifluoromethyl)phenyl)-3-oxopropanenitrile (0.87 g, 3.76 mmol) in MeOH (9 mL), and the resulting mixture was heated at 120° C. for 1 h under microwave. Then MeOH was removed under reduced pressure. The crude product was purified by reverse phase column chromatography to afford 0.32 g of Int-38 as a yellow solid in 33% yield.

Int-39: 3-(2-Chlorophenyl)-1-methyl-1H-pyrazol-5-amine

Methyl hydrazine (0.77 g, 16.70 mmol) was added to a stirred solution of 3-(2-chlorophenyl)-3-oxopropanenitrile (1.00 g, 5.57 mmol) in MeOH (5 mL), and the resulting mixture was heated at 120° C. for 1 h under microwave. Then MeOH was removed under reduced pressure. Crude compound was purified by reverse phase column chromatography to afford 0.4 g of Int-39 as an off white solid in 35% yield.

Int-40: 3-(2-Methylphenyl)-1-isopropyl-1H-pyrazol-5-amine

Int-40 was synthesized using a similar protocol that was utilized in the synthesis of Int-29.

Int-41: 7-bromo-4-morpholino-quinoline

A microwave vial was charged with 7-bromo-4-chloro-quinoline (1.0 equiv.), 1,4-dioxane and morpholine (4.0 equiv.). The vial was capped, and the reaction mixture was heated at 120° C. for 6 hrs. After complete conversion was observed by LCMS, the reaction mixture was diluted with water and extracted with EtOAc (3×). Combined organic extracts were washed with brine, dried over anhydrous $Na_2SO_4$, filtered and concentrated in vacuo to give the crude product. The crude product was purified on silica gel column using a 10% to 100% gradient of EtOAc in Hexanes as an eluent. Fractions, containing the product, were combined and concentrated in vacuo to give the desired product as an off-white solid.

Int-42: 7-bromo-N,N-dimethylquinolin-4-amine

A microwave vial was charged with 7-bromo-4-chloroquinoline (1.0 equiv.), 1,4-dioxane and 2M solution of dimethylamine in MeOH (4.0 equiv.). The vial was capped, and the reaction mixture was heated at 120° C. for 6 hrs. Then the reaction was diluted with water and extracted with EtOAc (3×). Combined organic extracts were washed with brine, dried over anhydrous $Na_2SO_4$, filtered and concentrated in vacuo to give the crude product. The crude product was purified on silica gel column. Fractions containing the product, were combined and concentrated in vacuo to give the desired product as a dark-yellow solid. MS m/z=253 $[M+H]^+$.

Int-43: 3-Bromo-N-(4-Chloro-3-(N,N-diethylsulfamoyl)phenyl)-quinoline-7-carboxamide Intermediate Int-43 was synthesized according to the General Experimental Procedure II starting from 3-bromo-quinoline-7-carboxylic acid and Int-25, and the product was obtained as an off-white solid in 43% yield.

Int-44: 7-bromo-4-isopropoxy-quinoline 5 mL microwave vial was charged with 1.0 mL of 2-propanol and cooled down to 0° C. Then 120 mg of NaH (60% dispersion in mineral oil) were slowly added. The ice bath was removed, and the mixture was stirred at rt for 10 min. Then 244.0 mg of 7-bromo-4-chloroquinoline was added, the vial was sealed and heated at 120° C. for 3 hrs. Then the reaction mixture was allowed to cool down to rt, quenched with water, and extracted with DCM (3×). Combined organic phases were washed with water and brine, dried over anhydrous $Na_2SO_4$ and concentrated in vacuo to give Int-44 as yellow oil. MS m/z=265.75 $[M+H]^+$.

Int-45: 3-bromo-N-(1-methyl-3-phenyl-1H-pyrazol-5-yl)quinoline-7-carboxamide

Intermediate Int-45 was synthesized according to the General Experimental Procedure II starting from 3-bromo-quinoline-7-carboxylic acid and 1-methyl-3-phenyl-1H-pyrazol-5-amine, and the product was obtained as an off-white solid in 63% yield.

Int-46: 3-bromo-N-(1-methyl-3-(o-tolyl)-1H-pyrazol-5-yl)quinoline-7-carboxamide

Intermediate Int-46 was synthesized according to the General Experimental Procedure II starting from 3-bromo-quinoline-7-carboxylic acid and 1-methyl-3-(o-tolyl)-1H-pyrazol-5-amine, and the product was obtained as an off-white solid in 74% yield.

Int-47: 5-bromo-N-(1-methyl-3-(o-tolyl)-1H-pyrazol-5-yl)thieno[2,3-b]pyridine-2-carboxamide Intermediate Int-47 was synthesized according to the General Experimental Procedure II starting from 5-bromothieno[2,3-b]pyridine-2-carboxylic acid and 1-methyl-3-(o-tolyl)-1H-pyrazol-5-amine, and the product was obtained as an off-white solid in 63% yield.

Example 2

Compound 1: N-(3-(tert-butyl)-1-methyl-1H-pyrazol-5-yl)quinoxaline-7-carboxamide Compound 1 was synthesized according to the protocol outlined in the General Experimental Procedure I. The product was obtained as an off-white solid in 15% yield.

Example 3

Compound 2: N-(3-tert-Butyl-1-methyl-1H-pyrazol-5-yl)thieno[2,3-b]pyridine-2-carboxamide Compound 2 was synthesized according to the General Experimental Procedure I starting from thieno[2,3-b]pyridine-2-carboxylic acid and 3-tert-butyl-1-methyl-1H-pyrazol-5-amine, and the product was obtained as an off-white solid in 76% yield.

Example 4

Compound 3: N-(3-tert-Butyl-1-methyl-1H-pyrazol-5-yl)-1,5-naphthyridine-3-carboxamide Compound 3 was synthesized according to the General Experimental Procedure I starting from 1,5-naphthyridine-3-carboxylic acid and 3-tert-butyl-1-methyl-1H-pyrazol-5-amine, and the product was obtained as an off-white solid in 52% yield.

Example 5

Compound 4: N-(3-tert-Butyl-1-methyl-1H-pyrazol-5-yl)-1,8-naphthyridine-2-carboxamide Compound 4 was synthesized according to the General Experimental Procedure I starting from 1,8-naphthyridine-2-carboxylic acid and 3-tert-butyl-1-methyl-1H-pyrazol-5-amine, and the product was obtained as a yellow solid in 74% yield.

Example 6

Compound 5: N-(3-tert-Butyl-1-methyl-1H-pyrazol-5-yl)-4-methoxyquinoline-7-carboxamide Compound 5 was synthesized according to the General Experimental Procedure V starting from 7-bromo-4-methoxyquinoline and 3-tert-butyl-1-methyl-1H-pyrazol-5-amine, and the product was obtained as a white solid in 52% yield.

Example 7

Compound 6: 4-Methoxy-N-[3-(morpholine-4-carbonyl)phenyl]quinoline-7-carboxamide Compound 6 was synthesized according to the General Experimental Procedure I starting from Int-8 and (3-aminophenyl)(morpholino)methanone, and the product was obtained as an off-white solid in 62% yield.

Example 8

Compound 7: 4-Methoxy-N-[4-(morpholin-4-yl)phenyl]quinoline-7-carboxamide

Compound 7 was synthesized according to the General Experimental Procedure I starting from Int-8 and 4-morpholinoaniline, and the product was obtained as a grey solid in 49% yield.

Example 9

Compound 8: N-[4-(4-Ethylpiperazin-1-yl)phenyl]-4-methoxyquinoline-7-carboxamide Compound 8 was synthesized according to the General Experimental Procedure I starting from Int-8 and 4-(4-ethylpiperazin-1-yl)aniline, and the product was obtained as a grey solid in 63% yield.

Example 10

Compound 9: N-(3-tert-Butyl-1-methyl-1H-pyrazol-5-yl)pyrido[2,3-b]pyrazine-7-carboxamide Compound 9 was synthesized according to the General Experimental Procedure I starting from pyrido[2,3-b]pyrazine-7-carboxylic acid and 3-tert-butyl-1-methyl-1H-pyrazol-5-amine, and the product was obtained as a yellow solid in 68% yield.

Example 11

Compound 10: 7-(6-((2-methoxyethyl)-1,4-diazepan-1-yl)sulfonyl)-1-methyl-1H-benzo[d]imidazol-2-yl)quinoline DIPEA (2.29 g, 17.7 mmol) was added to a stirred solution of quinoline-7-carboxylic acid (1 g, 5.7 mmol) in DMF (15 mL), followed by HATU (2.1 g, 8.5 mmol) at 0° C., and the reaction mixture was stirred for 15 min. Then Int-14 (1.91 g, 5.7 mmol) was added to the reaction mixture at 0° C. The reaction mixture was stirred at rt for 16 hrs. After completion of the reaction, the reaction mixture was diluted with water (250 mL) and extracted with EtOAc (2×50 mL). The combined organic layers were washed with water and brine, dried over anhydrous $Na_2SO_4$ and concentrated under reduced pressure. The resultant crude compound was purified by trituration with diethyl ether to afford 1.2 g of N-(2-methylamino-4-(4-(2-methoxyethyl)-1,4-diazepan-1-ylsulfonyl) phenyl)-quinoline-7-carboxamide as a brown solid. The solid was dissolved in 50 mL of acetic acid (50 mL), and 25 mL xylene was added at rt. Then the reaction mixture was heated at 120° C. for 16 h. After completion of the reaction, the reaction mixture was concentrated in vacuo to give crude material, which was passed through neutral alumina to afford 600 mg of the crude product, which was then purified by prep-HPLC. After purification, fractions were concentrated to minimum volume, filtered through 0.4μ syringe filter and concentrated in vacuo to afford 310 mg of Compound 10 as an off-white solid in 12% yield.

Example 12

Compound 11: 6-Methyl-7-(6-((4-methyl-1,4-diazepan-1-yl)sulfonyl)-1H-benzo[d]imidazol-2-yl)quinoline DIPEA (0.63 g, 4.8 mmol) was added to a stirred solution of Int-6 (0.3 g, 1.6 mmol) in DMF (15 mL), followed by HATU (0.6 g, 2.4 mmol) at 0° C., and the reaction mixture was stirred for 15 min. Then Int-11 (0.524 g, 1.6 mmol) was added to the reaction mixture at 0° C. The reaction mixture was stirred at rt for 16 hrs. The progress of the reaction was monitored by thin layer chromatography and LCMS. After completion of the reaction, the reaction mixture was diluted with water (250 mL) and extracted with EtOAc (2×30 mL). Combined organic layers were washed with water and brine, dried over anhydrous $Na_2SO_4$ and concentrated under reduced pressure. The resultant crude compound was purified by trituration with diethyl ether to afford 0.45 g of N-(2-amino-4-(4-(2-methoxyethyl)-1,4-diazepan-1-ylsulfonyl)phenyl)-6-methylquinoline-7-carboxamide as a brown solid. The solid was dissolved in 15 mL of acetic acid and 5 mL of xylene was added. Then the reaction mixture was heated at 120° C. for 16 hrs. Upon completion, the reaction mixture was concentrated in vacuo to give crude material, which was passed through neutral alumina. The resultant crude product was purified by prep-HPLC. Fractions containing the desired product were concentrated to minimum volume, filtered through 0.4µ syringe filter and dried in vacuo to afford 340 mg of Compound 11 as an off-white solid in 39% yield.

Example 13

Compound 12: N-(2-amino-4-(4-methyl-1,4-diazepan-1-ylsulfonyl)phenyl)-1,5-naphthyridine-3-carboxamide $T_3P$ 50% solution in EtOAc (5 mL) was added to a stirred solution of 1,5-naphthyridine-3-carboxylic acid (0.25 g, 1.43 mmol) in pyridine (2 mL) at 0° C., and the mixture was stirred for 15 min. Then Int-16 (0.405 g, 1.43 mmol) was added to the reaction mixture at 0° C. The reaction mixture was stirred at rt for 16 hrs. After completion of the reaction, the reaction mixture was passed through the filter column over neutral alumina twice to remove the excess of $T_3P$ to afford 300 mg of crude N-(2-amino-4-(4-methyl-1,4-diazepan-1-ylsulfonyl)phenyl)-1,5-naphthyridine-3-carboxamide as a brown solid. The solid was dissolved in 15 mL of acetic acid, 10 mL of xylene was added, and the mixture was heated at 100° C. for 3 hrs. After completion of the reaction, the mixture was diluted with water (25 mL) and extracted with EtOAc (2×50 mL). Combined organic layers were washed with water and brine, dried over anhydrous $Na_2SO_4$ and concentrated under reduced pressure. The resultant crude compound was purified by prep-HPLC to afford 38 mg of Compound 12 as an off-white solid.

Example 14

Compound 13: 3-(5-(4-(2-methoxyethyl)-1,4-diazepan-1-ylsulfonyl)-1-methyl-1H-benzo[d]-imidazol-2-yl)-1,5-naphthyridine $T_3P$ 50% solution in EtOAc (5 mL) was added to a stirred solution of 1,5-naphthyridine-3-carboxylic acid (0.25 g, 1.43 mmol) in pyridine (2 mL) at 0° C., and the reaction mixture was stirred for 15 min. Then Int-14 (0.48 g, 1.43 mmol) was added to the reaction mixture at 0° C., and it was stirred at rt for 16 hrs. After completion of the reaction, the reaction mixture was passed through the filter column over neutral alumina twice to remove the excess of $T_3P$ to give 0.25 g N-(2-amino-4-(4-(2-methoxyethyl)-1,4-diazepan-1-ylsulfonyl)phenyl)-N-methyl-1,5-naphthyridine-3-carboxamide as a brown solid. The solid was dissolved in 15 mL of acetic acid and 10 mL of xylene was added. The reaction mixture was heated at 100° C. for 3 hrs. After completion of the reaction, the reaction mixture was diluted with water (50 mL) and extracted with EtOAc (2×50 mL). Combined organic layers were washed with water and brine, dried over anhydrous $Na_2SO_4$ and concentrated under reduced pressure. The resultant crude compound was purified by prep-HPLC method to afford 61 mg of Compound 13 as an off-white solid.

Example 15

Compound 14: 3-(6-(4-(2-methoxyethyl)-1,4-diazepan-1-ylsulfonyl)-1H-benzo[d]imidazol-2-yl)-1,5-naphthyridine $T_3P$ 50% solution in EtOAc (5 mL) was added to a stirred solution of 1,5-naphthyridine-3-carboxylic acid (0.25 g, 1.43 mmol) in pyridine (2 mL) at 0° C., and the reaction mixture was stirred for 15 min. Then Int-11 (0.47 g, 1.43 mmol) was added to the reaction mixture at 0° C. The reaction mixture was stirred at rt for 16 hrs. After completion of the reaction, the reaction mixture was passed through the filter column over neutral alumina twice to remove the excess of $T_3P$ to afford 0.3 g of crude N-(2-amino-4-(4-(2-methoxyethyl)-1,4-diazepan-1-ylsulfonyl)phenyl)-1,5-naphthyridine-3-carboxamide as a brown solid. The solid was dissolved in 15 mL of acetic acid and 10 mL of xylene was added. The reaction mixture was heated at 100° C. for 3 hrs. After completion of the reaction, the mixture was diluted with water (15 mL) and extracted with EtOAc (2×50 mL). Combined organic layers were washed with water and brine, dried over anhydrous $Na_2SO_4$ and concentrated under reduced pressure. The resultant crude product was purified by prep-HPLC column chromatography to afford 38 mg of Compound 14 as an off-white solid.

Example 16

Compound 15: N-(4-(4-ethylpiperazin-1-yl)-3-fluorophenyl)-1,5-naphthyridine-3-carboxamide $T_3P$ 50% solution in EtOAc (5 mL) was added to a stirred solution of 1,5-naphthyridine-3-carboxylic acid (0.102 g, 0.58 mmol) in pyridine (2 mL) at 0° C. and the mixture was stirred for 15 min. Then 4-(4-ethylpiperazin-1-yl)-3-fluoroaniline (0.130 g, 0.58 mmol) was added to the reaction mixture at 0° C. The reaction mixture was stirred at rt for 16 hrs. After completion of the reaction, the reaction mixture was passed through the filter column over neutral alumina twice to remove the excess of $T_3P$. The crude product was purified by prep-HPLC and the fractions were concentrated to minimum volume, filtered through 0.4µ syringe filter and lyophilized to afford 0.032 g of Compound 15 as an off-white solid in 15% yield.

Example 17

Compound 16: 6-Chloro-7-(6-((4-methyl-1,4-diazepan-1-yl)sulfonyl)-1H-benzo[d]imidazol-2-yl)quinoline DIPEA (0.3 mL, 2.16 mmol) was added to a stirred solution of Int-3 (0.15 g, 0.72 mmol) in DMF (15 mL), followed by HATU (0.41 g, 1.08 mmol) at 0° C., and the mixture was stirred for 15 min. Then Int-16 (0.25 g, 0.87 mmol) was added to the reaction mixture at 0° C. The reaction mixture was stirred at rt for 16 hrs. After completion of the reaction, the reaction mixture was diluted with water (150 mL) and extracted with EtOAc (2×150 mL). Combined organic layers were washed with water and brine, dried over anhydrous Na$_2$SO$_4$ and concentrated under reduced pressure. The resultant crude product was triturated with diethyl ether to afford 0.24 g of N-(2-amino-4-((4-methyl-1,4-diazepan-1-yl)sulfonyl)phenyl)-6-chloroquinoline-7-carboxamide as a brown solid. The solid was dissolved in 15 mL of acetic acid and 4 mL of xylene were added. The reaction mixture was heated at 120° C. for 16 hrs. After completion of the reaction, the reaction mixture was concentrated in vacuo to give crude material, which was passed through neutral alumina. The resultant 0.2 g of the crude product was further purified by preparative HPLC, concentrated to minimum volume, filtered through 0.4 g syringe filter and concentrated in vacuo to afford 0.06 g of Compound 16 as an off-white solid in 31% yield.

Example 18

Compound 17: 6-Chloro-N-(1-methyl-3-phenyl-1H-pyrazol-5-yl)quinoline-7-carboxamide Compound 17 was synthesized according to the General Experimental Procedure I starting from Int-3 and 1-methyl-3-phenyl-1H-pyrazol-5-amine, and the product was obtained as a white solid in 33% yield.

Example 19

Compound 18: N-(3-tert-Butyl-1-phenyl-1H-pyrazol-5-yl)-6-chloroquinoline-7-carboxamide Compound 18 was synthesized according to the General Experimental Procedure I starting from Int-3 and 3-tert-butyl-1-phenyl-TH-pyrazol-5-amine, and the product was obtained as an orange solid in 26% yield.

Example 20

Compound 19: N-(3-tert-Butyl-1-methyl-1H-pyrazol-5-yl)-6-chloroquinoline-7-carboxamide Compound 19 was synthesized according to the General Experimental Procedure I starting from Int-3 and 3-tert-butyl-1-methyl-1H-pyrazol-5-amine, and the product was obtained as an off-white solid in 60% yield.

Example 21

Compound 20: 6-Chloro-7-(5-fluoro-6-(4-methyl-1,4-diazepan-1-ylsulfonyl)-1H-benzo[d]imidazol-2-yl)quinolone Compound 20 was synthesized according to the General Experimental Procedure VI starting from Int-3 and Int-19, and the product was obtained as an off-white solid in 32% yield.

Example 22

Compound 21: 6-Chloro-7-(5-fluoro-6-(4-(2-methoxyethyl)-1,4-diazepan-1-ylsulfonyl)-1H-benzo[d]imidazol-2-yl)quinoline Compound 21 was synthesized according to the General Experimental Procedure VI starting from Int-3 and Int-21, and the product was obtained as an off-white solid in 27% yield.

Example 23

Compound 22: 6-Chloro-N-[4-(4-ethylpiperazin-1-yl)-3-fluorophenyl]quinoline-7-carboxamide Compound 22 was synthesized according to the General Experimental Procedure I starting from Int-3 and 4-(4-ethylpiperazin-1-yl)-3-fluoroaniline, and the product was obtained as an off-white solid in 52% yield.

Example 24

Compound 23: 3-Phenoxy-N-[6-(trifluoromethyl)pyridin-3-yl]quinoline-7-carboxamide Compound 23 was synthesized according to the General Experimental Procedure IV starting from Int-27 and phenol, and the product was obtained as an off-white solid in 56% yield.

Example 25

Compound 24: 3-(Pyridin-3-yloxy)-N-[6-(trifluoromethyl)pyridin-3-yl]quinoline-7-carboxamide Compound 24 was synthesized according to the General Experimental Procedure IV starting from Int-27 and 3-hydroxypyridine, and the product was obtained as a white solid in 30% yield.

Example 26

Compound 25: 6-Chloro-N-[1-methyl-3-(2-methylpropyl)-1H-pyrazol-5-yl]quinoline-7-carboxamide Compound 25 was synthesized according to the General Experimental Procedure I starting from Int-3 and 1-methyl-3-(2-methylpropyl)-1H-pyrazol-5-amine, and the product was obtained as an off-white solid in 42% yield.

Example 27

Compound 26: N-[3-(4-tert-Butylphenyl)-1-methyl-1H-pyrazol-5-yl]-6-chloroquinoline-7-carboxamide Compound 26 was synthesized according to the General Experimental Procedure I starting from Int-3 and 3-(4-tert-butylphenyl)-1-methyl-1H-pyrazol-5-amine, and the product was obtained as an off-white solid in 26% yield.

Example 28

Compound 27: 6-Chloro-N-[1-methyl-3-(trifluoromethyl)-1H-pyrazol-5-yl]quinoline-7-carboxamide Compound 27 was synthesized according to the General Experimental Procedure I starting from Int-3 and 2-methyl-5-(trifluoromethyl)pyrazol-3-amine, and the product was obtained as an off-white solid in 46% yield.

Example 29

Compound 28: 6-Chloro-N-[3-(3-methoxyphenyl)-1-methyl-1H-pyrazol-5-yl]quinoline-7-carboxamide Compound 28 was synthesized according to the General Experimental Procedure I starting from Int-3 and 3-(3-methoxyphenyl)-1-methyl-1H-pyrazol-5-amine, and the product was obtained as an off-white solid in 45% yield.

Example 30

Compound 29: 6-Chloro-N-[3-(2-fluorophenyl)-1-methyl-1H-pyrazol-5-yl]quinoline-7-carboxamide Compound 29 was synthesized according to the General Experimental Procedure I starting from Int-3 and 5-amino-3-(2-fluorophenyl)-1-methylpyrazole, and the product was obtained as an off-white solid in 43% yield.

Example 31

Compound 30: 6-Chloro-N-[3-(2-methoxyphenyl)-1-methyl-1H-pyrazol-5-yl]quinoline-7-carboxamide Compound 30 was synthesized according to the General Experimental Procedure I starting from Int-3 and 5-(2-methoxyphenyl)-2-methylpyrazol-3-amine, and the product was obtained as an off-white solid in 43% yield.

Example 32

Compound 31: 6-Chloro-N-[1-methyl-3-(2-methylphenyl)-1H-pyrazol-5-yl]quinoline-7-carboxamide Compound 31 was synthesized according to the General Experimental Procedure I starting from Int-3 and 2-methyl-5-(2-methylphenyl)pyrazol-3-amine, and the product was obtained as an off-white solid in 53% yield.

Example 33

Compound 32: 6-Chloro-N-(3-(N,N-diethylsulfamoyl)phenyl)quinoline-7-carboxamide

Int-3 (0.15 g, 0.72 mmol) was added to a solution of $T_3P$ in EtOAc (50% in EtOAc), (2.3 g, 7.24 mmol), followed by pyridine (0.17 g, 2.14 mmol) and N,N-diethyl 3-aminobenzenesulfonamide (0.16 g, 0.72 mmol) at 0° C. After addition, reaction mixture was allowed to warm to rt and stirred for 5 hrs under nitrogen atmosphere. Progress of the reaction was monitored by TLC and LCMS. After completion, reaction mixture was diluted with $H_2O$ (100 mL) and extracted with EtOAc (3×100 mL). Combined organic layers were washed with $H_2O$ (50 mL), dried over anhydrous $Na_2SO_4$, and concentrated in vacuo. The crude product was purified by preparative HPLC to give 0.055 g of Compound 32 as an off-white solid in 18% yield.

Example 34

Compound 33: 6-Chloro-N-(3-(N,N-diethylsulfamoyl)-4-fluorophenyl)quinoline-7-carboxamide Int-3 (0.2 g, 0.96 mmol) was added to a solution of $T_3P$ in EtOAc (50% in EtOAc), (3.07 g, 9.6 mmol), followed by pyridine (0.23 g, 2.88 mmol) and Int-23 (0.16 g, 0.72 mmol) at 0° C. After addition, reaction mixture was allowed to warm to rt and stirred for 5 hrs under nitrogen atmosphere. After completion, reaction mixture was diluted with $H_2O$ (100 mL) and extracted with EtOAc (3×100 mL). Combined organic layers were washed with $H_2O$, dried over anhydrous $Na_2SO_4$, and concentrated in vacuo. The crude product was purified by recrystallization to afford 0.180 g of Compound 33 as an off-white solid in 43% yield.

Example 35

Compound 34: 6-Chloro-N-(4-chloro-3-(N,N-diethylsulfamoyl)phenyl)quinoline-7-carboxamide Int-3 (0.2 g, 0.96 mmol) was added to a solution of $T_3P$ in EtOAc (50% in EtOAc), (3.07 g, 9.6 mmol), followed by pyridine (0.23 g, 2.88 mmol) and Int-25 (0.25 g, 0.96 mmol) at 0° C. After addition, reaction mixture was allowed to warm to rt and stirred for 5 hrs under nitrogen atmosphere. After completion, reaction mixture was diluted with $H_2O$ (100 mL) and extracted with EtOAc (3×100 mL). Combined organic layers were washed with $H_2O$, dried over anhydrous $Na_2SO_4$, and concentrated in vacuo. The crude product was purified by preparative HPLC to give 0.135 g of Compound 34 as an off-white solid in 31% yield.

Example 36

Compound 35: 6-Chloro-N-[4-(4-cyclopentylpiperazin-1-yl)phenyl]quinoline-7-carboxamide Compound 35 was synthesized according to the General Experimental Procedure I starting from Int-3 and 4-(4-cyclopentylpiperazin-1-yl)aniline, and the product was obtained as an off-white solid in 26% yield.

Example 37

Compound 36: N-[3-tert-Butyl-1-(2,2,2-trifluoroethyl)-1H-pyrazol-5-yl]-6-chloroquinoline-7-carboxamide Compound 36 was synthesized according to the General Experimental Procedure I starting from Int-3 and 3-tert-butyl-1-(2,2,2-trifluoroethyl)-1H-pyrazol-5-amine, and the product was obtained as an off-white solid in 28% yield.

Example 38

Compound 37: 4-Phenoxy-N-[6-(trifluoromethyl)pyridin-3-yl]quinoline-7-carboxamide Compound 37 was synthesized according to the General Experimental Procedure V starting from Int-26 and 6-(trifluoromethyl)pyridine-3-amine, and the product was obtained as an off-white solid in 51% yield.

Example 39

Compound 38: 6-Chloro-N-[3-(3-fluorophenyl)-1-methyl-1H-pyrazol-5-yl]quinoline-7-carboxamide Compound 38 was synthesized according to the General Experimental Procedure I starting from Int-3 and 5-amino- 3-(3-fluorophenyl)-1-methylpyrazole, and the product was obtained as an off-white solid in 8% yield.

Example 40

Compound 39: 3-Bromo-N-[1-methyl-3-(trifluoromethyl)-1H-pyrazol-5-yl]quinoline-7-carboxamide Compound 39 was synthesized according to the General Experimental Procedure I starting from 3-bromoquinoline-7-carboxylic acid and 2-methyl-5-(trifluoromethyl) pyrazol-3-amine, and the product was obtained as a white solid in 74% yield.

Example 41

Compound 40: N-[1-Methyl-3-(trifluoromethyl)-1H-pyrazol-5-yl]-3-phenylquinoline-7-carboxamide Compound 40 was synthesized according to the General Experimental Procedure III starting from Compound 39 and phenyl boronic acid, and the product was obtained as an off-white solid in 36% yield.

Example 42

Compound 41: N-[1-Methyl-3-(trifluoromethyl)-1H-pyrazol-5-yl]-3-(3-methylphenyl) quinoline-7-carboxamide Compound 41 was synthesized according to the General Experimental Procedure III starting from Compound 39 and 3-methylphenylboronic acid, and the product was obtained as an off-white solid in 36% yield.

Example 43

Compound 42: 3-Bromo-N-(1-methyl-1H-pyrazol-5-yl)quinoline-7-carboxamide

Compound 42 was synthesized according to the General Experimental Procedure I starting from 3-bromoquinoline-7-carboxylic acid and 1-methyl-1H-pyrazol-5-amine, and the product was obtained as an off-white solid in 46% yield.

Example 44

Compound 43: 3-Bromo-N-(3-tert-butyl-1-methyl-1H-pyrazol-5-yl)quinoline-7-carboxamide Compound 43 was synthesized according to the General Experimental Procedure I starting from 3-bromoquinoline-7-carboxylic acid and 3-tert-butyl-1-methyl-1H-pyrazol-5-amine, and the product was obtained as an off-white solid in 43% yield.

Example 45

Compound 44: 6-Chloro-N-(1-methyl-3-(2-(trifluoromethyl)phenyl)-1H-pyrazol-5-yl)quinoline-7-carboxamide Compound 44 was synthesized according to the General Experimental Procedure II starting from Int-3 and Int-28, and the product was obtained as an off-white solid in 19% yield.

Example 46

Compound 45: N-(1-Methyl-1H-pyrazol-5-yl)-3-phenylquinoline-7-carboxamide

Compound 45 was synthesized according to the General Experimental Procedure III starting from Compound 42 and phenyl boronic acid, and the product was obtained as a white solid in 61% yield.

Example 47

Compound 46: N-(3-tert-Butyl-1-methyl-1H-pyrazol-5-yl)-3-phenylquinoline-7-carboxamide Compound 46 was synthesized according to the General Experimental Procedure III starting from Compound 43 and phenyl boronic acid, and the product was obtained as a yellow solid in 47% yield.

Example 48

Compound 47: 6-Chloro-N-[1-(propan-2-yl)-3-[2-(trifluoromethyl)phenyl]-1H-pyrazol-5-yl]quinoline-7-carboxamide Compound 47 was synthesized according to the General Experimental Procedure II starting from Int-3 and Int-29, and the product was obtained as an off-white solid in 31% yield.

Example 49

Compound 48: 6-Chloro-N-{1-methyl-3-[3-(trifluoromethyl)phenyl]-1H-pyrazol-5-yl}quinoline-7-carboxamide Compound 48 was synthesized according to the General Experimental Procedure II starting from Int-3 and Int-30, and the product was obtained as an off-white solid in 48% yield.

Example 50

Compound 49: 6-Chloro-N-[3-(3-chlorophenyl)-1-methyl-1H-pyrazol-5-yl]quinoline-7-carboxamide Compound 49 was synthesized according to the General Experimental Procedure II starting from Int-3 and Int-31, and the product was obtained as an off-white solid in 48% yield.

Example 51

Compound 50: 6-Chloro-N-[3-(5-fluoro-2-methylphenyl)-1-methyl-1H-pyrazol-5-yl]quinoline-7-carboxamide Compound 50 was synthesized according to the General Experimental Procedure II starting from Int-3 and Int-32, and the product was obtained as an off-white solid in 42% yield.

Example 52

Compound 51: 6-Chloro-N-[3-(5-chloro-2-methylphenyl)-1-methyl-1H-pyrazol-5-yl]quinoline-7-carboxamide Compound 51 was synthesized according to the General Experimental Procedure II starting from Int-3 and Int-33, and the product was obtained as an off-white solid in 44% yield.

Example 53

Compound 52: N-[1-methyl-3-(trifluoromethyl)-1H-pyrazol-5-yl]-3-(2-methylphenyl) quinoline-7-carboxamide Compound 52 was synthesized according to the General Experimental Procedure VI starting from Compound 39 and 2-methylphenyl boronic acid, and the product was obtained as an off-white solid in 90% yield.

Example 54

Compound 53: N-[1-methyl-3-(trifluoromethyl)-1H-pyrazol-5-yl]-3-[2-(trifluoromethyl) phenyl]quinoline-7-carboxamide Compound 53 was synthesized according to the General Experimental Procedure VI starting from Compound 39 and 2-(trifluoromethyl)phenyl boronic acid, and the product was obtained as an off-white solid in 70% yield.

Example 55

Compound 54: 3-(2-Fluorophenyl)-N-[1-methyl-3-(trifluoromethyl)-1H-pyrazol-5-yl]quinoline-7-carboxamide Compound 54 was synthesized according to the General Experimental Procedure VI starting from Compound 39 and 2-fluorophenylboronic acid, and the product was obtained as an off-white solid in 77% yield.

Example 56

Compound 55: N-[1-Methyl-3-(trifluoromethyl)-1H-pyrazol-5-yl]-3-[3-(trifluoromethyl) phenyl]quinoline-7-carboxamide Compound 55 was synthesized according to the General Experimental Procedure VI starting from Compound 39 and 3-(trifluoromethyl)phenyl boronic acid, and the product was obtained as a yellow solid in 56% yield.

Example 57

Compound 56: 6-Chloro-N-(3-(2-chloro-5-(trifluoromethyl)phenyl)-1-methyl-1H-pyrazol-5-yl)quinoline-7-carboxamide Compound 56 was synthesized according to the General Experimental Procedure II starting from Int-3 and Int-34, and the product was obtained as a brown solid in 20% yield.

Example 58

Compound 57: 6-Chloro-N-(3-(4-fluoro-2-methylphenyl)-1-methyl-1H-pyrazol-5-yl) quinoline-7-carboxamide Compound 57 was synthesized according to the General Experimental Procedure II starting from Int-3 and Int-35, and the product was obtained as an off-white solid in 31% yield.

Example 59

Compound 58: 6-Chloro-N-(3-(4-chloro-2-methylphenyl)-1-methyl-1H-pyrazol-5-yl)quinoline-7-carboxamide Compound 58 was synthesized according to the General Experimental Procedure II starting from Int-3 and Int-36, and the product was obtained as an off-white solid in 27% yield.

Example 60

Compound 59: 1-Methyl-3-(2-methyl-5-(trifluoromethyl)phenyl)-1H-pyrazol-5-amine

Compound 59 was synthesized according to the General Experimental Procedure II starting from Int-3 and Int-37, and the product was obtained as an off-white solid in 17% yield.

Example 61

Compound 60: 3-(3-Fluorophenyl)-N-[1-methyl-3-(trifluoromethyl)-1H-pyrazol-5-yl]quinoline-7-carboxamide Compound 60 was synthesized according to the General Experimental Procedure VI starting from Compound 39 and 3-fluorophenylboronic acid, and the product was obtained as an off-white solid in 57% yield.

Example 62

Compound 61: 3-(4-Fluorophenyl)-N-[1-methyl-3-(trifluoromethyl)-1H-pyrazol-5-yl]quinoline-7-carboxamide Compound 61 was synthesized according to the General Experimental Procedure VI starting from Compound 39 and 4-fluorophenylboronic acid, and the product was obtained as a light brown solid in 57% yield.

Example 63

Compound 62: N-[1-Methyl-3-(trifluoromethyl)-1H-pyrazol-5-yl]-3-(4-methylphenyl) quinoline-7-carboxamide Compound 62 was synthesized according to the General Experimental Procedure VI starting from Compound 39 and 4-methylphenylboronic acid, and the product was obtained as a light brown solid in 50% yield.

Example 64

Compound 63: 3-Bromo-N-[4-(4-ethylpiperazin-1-yl)-3-fluorophenyl]quinoline-7-carboxamide Compound 63 was synthesized according to the General Experimental Procedure I starting from 3-bromoquinoline-7-carboxylic acid and 4-(4-ethylpiperazin-1-yl)-3-fluoroaniline, and the product was obtained as off-white solid in 42% yield.

Example 65

Compound 64: N-[4-(4-ethylpiperazin-1-yl)-3-fluorophenyl]-3-phenylquinoline-7-carboxamide Compound 64 was synthesized according to the General Experimental Procedure VI starting from compound 63 and phenyl boronic acid, and the product was obtained as a yellow solid in 86% yield.

Example 66

Compound 65: 3-(3-chlorophenyl)-N-[1-methyl-3-(trifluoromethyl)-1H-pyrazol-5-yl]quinoline-7-carboxamide Compound 65 was synthesized according to the General Experimental Procedure VI starting from Compound 39 and 2-chlorophenylboronic acid, and the product was obtained as an off-white solid in 72% yield.

Example 67

Compound 66: 3-(2-Chlorophenyl)-N-[1-methyl-3-(trifluoromethyl)-1H-pyrazol-5-yl]quinoline-7-carboxamide Compound 66 was synthesized according to the General Experimental Procedure VI starting from Compound 39 and 2-chlorophenylboronic acid, and the product was obtained as a light-grey solid in 72% yield.

Example 68

Compound 67: N-[1-Methyl-3-(trifluoromethyl)-1H-pyrazol-5-yl]-3-(thiophen-3-yl)quinoline-7-carboxamide Compound 67 was synthesized according to the General Experimental Procedure VI starting from Compound 39 and thiophene-3-boronic acid, and the product was obtained as an off-white solid in 58% yield.

Example 69

Compound 68: 6-Chloro-N-{3-[5-fluoro-2-(trifluoromethyl)phenyl]-1-methyl-1H-pyrazol-5-yl}quinoline-7-carboxamide Compound 68 was synthesized according to the General Experimental Procedure II starting from Int-3 and Int-38, and the product was obtained as a white solid in 37% yield.

Example 70

Compound 69: 6-Chloro-N-[3-(2-chlorophenyl)-1-methyl-1H-pyrazol-5-yl]quinoline-7-carboxamide Compound 69 was synthesized according to the General Experimental Procedure II starting from Int-3 and Int-39, and the product was obtained as an off-white solid in 35% yield.

Example 71

Compound 70: 3-Bromo-N-[6-(trifluoromethyl)pyridin-3-yl]quinoline-7-carboxamide

Compound 70 was synthesized according to the General Experimental Procedure I starting from 3-bromoquinoline-7-carboxylic acid and 5-amino-2-(trifluoromethyl) pyridine, and the product was obtained as an off-white solid in 77% yield.

Example 72

Compound 71: 3-Phenyl-N-[6-(trifluoromethyl)pyridin-3-yl]quinoline-7-carboxamide Compound 71 was synthesized according to the General Experimental Procedure VII starting from Int-27 and phenyl boronic acid.

Example 73

Compound 72: 6-Chloro-N-[3-(2-methylphenyl)-1-(propan-2-yl)-1H-pyrazol-5-yl]quinoline-7-carboxamide Compound 72 was synthesized according to the General Experimental Procedure II starting from Int-3 and Int-40, and the product was obtained as an off-white solid in 26% yield.

Example 74

Compound 73: N-[1-Methyl-3-(trifluoromethyl)-1H-pyrazol-5-yl]-3-(thiophen-2-yl)quinoline-7-carboxamide Compound 73 was synthesized according to the General Experimental Procedure VI starting from Compound 39 and thiophene-2-boronic acid, and the product was obtained as an off-white solid in 55% yield.

Example 75

Compound 74: 3-(4-Fluorophenyl)-N-[1-methyl-3-(tert-butyl)-1H-pyrazol-5-yl]quinoline-7-carboxamide Compound 74 was synthesized according to the General Experimental Procedure VI starting from Compound 43 and 4-fluorophenyl boronic acid, and the product was obtained as an off-white solid in 65% yield.

Example 76

Compound 75: 3-(2,4-Difluorophenyl)-N-[1-methyl-3-(trifluoromethyl)-1H-pyrazol-5-yl]quinoline-7-carboxamide Compound 75 was synthesized according to the General Experimental Procedure VI starting from Compound 39 and 2,4-difluorophenyl boronic acid, and the product was obtained as an off-white solid in 60% yield.

Example 77

Compound 76: N-(1-Methyl-1H-pyrazol-5-yl)-4-phenoxyquinoline-7-carboxamide

Compound 76 was synthesized according to the General Experimental Procedure V starting from Int-26 and 1-methyl-5-aminopyrazole, and the product was obtained as a white solid in 23% yield.

Example 78

Compound 77: N-[1-methyl-3-(trifluoromethyl)-1H-pyrazol-5-yl]-3-(pyridin-3-yl)quinoline-7-carboxamide Compound 77 was synthesized according to the General Experimental Procedure VII starting from Compound 39 and pyridin-3-ylboronic acid, and the product was obtained as an off-white solid in 59% yield.

Example 79

Compound 78: N-[1-methyl-3-(trifluoromethyl)-1-pyrazol-yl]-3-(pyridin-4-yl)quinoline-7-carboxamide Compound 78 was synthesized according to the General Experimental Procedure VII starting from Compound 39 and pyridin-4-ylboronic acid, and the product was obtained as a light-yellow solid in 60% yield.

Example 80

Compound 79: 3-(4-(2-methoxyethoxy)phenyl-N-[1-methyl-3-(trifluoromethyl)-1H-pyrazol-5-yl]quinoline-7-carboxamide Compound 79 was synthesized according to the General Experimental Procedure VII starting from Compound 39 and 4-(2-methoxyethoxy)phenylboronic acid, and the product was obtained as an off-white solid in 57% yield.

Example 81

Compound 80: 4-morpholino-N-(6-(trifluoromethyl)pyridin-3-yl)quinoline-7-carboxamide Compound 80 was synthesized according to the General Experimental Procedure V starting from Int-41 and 3-amino-6-trifluoromethylpyridine, and the product was obtained as an off-white solid in 11% yield.

Example 82

Compound 81: 3-(o-tolyl)-N-(6-(trifluoromethyl)pyridin-3-yl)quinoline-7-carboxamide Compound 81 was synthesized according to the General Experimental Procedure VII starting from Int-27 and 2-methylphenylboronic acid, and the product was obtained as a white solid.

Example 83

Compound 82: 3-(m-tolyl)-N-(6-(trifluoromethyl)pyridin-3-yl)quinoline-7-carboxamide Compound 82 was synthesized according to the General Experimental Procedure VII starting from Int-27 and 3-methylphenylboronic acid, and the product was obtained as a white solid.

Example 84

Compound 83: 3-(thiazol-2-yl)-N-(6-(trifluoromethyl)pyridin-3-yl)quinoline-7-carboxamide Compound 83 was synthesized according to the General Experimental Procedure VII starting from Int-27 and thiazol-2-ylboronic acid, and the product was obtained as a white solid.

Example 85

Compound 84: N-(3-(tert-butyl)-1-methyl-1H-pyrazol-5-yl)-3-(2,4-difluorophenyl) quinoline-7-carboxamide Compound 84 was synthesized according to the General Experimental Procedure VII starting from Compound 43 and 2,4-difluorophenylboronic acid, and the product was obtained as a yellow solid in 80% yield.

Example 86

Compound 85: 3-(2-fluorophenyl)-N-(6-(trifluoromethyl)pyridin-3-yl)quinoline-7-carboxamide Compound 85 was synthesized according to the General Experimental Procedure VII starting from Int-27 and 2-fluorophenylboronic acid, and the product was obtained as an off-white solid.

Example 87

Compound 86: 3-(4-fluorophenyl)-N-(6-(trifluoromethyl)pyridin-3-yl)quinoline-7-carboxamide Compound 86 was synthesized according to the General Experimental Procedure VII starting from Int-27 and 4-fluorophenylboronic acid, and the product was obtained as an off-white solid.

Example 88

Compound 87: 3-(2,4-difluorophenyl)-N-(6-(trifluoromethyl)pyridin-3-yl)quinoline-7-carboxamide Compound 87 was synthesized according to the General Experimental Procedure VII starting from Int-27 and 2,4-difluorophenylboronic acid, and the product was obtained as an off-white solid.

Example 89

Compound 88: 3-(thiophen-2-yl)-N-(6-(trifluoromethyl)pyridin-3-yl)quinoline-7-carboxamide Compound 88 was synthesized according to the General Experimental Procedure VII starting from Int-27 and 2-thienylboronic acid, and the product was obtained as an off-white solid.

Example 90

Compound 89: 3-(thiophen-3-yl)-N-(6-(trifluoromethyl)pyridin-3-yl)quinoline-7-carboxamide Compound 89 was synthesized according to the General Experimental Procedure VII starting from Int-27 and 3-thienylboronic acid, and the product was obtained as an off-white solid.

Example 91

Compound 90: 6-chloro-N-(1-methyl-4-phenyl-1H-imidazol-2-yl)quinoline-7-carboxamide Compound 90 was synthesized according to the General Experimental Procedure II starting from Int-3 and 1-methyl-4-phenyl-1H-imidazol-2-amine, and the product was obtained as an off-white solid

Example 92

Compound 91: N-(4-Chloro-3-(N,N-diethylsulfamoyl)phenyl)-3-phenylquinoline-7-carboxamide Compound 91 was synthesized according to the General Experimental Procedure VII starting from Int-43 and phenyl boronic acid, and the product was obtained as an off-white solid in 55% yield.

Example 93

Compound 92: N-(3-(tert-butyl)-1-methyl-1H-pyrazol-5-yl)-3-(2-fluorophenyl)quinoline-7-carboxamide Compound 92 was synthesized according to the General Experimental Procedure VII starting from Compound 43 and 2-fluorophenylboronic acid, and the product was obtained as an off-white solid in 74% yield.

Example 94

Compound 93: N-(1-methyl-3-(trifluoromethyl)-1H-pyrazol-5-yl)-3-(thiazol-2-yl)quinoline-7-carboxamide Compound 93 was synthesized according to the General Experimental Procedure VII starting from Compound 39 and thiazol-2-ylboronic acid, and the product was obtained as an off-white solid.

Example 95

Compound 94: N-(4-Chloro-3-(N,N-diethylsulfamoyl)phenyl)-3-(4-fluorophenyl) quinoline-7-carboxamide Compound 94 was synthesized according to the General Experimental Procedure VII starting from Int-43 and 4-fluorophenylboronic acid, and the product was obtained as an off-white solid in 64% yield.

Example 96

Compound 95: 3-(4-fluorophenyl)-N-(1-methyl-3-(o-tolyl)-1H-pyrazol-5-yl)quinoline-7-carboxamide Compound 95 was synthesized according to the General Experimental Procedure VII starting from Int-46 and 4-fluorophenylboronic acid, and the product was obtained as an off-white solid in 54% yield.

Example 97

Compound 96: 3-(2,4-difluorophenyl)-N-(1-methyl-3-(o-tolyl)-1H-pyrazol-5-yl)quinoline-7-carboxamide Compound 96 was synthesized according to the General Experimental Procedure VII starting from Int-46 and 2,4-difluorophenylboronic acid, and the product was obtained as an off-white solid in 43% yield.

Example 98

Compound 97: N-(1-methyl-3-(o-tolyl)-1H-pyrazol-5-yl)-3-(thiophen-2-yl)quinoline-7-carboxamide Compound 97 was synthesized according to the General Experimental Procedure VII starting from Int-46 and 2-thienylboronic acid, and the product was obtained as an off-white solid.

Example 99

Compound 98: 3-(3-fluoropyridin-4-yl)-N-[1-methyl-3-(trifluoromethyl)-1H-pyrazol-5-yl]quinoline-7-carboxamide Compound 98 was synthesized according to the General Experimental Procedure VII starting from Compound 39 and 3-fluoropyridine-4-boronic acid, and the product was obtained as an off-white solid in 39% yield.

Example 100

Compound 99: 4-Isopropoxy-N-[1-methyl-3-(trifluoromethyl)-1H-pyrazol-5-yl]quinoline-7-carboxamide Compound 99 was synthesized according to the General Experimental Procedure V starting from Int-44 and 1-methyl-3-(trifluoromethyl)-1H-pyrazol-5-amine, and the product was obtained as an off-white solid in 23% yield.

Example 101

Compound 100: N-(1-methyl-3-(trifluoromethyl)-1H-pyrazol-5-yl)-3-(pyridine-2-yl)quinoline-7-carboxamide Compound 100 was synthesized according to the General Experimental Procedure VIII starting from Compound 39 and pyridine-2-boronic acid pinacol ester, and the product was obtained as an off-white solid in 46% yield.

Example 102

Compound 101: 3-(5-fluoropyridin-2-yl)-N-(1-methyl-3-(trifluoromethyl)-1H-pyrazol-5-yl)quinoline-7-carboxamide Compound 101 was synthesized according to the General Experimental Procedure VIII starting from Compound 39 and 5-fluoropyridine-2-boronic acid pinacol ester, and the product was obtained as an off-white solid in 65% yield.

Example 103

Compound 102: 4-(Dimethylamino)-N-[1-methyl-3-(trifluoromethyl)-1H-pyrazol-5-yl]quinoline-7-carboxamide Compound 102 was synthesized according to the General Experimental Procedure V starting from starting from Int-42 and 1-methyl-3-(trifluoromethyl)-1H-pyrazol-5-amine, and the product was obtained as an off-white solid in 20% yield.

Example 104

Compound 103: N-(1-methyl-3-(trifluoromethyl)-1H-pyrazol-5-yl)-3-(4-trifluoromethoxy)phenyl)quinoline-7-carboxamide Compound 103 was synthesized according to the General Experimental Procedure II starting from Compound 39 and 4-(trifluoromethoxy)phenylboronic acid, and the product was obtained as an off-white solid in 62% yield.

Example 105

Compound 104: 3-(2,6-Difluorophenyl)-N-[1-methyl-3-(trifluoromethyl)-1H-pyrazol-5-yl]quinoline-7-carboxamide Compound 104 was synthesized according to the General Experimental Procedure VIII starting from Compound 39 and 2,6-difluorophenylboronic acid MIDA ester, and the product was obtained as an off-white solid in 15% yield.

Example 106

Compound 105: N-[1-methyl-3-(trifluoromethyl)-1H-pyrazol-5-yl]-3-(2-(trifluoromethoxy)phenyl)quinoline-7-carboxamide Compound 105 was synthesized according to the General Experimental Procedure VII starting from Compound 39 and 2-(trifluoromethoxy)phenylboronic acid, and the product was obtained as an off-white solid in 62% yield.

Example 107

Compound 106: N-[1-methyl-3-(trifluoromethyl)-1H-pyrazol-5-yl]-3-(thiazol-5-yl)quinoline-7-carboxamide Compound 106 was synthesized according to the General Experimental Procedure VIII starting from Compound 39 and thiazol-5-ylboronic acid pinacol ester, and the product was obtained as an off-white solid in 51% yield.

Example 108

Compound 107: 3-(1-methyl-1H-pyrazol-4-yl)-N-[1-methyl-3-(trifluoromethyl)-1H-pyrazol-5-yl]quinoline-7-carboxamide Compound 107 was synthesized according to the General Experimental Procedure VIII starting from Compound 39 and 1-methylpyrazole-4-boronic acid, pinacol ester, and the product was obtained as an off-white solid in 75% yield.

Example 109

Compound 108: 3-(1-methyl-1H-pyrazol-3-yl)-N-[1-methyl-3-(trifluoromethyl)-1H-pyrazol-5-yl]quinoline-7-carboxamide Compound 108 was synthesized according to the General Experimental Procedure VIII starting from Compound 39 and 1-methyl-1H-pyrazole-3-boronic acid pinacol ester, and the product was obtained as an off-white solid in 60% yield.

Example 110

Compound 109: 3-(3,5-difluoropyridin-4-yl)-N-[1-methyl-3-(trifluoromethyl)-1H-pyrazol-5-yl]quinoline-7-carboxamide Compound 109 was synthesized according to the General Experimental Procedure VIII starting from Compound 39 and 3,5-difluoropyridine-4-boronic acid pinacol ester, and the product was obtained as an off-white solid in 22% yield.

Example 111

Compound 110: 3-(isoxazole-4-yl)-N-[1-methyl-3-(trifluoromethyl)-1H-pyrazol-5-yl]quinoline-7-carboxamide Compound 110 was synthesized according to the General Experimental Procedure VIII starting from Compound 39 and 4-isoxazoleboronic acid pinacol ester, and the product was obtained as a yellow solid in 39% yield.

Example 112

Compound 111: 3-(4-hydroxyphenyl)-N-[1-methyl-3-(trifluoromethyl)-1H-pyrazol-5-yl]quinoline-7-carboxamide Compound 110 was synthesized according to the General Experimental Procedure VII starting from Compound 39 and 4-hydroxyphenylboronic acid, and the product was obtained as an off-white solid in 49% yield.

Example 113

Compound 112: N-(4-Chloro-3-(N,N-diethylsulfamoyl)phenyl)-3-(thiazol-2-yl)quinoline-7-carboxamide Compound 112 was synthesized according to the General Experimental Procedure VII starting from Int-43 and thiazol-2-ylboronic acid, and the product was obtained as an off-white solid in 60% yield.

Example 114

Compound 113: N-(4-Chloro-3-(N,N-diethylsulfamoyl)phenyl)-3-(2,4-difluorophenyl) quinoline-7-carboxamide Compound 113 was synthesized according to the General Experimental Procedure VII starting from Int-43 and 2,4-difluorophenylboronic acid, and the product was obtained as an off-white solid.

Example 115

Compound 114: N-(4-Chloro-3-(N,N-diethylsulfamoyl)phenyl)-3-(thiophen-2-yl) quinoline-7-carboxamide Compound 114 was synthesized according to the General Experimental Procedure VII starting from Int-43 and 2-thienylboronic acid, and the product was obtained as a yellow solid.

Example 116

Compound 115: N-(1-methyl-3-(o-tolyl)-1H-pyrazol-5-yl)-3-(thiazol-2-yl)quinoline-7-carboxamide Compound 115 was synthesized according to the General Experimental Procedure VII starting from Int-46 and thiazol-2-ylboronic acid, and the product was obtained as an off-white solid.

Example 117

Compound 116: 3-(1-methyl-1H-pyrazol-5-yl)-N-[1-methyl-3-(trifluoromethyl)-1H-pyrazol-5-yl]quinoline-7-carboxamide Compound 116 was synthesized according to the General Experimental Procedure VIII starting from Compound 39 and 1-methyl-1H-pyrazole-5-boronic acid pinacol ester, and the product was obtained as an off-white solid in 58% yield.

Example 118

Compound 117: 3-(2-hydroxyphenyl)-N-[1-methyl-3-(trifluoromethyl)-1H-pyrazol-5-yl]quinoline-7-carboxamide Compound 117 was synthesized according to the General Experimental Procedure VII starting from Compound 39 and 2-hydroxyphenylboronic acid, and the product was obtained as an off-white solid in 57% yield.

Example 119

Compound 118: N-[1-methyl-3-(trifluoromethyl)-1H-pyrazol-5-yl]-3-(pyrimidin-2-yl)quinoline-7-carboxamide Compound 118 was synthesized according to the General Experimental Procedure IX starting from Compound 39 and 2-bromopyrimidine, and the product was obtained as an off-white solid in 50% yield.

Example 120

Compound 119: 3-(3-fluoropyridin-2-yl)-N-[1-methyl-3-(trifluoromethyl)-1H-pyrazol-5-yl]quinoline-7-carboxamide Compound 119 was synthesized according to the General Experimental Procedure IX starting from Compound 39 and 2-bromo-3-fluoropyridine, and the product was obtained as an off-white solid in 39% yield.

Example 121

Compound 120: 3-(isothiazol-4-yl)-N-[1-methyl-3-(trifluoromethyl)-1H-pyrazol-5-yl]quinoline-7-carboxamide Compound 120 was synthesized according to the General Experimental Procedure IX starting from Compound 39 and 4-bromo-isothiazole, and the product was obtained as an off-white solid in 39% yield.

Example 122

Compound 121: N-[1-methyl-3-(trifluoromethyl)-1H-pyrazol-5-yl]-3-(thiazol-4-yl)quinoline-7-carboxamide Compound 121 was synthesized according to the General Experimental Procedure VII starting from Compound 39 and 4-bromothiazole, and the product was obtained as a yellow solid in 43% yield.

Example 123

Compound 122: N-[1-methyl-3-(trifluoromethyl)-1H-pyrazol-5-yl]-3-(pyrimidin-4-yl) quinoline-7-carboxamide Compound 122 was synthesized according to the General Experimental Procedure IX starting from Compound 39 and 4-bromopyrimidine, and the product was obtained as a yellow solid in 25% yield.

Example 124

Compound 123: 3-(5-fluoropyrimidin-2-yl)-N-[1-methyl-3-(trifluoromethyl)-1H-pyrazol-5-yl]quinoline-7-carboxamide Compound 123 was synthesized according to the General Experimental Procedure IX starting from Compound 39 and 2-bromo-5-fluoropyrimidine, and the product was obtained as a greenish-yellow solid in 43% yield.

Example 125

Compound 124: 3-(3,5-difluoropyridin-2-yl)-N-[1-methyl-3-(trifluoromethyl)-1H-pyrazol-5-yl]quinoline-7-carboxamide Compound 124 was synthesized according to the General Experimental Procedure VII starting from Compound 39 and 2-bromo-3,5-difluoropyridine, and the product was obtained as an off-white solid in 49% yield.

Example 126

Compound 125: 3-(3-fluoropyridin-4-yl)-N-(1-methyl-3-phenyl-1H-pyrazol-5-yl) quinoline-7-carboxamide Compound 125 was synthesized according to the General Experimental Procedure VII starting from Int-45 and 3-fluoropyridine-4-boronic acid, and the product was obtained as an off-white solid.

Example 127

Compound 126: 3-(1-methyl-1H-imidazol-5-yl)-N-[1-methyl-3-(trifluoromethyl)-1H-pyrazol-5-yl]quinoline-7-carboxamide Compound 126 was synthesized according to the General Experimental Procedure IX starting from Compound 39 and 5-bromo-1-methyl-1H-imidazole, and the product was obtained as an off-white solid in 19% yield.

Example 128

Compound 127: 3-(1-methyl-1H-imidazol-2-yl)-N-[1-methyl-3-(trifluoromethyl)-1H-pyrazol-5-yl]quinoline-7-carboxamide Compound 127 was synthesized according to the General Experimental Procedure IX starting from Compound 39 and 2-bromo-1-methyl-1H-imidazole, and the product was obtained as an off-white solid in 16% yield.

Example 129

Compound 128: 3-(5-fluoropyridin-2-yl)-N-(1-methyl-3-phenyl-1H-pyrazol-5-yl) quinoline-7-carboxamide Compound 128 was synthesized according to the General Experimental Procedure VIII starting from Int-45 and 5-fluoropyridine-2-boronic acid pinacol ester, and the product was obtained as an off-white solid.

Example 130

Compound 129: 5-phenyl-N-(6-(trifluoromethyl)pyridin-3-yl))thieno[2,3-b]pyridine-2-carboxamide Compound 129 was synthesized according to the General Experimental Procedure VII starting from 5-bromo-N-(6-(trifluoromethyl)pyridin-3-yl))thieno[2,3-b]pyridine-2-carboxamide and phenyl boronic acid, and the product was obtained as an off-white solid.

Example 131

Compound 130: 5-phenyl-N-[1-methyl-3-(trifluoromethyl)-1H-pyrazol-5-yl]thieno[2,3-b]pyridine-2-carboxamide Compound 130 was synthesized according to the General Experimental Procedure VII starting from 5-bromo-N-[1-methyl-3-(trifluoromethyl)-1H-pyrazol-5-yl]thieno[2,3-b]pyridine-2-carboxamide and phenyl boronic acid, and the product was obtained as an off-white solid.

Example 132

Compound 131: 5-phenyl-N-[4-(4-ethylpiperazin-1-yl)phenyl]thieno[2,3-b]pyridine-2-carboxamide Compound 131 was synthesized according to the General Experimental Procedure VII starting from 5-bromo-N-[4-(4-ethylpiperazin-1-yl)phenyl]thieno[2,3-b]pyridine-2-carboxamide and phenyl boronic acid, and the product was obtained as a pale-green solid.

Example 133

Compound 132: 5-phenyl-N-[4-(4-ethylpiperazin-1-yl)-3-fluorophenyl]thieno[2,3-b]pyridine-2-carboxamide Compound 132 was synthesized according to the General Experimental Procedure VII starting from 5-bromo-N-[4-(4-ethylpiperazin-1-yl)-3-fluorophenyl]thieno[2,3-b]pyridine-2-carboxamide, and the product was obtained as an off-white solid.

Example 134

Compound 133: N-(3-(tert-butyl)-1-methyl-1H-pyrazol-5-yl)-5-phenyl-thieno[2,3-b]pyridine-2-carboxamide Compound 133 was synthesized according to the General Experimental Procedure VII starting from 5-bromo-N-(3-(tert-butyl)-1-methyl-1H-pyrazol-5-yl)-thieno[2,3-b]pyridine-2-carboxamide, and the product was obtained as an off-white solid.

Example 135

Compound 134: N-[4-chloro-3-(N,N-diethylsulfamoyl)phenyl]-5-phenyl-thieno[2,3-b]pyridine-2-carboxamide Compound 134 was synthesized according to the General Experimental Procedure VII starting from 5-bromo-N-[4- chloro-3-(N,N-diethylsulfamoyl)phenyl]thieno[2,3-b]pyridine-2-carboxamide, and the product was obtained as a white solid.

Example 136

Compound 135: N-[4-(morpholin-4-yl)phenyl]-5-phenyl-thieno[2,3-b]pyridine-2-carboxamide Compound 135 was synthesized according to the General Experimental Procedure VII starting from 5-bromo-N-[4-(morpholin-4-yl)phenyl]thieno[2,3-b]pyridine-2-carboxamide, and the product was obtained as a pale-green solid.

Example 137

Compound 136: 5-(4-fluorophenyl)-N-(1-methyl-3-(o-tolyl)-1H-pyrazol-5-yl)thieno[2,3-b]pyridine-2-carboxamide Compound 136 was synthesized according to the General Experimental Procedure VII starting from 5-bromo-N-(1-methyl-3-(o-tolyl)-1H-pyrazol-5-yl)thieno[2,3-b]pyridine-2-carboxamide and 4-fluorophenylboronic acid, and the product was obtained as an off-white solid.

Example 138

Compound 137: 5-(2,4-difluorophenyl)-N-(1-methyl-3-(o-tolyl)-1H-pyrazol-5-yl)thieno[2,3-b]pyridine-2-carboxamide Compound 137 was synthesized according to the General Experimental Procedure VII starting from 5-bromo-N-(1-methyl-3-(o-tolyl)-1H-pyrazol-5-yl)thieno[2,3-b]pyridine-2-carboxamide and 2,4-difluorophenylboronic acid, and the product was obtained as an off-white solid.

Example 139

Compound 138: N-(1-methyl-3-(o-tolyl)-1H-pyrazol-5-yl)-5-(thiophen-2-yl)thieno[2,3-b]pyridine-2-carboxamide Compound 138 was synthesized according to the General Experimental Procedure VII starting from 5-bromo-N-(1-methyl-3-(o-tolyl)-1H-pyrazol-5-yl)thieno[2,3-b]pyridine-2-carboxamide and 2-thienylboronic acid, and the product was obtained as an off-white solid.

Example 140

Compound 139: N-(1-methyl-3-(o-tolyl)-1H-pyrazol-5-yl)-5-(thiazol-2-yl)thieno[2,3-b]pyridine-2-carboxamide Compound 139 was synthesized according to the General Experimental Procedure VII starting from 5-bromo-N-(1-methyl-3-(o-tolyl)-1H-pyrazol-5-yl)thieno[2,3-b]pyridine-2-carboxamide and thiazol-2-ylboronic acid, and the product was obtained as a white solid.

Example 141

Compound 140: N-[4-chloro-3-(N,N-diethylsulfamoyl)phenyl]-5-(2-fluorophenyl)-thieno[2,3-b]pyridine-2-carboxamide Compound 140 was synthesized according to the General Experimental Procedure VII starting from 5-bromo-N-[4-chloro-3-(N,N-diethylsulfamoyl)phenyl]thieno[2,3-b]pyridine-2-carboxamide and 2-fluorophenylboronic acid, and the product was obtained as an off-white solid.

Example 142

Compound 141: N-[4-chloro-3-(N,N-diethylsulfamoyl)phenyl]-5-(4-fluorophenyl)-thieno[2,3-b]pyridine-2-carboxamide Compound 141 was synthesized according to the General Experimental Procedure VII starting from 5-bromo-N-[4-chloro-3-(N,N-diethylsulfamoyl)phenyl]thieno[2,3-b]pyridine-2-carboxamide and 4-fluorophenylboronic acid, and the product was obtained as an off-white solid.

Example 143

Compound 142: N-[4-chloro-3-(N,N-diethylsulfamoyl)phenyl]-5-(pyridin-4-yl)-thieno[2,3-b]pyridine-2-carboxamide Compound 142 was synthesized according to the General Experimental Procedure VII starting from 5-bromo-N-[4-chloro-3-(N,N-diethylsulfamoyl)phenyl]thieno[2,3-b]pyridine-2-carboxamide and pyridine-4-boronic acid, and the product was obtained as an off-white solid.

Example 144

Compound 143: N-[4-chloro-3-(N,N-diethylsulfamoyl)phenyl]-5-(thiazol-2-yl)-thieno[2,3-b]pyridine-2-carboxamide Compound 143 was synthesized according to the General Experimental Procedure VII starting from 5-bromo-N-[4-chloro-3-(N,N-diethylsulfamoyl)phenyl]thieno[2,3-b]pyridine-2-carboxamide and thiazol-2-ylboronic acid, and the product was obtained as an off-white solid.

Example 145

Compound 144: N-[4-chloro-3-(N,N-diethylsulfamoyl)phenyl]-5-(pyridin-2-yl)-thieno[2,3-b]pyridine-2-carboxamide Compound 144 was synthesized according to the General Experimental Procedure VIII starting from 5-bromo-N-[4-chloro-3-(N,N-diethylsulfamoyl)phenyl]thieno[2,3-b]pyridine-2-carboxamide and pyridine-2-boronic acid pinacol ester, and the product was obtained as an off-white solid.

Example 146

Compound 145: N-[4-chloro-3-(N,N-diethylsulfamoyl)phenyl]-5-(3-fluoropyridin-4-yl)-thieno[2,3-b]pyridine-2-carboxamide Compound 145 was synthesized according to the General Experimental Procedure VII starting from 5-bromo-N-[4-chloro-3-(N,N-diethylsulfamoyl)phenyl]thieno[2,3-b]pyridine-2-carboxamide and 3-fluoropyridine-4-boronic acid, and the product was obtained as an off-white solid.

Example 147

Compound 146: N-[4-chloro-3-(N,N-dimethylsulfamoyl)phenyl]-5-phenyl-thieno[2,3-b]pyridine-2-carboxamide Compound 146 was synthesized according to the General Experimental Procedure VII starting from 5-bromo-N-[4-chloro-3-(N,N-diethylsulfamoyl)phenyl]thieno[2,3-b]pyridine-2-carboxamide and phenyl boronic acid, and the product was obtained as an off-white solid.

Example 148

Compound 147: N-[4-chloro-3-(N,N-dimethylsulfamoyl)phenyl]-5-(2-fluorophenyl)-thieno[2,3-b]pyridine-2-carboxamide Compound 147 was synthesized according to the General Experimental Procedure VII starting from 5-bromo-N-[4-chloro-3-(N,N-dimethylsulfamoyl)phenyl]thieno[2,3-b]pyridine-2-carboxamide and 2-fluorophenylboronic acid, and the product was obtained as an off-white solid.

Example 149

Compound 148: N-[4-chloro-3-(N,N-dimethylsulfamoyl)phenyl]-5-(4-fluorophenyl)-thieno[2,3-b]pyridine-2-carboxamide Compound 148 was synthesized according to the General Experimental Procedure VII starting from 5-bromo-N-[4-chloro-3-(N,N-dimethylsulfamoyl)phenyl]thieno[2,3-b]pyridine-2-carboxamide and 4-fluorophenylboronic acid, and the product was obtained as an off-white solid.

Example 150

Compound 149: N-[4-chloro-3-(N,N-dimethylsulfamoyl)phenyl]-5-(pyridin-4-yl)-thieno[2,3-b]pyridine-2-carboxamide Compound 149 was synthesized according to the General Experimental Procedure VII starting from 5-bromo-N-[4-chloro-3-(N,N-dimethylsulfamoyl)phenyl]thieno[2,3-b]pyridine-2-carboxamide and pyridine-4-boronic acid, and the product was obtained as an off-white solid.

Example 151

Compound 150: N-[4-chloro-3-(N,N-dimethylsulfamoyl)phenyl]-5-(thiazol-2-yl)-thieno[2,3-b]pyridine-2-carboxamide Compound 150 was synthesized according to the General Experimental Procedure VII starting from 5-bromo-N-[4-chloro-3-(N,N-dimethylsulfamoyl)phenyl]thieno[2,3-b]pyridine-2-carboxamide and thiazol-2-ylboronic acid, and the product was obtained as an off-white solid.

Example 152

Compound 151: N-[4-chloro-3-(N,N-diethylsulfamoyl)phenyl]-5-(5-fluoropyridin-2-yl)-thieno[2,3-b]pyridine-2-carboxamide Compound 151 was synthesized according to the General Experimental Procedure VIII starting from 5-bromo-N-[4-chloro-3-(N,N-diethylsulfamoyl)phenyl]thieno[2,3-b]pyridine-2-carboxamide and 5-fluoropyridine-2-boronic acid pinacol ester, and the product was obtained as an off-white solid.

Example 153

Compound 152: N-[4-chloro-3-(N,N-dimethylsulfamoyl)phenyl]-5-(pyridin-2-yl)-thieno[2,3-b]pyridine-2-carboxamide Compound 152 was synthesized according to the General Experimental Procedure VII starting from 5-bromo-N-[4-chloro-3-(N,N-dimethylsulfamoyl)phenyl]thieno[2,3-b]pyridine-2-carboxamide and pyridine-2-boronic acid, and the product was obtained as an off-white solid.

Example 154

Compound 153: N-[4-chloro-3-(N,N-dimethylsulfamoyl)phenyl]-5-(3-fluoropyridin-4-yl)-thieno[2,3-b]pyridine-2-carboxamide Compound 153 was synthesized according to the General Experimental Procedure VII starting from 5-bromo-N-[4-chloro-3-(N,N-dimethylsulfamoyl)phenyl]thieno[2,3-b]pyridine-2-carboxamide and 3-fluoropyridine-4-boronic acid, and the product was obtained as an off-white solid.

Example 155

Compound 154: N-[4-chloro-3-(N,N-dimethylsulfamoyl)phenyl]-5-(5-fluoropyridin-2-yl)-thieno[2,3-b]pyridine-2-carboxamide Compound 154 was synthesized according to the General Experimental Procedure VIII starting from 5-bromo-N-[4-chloro-3-(N,N-dimethylsulfamoyl)phenyl]thieno[2,3-b]pyridine-2-carboxamide and 5-fluoropyridine-2-boronic acid pinacol ester, and the product was obtained as an off-white solid.

The characterization data of the compounds are summarized in Table 3.

TABLE 3

| No. | MS (ESI) m/z | $^1$H NMR (400 MHz) |
|---|---|---|
| 1 | 309 [M + H]$^+$ | δ 10.64 (s, 1H), 9.11-9.07 (m, 2H), 8.76 (d, J = 1.5 Hz, 1H), 8.34 (dd, J = 8.7, 1.8 Hz, 1H), 8.25 (d, J = 8.7 Hz, 1H), 6.19 (s, 1H), 3.69 (s, 3H), 1.25 (s, 9H). |
| 2 | 315.2 [M + H]$^+$ | δ 10.64 (s, 1H), 8.70 (dd, J = 4.6, 1.6 Hz, 1H), 8.46 (dd, J = 8.1, 1.6 Hz, 1H), 8.30 (s, 1H), 7.55 (dd, J = 8.1, 4.6 Hz, 1H), 6.16 (s, 1H), 3.66 (s, 3H), 1.24 (s, 9H). |

TABLE 3-continued

| No. | MS (ESI) m/z | ¹H NMR (400 MHz) |
|---|---|---|
| 3 | 310.1 [M + H]⁺ | δ 10.73 (s, 1H), 9.44 (d, J = 2.0 Hz, 1H), 9.14 (dd, J = 4.1, 1.5 Hz, 1H), 9.02 (s, 1H), 8.55 (d, J = 8.5 Hz, 1H), 7.93 (dd, J = 8.6, 4.1 Hz, 1H), 6.22 (s, 1H), 3.70 (s, 3H), 1.25 (s, 9H). |
| 4 | 310.2 [M + H]⁺ | δ 10.84 (s, 1H), 9.25 (dd, J = 4.2, 2.0 Hz, 1H), 8.76 (d, J = 8.4 Hz, 1H), 8.63 (dd, J = 8.2, 1.9 Hz, 1H), 8.32 (d, J = 8.3 Hz, 1H), 7.79 (dd, J = 8.2, 4.2 Hz, 1H), 6.22 (s, 1H), 3.70 (s, 3H), 1.25 (s, 9H). |
| 5 | 339.1 [M + H]⁺ | δ 10.54 (s, 1H), 8.86 (d, J = 5.2 Hz, 1H), 8.61 (s, 1H), 8.26 (d, J = 8.7 Hz, 1H), 8.05 (dd, J = 8.7, 1.6 Hz, 1H), 7.15 (d, J = 5.2 Hz, 1H), 6.17 (s, 1H), 4.09 (s, 3H), 3.67 (s, 3H), 1.25 (s, 9H). |
| 6 | 392.0 [M + H]⁺ | δ 10.69 (s, 1H), 8.87 (d, J = 5.2 Hz, 1H), 8.62 (d, J = 1.6 Hz, 1H), 8.27 (d, J = 8.7 Hz, 1H), 8.07 (dd, J = 8.7, 1.8 Hz, 1H), 7.95-7.88 (m, 2H), 7.46 (t, J = 7.8 Hz, 1H), 7.19-7.13 (m, 2H), 4.09 (s, 3H), 3.63 (bs, 6H), 3.40 (bs, 2H). |
| 7 | 363.9 [M + H]⁺ | δ 10.38 (s, 1H), 8.85 (d, J = 5.2 Hz, 1H), 8.58 (s, 1H), 8.24 (d, J = 8.7 Hz, 1H), 8.06 (dd, J = 8.7, 1.5 Hz, 1H), 7.70 (d, J = 9.0 Hz, 2H), 7.13 (d, J = 5.2 Hz, 1H), 6.96 (d, J = 9.0 Hz, 2H), 4.08 (s, 3H), 3.75 (t, J = 4.7 Hz, 4H), 3.08 (t, J = 4.7 Hz, 4H). |
| 8 | 391.2 [M + H]⁺ | δ 8.81 (d, J = 5.2 Hz, 1H), 8.44 (d, J = 1.3 Hz, 1H), 8.30 (d, J = 8.7 Hz, 1H), 8.09-8.01 (m, 2H), 7.64-7.54 (m, 2H), 7.01-6.93 (m, 2H), 6.81 (d, J = 5.2 Hz, 1H), 4.08 (s, 3H), 3.22 (t, J = 5.0 Hz, 4H), 2.63 (t, J = 5.0 Hz, 4H), 2.49 (q, J = 7.2 Hz, 2H), 1.14 (t, J = 7.2 Hz, 3H). |
| 9 | 311.1 [M + H]⁺ | δ 10.79 (bs, 1H), 9.60 (d, J = 2.4 Hz, 1H), 9.26 (d, J = 1.8 Hz, 1H), 9.20 (d, J = 1.8 Hz, 1H), 9.13 (d, J = 2.4 Hz, 1H), 6.23 (s, 1H), 3.71 (s, 3H), 1.25 (s, 9H). |
| 10 | 480.3 [M + H]⁺ | δ 9.04 (dd, J = 4.4, 1.6 Hz, 1H), 8.53 (s, 1H), 8.48 (dd, J = 8.4, 0.8 Hz, 1H), 8.21 (d, J = 8.4, 1H) 8.13 (m, 2H), 7.92 (d, J =8.4 Hz, 1H), 7.74 (dd, J = 8.4, 1.6 Hz, 1H), 7.67 (dd, J = 8.4, 4.4 Hz, 1H), 4.06 (s, 3H), 3.33 (m, 2H), 3.32 (m, 4 H), 3.19 (s, 3H), 2.68 (m, 2H), 2.58 (m, 4H), 1.69 (quint, J = 5.6 Hz, 2H). |
| 11 | 480.1 [M + H]⁺ | δ 13.45 (br s, 1H), 8.95 (dd, J = 4.0, 1.6 Hz, 1H), 8.496 (s, 1H), 8.37 (d, J = 7.6 Hz, 1H), 8.11 (br. s, 1H), 8.00 (s, 1H), 7.78 (br. s, 1H), 7.66 (br s, 1H), 7.60 (dd, J = 8.4, 4.4 Hz, 1H), 3.35 (m, 2H), 3.32 (m, 4 H), 3.188 (s, 3H), 2.83 (s, 3H), 2.69 (m, 2H), 2.60 (m, 4H), 1.71 (quint, J = 5.2 Hz, 2H). |
| 12 | 423.3 [M + H]⁺ | δ 13.73 (br s, 1H), 9.83 (d, J = 2.4 Hz, 1H), 9.16 (d, J = 1.2 Hz, 1H), 9.13 (dd, J = 4.0, 1.6 Hz, 1H), 8.53 (d, J = 8.0 Hz, 1H), 8.08 (s, 1H), 7.88 (m, 2H), 7.67 (dd, J = 8.4, 1.6 Hz, 1H), 3.33 (m, 4H), 2.53 (m, 2H), 2, 46 (m, 2H), 2.21 (s, 3H), 1.71 (quint, J = 5.2 Hz, 2H). |
| 13 | 481.1 [M + H]⁺ | δ 9.50 (d, J = 2.0 Hz, 1H), 9.15 (dd, J = 4.0, 1.6 Hz, 1H), 8.96 (dd, J = 2.0, 0.8 Hz, 1H), 8.57 (dq, J = 8.4, 0.8 Hz, 1H), 8.17 (d, J = 1.2 Hz, 1H), 7.96 (d, J = 8.4 Hz, 1H), 7.93 (dd, J = 8.8, 4.4 Hz, 1H), 7.77 (dd, J = 8.8, 1.6 Hz, 1H), 4.10 (s, 3H), 3.31 (m, 6H), 3.19 (s, 3H), 2.68 (m, 2H), 2.58 (m, 4H), 1.69 (quint, J = 5.2 Hz, 2H). |
| 14 | 467.34 [M + H]⁺ | δ 9.82 (d, J = 2.0 Hz, 1H), 9.15 (dd, J = 1.2 Hz, 1H), 9.12 (dd, J = 4.0, 1.6 Hz, 1H), 8.52 (dd, J = 8.4, 0.8 Hz, 1H), 8.07 (d, J = 1.2 Hz, 1H), 7.87 (m, 2H), 7.65 (dd, J = 8.4, 1.6 Hz, 1H), 3.32 (m, 6H), 3.18 (s, 3H), 2.68 (m, 2H), 2.58 (m, 4H), 1.69 (quint, J = 5.2 Hz, 2H). |
| 15 | 380.33 [M + H]⁺ | δ 10.725 (s, 1H), 9.44 (d, J = 2.4 Hz, 1H), 9.13 (dd, J = 4.4, 1.6 Hz, 1H), 9.01 (d, J = 1.6 Hz, 1H), 8.53 (d, J = 8.0 Hz, 1H), 7.91 (dd, J = 8.4, 4.0 Hz, 1H), 7.75 (dd, J = 14.8, 2.4 Hz, 1H), 7.52 (dd, J = 8.8, 1.6 Hz, 1H), 7.07 (t, J = 9.6 Hz, 1H), 3.01 (t, J = 4.4 Hz, 4H), 2.50 (t, J =4.4 Hz, 4H), 2.38 (q, J = 7.2 Hz, 2H), 1.03 (t, J = 7.2 Hz, 3H). |
| 16 | 456.0 [M + H]⁺ | δ 13.45 (br s, 1H), 9.05 (dd, J = 4.4, 1.6 Hz, 1H), 8.56 (s, 1H), 8.48 (dd, J = 8.4, 0.8 Hz, 1H), 8.42 (s, 1H), 8.15 (br. s, 1H), 7.81 (br. s, 1H), 7.71 (dd, J = 8.4, 4.4 Hz, 1H), 7.69 (br. s, 1H), 3.32 (m, 4 H), 2.55 (m, 2H), 2.23 (s, 3H), 1.73 (quint, J = 5.2 Hz, 2H). |
| 17 | 363.1 [M + H]⁺ | δ 10.89 (s, 1H), 9.04 (dd, J = 4.3, 1.7 Hz, 1H), 8.46 (dd, J = 8.1 Hz, 1H), 8.34 (s, 1H), 8.33 (s, 1H), 7.85-7.79 (m, 2H), 7.70 (dd, J = 8.3, 4.2 Hz, 1H), 7.41 (t, J = 7.6 Hz, 2H), 7.35-7.28 (m, 1H), 6.85 (s, 1H), 3.84 (s, 3H). |
| 18 | 405.1 [M + H]⁺ | δ 10.69 (s, 1H), 9.00 (dd, J = 4.2, 1.6 Hz, 1H), 8.41 (d, J = 8.3 Hz, 1H), 8.26 (s, 1H), 8.10 (s, 1H), 7.67 (dd, J = 8.4, 4.2 Hz, 1H), 7.60-7.57 (m, 2H), 7.54-7.49 (m, 2H), 7.43-7.37 (m, 1H), 6.52 (s, 1H), 1.33 (s, 9H). |
| 19 | 344.4 [M + H]⁺ and 340.96 [M − H] | δ 10.70 (s, 1H), 9.02 (dd, J = 4.2, 1.7 Hz, 1H), 8.44 (dd, J = 8.5, 1.1 Hz, 1H), 8.31 (s, 1H), 8.28 (s, 1H), 7.68 (dd, J = 8.4, 4.2 Hz, 1H), 6.26 (s, 1H), 3.71 (s, 3H), 1.25 (s, 9H). |
| 20 | 474.25 [M + H]⁺ | δ 13.52 (bs, 1H), 9.04 (dd, J = 4.2, 1.6 Hz, 1H), 8.54 (s, 1H), 8.48 (d, J = 8.0 Hz, 1H), 8.41 (s, 1H), 8.09 (d, J =5.9 Hz, 1H), 7.76 (d, J = 10.6 Hz, 1H), 7.71 (dd, J =8.4, 4.2 Hz, 1H), 3.44-3.42 (m, 2H), 3.38 (t, J = 6.2 Hz, 3H), 2.57-2.55 (m, 2H), 2.54-2.50 (m, 2H), 2.24 (s, 3H), 1.78 (quint, J = 5.7 Hz, 2H). |
| 21 | 518.38 [M + H]⁺ | δ 13.53 (bs, 1H), 9.04 (dd, J = 4.2, 1.7 Hz, 1H), 8.54 (s, 1H), 8.48 (dd, J = 8.5, 0.9 Hz, 1H), 8.42 (s, 1H), 8.09 (bs, 1H), 7.73 (bs, 1H), 7.71 (dd, J = 8.3, 4.2 Hz, 1H), 3.42-3.33 (m, 6H), 3.20 (s, 3H), 2.73-2.71 (m, 2H), 2.69-2.64 (m, 2H), 2.62 (t, J = 5.9 Hz, 2H), 1.75 (quint, J = 5.7 Hz, 2H). |
| 22 | 413.0 [M + H]⁺ | δ 10.72 (s, 1H), 9.01 (dd, J = 4.2, 1.7 Hz, 1H), 8.44 (dd, J = 8.5, 1.0 Hz, 1H), 8.29 (s, 1H), 8.21 (s, 1H), 7.69-7.64 (m, 2H), 7.39 (d, J = 8.7, 1.9 Hz, 1H), 7.05 (t, J = 9.3 Hz, 1H), 2.99 (t, J = 4.6 Hz, 4H), 2.57-2.47 (m, 4H), 2.38 (q, J = 7.2 Hz, 2H), 1.03 (t, J = 7.2 Hz, 3H). |

TABLE 3-continued

| No. | MS (ESI) m/z | ¹H NMR (400 MHz) |
|---|---|---|
| 23 | 410.4 [M + H]⁺ | δ 11.08 (s, 1H), 9.17 (d, J = 2.4 Hz, 1H), 8.97 (d, J = 2.8 Hz, 1H), 8.77 (s, 1H), 8.56 (dd, J = 8.1, 2.4 Hz, 1H), 8.11 (dd, J = 8.6, 1.7 Hz, 1H), 8.08 (d, J = 8.4 Hz, 1H), 7.96 (d, J = 8.6 Hz, 1H), 7.81 (d, J = 2.8 Hz, 1H), 7.54-7.49 (m, 2H), 7.33-7.24 (m, 3H). |
| 24 | 411.4 [M + H]⁺ | δ 9.09 (d, J = 2.4 Hz, 1H), 8.94 (d, J = 2.8 Hz, 1H), 8.69 (d, J = 1.8 Hz, 1H), 8.57-8.53 (m, 2H), 8.48 (dd, J = 4.7, 1.1 Hz, 1H), 8.13 (dd, J = 8.6, 1.8 Hz, 1H), 7.99 (d, J = 8.5 Hz, 1H), 7.86 (s, 1H), 7.85 (d, J = 6.8 Hz, 1H), 7.72 (ddd, J = 8.4, 2.8, 1.3 Hz, 1H), 7.57 (ddd, J = 8.4, 4.8, 0.6 Hz, 1H). |
| 25 | 343.9 [M + H]⁺ | δ 10.71 (s, 1H), 9.02 (dd, J = 4.2, 1.7 Hz, 1H), 8.44 (d, J = 8.1 Hz, 1H), 8.30 (s, 1H), 8.29 (s, 1H), 7.68 (dd, J = 8.3, 4.2 Hz, 1H), 6.19 (s, 1H), 3.70 (s, 3H), 2.36 (d, J = 7.1 Hz, 2H), 1.87 (septet, J = 6.7 Hz, 1H), 0.92 (s, 3H), 0.90 (s, 3H). |
| 26 | 419.9 [M + H]⁺ | δ 10.88 (s, 1H), 9.03 (dd, J = 4.2, 1.7 Hz, 1H), 8.46 (d, J = 8.3 Hz, 1H), 8.34 (s, 1H), 8.33 (s, 1H), 7.74-7.72 (m, 2H), 7.69 (dd, J = 8.4, 4.3 Hz, 1H), 7.43 (d, J = 8.5 Hz, 2H), 6.81 (s, 1H), 3.83 (s, 3H), 1.31 (s, 9H). |
| 27 | 355.24 [M + H]⁺ | δ 11.14 (s, 1H), 9.03 (dd, J = 4.2, 1.7 Hz, 1H), 8.45 (d, J = 8.3 Hz, 1H), 8.37 (s, 1H), 8.33 (s, 1H), 7.70 (dd, J = 8.3, 4.2 Hz, 1H), 6.86 (s, 1H), 3.89 (s, 3H). |
| 28 | 393.0 [M + H]⁺ and 391.0 [M − H] | δ 10.89 (s, 1H), 9.04 (dd, J = 4.2, 1.7 Hz, 1H), 8.46 (dd, J = 8.3, 1.3 Hz, 1H), 8.34(s, 1H), 8.33 (s, 1H), 7.70 (dd, J = 8.4, 4.2 Hz, 1H), 7.39 (dt, J = 7.6, 1.2 Hz, 1H), 7.35-7.30 (m, 2H), 6.89-6.86 (m, 1H), 6.87 (s, 1H), 3.84 (s, 3H), 3.81 (s, 3H). |
| 29 | 381.0 [M + H]⁺ and 379.0 [M − H] | δ 10.94 (s, 1H), 9.04 (dd, J = 4.2, 1.7 Hz, 1H), 8.46 (d, J = 8.3 Hz, 1H), 8.37 (s, 1H), 8.33 (s, 1H), 7.96 (td, J = 7.8, 1.8 Hz, 1H), 7.70 (dd, J = 8.4, 4.2 Hz, 1H), 7.42-7.33 (m, J = 5.4, 1.7 Hz, 1H), 7.33-7.25 (m, 2H), 6.81 (d, J = 4.1 Hz, 1H), 3.87 (s, 3H). |
| 30 | 393.1 [M + H]⁺ and 391.0 [M − H] | δ 10.82 (s, 1H), 9.04 (dd, J = 4.2, 1.7 Hz, 1H), 8.45 (dd, J = 8.4, 1.4 Hz, 1H), 8.35 (s, 1H), 8.33 (s, 1H), 7.88 (dd, J = 7.7, 1.8 Hz, 1H), 7.69 (dd, J = 8.4, 4.2 Hz, 1H), 7.31 (ddd, J = 8.3, 7.3, 1.7 Hz, 1H), 7.11 (d, J = 7.6 Hz, 1H), 6.99 (td, J = 7.5, 1.0 Hz, 1H), 6.85 (s, 1H), 3.88 (s, 3H), 3.84 (s, 3H). |
| 31 | 377.0 [M + H]⁺ and 375.0 [M − H] | δ 10.89 (s, 1H), 9.04 (dd, J = 4.2, 1.7 Hz, 1H), 8.45 (dd, J = 8.3, 1.3 Hz, 1H), 8.35 (s, 1H), 8.33 (s, 1H), 7.70 (dd, J = 8.3, 4.2 Hz, 1H), 7.59-7.55 (m, 1H), 7.29-7.22 (m, 3H), 6.66 (s, 1H), 3.85 (s, 3H), 2.49 (s, 3H). |
| 32 | 418.24 [M + H]⁺ | δ 11.04 (s, 1H), 9.03 (dd, J = 4.2, 1.7 Hz, 1H), 8.44 (d, J = 8.2 Hz, 1H), 8.31-8.29 (m, 3H), 7.96 (d, J = 8.0 Hz, 1H), 7.69 (dd, J = 8.4, 4.2 Hz, 1H), 7.62 (t, J = 7.9 Hz, 1H), 7.55 (dt, J = 8.0, 1.4 Hz, 1H), 3.19 (q, J = 7.1 Hz, 4H), 1.08 (t, J = 7.1 Hz, 6H). |
| 33 | 436.27 [M + H]⁺ | δ 11.03 (s, 1H), 9.02 (dd, J = 4.2, 1.7 Hz, 1H), 8.44 (dd, J = 8.5, 1.1 Hz, 1H), 8.33 (dd, J = 6.4, 2.7 Hz, 1H), 8.32-8.30 (m, 2H), 7.99 (ddd, J = 8.9, 4.2, 2.8 Hz, 1H), 7.69 (dd, J = 8.4, 4.2 Hz, 1H), 7.50 (dd, J = 10.1, 9.1 Hz, 1H), 3.29 (dd, J = 7.1 Hz, 4H), 1.09 (t, J = 7.1 Hz, 6H). |
| 34 | 450.0 [M + H]⁺ | δ 11.13 (s, 1H), 9.03 (dd, J = 4.2, 1.7 Hz, 1H), 8.45 (dd, J = 8.5, 1.1 Hz, 1H), 8.45 (d, J = 2.6 Hz, 1H), 8.32 (s, 1H), 8.31 (s, 1H), 8.00 (dd, J = 8.7, 2.6 Hz, 1H), 7.70 (d, J = 8.7 Hz, 1H), 7.69 (dd, J = 8.3, 4.3 Hz, 1H), 3.34 (q, J = 7.0 Hz, 4H), 1.09 (t, J = 7.1 Hz, 6H). |
| 35 | 435.1 [M + H]⁺ | δ 10.46 (s, 1H), 9.00 (dd, J = 4.2, 1.7 Hz, 1H), 8.43 (dd, J = 8.5, 1.1 Hz, 1H), 8.27 (s, 1H), 8.17 (s, 1H), 7.66 (dd, J = 8.4, 4.2 Hz, 1H), 7.63-7.57 (m, 2H), 6.98-6.91 (m, 2H), 3.09 (t, J = 4.9 Hz, 4H), 2.55 (t, J = 4.8 Hz, 4H), 2.49-2.44 (m, 1H), 1.85-1.77 (m, 2H), 1.67-1.57 (m, 2H), 1.56-1.44 (m, 2H), 1.42-1.28 (m, 2H). |
| 36 | 411.0 [M + H]⁺ and 409.0 [M − H] | δ 10.91 (s, 1H), 9.02 (dd, J = 4.2, 1.7 Hz, 1H), 8.45 (d, J = 8.5 Hz, 1H), 8.32 (s, 1H), 8.21 (s, 1H), 7.69 (dd, J = 8.4, 4.2 Hz, 1H), 6.50(s, 1H), 5.07 (q, J = 9.1 Hz, 2H), 1.27 (s, 9H). |
| 37 | 410.3 [M + H]⁺ and 408.0 [M − H] | δ 11.17 (s, 1H), 9.19 (d, J = 2.4 Hz, 1H), 8.83 (d, J = 5.1 Hz, 1H), 8.79 (d, J = 1.7 Hz, 1H), 8.58 (dd, J = 8.5, 2.0 Hz, 1H), 8.49 (d, J = 8.8 Hz, 1H), 8.20 (dd, J = 8.7, 1.8 Hz, 1H), 7.97 (d, J = 8.4 Hz, 1H), 7.60-7.55 (m, 2H), 7.41-7.35 (m, 3H), 6.72 (d, J = 5.2 Hz, 1H). |
| 38 | 380.9 [M + H]⁺ and 379.0 [M − H] | δ 8.99 (dd, J = 4.3, 1.7 Hz, 1H), 8.43 (d, J =8.3 Hz, 1H), 8.32 (s, 1H), 8.22 (s, 1H), 7.68 (dd, J = 8.4, 4.3 Hz, 1H), 7.62 (dt, J = 7.8, 1.1 Hz, 1H), 7.54 (ddd, J = 10.4, 2.5, 1.5 Hz, 1H), 7.43 (dt, J = 8.0, 6.0 Hz, 1H), 7.08-7.03 (m, 1H), 6.85 (s, 1H), 3.92 (s, 3H). |
| 39 | 400.8 [M + H]⁺ and 396.9 [M − H] | δ 10.95 (s, 1H), 9.11 (d, J = 2.3 Hz, 1H), 8.88 (dd, J = 2.3, 0.7 Hz, 1H), 8.73 (s, 1H), 8.20-8.15 (m, 2H), 6.80 (s, 1H), 3.87 (s, 3H). |
| 40 | 397.0 [M + H]⁺ and 395.0 [M − H] | δ 10.94 (s, 1H), 9.42 (d, J = 2.3 Hz, 1H), 8.84-8.74 (m, J = 4.0 Hz, 2H), 8.23 (d, J = 8.5 Hz, 1H), 8.15 (dd, J = 8.6, 1.4 Hz, 1H), 7.96 (d, J = 7.3 Hz, 2H), 7.59 (t, J = 7.5 Hz, 2H), 7.51 (t, J = 7.3 Hz, 1H), 6.81 (s, 1H), 3.89 (s, 3H). |
| 41 | 411.0 [M + H]⁺ and 409.0 [M − H] | δ 10.94 (s, 1H), 9.40 (d, J = 2.3 Hz, 1H), 8.82-8.77 (m, 2H), 8.22 (d, J = 8.5 Hz, 1H), 8.16-8.14 (m, 1H), 7.78 (s, 1H), 7.75 (d, J = 8.1 Hz, 1H), 7.47 (t, J = 7.6 Hz, 1H), 7.32 (d, J = 7.8 Hz, 1H), 6.81 (s, 1H), 3.89 (s, 3H), 2.44 (s, 3H). |
| 42 | 332.8 [M + H]⁺ and 330.9 [M − H] | δ 10.67 (s, 1H), 9.09 (d, J = 2.3 Hz, 1H), 8.87 (d, J =2.0 Hz, 1H), 8.71 (s, 1H), 8.17 (dd, J = 8.5, 1.5 Hz, 1H), 8.12 (d, J = 8.5 Hz, 1H), 7.42 (d, J = 1.9 Hz, 1H), 6.30 (d, J = 1.9 Hz, 1H), 3.75 (s, 3H). |

TABLE 3-continued

| No. | MS (ESI) m/z | $^1$H NMR (400 MHz) |
|---|---|---|
| 43 | 388.9 [M + H]$^+$ and 387.0 [M − H]$^-$ | δ 10.58 (s, 1H), 9.09 (d, J = 2.3 Hz, 1H), 8.86 (dd, J = 2.3, 0.7 Hz, 1H), 8.68 (s, 1H), 8.16-8.11 (m, 2H), 6.18 (s, 1H), 3.67 (s, 3H), 1.25 (s, 9H). |
| 44 | 431.29 [M + H]$^+$ | δ 10.94(s, 1H), 9.03 (dd, J = 4.2, 1.7 Hz, 1H), 8.45 (d, J = 7.7 Hz, 1H), 8.37 (s, 1H), 8.32 (s, 1H), 7.84 (d, J = 7.9 Hz, 1H), 7.75-7.68 (m, 3H), 7.63-7.57 (m, 1H), 6.64 (s, 1H), 3.86 (s, 3H). |
| 45 | 329.0 [M + H]$^+$ and 327.0 [M − H]$^-$ | δ 10.67 (bs, 1H), 9.39 (d, J = 2.3 Hz, 1H), 8.81-8.74 (m, 2H), 8.23-8.14 (m, 2H), 8.00-7.94 (m, 2H), 7.63-7.57 (m, 2H), 7.54-7.47 (m, 1H), 7.41 (d, J = 1.8 Hz, 1H), 6.32 (d, J = 1.9 Hz, 1H), 3.76(s, 3H). |
| 46 | 385.0 [M + H]$^+$ and 383.1 [M − H]$^-$ | δ 10.58 (s, 1H), 9.39 (d, J = 2.2 Hz, 1H), 8.80-8.77 (m, 1H), 8.72 (s, 1H), 8.19 (d, J = 8.4 Hz, 1H), 8.15 (d, J = 8.7 Hz, 1H), 7.96 (s, 1H), 7.94 (s, 1H), 7.59 (t, J = 7.5 Hz, 2H), 7.54-7.47 (m, 1H), 6.20 (s, 1H), 3.69 (s, 3H), 1.25 (s, 9H). |
| 47 | 457.0 [M + H]$^+$ | δ 10.82 (s, 1H), 9.03 (dd, J = 4.2, 1.7 Hz, 1H), 8.45 (d, J = 8.4 Hz, 1H), 8.33 (s, 1H), 8.32 (s, 1H), 7.84 (d, J = 8.0 Hz, 1H), 7.74 (d, J = 4.0 Hz, 2H), 7.69 (dd, J = 8.0, 4.2 Hz, 1H), 7.65-7.55 (m, 1H), 6.62 (s, 1H), 4.74 (quintet, J = 6.5 Hz, 1H), 1.44 (d, J = 6.5 Hz, 6H). |
| 48 | 431.31 [M + H]$^+$ | δ 10.94 (s, 1H), 9.04 (dd, J = 4.2, 1.6 Hz, 1H), 8.46 (d, J = 8.5 Hz, 1H), 8.35 (s, 1H), 8.34 (s, 1H), 8.19-8.09 (m, 2H), 7.70 (dd, J = 8.4, 4.2 Hz, 1H), 7.67-7.64 (m, 2H), 7.03 (s, 1H), 3.88 (s, 3H). |
| 49 | 394.9 [M + H]$^+$ | δ 10.93 (s, 1H), 9.04 (dd, J = 4.2, 1.7 Hz, 1H), 8.46 (d, J = 8.4 Hz, 1H), 8.34 (s, 1H), 8.33 (s, 1H), 7.85 (t, J = 1.7 Hz, 1H), 7.79 (dt, J = 7.8, 1.3 Hz, 1H), 7.70 (dd, J = 8.4, 4.2 Hz, 1H), 7.45 (t, J = 7.8 Hz, 1H), 7.37 (ddd, J = 8.0, 2.1, 1.0 Hz, 1H), 6.95 (s, 1H), 3.86 (s, 3H). |
| 50 | 393.0 [M + H]$^+$ | δ 10.93 (s, 1H), 9.03 (dd, J = 4.2, 1.6 Hz, 1H), 8.45 (d, J = 8.2 Hz, 1H), 8.34 (s, 1H), 8.33 (s, 1H), 7.69 (dd, J = 8.3, 4.2 Hz, 1H), 7.38 (dd, J = 10.4, 2.8 Hz, 1H), 7.31 (dd, J = 8.3, 6.1 Hz, 1H), 7.08 (dt, J = 8.4, 2.8 Hz, 1H), 6.74 (s, 1H), 3.86 (s, 3H), 2.47 (s, 3H). |
| 51 | 411.38 [M + H]$^+$ | δ 10.93 (s, 1H), 9.03 (dd, J = 4.2, 1.7 Hz, 1H), 8.45 (d, J = 8.3 Hz, 1H), 8.34 (s, 1H), 8.32 (s, 1H), 7.69 (dd, J = 8.4, 4.2 Hz, 1H), 7.61 (d, J = 1.8 Hz, 1H), 7.36-7.26 (m, 2H), 6.75 (s, 1H), 3.86 (s, 3H), 2.48 (s, 3H). |
| 52 | 410.95 [M + H]$^+$ and 409.00 [M − H]$^-$ | δ 10.94 (s, 1H), 9.06 (d, J = 2.2 Hz, 1H), 8.79 (s, 1H), 8.50 (d, J = 1.9 Hz, 1H), 8.21 (d, J = 8.4 Hz, 1H), 8.16 (dd, J = 8.5, 1.7 Hz, 1H), 7.46-7.35 (m, 4H), 6.82 (s, 1H), 3.88 (s, 3H), 2.33 (s, 3H). |
| 53 | 464.90 [M + H]$^+$ and 463.00 [M − H]$^-$ | δ 10.96 (s, 1H), 8.99 (d, J = 1.8 Hz, 1H), 8.80 (s, 1H), 8.50 (d, J = 2.1 Hz, 1H), 8.23 (d, J = 8.5 Hz, 1H), 8.18 (dd, J = 8.5, 1.7 Hz, 1H), 7.96 (d, J = 7.6 Hz, 1H), 7.85 (t, J = 7.3 Hz, 1H), 7.75 (t, J = 7.6 Hz, 1H), 7.65 (d, J = 7.5 Hz, 1H), 6.82 (s, 1H), 3.89 (s, 3H). |
| 54 | 414.90 [M + H]$^+$ and 412.95 [M − H]$^-$ | δ 10.96 (s, 1H), 9.24 (t, J = 2.1 Hz, 1H), 8.79 (s, 1H), 8.71 (s, 1H), 8.25 (d, J = 8.5 Hz, 1H), 8.17 (dd, J = 8.5, 1.7 Hz, 1H), 7.81 (td, J = 7.9, 1.7 Hz, 1H), 7.60-7.54 (m, 1H), 7.48-7.41 (m, 1H), 7.44 (d, J = 8.0 Hz, 1H), 6.82 (s, 1H), 3.89 (s, 3H). |
| 55 | 464.90 [M + H]$^+$ and 463.00 [M − H]$^-$ | δ 10.95 (s, 1H), 9.47 (d, J = 2.4 Hz, 1H), 8.93 (d, J = 2.4 Hz, 1H), 8.79 (s, 1H), 8.31-8.28 (m, 2H), 8.24 (d, J = 8.4 Hz, 1H), 8.18 (dd, J = 8.5, 1.7 Hz, 1H), 7.91-7.78 (m, 2H), 6.82 (s, 1H), 3.89 (s, 3H). |
| 56 | 463.0 [M − H]$^-$ | δ 11.01 (s, 1H), 9.04 (dd, J = 4.2, 1.7 Hz, 1H), 8.46 (d, J = 8.4 Hz, 1H), 8.38 (s, 1H), 8.33 (s, 1H), 8.15 (d, J = 2.2 Hz, 1H), 7.82 (d, J = 8.4 Hz, 1H), 7.74 (dd, J = 8.5, 2.3 Hz, 1H), 7.70 (dd, J = 8.4, 4.2 Hz, 1H), 7.07 (s, 1H), 3.91 (s, 3H). |
| 57 | 393.0 [M − H]$^-$ | δ 10.90 (bs, 1H), 9.02 (d, J = 3.0 Hz, 1H), 8.44 (d, J = 8.4 Hz, 1H), 8.31 (s, 1H), 8.30 (s, 1H), 7.68 (dd, J = 8.2, 4.3 Hz, 1H), 7.58 (dd, J = 8.3, 6.5 Hz, 1H), 7.13 (dd, J = 10.3, 2.4 Hz, 1H), 7.06 (dt, J = 8.4, 2.4 Hz, 1H), 6.65 (s, 1H), 3.82 (s, 3H), 2.50 (s, 3H). |
| 58 | 409.0 [M − H]$^-$ | δ 10.92 (s, 1H), 9.04 (dd, J = 4.2, 1.7 Hz, 1H), 8.46 (d, J = 8.4 Hz, 1H), 8.35 (s, 1H), 8.33 (s, 1H), 7.70 (dd, J = 8.4, 4.2 Hz, 1H), 7.60 (d, J = 8.3 Hz, 1H), 7.38 (d, J = 2.0 Hz, 1H), 7.30 (dd, J = 8.3, 2.0 Hz, 1H), 6.70 (s, 1H), 3.85 (s, 3H), 2.50 (s, 3H). |
| 59 | 442.99 [M − H]$^-$ | δ 10.94 (s, 1H), 9.04 (dd, J = 4.2, 1.6 Hz, 1H), 8.46 (d, J = 8.4 Hz, 1H), 8.35 (s, 1H), 8.33 (s, 1H), 7.89 (d, J = 1.6 Hz, 1H), 7.70 (dd, J = 8.4, 4.2 Hz, 1H), 7.60 (dd, J = 8.0, 1.6 Hz, 1H), 7.53 (d, J = 8.0 Hz, 1H), 6.81 (s, 1H), 3.88 (s, 3H), 2.59 (s, 3H). |
| 60 | 414.90 [M + H]$^+$ and 413.00 [M − H]$^-$ | δ 10.95 (s, 1H), 9.44 (d, J = 2.3 Hz, 1H), 8.86 (d, J = 2.3 Hz, 1H), 8.78 (s, 1H), 8.22 (d, J = 8.5 Hz, 1H), 8.16 (dd, J = 8.5, 1.7 Hz, 1H), 7.87 (dt, J = 10.2, 2.1 Hz, 1H), 7.83 (d, J = 7.8 Hz, 1H), 7.63 (td, J = 8.0, 6.2 Hz, 1H), 7.34 (dt, J = 8.9, 2.5 Hz, 1H), 6.81 (s, 1H), 3.89 (s, 3H). |
| 61 | 414.90 [M + H]$^+$ and 412.95 [M − H]$^-$ | δ 10.94 (s, 1H), 9.40 (d, J = 2.3 Hz, 1H), 8.81-8.75 (m, 2H), 8.21 (d, J = 8.5 Hz, 1H), 8.15 (dd, J = 8.5, 1.7 Hz, 1H), 8.04-7.99 (m, 2H), 7.46-7.40 (m, 2H), 6.81 (s, 1H), 3.88 (s, 3H). |
| 62 | 410.95 [M + H]$^+$ and 409.00 [M − H]$^-$ | δ 10.93 (s, 1H), 9.40 (d, J = 2.3 Hz, 1H), 8.80-8.72 (m, 2H), 8.21 (d, J = 8.5 Hz, 1H), 8.14 (dd, J = 8.5, 1.7 Hz, 1H), 7.86 (d, J = 8.2 Hz, 2H), 7.40 (d, J = 7.9 Hz, 2H), 6.81 (s, 1H), 3.88 (s, 3H), 2.40 (s, 3H). |
| 63 | 458.80 [M + H]$^+$ and 456.95 [M − H]$^-$ | δ 10.60 (s, 1H), 9.08 (d, J = 2.3 Hz, 1H), 8.85 (dd, J = 2.3, 0.7 Hz, 1H), 8.68-8.65 (m, 1H), 8.15 (dd, J = 8.6, 1.7 Hz, 1H), 8.11 (d, J = 8.4 Hz, 1H), 7.74 (dd, J = 15.0, 2.4 Hz, 1H), 7.52 (dd, J = 8.7, 1.7 Hz, 1H), 7.05 (dd, J = 9.8, 9.0 Hz, 1H), 3.00 (t, J = 4.5 Hz, 4H), 2.56-2.51 (m, 4H), 2.38 (q, J = 7.2 Hz, 2H), 1.03 (t, J = 7.2 Hz, 3H). |

TABLE 3-continued

| No. | MS (ESI) m/z | ¹H NMR (400 MHz) |
|---|---|---|
| 64 | 455.00 [M + H]⁺ | δ 10.60 (s, 1H), 9.39 (d, J = 2.4 Hz, 1H), 8.76 (d, J = 2.3 Hz, 1H), 8.73-8.68 (m, 1H), 8.19 (d, J = 8.4 Hz, 1H), 8.14 (dd, J = 8.5, 1.7 Hz, 1H), 7.98-7.95 (m, 1H), 7.94-7.92 (m, 1H), 7.77 (dd, J = 15.0, 2.4 Hz, 1H), 7.61-7.48 (m, 4H), 7.06 (dd, J = 9.8, 9.0 Hz, 1H), 3.01 (t, J = 4.6 Hz, 4H), 2.58-2.52 (m, 4H), 2.38 (q, J = 7.2 Hz, 2H), 1.03 (t, J = 7.2 Hz, 3H). |
| 65 | 430.90 [M + H]⁺ and 428.95 [M − H] | δ 10.95 (s, 1H), 9.43 (d, J = 2.3 Hz, 1H), 8.87 (d, J = 2.4 Hz, 1H), 8.78 (s, 1H), 8.22 (d, J = 8.5 Hz, 1H), 8.16 (dd, J = 8.5, 1.7 Hz, 1H), 8.07 (d, J = 1.8 Hz, 1H), 7.95 (dt, J = 7.8, 1.5 Hz, 1H), 7.62 (t, J = 7.8 Hz, 1H), 7.57 (ddd, J = 8.0, 2.0, 1.2 Hz, 1H), 6.81 (s, 1H), 3.89 (s, 3H). |
| 66 | 430.90 [M + H]⁺ and 428.95 [M − H] | δ 10.96 (s, 1H), 9.12 (d, J = 2.2 Hz, 1H), 8.79 (s, 1H), 8.60 (d, J = 2.2 Hz, 1H), 8.24 (d, J = 8.4 Hz, 1H), 8.18 (dd, J = 8.5, 1.7 Hz, 1H), 7.72-7.64 (m, 2H), 7.59-7.51 (m, 2H), 6.82 (s, 1H), 3.89 (s, 3H). |
| 67 | 402.85 [M + H]⁺ and 400.95 [M − H] | δ 10.91 (s, 1H), 9.51 (d, J = 2.3 Hz, 1H), 8.79 (d, J = 2.0 Hz, 1H), 8.74 (s, 1H), 8.33 (dd, J = 2.8, 1.3 Hz, 1H), 8.15 (d, J = 8.4 Hz, 1H), 8.12 (dd, J = 8.5, 1.6 Hz, 1H), 7.86 (dd, J = 5.1, 1.3 Hz, 1H), 7.80 (dd, J = 5.0, 2.9 Hz, 1H), 6.80 (s, 1H), 3.88 (s, 3H). |
| 68 | 447.19 [M + H]⁺ | δ 10.97 (s, 1H), 9.03 (dd, J = 4.2, 1.7 Hz, 1H), 8.45 (d, J = 8.6 Hz, 1H), 8.37 (s, 1H), 8.32 (s, 1H), 7.92 (dd, J = 8.9, 5.6 Hz, 1H), 7.69 (dd, J = 8.3, 4.2 Hz, 1H), 7.55 (dd, J = 9.7, 2.6 Hz, 1H), 7.45 (dt, J = 8.3, 2.6 Hz, 1H), 6.71 (d, J = 0.8 Hz, 1H), 3.87 (s, 3H). |
| 69 | 397.39 [M + H]⁺ | δ 10.93 (s, 1H), 9.04 (dd, J = 4.2, 1.7 Hz, 1H), 8.46 (d, J = 8.6 Hz, 1H), 8.36 (s, 1H), 8.33 (s, 1H), 7.82 (dd, J = 7.6, 1.9 Hz, 1H), 7.69 (dd, J = 8.4, 4.2 Hz, 1H), 7.54 (dd, J = 7.5, 1.8 Hz, 1H), 7.43-7.35 (m, 2H), 6.92 (s, 1H), 3.87 (s, 3H). |
| 70 | 397.9 [M + H]⁺ | δ 11.14 (s, 1H), 9.16 (d, J = 2.4 Hz, 1H), 9.11 (d, J = 2.3 Hz, 1H), 8.88 (d, J = 2.3 Hz, 1H), 8.77-8.73 (m, 1H), 8.55 (dd, J = 8.6, 2.4 Hz, 1H), 8.19 (dd, J = 8.6, 1.7 Hz, 1H), 8.15 (d, J = 8.4 Hz, 1H), 7.96 (d, J = 8.7 Hz, 1H). |
| 71 | 394.36 [M + H]⁺ | δ 11.13 (s, 1H), 9.42 (d, J = 2.2 Hz, 1H), 9.19 (d, J = 2.0 Hz, 1H), 8.80 (s, 1H), 8.79 (d, J = 1.8 Hz, 1H), 8.58 (dd, J = 8.4, 2.0 Hz, 1H), 8.24 (d, J = 8.4 Hz, 1H), 8.18 (dd, J = 8.5, 1.4 Hz, 1H), 8.02-7.93 (m, 3H), 7.62-7.58 (m, 2H), 7.53-7.49 (m, 1H). |
| 72 | 405.23 [M + H]⁺ | δ 10.75 (s, 1H), 9.04 (dd, J = 4.2, 1.7 Hz, 1H), 8.46 (dd, J = 8.4, 1.0 Hz, 1H), 8.33 (s, 1H), 8.32 (s, 1H), 7.69 (dd, J = 8.4, 4.2 Hz, 1H), 7.62-7.55 (m, 1H), 7.31-7.21 (m, 3H), 6.63 (s, 1H), 4.72 (septet, J = 6.5 Hz, 1H), 2.51 (s, 3H), 1.45 (d, J = 6.5 Hz, 6H). |
| 73 | 402.90 [M + H]⁺ and 400.95 [M − H] | δ 10.91 (s, 1H), 9.44 (d, J = 2.3 Hz, 1H), 8.73 (s, 1H), 8.70 (d, J = 2.3 Hz, 1H), 8.20 (d, J = 8.4 Hz, 1H), 8.12 (dd, J = 8.5, 1.7 Hz, 1H), 7.92 (dd, J = 3.6, 1.1 Hz, 1H), 7.77 (dd, J = 5.1, 1.1 Hz, 1H), 7.28 (dd, J = 5.1, 3.6 Hz, 1H), 6.80 (s, 1H), 3.88 (s, 3H). |
| 74 | 403.15 [M + H]⁺ and 401.00 [M − H] | δ 10.56 (s, 1H), 9.38 (d, J = 2.3 Hz, 1H), 8.76 (d, J = 2.2 Hz, 1H), 8.72 (s, 1H), 8.19 (d, J = 8.7 Hz, 1H), 8.13 (dd, J = 8.5, 1.4 Hz, 1H), 8.07-7.98 (m, 2H), 7.50-7.41 (m, 2H), 6.19 (s, 1H), 3.69 (s, 3H), 1.26 (s, 9H). |
| 75 | 432.85 [M + H]⁺ and 430.95 [M − H] | δ 10.95 (s, 1H), 9.21 (t, J = 2.0 Hz, 1H), 8.78 (s, 1H), 8.69 (s, 1H), 8.24 (d, J = 8.6 Hz, 1H), 8.17 (dd, J = 8.5, 1.5 Hz, 1H), 7.88 (ddd, J = 15.4, 8.8, 6.6 Hz, 1H), 7.53 (ddd, J = 11.2, 9.1, 2.3 Hz, 1H), 7.34 (ddd, J = 10.6, 8.5, 2.1 Hz, 1H), 6.81 (s, 1H), 3.89 (s, 3H). |
| 76 | n/a | 1H-NMR (400 MHz, DMSO-d₆): δ 10.68 (s, 1H), 8.82 (d, J = 5.1 Hz, 1H), 8.73 (d, J = 1.0 Hz, 1H), 8.46 (d, J = 8.6 Hz, 1H), 8.17 (dd, J = 8.7, 1.6 Hz, 1H), 7.59-7.55 (m, 2H), 7.43 (d, J = 1.9 Hz, 1H), 7.41-7.34(m, 3H), 6.72(d, J = 5.1 Hz, 1H), 6.31 (d, J = 1.8 Hz, 1H), 3.76 (s, 3H). |
| 77 | 396.00 [M − H] and 397.90 [M + H]⁺ | δ 10.95 (s, 1H), 9.46 (d, J = 2.4 Hz, 1H), 9.17 (d, J = 2.0 Hz, 1H), 8.90 (d, J = 2.4 Hz, 1H), 8.79 (s, 1H), 8.70 (dd, J = 4.0, 1.5 Hz, 1H), 8.38 (dt, J = 8.8, 4.0 Hz, 1H), 8.23 (d, J = 8.0 Hz, 1H), 8.17 (dd, J = 8.8, 4.0 Hz, 1H), 7.62 (dd, J = 8.8, 4.0 Hz, 1H), 6.81 (s, 1H), 3.89 (s, 3H). |
| 78 | 396.00 [M − H] and 397.90 [M + H]⁺ | δ 10.95 (s, 1H), 9.50 (d, J = 2.4 Hz, 1H), 8.98 (d, J = 2.0 Hz, 1H), 8.79 (s, 1H), 8.77 (dd, J = 4.4, 1.6 Hz, 2H), 8.26 (d, J = 8.4 Hz, 1H), 8.19 (dd, J = 8.4, 1.6 Hz, 2H), 8.01 (dd, J = 4.4, 1.6 Hz, 2H), 6.81 (s, 1H), 3.89 (s, 3H). |
| 79 | 469.05 [M − H] and 471.00 [M + H]⁺ | δ 10.91 (s, 1H), 9.39 (d, J = 2.4 Hz, 1H), 9.75 (d, J = 2.0 Hz, 1H), 8.71 (d, J = 2.0 Hz, 1H), 8.18 (d, J = 8.4 Hz, 1H), 8.12 (d, J = 8.4, 1.6 Hz, 1H), 7.90 (dd, J = 4.4, 1.6 Hz, 2H), 7.14 (dd, J = 4.4, 1.6Hz, 2H), 6.80 (s, 1H), 4.18-4.21 (m, 2H), 3.88 (s, 3H), 3.69-3.72 (m, 2H). |
| 80 | 403.4 [M + H]⁺ | δ 9.08 (d, J = 2.4 Hz, 1H), 8.77 (d, J = 4.4 Hz, 1H), 8.56 (d, J = 1.6 Hz, 1H), 8.54 (d, J = 1.6 Hz, 1H), 8.26 (d, J = 8.4 Hz, 1H), 8.08 (dd, J = 8.4, 1.6 Hz, 1H), 7.85 (d, J = 8.4 Hz, 1H), 7.13 (d, J = 4.4 Hz, 1H), 3.99-4.01 (m, 4H). |
| 81 | 408.10 [M + H]⁺ | δ 11.1 (s, 1H), 9.15 (d, J = 2.4 Hz, 1H), 9.05 (d, J = 2.0 Hz, 1H), 8.82 (s, 1H), 8.57 (dd, J = 8.4, 2.4 Hz, 1H), 8.48 (d, J = 1.6 Hz, 1H), 8.18-8.23 (m, 2H), 7.94 (d, J = 8.4 Hz, 1H), 7.35-7.44 (m, 4H), 2.34 (s, 3H). |
| 82 | 408.21 [M + H]⁺ | δ 11.12 (s, 1H), 9.40 (d, J = 2.4 Hz, 1H), 9.18 (d, J = 2.4 Hz, 1H), 8.80 (s, 1H), 8.77 (d, J = 2.0 Hz, 1H), 8.57 (dd, J = 8.4, 2.4 Hz, 1H), 8.22 (d, J = 8.4 Hz, 1H), 8.16 (dd, J = 8.4, 1.6 Hz, 1H), 7.97 (d, J =8.4 Hz, 1H), 7.78 (s, 1H), 7.74 (d, J = 8.0 Hz, 1H), 7.47 (t, J = 7.6 Hz, 1H), 7.31 (d, J = 7.6 Hz, 1H), 2.45 (s, 3H). |

TABLE 3-continued

| No. | MS (ESI) m/z | $^1$H NMR (400 MHz) |
|---|---|---|
| 83 | 401.26 [M + H]$^+$ | δ 11.15 (s, 1H), 9.62 (d, J = 2.4 Hz, 1H), 9.18 (d, J = 2.4 Hz, 1H), 9.05 (d, J = 2.0 Hz, 1H), 8.80 (s, 1H), 8.57 (dd, J = 8.4, 2.4 Hz, 1H), 8.33 (d, J = 8.4 Hz, 1H), 8.20 (dd, J = 8.4, 1.6 Hz, 1H), 8.10 (d, J = 3.2 Hz, 1H), 8.00 (d, J = 3.2 Hz, 1H), 7.97 (d, J = 8.4 Hz, 1H). |
| 84 | 419.05 [M − H] and 421.35 [M + H]$^+$ | δ 10.59 (s, 1H), 9.19 (t, J = 2.0 Hz, 1H), 8.74 (s, 1H), 8.67 (s, 1H), 8.22 (d, J = 8.4 Hz, 1H), 8.15 (dd, J = 8.4, 2.0 Hz, 1H), 7.88 (ddd, J = 15.2, 8.8, 6.4 Hz, 1H), 7.52 (ddd, J = 11.2, 9.2, 2.4 Hz, 1H), 7.34 (ddd, J = 10.4, 8.0, 2.1 Hz, 1H), 6.19 (s, 1H), 3.69 (s, 3H), 1.26 (s, 9H). |
| 85 | 412.20 [M + H]$^+$ | δ 11.15 (s, 1H), 9.24 (t, J = 2.0 Hz, 1H), 9.19 (d, J = 2.4 Hz, 1H), 8.82 (s, 1H), 8.71 (s, 1H), 8.58 (dd, J = 8.4, 2.4 Hz, 1H), 8.26 (d, J = 8.4 Hz, 1H), 8.20 (dd, J = 8.4, 1.6 Hz, 1H), 7.97 (d, J = 8.4 Hz, 1H), 7.80 (ddd, J = 9.6, 7.6, 1.6 Hz, 1H), 7.56-7.59 (m, 1H), 7.43-7.47 (m, 2H). |
| 86 | 412.30 [M + H]$^+$ | δ 11.13 (s, 1H), 9.40 (d, J = 2.4 Hz, 1H), 9.19 (d, J = 2.4 Hz, 1H), 8.80 (s, 1H), 8.77 (d, J = 2.2 Hz, 1H), 8.58 (dd, J = 8.4, 2.1 Hz, 1H), 8.22 (d, J = 8.5 Hz, 1H), 8.18 (dd, J = 8.8, 1.6 Hz, 1H), 7.96-8.03 (m, 3H), 7.41-7.45 (m, 2H). |
| 87 | 430.18 [M + H]$^+$ | δ 11.15 (s, 1H), 9.21 (t, J = 2.4 Hz, 1H), 9.18 (d, J = 2.0 Hz, 1H), 8.82 (s, 1H), 8.69 (s, 1H), 8.58 (dd, J = 8.4, 2.4 Hz, 1H), 8.25 (d, J = 8.8 Hz, 1H), 8.20 (dd, J = 8.4, 1.6 Hz, 1H), 7.97 (d, J = 8.4 Hz, 1H), 7.88 (ddd, J = 15.2, 8.8, 6.4 Hz, 1H), 7.53 (ddd, J = 11.2, 9.2, 2.4 Hz, 1H), 7.34 (ddd, J = 10.4, 8.0, 2.1 Hz, 1H). |
| 88 | 400.15 [M + H]$^+$ | δ 11.11 (s, 1H), 9.44 (d, J = 2.4 Hz, 1H), 9.18 (d, J = 2.4 Hz, 1H), 8.76 (s, 1H), 8.58 (dd, J = 8.4, 2.4 Hz, 1H), 8.21 (d, J = 8.8 Hz, 1H), 8.15 (dd, J = 8.4, 1.6 Hz, 1H), 7.96 (d, J = 8.4 Hz, 1H), 7.91 (dd, J = 3.6, 1.2 Hz, 1H), 7.77 (dd, J = 4.8, 1.2 Hz, 1H), 7.28 (dd, J = 4.8, 3.6 Hz, 1H). |
| 89 | 400.19 [M + H]$^+$ | δ 11.11 (s, 1H), 9.51 (d, J = 2.4 Hz, 1H), 9.18 (d, J = 2.4 Hz, 1H), 8.79 (d, J = 2.4 Hz, 1H), 8.77 (s, 1H), 8.58 (dd, J = 8.4, 2.4 Hz, 1H), 8.32 (dd, J = 2.8, 1.2 Hz, 1H), 8.16 (s, 2H), 7.96 (d, J = 8.8 Hz, 1H), 7.86 (dd, J = 5.2, 1.2 Hz, 1H), 7.80 (dd, J = 5.2, 2.8 Hz, 1H). |
| 90 | 363.22 [M + H]$^+$ | δ 10.99 (s, 1H), 9.03 (d, J = 2.8 Hz, 1H), 8.44 (d, J = 8.0 Hz, 1H), 8.32 (s, 1H), 8.31 (s, 1H), 7.67-7.75 (m, 4H), 7.37 (t, J = 7.6 Hz, 1H), 7.21 (t, J = 7.6 Hz, 1H), 3.66 (s, 3H). |
| 91 | 492.31 [M + H]$^+$ | δ 10.97 (s, 1H), 9.40 (d, J = 1.6 Hz, 1H), 8.77 (s, 2H), 8.61 (d, J = 2.4 Hz, 1H), 8.16-8.22 (m, 3H), 7.95 (d, J = 7.6 Hz, 2H), 7.70 (d, J = 8.8 Hz, 1H), 7.59 (t, J = 7.6 Hz, 1H), 7.52 (t, J = 7.6 Hz, 1H), 3.36 (q, J = 6.8 Hz, 4H), 1.1 (q, J = 6.8 Hz, 6H). |
| 92 | 401.05 [M − H] and 403.40 [M + H]$^+$ | δ 9.19 (t, J = 2.4 Hz, 1H), 8.71 (s, 1H), 8.64 (s, 1H), 8.19 (m, 2H), 7.73 (dt, J = 8.4, 2.4 Hz, 1H), 7.50-7.56 (m, 1H), 7.32-7.42 (m, 2H), 6.23 (s, 1H), 3.78 (s, 3H), 1.33 (s, 9H). |
| 93 | 402.24 [M − H] and 404.18 [M + H]$^+$ | δ 10.95 (s, 1H), 9.61 (d, J = 2.4 Hz, 1H), 9.05 (d, J = 2.4 Hz, 1H), 8.77 (s, 1H), 8.32 (d, J = 8.4 Hz, 1H), 8.17 (dd, J = 8.4, 1.7 Hz, 1H), 8.10 (d, J = 3.2 Hz, 1H), 8.00 (d, J = 3.2 Hz, 1H), 6.81 (s, 1H), 3.89 (s, 3H). |
| 94 | 512.63 [M + H]$^+$ | δ 10.97 (s, 1H), 9.39 (d, J = 2.4 Hz, 1H), 8.77 (s, 1H), 8.76 (d, J = 2.0 Hz, 1H), 8.60 (d, J = 2.4 Hz, 1H), 8.15-8.21 (m, 3H), 8.01 (ddd, J = 8.8, 5.2, 2.0 Hz, 1H), 7.70 (d, J = 8.8 Hz, 1H), 7.43 (t, J = 8.8 Hz, 2H), 3.35 (q, J = 7.2 Hz, 4H), 1.1 (t, J = 7.2 Hz, 6H). |
| 95 | 437.36 [M + H]$^+$ | δ 10.76 (s, 1H), 9.39 (d, J = 2.0 Hz, 1H), 8.77 (s, 2H), 8.16-8.22 (m, 2H), 8.01 (dd, J = 8.8, 5.6 Hz, 2H), 7.56-7.59 (m, 1H), 7.43 (t, J = 8.8 Hz, 1H), 7.23-7.29 (m, 3H), 6.60 (s, 1H), 3.84 (s, 3H), 2.50 (s, 3H). |
| 96 | 455.34 [M + H]$^+$ | δ 10.92 (s, 1H), 9.21 (t, J = 2.0 Hz, 1H), 8.79 (s, 1H), 8.68 (s, 1H), 8.24 (d, J = 8.4 Hz, 1H), 8.19 (dd, J = 8.4, 1.2 Hz, 1H), 7.88 (ddd, J = 15.2, 8.8, 6.4 Hz, 1H), 7.55-7.59 (m, 1H), 7.53 (ddd, J = 11.2, 9.2, 2.4 Hz, 1H), 7.34 (ddd, J = 10.6, 8.5, 2.0 Hz, 1H), 7.23-7.29 (m 3H), 6.61 (s, 1H), 3.84 (s, 3H), 2.49 (s, 3H). |
| 97 | 425.31 [M + H]$^+$ | δ 10.73 (s, 1H), 9.43 (d, J = 2.0 Hz, 1H), 8.74 (s, 1H), 8.69 (d, J = 2.0 Hz, 1H), 8.20 (d, J = 8.4 Hz, 1H), 8.15 (d, J = 8.4 Hz, 1H), 7.91 (dd, J = 3.6, 0.8 Hz, 1H), 7.76 (dd, J = 5.2, 1.2 Hz, 1H), 7.56-7.59 (m, 1H), 7.22-7.30 (m, 4H), 6.60 (s, 1H), 3.83 (s, 3H), 2.49 (s, 3H). |
| 98 | 413.95 [M − H] and 415.85 [M + H]$^+$ | δ 10.97 (s, 1H), 9.30 (t, J = 1.4 Hz, 1H), 8.86 (s, 1H), 8.78 (s, 1H), 8.64 (d, J = 5.2 Hz, 1H), 8.30 (d, J = 8.4 Hz, 1H), 8.20 (dd, J = 8.4, 1.6 Hz, 1H), 7.90 (dd, J = 6.8, 5.2 Hz, 1H), 6.82 (s, 1H), 3.89 (s, 3H). |
| 99 | 377.05 [M − H] and 378.80 [M + H]$^+$ | δ 10.89 (s, 1H), 8.84 (d, J = 5.2 Hz, 1H), 8.64 (d, J = 1.6 Hz, 1H), 8.26 (d, J = 8.4 Hz, 1H), 8.05 (dd, J = 8.4, 1.6 Hz, 1H), 7.17 (d, J = 5.2 Hz, 1H), 6.79 (s, 1H), 5.00 (sept, J = 5.6 Hz, 1H), 3.86 (s, 3H), 1.45 (d, J = 5.6 Hz, 6H). |
| 100 | 396.00 [M − H] and 397.95 [M + H]$^+$ | δ 10.94 (s, 1H), 9.76 (d, J = 2.4 Hz, 1H), 9.15 (d, J = 2.4 Hz, 1H), 8.80 (d, J = 4.2 Hz, 1H), 8.76 (s, 1H), 8.30 (d, J = 8.4 Hz, 1H), 8.27 (d, J = 8.0 Hz, 1H), 8.16 (dd, J = 8.8, 1.6 Hz, 1H), 8.03 (dt, J = 8.0, 1.6 Hz, 1H), 7.52 (dd, J = 7.2, 4.8 Hz, 1H), 6.81 (s, 1H), 3.88 (s, 3H). |
| 101 | 413.95 [M − H] and 415.90 [M + H]$^+$ | δ 10.94 (s, 1H), 9.72 (d, J = 2.4 Hz, 1H), 9.12 (d, J = 2.4 Hz, 1H), 8.80 (d, J = 2.8 Hz, 1H), 8.77 (s, 1H), 8.38 (dd, J = 8.8, 4.4 Hz, 1H), 8.27 (d, J = 8.4 Hz, 1H), 8.17 (dd, J = 8.8, 1.6 Hz, 1H), 8.00 (dt, J = 8.8, 3.2 Hz, 1H), 7.52 (dt, J = 7.6, 4.2 Hz, 1H), 6.81 (s, 1H), 3.89 (s, 3H). |

TABLE 3-continued

| No. | MS (ESI) m/z | ¹H NMR (400 MHz) |
|---|---|---|
| 102 | 362.00 [M − H] and 364.30 [M + H]⁺ | δ 10.86 (s, 1H), 8.70 (d, J = 5.2 Hz, 1H), 8.61 (d, J = 1.6 Hz, 1H), 8.22 (d, J = 8.4 Hz, 1H), 7.99 (dd, J = 8.4, 1.6 Hz, 1H), 6.96 (d, J = 5.2 Hz, 1H), 6.79 (s, 1H), 3.86 (s, 3H), 3.04 (s, 6H). |
| 103 | 479.00 [M − H] and 480.90 [M + H]⁺ | δ 10.95 (s, 1H), 9.42 (d, J = 2.4 Hz, 1H), 8.82 (d, J = 2.4 Hz, 1H), 8.78 (s, 1H), 8.23 (d, J =8.8 Hz, 1H), 8.16 (dd, J = 8.8, 1.6 Hz, 1H), 8.08-8.10 (m, 2H), 7.59 (d, J = 8.2 Hz, 1H), 6.81 (s, 1H), 3.89 (s, 3H). |
| 104 | 430.95 [M − H] and 432.95 [M + H]⁺ | δ 10.97 (s, 1H), 9.12 (d, J = 2.4 Hz, 1H), 8.80 (s, 1H), 8.69 (s, 1H), 8.25 (d, J = 8.8 Hz, 1H), 8.16 (dd, J = 8.8, 1.6 Hz, 1H), 7.59-7.66 (m, 1H), 7.34-7.40 (m, 2H), 6.82 (s, 1H), 3.89 (s, 3H). |
| 105 | 479.00 [M − H] and 480.85 [M + H]⁺ | δ 10.95 (s, 1H), 9.15 (d, J = 2.4 Hz, 1H), 8.79 (s, 1H), 8.64 (d, J = 2.4 Hz, 1H), 8.25 (d, J = 8.8 Hz, 1H), 8.16 (dd, J = 8.8, 1.6 Hz, 1H), 7.80-7.82 (m, 1H), 7.59-7.69 (m, 3H), 6.82 (s, 1H), 3.89 (s, 3H). |
| 106 | 403.85 [M + H]⁺ | δ 10.93 (s, 1H), 9.47 (d, J = 2.4 Hz, 1H), 9.27 (s, 1H), 8.78 (d, J = 2.4 Hz, 1H), 8.75 (s, 1H), 8.70 (s, 1H), 8.21 (d, J = 8.4 Hz, 1H), 8.15 (dd, J = 8.4, 1.6 Hz, 1H), 6.80 (s, 1H), 3.88 (s, 3H). |
| 107 | 399.00 [M − H] and 400.95 [M + H]⁺ | δ 10.88 (s, 1H), 9.34 (d, J = 2.4 Hz, 1H), 8.70 (s, 1H), 8.60 (d, J = 2.4 Hz, 1H), 8.48 (s, 1H), 8.18 (s, 1H), 8.06-8.12 (m, 2H), 6.79 (s, 1H), 3.93 (s, 3H), 3.87 (s, 3H). |
| 108 | 399.00 [M − H] and 400.95 [M + H]⁺ | δ 10.90 (s, 1H), 9.51 (d, J = 2.4 Hz, 1H), 8.79 (d, J = 2.4 Hz, 1H), 8.73 (s, 1H), 8.19 (d, J = 8.4 Hz, 1H), 8.11 (dd, J = 8.4, 1.4 Hz, 1H), 7.88 (d, J = 2.6 Hz, 1H), 7.02 (d, J = 2.6 Hz, 1H), 6.81 (s, 1H), 3.97 (s, 3H), 3.88 (s, 3H). |
| 109 | 432.00 [M − H] and 433.85 [M + H]⁺ | δ 11.00 (s, 1H), 9.20 (d, J = 2.1 Hz, 1H), 8.83 (s, 1H), 8.82 (s, 1H), 8.79 (s, 2H), 8.30 (d, J = 8.2 Hz, 1H), 8.21 (dd, J = 8.2, 2.1 Hz, 1H), 6.82 (s, 1H), 3.89 (s, 3H). |
| 110 | 386.00 [M − H] and 387.90 [M + H]⁺ | δ 10.70 (s, 1H), 9.36 (d, J = 2.4 Hz, 1H), 8.88 (s, 1H), 8.58 (d, J = 2.4 Hz, 1H), 8.54 (s, 1H), 7.90 (dd, J = 8.0, 1.4 Hz, 1H), 7.83 (d, J = 8.0 Hz, 1H), 6.76 (s, 1H), 3.86 (s, 3H). |
| 111 | 411.00 [M − H] and 412.90 [M + H]⁺ | δ 10.90 (s, 1H), 9.83 (s, 1H), 9.35 (d, J = 2.4 Hz, 1H), 8.73 (s, 1H), 8.65 (d, J = 2.4 Hz, 1H), 8.17 (d, J = 8.2 Hz, 1H), 8.11 (dd, J = 8.2, 1.4 Hz, 1H), 7.80 (d, J = 8.4 Hz, 2H), 6.96 (d, J = 8.4 Hz, 2H), 6.80 (s, 1H), 3.88 (s, 3H). |
| 112 | 501.30 [M + H]⁺ | δ 10.99 (s, 1H), 9.61 (d, J = 2.0 Hz, 1H), 9.04 (d, J = 2.0 Hz, 1H), 8.77 (s, 1H), 8.60 (d, J = 2.4 Hz, 1H), 8.31 (d, J = 8.8 Hz, 1H), 8.16-8.20 (m, 2H), 8.10 (d, J = 3.2 Hz, 1H), 8.00 (d, J = 3.2 Hz, 1H), 7.70 (d, J = 8.8 Hz, 1H), 3.36 (q, J = 7.2 Hz, 4H), 1.09 (q, J = 7.2 Hz, 6H). |
| 113 | 530.18 [M + H]⁺ | δ 10.99 (s, 1H), 9.20 (t, J = 2.4 Hz, 1H), 8.79 (s, 1H), 8.67 (s, 1H), 8.60 (d, J = 2.4 Hz, 1H), 8.22 (d, J = 8.4 Hz, 1H), 8.19 (dd, J = 8.4, 2.4 Hz, 1H), 7.88 (ddd, J = 15.6, 8.8, 6.4 Hz, 1H), 7.70 (d, J = 8.8 Hz, 1H), 7.52 (ddd, J = 11.6, 9.6, 2.8 Hz, 1H), 7.34 (dt, J = 8.4, 2.0 Hz, 1H), 3.36 (q, J = 6.8 Hz, 4H), 1.09 (q, J = 6.8 Hz, 6H). |
| 114 | 498.14 [M − H] | δ 10.94 (s, 1H), 9.43 (d, J = 2.4 Hz, 1H), 8.74 (s, 1H), 8.68 (d, J = 2.0 Hz, 1H), 8.60 (d, J = 2.8 Hz, 1H), 8.16-8.20 (m, 2H), 8.14 (dd, J = 8.4, 2.4 Hz, 1H), 7.91 (dd, J = 3.6, 0.8 Hz, 1H), 7.76 (d, J = 5.2, 1.2 Hz, 1H), 7.70 (dd, J = 8.8 Hz, 1H), 7.28 (dd, J = 4.8, 3.6 Hz, 1H), 3.36 (q, J = 6.8 Hz, 4H), 1.09 (q, J = 6.8 Hz, 6H). |
| 115 | 426.38 [M + H]⁺ | δ 10.78 (s, 1H), 9.61 (d, J = 2.4 Hz, 1H), 9.05 (d, J = 2.0 Hz, 1H), 8.78 (s, 1H), 8.32 (d, J = 8.8 Hz, 1H), 8.20 (dd, J = 8.4, 1.2 Hz, 1H), 8.11 (d, J = 3.2 Hz, 1H), 8.00 (d, J = 3.2 Hz, 1H), 7.56-7.59 (m, 1H), 7.22-7.29 (m, 3H), 6.61 (s, 1H), 3.84 (s, 3H), 2.49 (s, 3H). |
| 116 | 399.00 [M − H] and 400.95 [M + H]⁺ | δ 10.96 (s, 1H), 9.23 (d, J = 2.4 Hz, 1H), 8.78 (s, 1H), 8.72 (d, J = 2.4 Hz, 1H), 8.24 (d, J = 8.0 Hz, 1H), 8.18 (dd, J = 8.0, 1.4 Hz, 1H), 7.60 (d, J = 2.1 Hz, 1H), 6.81 (s, 1H), 6.76 (d, J = 2.1 Hz, 1H), 4.02 (s, 3H), 3.88 (s, 3H). |
| 117 | 411.00 [M − H] and 412.90 [M + H]⁺ | δ 10.92 (s, 1H), 9.96 (s, 1H), 9.25 (d, J = 2.4 Hz, 1H), 8.75 (s, 1H), 8.58 (d, J = 2.4 Hz, 1H), 8.19 (d, J = 8.0 Hz, 1H), 8.12 (dd, J = 8.0, 1.4 Hz, 1H), 7.51 (dd, J = 7.6, 1.4 Hz, 1H), 7.30 (dt, J = 8.2, 1.4 Hz, 1H), 7.05 (d, J = 8.1 Hz, 1H), 6.99 (t, J = 8.1 Hz, 1H), 6.81 (s, 1H), 3.89 (s, 3H). |
| 118 | 397.00 [M − H] and 398.90 [M + H]⁺ | δ 10.97 (s, 1H), 9.94 (d, J = 2.4 Hz, 1H), 9.41 (d, J = 2.4 Hz, 1H), 9.06 (d, J = 4.6 Hz, 2H), 8.79 (s, 1H), 8.40 (d, J = 8.0 Hz, 1H), 8.17 (dd, J = 8.0, 1.4 Hz, 1H), 7.61 (t, J = 4.6 Hz, 1H), 6.82 (s, 1H), 3.89 (s, 3H). |
| 119 | 413.95 [M + H]⁺ and 415.90 [M + H]⁺ | δ 10.97 (s, 1H), 9.56 (s, 1H), 9.01 (s, 1H), 8.79 (s, 1H), 8.67-8.69 (m, 1H), 8.34 (d, J = 8.4 Hz, 1H), 8.17 (dd, J = 8.4, 1.4 Hz, 1H), 8.00 (dd, J = 8.4, 7.8 Hz, 1H), 7.61-7.65 (m, 1H), 6.82 (s, 1H), 3.89 (s, 3H). |
| 120 | 401.95 [M − H] and 403.85 [M + H]⁺ | 1H-NMR (400 MHz, DMSO-do): δ 10.94 (s, 1H), 9.75 (s, 1H), 9.53 (d, J = 2.4 Hz, 1H), 9.33 (s, 1H), 8.93 (d, J = 2.4 Hz, 1H), 8.76 (s, 1H), 8.14-8.19 (m, 2H), 6.80 (s, 1H), 3.88 (s, 3H). |
| 121 | 401.95 [M − H] and 403.85 [M + H]⁺ | δ 10.93 (s, 1H), 9.68 (d, J = 2.4 Hz, 1H), 9.36 (d, J = 2.4 Hz, 1H), 9.02 (d, J = 2.4 Hz, 1H), 8.76 (s, 1H), 8.61 (d, J = 2.8 Hz, 1H), 8.25 (d, J = 8.4 Hz, 1H), 8.13 (dd, J = 8.4, 2.4 Hz, 1H), 6.81 (s, 1H), 3.88 (s, 3H). |
| 122 | 397.00 [M − H] and 398.90 [M + H]⁺ | δ 10.99 (s, 1H), 9.80 (d, J = 2.4 Hz, 1H), 9.40 (d, J = 1.6 Hz, 1H), 9.33 (d, J = 2.4 Hz, 1H), 9.02 (d, J = 7.2 Hz, 1H), 8.80 (s, 1H), 8.41 (dd, J = 7.2, 1.2 Hz, 1H), 8.34 (d, J = 8.4 Hz, 1H), 8.19 (dd, J = 8.4, 2.4 Hz, 1H), 6.82 (s, 1H), 3.89 (s, 3H). |

TABLE 3-continued

| No. | MS (ESI) m/z | $^1$H NMR (400 MHz) |
|---|---|---|
| 123 | 415.00 [M − H] and 416.85 [M + H]⁺ | δ 10.97 (s, 1H), 9.89 (d, J = 2.4 Hz, 1H), 9.36 (d, J = 1.6 Hz, 1H), 9.14 (s, 1H), 8.78 (s, 1H), 8.40 (d, J = 8.2 Hz, 1H), 8.17 (dd, J = 8.2, 2.4 Hz, 1H), 6.82 (s, 1H), 3.89 (s, 3H). |
| 124 | 432.00 [M − H] and 433.90 [M + H]⁺ | δ 10.97 (s, 1H), 9.51 (s, 1H), 8.97 (s, 1H), 8.79 (s, 1H), 8.78 (s, 1H), 8.33 (d, J = 8.4 Hz, 1H), 8.23 (ddd, J = 12.4, 9.8, 4.2 Hz, 1H), 8.17 (dd, J = 9.8, 4.2 Hz, 1H), 6.82 (s, 1H), 3.89 (s, 3H). |
| 125 | 424.25 [M + H]⁺ | δ 10.81 (s, 1H), 9.32 (t, J = 2.0 Hz, 1H), 8.87 (s, 1H), 8.80-8.82 (m, 2H), 8.64 (d, J = 5.2 Hz, 1H), 8.29 (d, J = 8.4 Hz, 1H), 8.22 (dd, J = 8.4, 1.6 Hz, 1H), 7.93 (dd, J = 6.8, 5.2 Hz, 1H), 7.82 (d, J = 7.6 Hz, 1H), 7.42 (d, J = 7.6 Hz, 1H), 7.31 (d, J = 7.2 Hz, 1H), 6.80 (s, 1H), 3.83 (s, 3H). |
| 126 | 400.95 [M + H]⁺ | δ 10.92 (s, 1H), 9.24 (d, J = 2.4 Hz, 1H), 8.75 (s, 1H), 8.63 (d, J = 2.4 Hz, 1H), 8.20 (d, J = 8.4 Hz, 1H), 8.16 (dd, J = 8.4, 1.6 Hz, 1H), 7.87 (s, 1H), 7.46 (d, J = 1.4 Hz, 1H), 6.81 (s, 1H), 3.88 (s, 3H). |
| 127 | 399.0 [M − H] and 400.90 [M + H]⁺ | δ 10.94 (s, 1H), 9.43 (d, J = 2.4 Hz, 1H), 8.80 (s, 1H), 8.76 (s, 1H), 8.25 (d, J = 8.4 Hz, 1H), 8.18 (d, J = 8.4 Hz, 1H), 7.43 (s, 1H), 7.14 (s, 1H), 6.81 (s, 1H), 3.95 (s, 3H), 3.88 (s, 3H). |
| 128 | 424.36 [M + H]⁺ | δ 10.78 (s, 1H), 9.73 (d, J = 2.0 Hz, 1H), 9.12 (d, J = 1.6 Hz, 1H), 8.81 (d, J = 2.8 Hz, 1H), 8.79 (s, 1H), 8.38 (dd, J = 8.8, 4.0 Hz, 1H), 8.27 (d, J = 8.4 Hz, 1H), 8.18 (d, J = 8.4 Hz, 1H), 7.99 (dt, J = 8.8, 2.8 Hz, 1H), 7.81 (d, J = 7.6 Hz, 1H), 7.42 (t, J = 7.6 Hz, 1H), 7.31 (t, J = 7.2 Hz, 1H), 6.80 (s, 1H), 3.83 (s, 3H). |
| 129 | 400.23 [M + H]⁺ | δ 11.23 (s, 1H), 9.12 (d, J = 2.0 Hz, 1H), 9.04 (d, J = 2.0 Hz, 1H), 8.76 (d, J = 2.0 Hz, 1H), 8.47-8.51 (m, 2H), 7.97 (d, J = 8.4 Hz, 1H), 7.85 (d, J = 8.4 Hz, 2H), 7.57 (t, J = 8.0 Hz, 2H), 7.48 (t, J = 7.6 Hz, 1H). |
| 130 | 403.25 [M + H]⁺ | δ 11.06 (s, 1H), 9.04 (d, J = 2.0 Hz, 1H), 8.76 (d, J = 2.0 Hz, 1H), 8.41 (s, 1H), 7.84-7.86 (m, 2H), 7.57 (t, J = 8.0 Hz, 2H), 7.46 (t, J = 7.6 Hz, 1H), 6.79 (s, 1H), 3.87 (s, 3H). |
| 131 | 443.36 [M + H]⁺ | δ 10.50 (s, 1H), 8.99 (d, J = 2.0 Hz, 1H), 8.67 (d, J = 2.0 Hz, 1H), 8.35 (s, 1H), 7.83 (d, J = 7.2 Hz, 2H), 7.61 (d, J = 8.8 Hz, 2H), 7.56 (t, J = 7.6 Hz, 2H), 7.47 (t, J = 7.6 Hz, 1H), 6.96 (d, J = 9.2 Hz, 2H), 3.11-3.14 (m, 4H), 2.48-2.50 (m, 4H), 2.36 (q, J = 7.2 Hz, 2H), 1.04 (t, J = 7.2 Hz, 3H). |
| 132 | 461.38 [M + H]⁺ | δ 10.71 (s, 1H), 9.00 (d, J = 2.4 Hz, 1H), 8.70 (d, J = 2.0 Hz, 1H), 8.37 (s, 1H), 7.83-7.85 (m, 2H), 7.67 (dd, J = 15.2, 2.4 Hz, 1H), 7.56 (t, J = 7.6 Hz, 2H), 7.45-7.48 (m, 2H), 7.06 (t, J = 9.2 Hz, 1H), 2.99-3.02 (m, 4H), 2.48-2.50 (m, 4H), 2.38 (q, J = 7.2 Hz, 2H), 1.04 (t, J = 7.2 Hz, 3H). |
| 133 | 391.32 [M + H]⁺ | δ 10.71 (s, 1H), 9.02 (d, J = 2.0 Hz, 1H), 8.36 (s, 1H), 7.84 (d, J = 7.2 Hz, 2H), 7.56 (t, J = 7.2 Hz, 2H), 7.47 (t, J = 7.2 Hz, 1H), 6.17 (s, 1H), 3.67 (s, 3H), 1.25 (s, 9H). |
| 134 | 498.23 [M − H] | δ 11.06 (s, 1H), 9.02 (d, J = 2.0 Hz, 1H), 8.73 (d, J = 2.0 Hz, 1H), 8.51 (d, J = 2.4 Hz, 1H), 8.44 (s, 1H), 8.11 (dd, J = 8.8, 2.8 Hz, 1H), 7.83-7.86 (m, 2H), 7.70 (d, J = 8.8 Hz, 1H), 7.57 (t, J = 7.2 Hz, 2H), 7.47 (t, J = 7.2 Hz, 1H), 3.34 (q, J = 7.2 Hz, 4H), 1.09 (q, J = 7.2 Hz, 6H). |
| 135 | 414.26 [M − H] | δ 10.52 (s, 1H), 8.99 (d, J = 2.0 Hz, 1H), 8.68 (d, J = 2.0 Hz, 1H), 8.35 (s, 1H), 7.83-7.86 (m, 2H), 7.64 (d, J = 9.2 Hz, 1H), 7.56 (t, J = 8.0 Hz, 2H), 7.47 (t, J = 7.6 Hz, 1H), 6.98 (d, J = 9.2 Hz, 1H), 3.75 (t, J = 4.8 Hz, 4H), 3.10 (t, J = 4.8 Hz, 6H). |
| 136 | 441.28 [M − H] | δ 10.90 (s, 1H), 9.02 (d, J = 2.0 Hz, 1H), 8.74 (d, J = 2.4 Hz, 1H), 8.40 (s, 1H), 7.89-7.93 (m, 2H), 7.55-7.58 (m, 1H), 7.40 (t, J = 8.8 Hz, 1H), 7.22-7.28 (m, 2H), 6.58 (s, 1H), 3.81 (s, 3H), 2.48 (s, 3H). |
| 137 | 461.35 [M + H]⁺ | δ 10.94 (s, 1H), 8.86 (t, J = 2.0 Hz, 1H), 8.66 (s, 1H), 8.42 (s, 1H), 7.77 (ddd, J = 15.6, 8.8, 6.8 Hz, 1H), 7.55-7.58 (m, 1H), 7.50 (ddd, J = 11.6, 8.8, 2.8 Hz, 1H), 7.22-7.32 (m, 4H), 6.58 (s, 1H), 3.81 (s, 3H), 2.48 (s, 3H). |
| 138 | 429.23 [M − H] | δ 10.90 (s, 1H), 9.06 (d, J = 2.4 Hz, 1H), 8.71 (d, J = 2.0 Hz, 1H), 8.37 (s, 1H), 7.77 (dd, J = 3.6, 0.8 Hz, 1H), 7.70 (dd, J = 5.2, 0.8 Hz, 1H), 7.55-7.58 (m, 1H), 7.22-7.27 (m, 4H), 6.58 (s, 1H), 3.81 (s, 3H), 2.48 (s, 3H). |
| 139 | 432.20 [M + H]⁺ | δ 10.96 (s, 1H), 9.28 (d, J = 2.0 Hz, 1H), 9.00 (d, J = 2.0 Hz, 1H), 8.43 (s, 1H), 8.05 (d, J = 3.2 Hz, 1H), 7.95 (d, J = 3.6 Hz, 1H), 7.55-7.58 (m, 1H), 7.22-7.28 (m, 3H), 6.59 (s, 1H), 3.81 (s, 3H), 2.48 (s, 3H). |
| 140 | 515.90 [M − H] | δ 11.08 (s, 1H), 8.88 (t, J = 2.0 Hz, 1H), 8.66 (t, J = 2.0 Hz, 1H), 8.51 (d, J = 2.8 Hz, 1H), 8.45 (s, 1H), 8.11 (dd, J = 8.8, 2.4 Hz, 1H), 7.69-7.74 (m, 2H), 7.51-7.56 (m, 1H), 7.40-7.45 (m, 2H), 3.34 (q, J = 7.2 Hz, 4H), 1.09 (t, J = 7.2 Hz, 6H). |
| 141 | 518.21 [M + H]⁺ | δ 11.06 (s, 1H), 9.01 (d, J = 2.4 Hz, 1H), 8.72 (d, J = 2.0 Hz, 1H), 8.51 (d, J = 2.4 Hz, 1H), 8.43 (s, 1H), 8.11 (dd, J = 8.8, 2.4 Hz, 1H), 7.89-7.92 (m, 2H), 7.70 (d, J = 8.8 Hz, 1H), 7.40 (t, J = 8.8 Hz, 2H), 3.35 (q, J = 7.2 Hz, 4H), 1.09 (t, J = 7.2 Hz, 6H). |
| 142 | 499.24 [M − H] | δ 11.08 (s, 1H), 9.15 (d, J = 2.0 Hz, 1H), 8.90 (d, J = 2.0 Hz, 1H), 8.74 (dd, J = 6.4, 1.6 Hz, 2H), 8.51 (d, J = 2.4 Hz, 1H), 8.47 (s, 1H), 8.11 (dd, J = 8.8, 2.4 Hz, 1H), 7.92 (dd, J = 6.4, 1.6 Hz, 2H), 7.71 (d, J = 8.8 Hz, 1H), 3.34 (q, J = 7.2 Hz, 4H), 1.09 (t, J = 7.2 Hz, 6H). |

TABLE 3-continued

| No. | MS (ESI) m/z | $^1$H NMR (400 MHz) |
|---|---|---|
| 143 | 507.12 [M + H]$^+$ | δ 11.11 (s, 1H), 9.27 (d, J = 2.0 Hz, 1H), 8.99 (d, J = 2.4 Hz, 1H), 8.51 (d, J = 2.4 Hz, 1H), 8.46 (s, 1H), 8.11 (dd, J = 8.8, 2.4 Hz, 1H), 8.05 (d, J = 3.2 Hz, 1H), 7.94 (d, J = 3.2 Hz, 1H), 7.71 (d, J = 8.8 Hz, 1H), 3.34 (q, J = 6.8 Hz, 4H), 1.09 (t, J = 6.8 Hz, 6H). |
| 144 | 517.12 [M − H] | δ 11.09 (s, 1H), 9.41 (d, J = 2.0 Hz, 1H), 9.08 (d, J = 2.0 Hz, 1H), 8.76 (d, J = 4.0 Hz, 1H), 8.51 (d, J = 2.4 Hz, 1H), 8.47 (s, 1H), 8.20 (d, J = 8.0 Hz, 1H), 8.12 (dd, J = 8.8, 2.8 Hz, 1H), 7.99 (dt, J = 8.0, 2.0 Hz, 1H), 7.71 (d, J = 8.8 Hz, 1H), 7.47 (dd, J = 6.8, 4.8 Hz, 1H), 3.34 (q, J = 6.8 Hz, 4H), 1.09 (t, J = 6.8 Hz, 6H). |
| 145 | 517.12 [M − H] | δ 11.09 (s, 1H), 8.98 (d, J = 2.0 Hz, 1H), 8.80-8.81 (m, 1H), 8.78 (d, J = 2.4 Hz, 1H), 8.61 (dd, J = 5.2, 0.8 Hz, 1H), 8.50 (d, J = 2.4 Hz, 1H), 8.48 (s, 1H), 8.11 (dd, J = 8.8, 2.8 Hz, 1H), 7.84 (dd, J = 6.8, 4.8 Hz, 1H), 7.71 (d, J = 8.4 Hz, 1H), 3.34 (q, J = 6.8 Hz, 4H), 1.09 (t, J = 6.8 Hz, 6H). |
| 146 | 470.08 [M − H] | δ 11.07 (s, 1H), 9.02 (d, J = 2.4 Hz, 1H), 8.72 (d, J = 2.0 Hz, 1H), 8.45 (d, J = 2.4 Hz, 1H), 8.43 (s, 1H), 8.12 (dd, J = 8.8, 2.8 Hz, 1H), 7.84 (d, J = 8.8 Hz, 2H), 7.72 (d, J = 8.8 Hz, 1H), 7.56 (t, J = 7.2 Hz, 1H), 7.48 (t, J = 7.2 Hz, 1H), 2.86 (s, 6H). |
| 147 | 490.23 [M + H]$^+$ | δ 11.07 (s, 1H), 8.87 (t, J = 2.0 Hz, 1H), 8.66 (t, J = 1.6 Hz, 1H), 8.45 (d, J = 2.0 Hz, 1H), 8.44 (s, 1H), 8.12 (dd, J = 8.8, 2.8 Hz, 1H), 7.69-7.74 (m, 2H), 7.51-7.56 (m, 1H), 7.40-7.42 (m, 1H), 2.85 (s, 6H). |
| 148 | 490.07 [M + H]$^+$ | δ 11.07 (s, 1H), 9.01 (d, J = 2.0 Hz, 1H), 8.72 (d, J = 2.0 Hz, 1H), 8.45 (d, J = 2.4 Hz, 1H), 8.43 (s, 1H), 8.12 (dd, J = 8.8, 2.4 Hz, 1H), 7.87-7.92 (m, 2H), 7.73 (d, J = 8.8 Hz, 1H), 7.37-7.43 (m, 2H), 2.85 (s, 6H). |
| 149 | 471.18 [M − H] | δ 11.10 (s, 1H), 9.15 (d, J = 2.0 Hz, 1H), 8.90 (d, J = 2.0 Hz, 1H), 8.74 (dd, J = 4.4, 1.6 Hz, 2H), 8.47 (s, 1H), 8.45 (d, J = 2.8 Hz, 1H), 8.13 (dd, J = 8.8, 2.4 Hz, 1H), 7.91 (dd, J = 4.4, 1.6 Hz, 2H), 7.72 (d, J = 8.8 Hz, 1H), 2.86 (s, 6H). |
| 150 | 477.00 [M − H] | δ 11.12 (s, 1H), 9.27 (d, J = 2.0 Hz, 1H), 8.99 (d, J = 2.4 Hz, 1H), 8.46 (s, 1H), 8.44 (d, J = 2.8 Hz, 1H), 8.13 (dd, J = 8.8, 2.4 Hz, 1H), 8.05 (d, J = 3.2 Hz, 1H), 7.94 (d, J = 3.2 Hz, 1H), 7.73 (d, J = 8.8 Hz, 1H), 2.86(s, 6H). |
| 151 | 519.19 [M + H]$^+$ | δ 11.07(s, 1H), 9.37 (d, J = 1.6 Hz, 1H), 9.04 (d, J = 1.6 Hz, 1H), 8.76 (d, J = 2.8 Hz, 1H), 8.51 (d, J = 2.0 Hz, 1H), 8.46 (s, 1H), 8.30 (dd, J = 8.4, 4.0 Hz, 1H), 8.11 (dd, J = 8.8, 2.4 Hz, 1H), 7.96 (dt, J = 8.4, 2.8 Hz, 1H), 7.71 (d, J = 8.8 Hz, 1H), 3.34 (q, J = 6.8 Hz, 4H), 1.09 (t, J = 6.8 Hz, 6H). |
| 152 | 471.08 [M + H]$^+$ | δ 11.09 (s, 1H), 9.41 (d, J = 2.0 Hz, 1H), 9.08 (d, J = 2.0 Hz, 1H), 8.76 (d, J = 4.0 Hz, 1H), 8.47 (s, 1H), 8.45 (d, J = 2.8 Hz, 1H), 8.20 (d, J = 8.0 Hz, 1H), 8.13 (dd, J = 8.8, 2.8 Hz, 1H), 7.99 (dt, J = 8.0, 2.0 Hz, 1H), 7.73 (d, J = 8.8 Hz, 1H), 7.47 (dd, J = 6.8, 4.8 Hz, 1H), 2.86 (s, 6H). |
| 153 | 489.20 [M − H] | δ 11.09 (s, 1H), 8.98 (d, J = 2.0 Hz, 1H), 8.80-8.81 (m, 1H), 8.78 (d, J = 2.4 Hz, 1H), 8.61 (dd, J = 5.2, 0.8 Hz, 1H), 8.50 (d, J = 2.4 Hz, 1H), 8.48 (s, 1H), 8.11 (dd, J = 8.8, 2.8 Hz, 1H), 7.84 (dd, J = 6.8, 4.8 Hz, 1H), 7.71 (d, J = 8.4 Hz, 1H), 2.85 (s, 6H). |
| 154 | 491.16 [M + H]$^+$ | δ 11.09 (s, 1H), 9.37 (d, J = 2.4 Hz, 1H), 9.04 (d, J = 2.0 Hz, 1H), 8.76 (d, J = 3.2 Hz, 1H), 8.44-8.45 (m, 2H), 8.29 (dd, J = 8.4, 4.0 Hz, 1H), 8.12 (dd, J = 8.8, 2.8 Hz, 1H), 7.95 (dt, J = 8.8, 3.2 Hz, 1H), 7.72 (d, J = 8.8 Hz, 1H), 2.86 (s, 6H). |

Example 156

INDIGO AhR Reporter Assay

INDIGO's Aryl Hydrocarbon Receptor (AhR) Reporter Cells include the luciferase reporter gene functionally linked to an AhR-responsive promoter. Thus, quantifying changes in luciferase expression in the treated reporter cells provides a sensitive surrogate measure of the changes in AhR activity. The principle application of this reporter assay is in the screening of test samples to quantify any functional activity, either agonist or antagonist, that they may exert against human AhR. Reporter Cells incorporate the cDNA encoding beetle luciferase, a 62 kD protein originating from the North American firefly (Photinus pyralis). Luciferase catalyzes the mono-oxidation of D-luciferin in a $Mg^{2+}$-dependent reaction that consumes 02 and ATP as co-substrates, and yields as products oxyluciferin, AMP, PPi, $CO_2$, and photon emission. Luminescence intensity of the reaction is quantified using a luminometer, and is reported in terms of Relative Light Units (RLU's). In brief, 200 μl of Reporter Cells was dispensed into wells of the assay plate and pre-incubated for 4-6 hours. Following the pre-incubation period, culture media were discarded and 200 l/well of the prepared 1×-concentration treatment media were added. Following 22-24 hours of incubation, treatment media were discarded and Luciferase Detection Reagent was added. The intensity of light emission (in units of "Relative Light Units" (RLU)) from each assay well was quantified using a plate-reading luminometer. The assay was run as a competitive binding assay in the antagonist mode with 50 nM of VAF347, a known AhR agonist.

In Table 4, $IC_{50}$ values are reported as A, B, C, or D. A represents an $IC_{50}$ value of less than 100 nM. B represents an $IC_{50}$ value of equal or greater than 100 nM and less than 500 nM. C represents an $IC_{50}$ value of equal or greater than 500 nM and less than 1 μM. D represents an $IC_{50}$ value of equal or greater than 1 μM.

TABLE 4

| Compound | IC$_{50}$ |
|---|---|
| CH223191 | B |
| Compound 19 | B |
| Compound 27 | A |
| Compound 29 | B |
| Compound 31 | A |
| Compound 33 | C |
| Compound 34 | B |
| Compound 40 | A |
| Compound 44 | B |
| Compound 48 | B |
| Compound 50 | A |
| Compound 51 | A |
| Compound 52 | B |
| Compound 53 | C |
| Compound 55 | D |
| Compound 48 | B |
| Compound 54 | A |
| Compound 57 | B |
| Compound 58 | B |
| Compound 59 | B |
| Compound 60 | D |
| Compound 61 | A |
| Compound 62 | B |
| Compound 64 | D |
| Compound 65 | D |
| Compound 66 | B |
| Compound 67 | A |
| Compound 73 | A |
| Compound 74 | B |
| Compound 75 | A |
| Compound 76 | D |
| Compound 77 | D |
| Compound 78 | B |
| Compound 80 | D |
| Compound 81 | B |
| Compound 83 | C |
| Compound 90 | C |
| Compound 93 | A |
| Compound 95 | A |
| Compound 96 | A |
| Compound 97 | A |
| Compound 98 | B |
| Compound 99 | D |
| Compound 100 | A |
| Compound 101 | A |
| Compound 123 | A |
| Compound 124 | A |
| Compound 125 | B |
| Compound 128 | A |
| Compound 141 | B |
| Compound 142 | B |
| Compound 144 | C |
| Compound 145 | B |
| Compound 148 | B |
| Compound 151 | D |
| Compound 153 | C |
| Compound 172 | C |

CH223191 is known AhR antagonist with the structure:

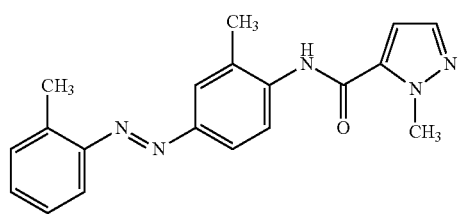 [SMILES: Cc1ccccc1/N=N/c1ccc(NC(=O)c2ccnn2C)c(C)c1]

What is claimed is:

1. A compound having the structure of Formula (Ia-1):

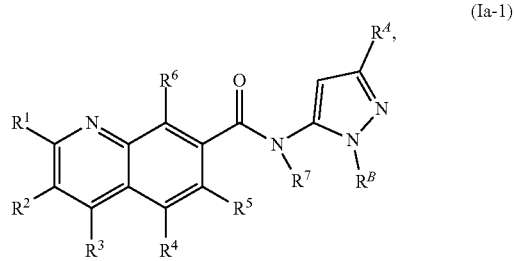

or a pharmaceutically acceptable salt thereof, wherein $R^A$ is selected from the group consisting of $C_{1-6}$ alkyl, $C_{1-6}$ haloalkyl, $C_{1-6}$ alkoxy, $C_{1-6}$ haloalkoxy, and $-(CH_2)_m R^{19}$;

$R^B$ is selected from the group consisting of $CH_3$, $CF_3$, $CH_2CF_3$, isopropyl, and phenyl;

each of $R^1$ and $R^3$ is H;

$R^2$ is thienyl, thiazolyl, isothiazolyl, pyrazolyl, oxazolyl, isoxazolyl, imidazolyl, pyridyl, pyrimidinyl, or phenyl, each optionally substituted with one or more substituents independently selected from the group consisting of halo, hydroxy, $C_{1-6}$ alkyl, $C_{1-6}$ haloalkyl, $C_{1-6}$ alkoxy, $C_{1-6}$ haloalkoxy, ($C_{1-6}$ alkoxy) $C_{1-6}$ alkyl, and $-O(C_{1-6}$ alkoxy)$C_{1-6}$ alkyl;

each $R^4$, $R^5$ and $R^6$ is independently H, halo or $C_{1-6}$ alkyl;

$R^7$ is H or methyl;

each of $R^9$ and $R^{10}$ is independently selected from the group consisting of H, optionally substituted $C_{1-6}$ alkyl, optionally substituted $C_{6-10}$ aryl, optionally substituted $C_{7-14}$ aralkyl, and optionally substituted $C_{3-7}$ carbocyclyl; or $R^9$ and $R^{10}$ together with the nitrogen atom to which they are attached form a 3 to 7 membered heterocyclyl optionally substituted with one or more $R^{22}$;

$R^{19}$ is selected from the group consisting of phenyl, 3 to 7 membered heterocyclyl, 5 to 6 membered heteroaryl, and $-NR^9R^{10}$, wherein each phenyl, 3 to 7 membered heterocyclyl, and 5 to 6 membered heteroaryl is optionally substituted with one or more $R^{22}$;

each $R^{22}$ is independently selected from the group consisting of $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl, $-O-(C_{1-6}$ alkoxy)$C_{1-6}$ alkyl, $C_{3-7}$ cycloalkyl, $-(CH_2CH_2O)_p CH_2CH_2N_3$, halo, hydroxy, SEM, nitro, azido, and cyano; or two germinal $R^{22}$ form oxo; and each m and p is independently an integer selected from 0 to 6.

2. The compound of claim 1, wherein $R^A$ is tert-butyl, isobutyl, or $-CF_3$.

3. The compound of claim 1, wherein $R^2$ is phenyl or pyridyl, each optionally substituted with one or more substituents independently selected from the group consisting of halo, $C_{1-6}$ alkyl, $C_{1-6}$ haloalkyl, $C_{1-6}$ alkoxy, and $C_{1-6}$ haloalkoxy.

4. The compound of claim 1, selected from the group consisting of
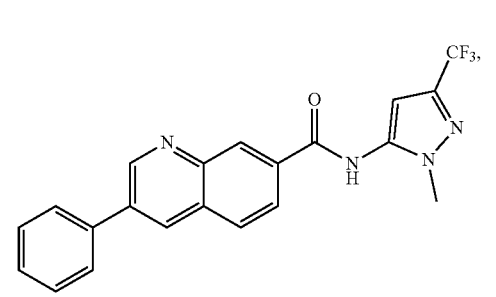
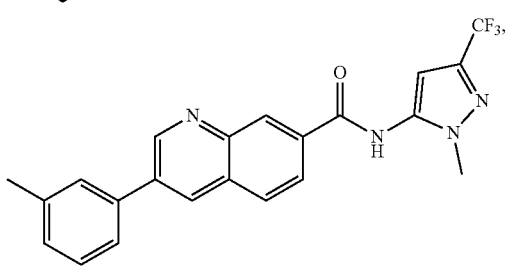
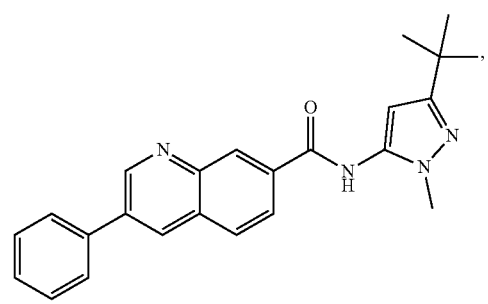
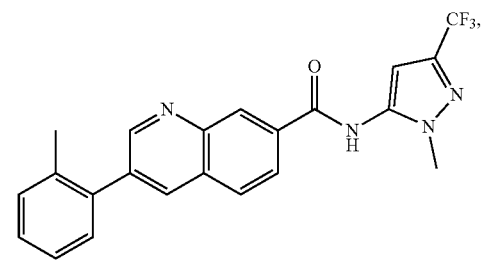
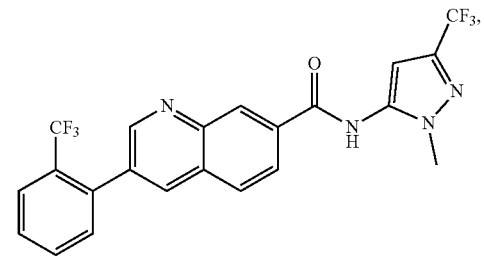
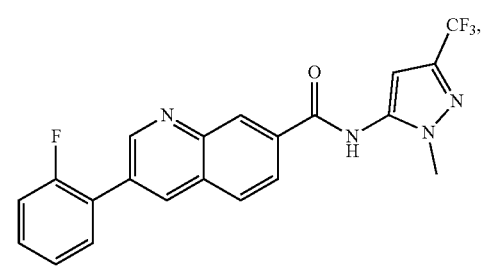
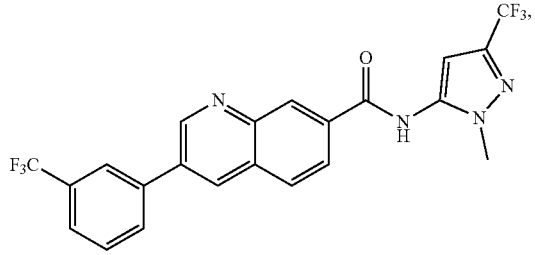
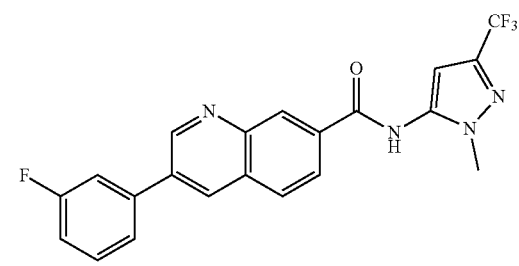
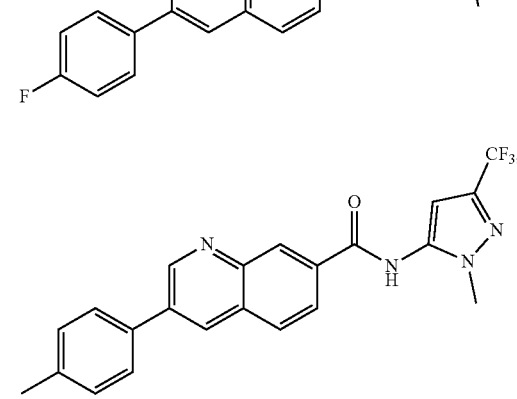
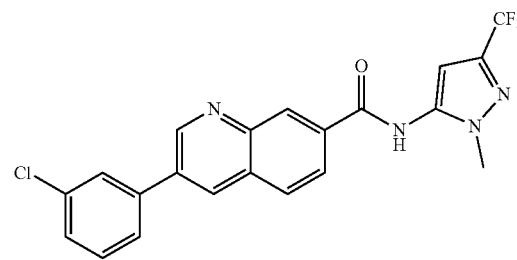
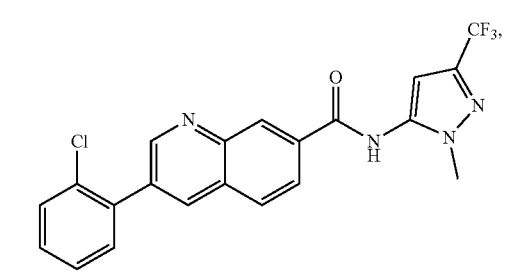

-continued
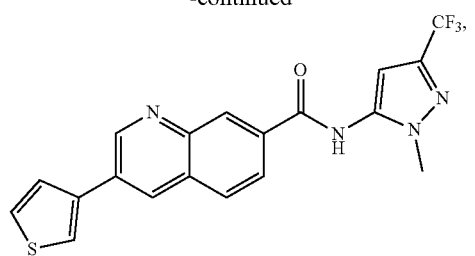
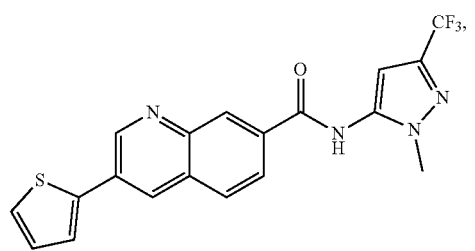
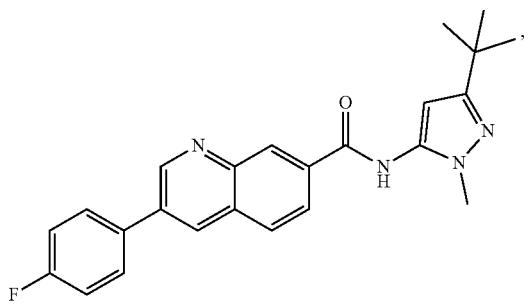
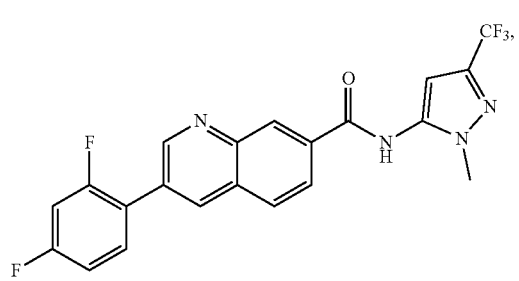
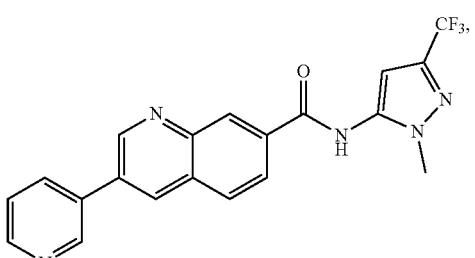
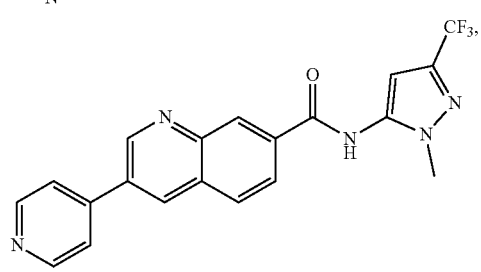
-continued
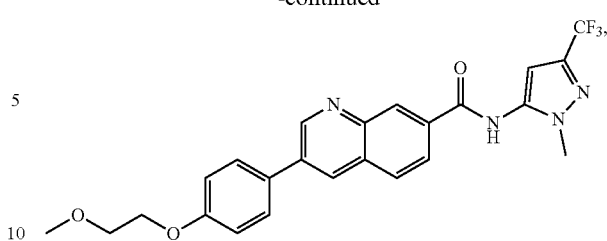
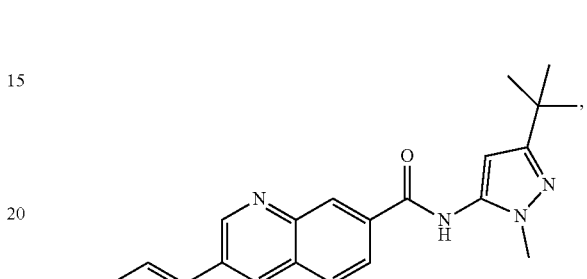
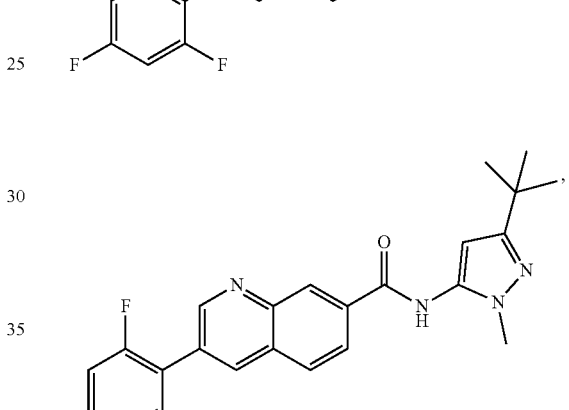
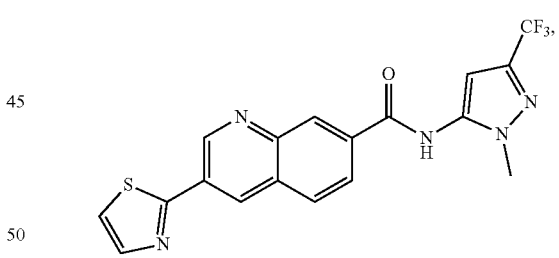
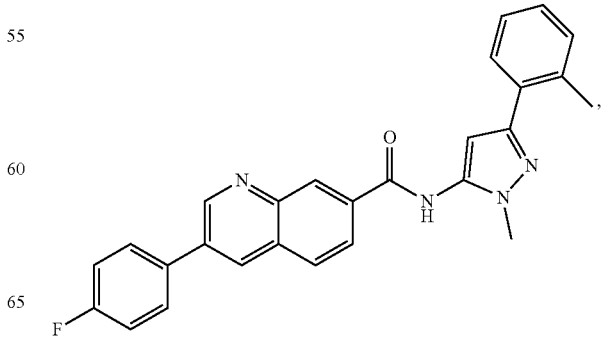

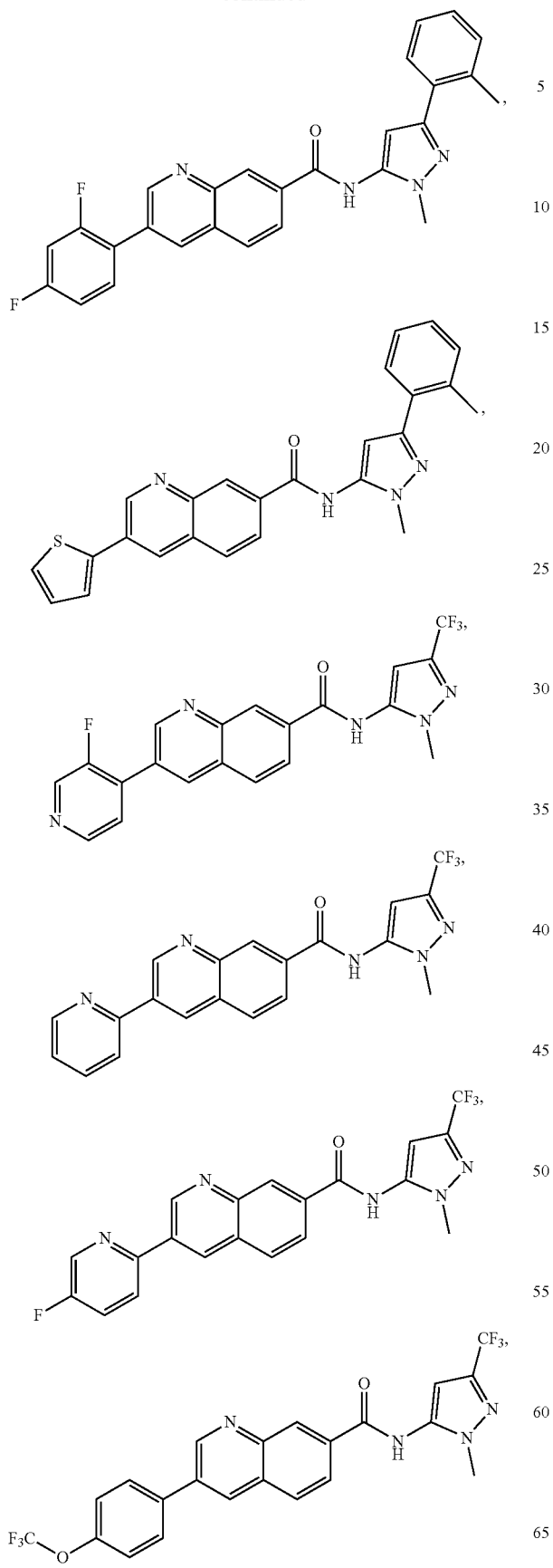
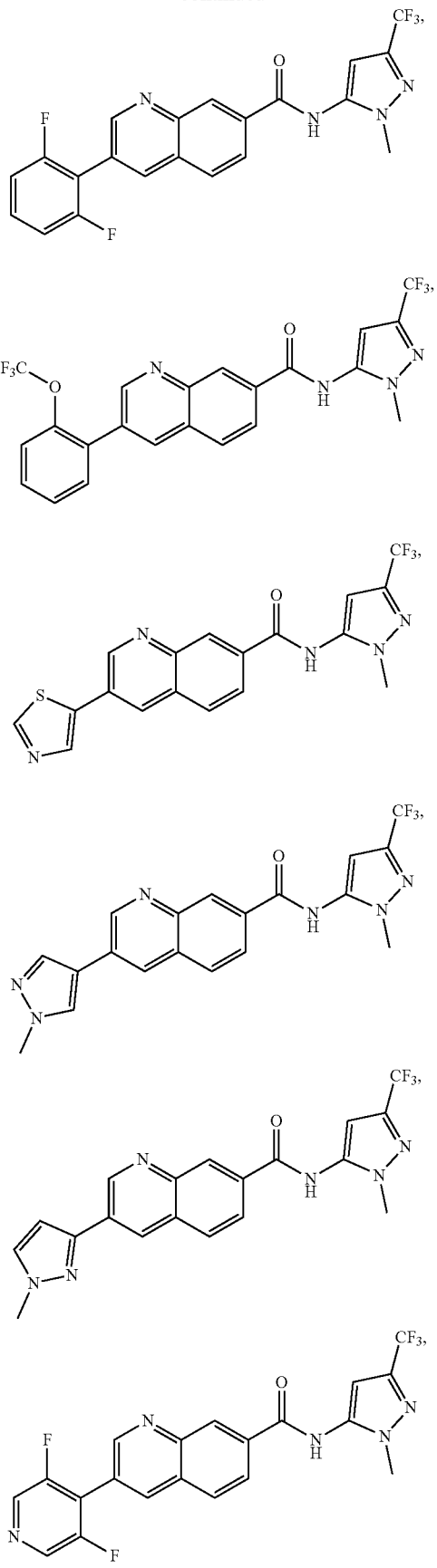

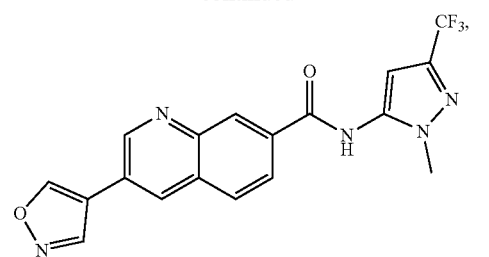
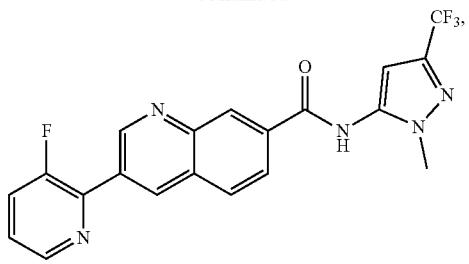
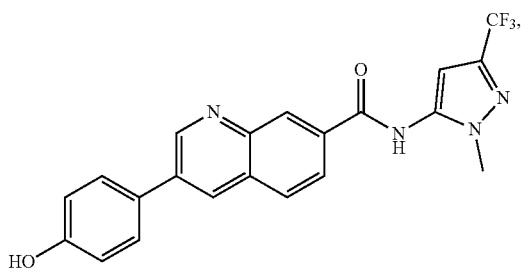
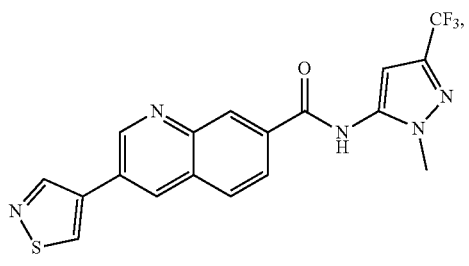
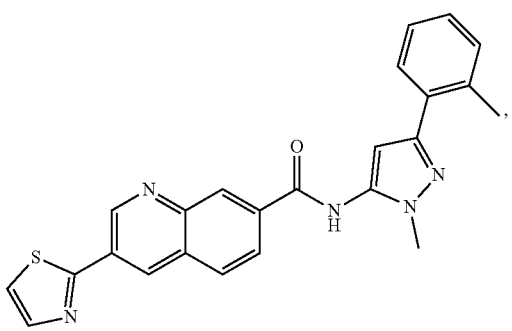
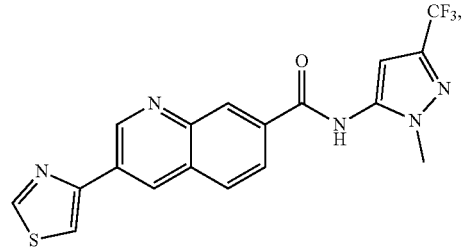
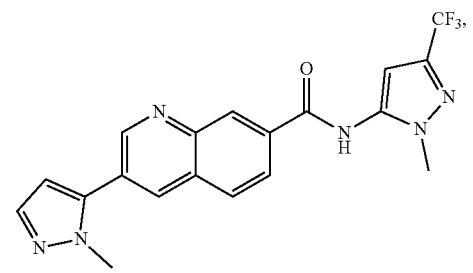
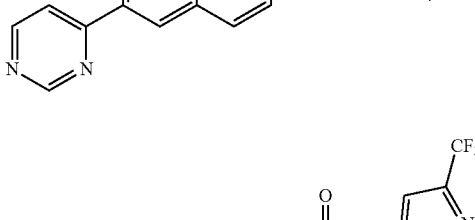
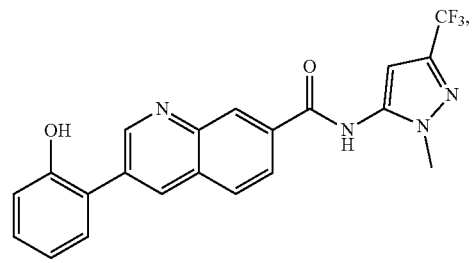 [SMILES: Cn1nc(C(F)(F)F)cc1NC(=O)c1ccc2cc(-c3ccccc3)cnc2c1]
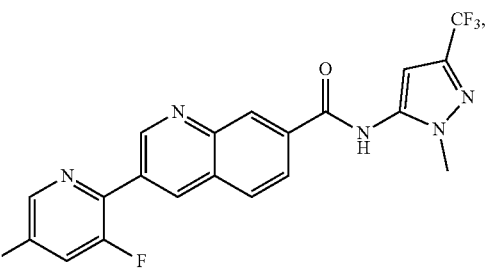
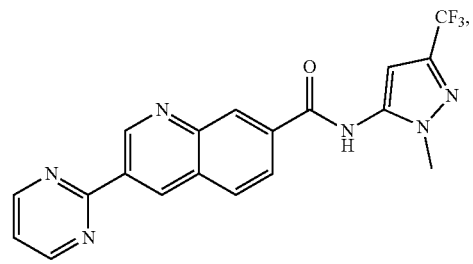

-continued

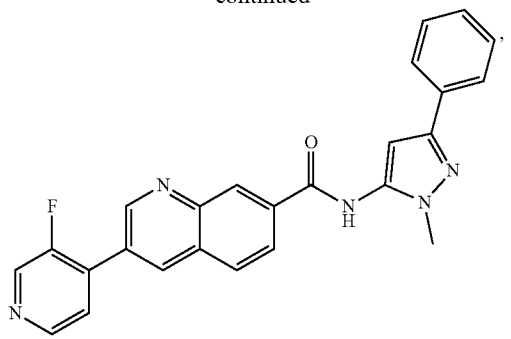

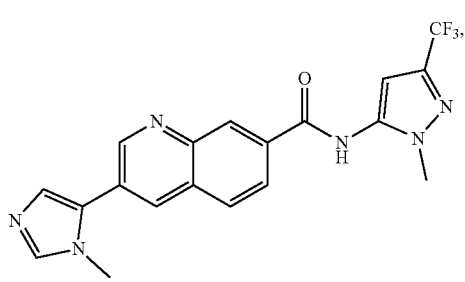

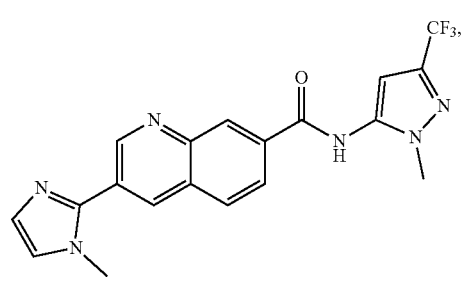

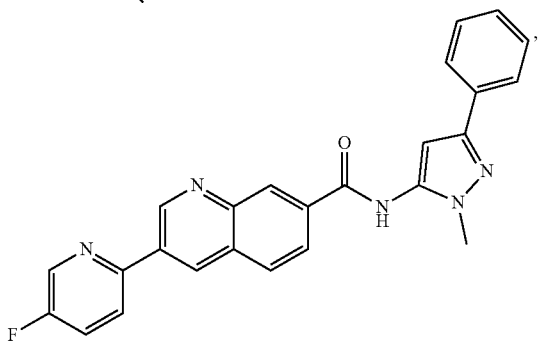

and pharmaceutically acceptable salts thereof.

5. The compound of claim 1, wherein $R^A$ is tert-butyl, isobutyl, or —$CF_3$, and wherein $R^2$ is phenyl or pyridyl, each optionally substituted with one or more substituents independently selected from the group consisting of halo, $C_{1-6}$ alkyl, $C_{1-6}$ haloalkyl, $C_{1-6}$ alkoxy, and $C_{1-6}$ haloalkoxy.

6. The compound of claim 5, wherein $R^A$ is —$CF_3$.

7. The compound of claim 5, wherein $R^B$ is methyl.

8. The compound of claim 6, wherein $R^2$ is phenyl, unsubstituted or substituted with one or more substituents independently selected from the group consisting of halo, $C_{1-6}$ alkyl, $C_{1-6}$ haloalkyl, $C_{1-6}$ alkoxy, and $C_{1-6}$ haloalkoxy.

9. The compound of claim 8, selected from

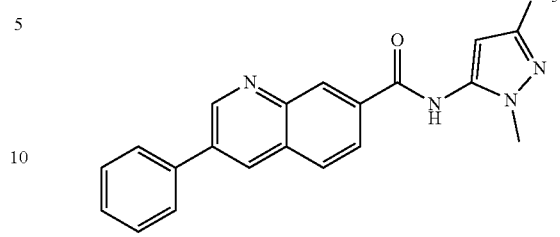

and pharmaceutically acceptable salt thereof.

10. The compound of claim 6, wherein $R^2$ is pyridyl, unsubstituted or substituted with one or more substituents independently selected from the group consisting of halo, $C_{1-6}$ alkyl, $C_{1-6}$ haloalkyl, $C_{1-6}$ alkoxy, and $C_{1-6}$ haloalkoxy.

11. The compound of claim 10, selected from the group consisting of

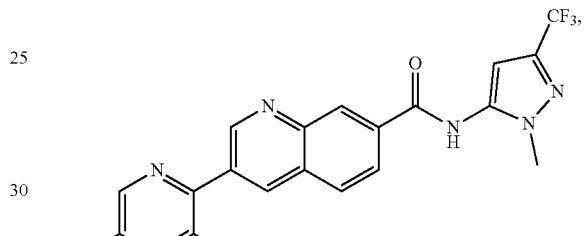

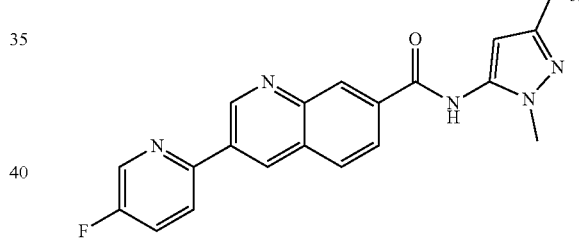

and pharmaceutically acceptable salt thereof.

12. A pharmaceutical composition comprising a compound of claim 1, or a pharmaceutically acceptable salt thereof, and a pharmaceutically acceptable carrier or excipient.

13. A method of treating or ameliorating an AhR-mediated disorder in a subject in need thereof, comprising administering a compound of claim 1, or a pharmaceutically acceptable salt thereof, to the subject.

14. The method of claim 13, wherein the AhR-mediated disorder is an inflammatory disorder or a cancer.

15. The method of claim 14, wherein the cancer is selected from the group consisting of breast cancer, melanoma, renal cancer, prostate cancer, colon cancer, lung cancer, bladder cancer, brain cancer, cervical cancer, head and neck cancer, esophageal and gastric cancers, osteosarcoma, multiple myeloma, acute myeloid leukemia, lymphomas, neuroendocrine cancer, hepatocellular carcinoma, renal cell cancer, pancreatic cancer, thyroid cancer, glioblastoma, ovarian and endometrial cancer.

* * * * *